US010272085B2

(12) United States Patent
McGowan et al.

(10) Patent No.: US 10,272,085 B2
(45) Date of Patent: Apr. 30, 2019

(54) PYRIMIDINE DERIVATIVES FOR THE TREATMENT OF VIRAL INFECTIONS

(71) Applicant: Janssen Sciences Ireland UC, Little Island, Co Cork (IE)

(72) Inventors: David McGowan, Brussels (BE); Pierre Jean-Marie Bernard Raboisson, Rosieres (BE); Werner Embrechts, Beerse (BE); Tim Hugo Maria Jonckers, Heist-op-den-Berg (BE); Stefaan Julien Last, Lint (BE); Serge Maria Aloysius Pieters, AR Hulst (NL); Jaromir Vlach, La Roche sur Foron (FR)

(73) Assignee: Janssen Sciences Ireland UC, Little Island, Co Cork (IE)

( * ) Notice: Subject to any disclaimer, the term of this patent is extended or adjusted under 35 U.S.C. 154(b) by 0 days.

(21) Appl. No.: 15/209,637

(22) Filed: Jul. 13, 2016

(65) Prior Publication Data

US 2017/0239245 A1    Aug. 24, 2017

Related U.S. Application Data

(62) Division of application No. 14/110,054, filed as application No. PCT/EP2012/056388 on Apr. 10, 2012, now Pat. No. 9,422,250.

(30) Foreign Application Priority Data

Apr. 8, 2011 (EP) ..................... 11161595

(51) Int. Cl.
*A61K 31/505* (2006.01)
*A61K 31/5377* (2006.01)
*A61K 31/506* (2006.01)
*C07D 239/48* (2006.01)
*C07D 401/12* (2006.01)
*C07D 403/12* (2006.01)
*C07D 405/12* (2006.01)
*C07D 413/12* (2006.01)
*C07D 471/04* (2006.01)
*C07D 487/04* (2006.01)
*C07D 495/04* (2006.01)

(52) U.S. Cl.
CPC .......... *A61K 31/505* (2013.01); *A61K 31/506* (2013.01); *A61K 31/5377* (2013.01); *C07D 239/48* (2013.01); *C07D 401/12* (2013.01); *C07D 403/12* (2013.01); *C07D 405/12* (2013.01); *C07D 413/12* (2013.01); *C07D 471/04* (2013.01); *C07D 487/04* (2013.01); *C07D 495/04* (2013.01)

(58) Field of Classification Search
CPC .... A61K 31/353; A61K 31/50; A61K 31/495; A61K 31/505; C07D 239/04; C07D 239/48; C07D 401/12; C07D 413/12; C07D 471/04; C07D 403/12; C07D 405/12; C07D 487/04; C07D 495/04
See application file for complete search history.

(56) References Cited

U.S. PATENT DOCUMENTS

| | | | |
|---|---|---|---|
| 6,503,908 B1 | 1/2003 | Maw | |
| 6,583,148 B1 | 6/2003 | Kelley et al. | |
| 7,030,118 B2 | 4/2006 | Lombardo et al. | |
| 7,091,232 B2 | 8/2006 | Chow et al. | |
| 7,498,409 B2 | 3/2009 | Vlach et al. | |
| 7,531,547 B2 | 5/2009 | Dillon et al. | |
| 7,923,554 B2 | 4/2011 | Hoornaert et al. | |
| 8,022,077 B2 | 9/2011 | Simmen et al. | |
| 8,455,458 B2 | 6/2013 | Marcum et al. | |
| 8,486,952 B2 | 7/2013 | Boy et al. | |
| 8,637,525 B2 | 1/2014 | Boy et al. | |
| 8,916,575 B2 | 12/2014 | McGowan et al. | |
| 9,133,192 B2 | 9/2015 | McGowan et al. | |
| 9,284,304 B2 | 3/2016 | McGowan et al. | |
| 9,365,571 B2 | 6/2016 | McGowan et al. | |
| 9,376,448 B2 | 6/2016 | Charifson et al. | |
| 9,416,114 B2 | 8/2016 | Gembus et al. | |
| 9,422,250 B2 * | 8/2016 | McGowan | C07D 239/48 |
| 9,499,549 B2 | 11/2016 | McGowan et al. | |
| 9,556,176 B2 | 1/2017 | Bonfanti et al. | |
| 9,556,199 B2 | 1/2017 | McGowan et al. | |
| 9,598,378 B2 | 3/2017 | McGowan et al. | |
| 9,663,474 B2 | 5/2017 | Last et al. | |
| 9,878,996 B2 | 1/2018 | Silverman et al. | |
| 2005/0054590 A1 | 3/2005 | Averett | |
| 2006/0258682 A1 | 11/2006 | Liao et al. | |
| 2007/0225303 A1 | 9/2007 | Ogita et al. | |
| 2009/0285782 A1 | 11/2009 | Gao et al. | |

(Continued)

FOREIGN PATENT DOCUMENTS

| | | |
|---|---|---|
| CN | 101784548 A | 7/2010 |
| EP | 0882727 | 12/1998 |

(Continued)

OTHER PUBLICATIONS

International Search Report for PCT/EP2012/056388, dated May 31, 2012.

(Continued)

*Primary Examiner* — Alexander R Pagano
*Assistant Examiner* — Ebenezer O Sackey

(57) ABSTRACT

This invention relates to pyrimidine derivatives, processes for their preparation, pharmaceutical compositions, and their use in treating viral infections such as HCV or HBV.

20 Claims, No Drawings

Specification includes a Sequence Listing.

(56) References Cited

U.S. PATENT DOCUMENTS

| | | |
|---|---|---|
| 2010/0143299 A1 | 6/2010 | Gao et al. |
| 2014/0148433 A1 | 5/2014 | Follmann et al. |
| 2015/0274676 A1 | 10/2015 | McGowan et al. |
| 2015/0299221 A1 | 10/2015 | Bonfanti et al. |
| 2015/0336907 A1 | 11/2015 | Gembus et al. |
| 2016/0304531 A1 | 10/2016 | Bonfanti et al. |

FOREIGN PATENT DOCUMENTS

| | | |
|---|---|---|
| EP | 0899263 A3 | 3/1999 |
| EP | 1552842 A1 | 6/2003 |
| EP | 1110951 A1 | 6/2006 |
| EP | 1939198 A1 | 7/2008 |
| EP | 1970373 A1 | 9/2008 |
| EP | 2133353 A1 | 12/2009 |
| EP | 2138497 A1 | 12/2009 |
| JP | 64063582 | 3/1989 |
| JP | 2000053653 | 2/2000 |
| JP | 2000053654 | 2/2000 |
| JP | 2008222557 A | 9/2008 |
| JP | 2009528989 A | 8/2009 |
| JP | 2010522151 A | 7/2010 |
| JP | 2010532353 A | 10/2010 |
| WO | 199801448 A1 | 1/1998 |
| WO | 199808847 A1 | 3/1998 |
| WO | WO 98/14448 A1 | 9/1998 |
| WO | 199850370 A1 | 11/1998 |
| WO | 199932122 A1 | 7/1999 |
| WO | 199940091 A1 | 8/1999 |
| WO | 199941253 A1 | 8/1999 |
| WO | WO 99/28321 A1 | 10/1999 |
| WO | 200006577 A1 | 2/2000 |
| WO | WO 00/61562 A1 | 10/2000 |
| WO | 2002087513 A2 | 11/2002 |
| WO | 2002088080 A2 | 11/2002 |
| WO | 2003055890 A1 | 7/2003 |
| WO | 2004029054 A1 | 8/2004 |
| WO | 2005007672 A2 | 1/2005 |
| WO | 2005092892 A1 | 10/2005 |
| WO | 2005092893 A1 | 10/2005 |
| WO | 2006015985 A1 | 2/2006 |
| WO | 2006050843 A1 | 5/2006 |
| WO | 2006120252 A2 | 11/2006 |
| WO | WO 2006/117670 A1 | 11/2006 |
| WO | 2007034881 A1 | 3/2007 |
| WO | 2007056208 A1 | 5/2007 |
| WO | 2007063934 A1 | 6/2007 |
| WO | WO 2007/084413 A | 7/2007 |
| WO | 2007093901 A1 | 8/2007 |
| WO | 2008009078 A2 | 1/2008 |
| WO | 2008073785 A2 | 6/2008 |
| WO | 2008075103 A1 | 6/2008 |
| WO | 2008114008 A1 | 9/2008 |
| WO | 2008114817 A1 | 9/2008 |
| WO | 2008114819 A1 | 9/2008 |
| WO | 2008115319 A2 | 9/2008 |
| WO | 2008147697 A1 | 12/2008 |
| WO | 2009005687 A1 | 1/2009 |
| WO | WO 2009/023179 A | 2/2009 |
| WO | 2009030998 A1 | 3/2009 |
| WO | WO 2009/067081 A1 | 5/2009 |
| WO | 2009080836 A2 | 7/2009 |
| WO | 2009099650 A2 | 8/2009 |
| WO | 2009032668 A3 | 9/2009 |
| WO | 2009134624 A1 | 11/2009 |
| WO | 2010006025 A1 | 1/2010 |
| WO | 2010007116 A3 | 1/2010 |
| WO | WO 2010/133885 A | 11/2010 |
| WO | 2011014535 A1 | 2/2011 |
| WO | 2011049825 A1 | 4/2011 |
| WO | 2011049987 | 4/2011 |
| WO | 2011062253 A1 | 5/2011 |
| WO | 2011062372 A3 | 5/2011 |
| WO | 2012066335 A1 | 5/2012 |
| WO | 2012067269 A1 | 5/2012 |
| WO | 2012136834 | 10/2012 |
| WO | 2012156498 A1 | 11/2012 |
| WO | 2013068438 A1 | 5/2013 |
| WO | 2013117615 A1 | 8/2013 |
| WO | 2014053595 A1 | 4/2014 |

OTHER PUBLICATIONS

Takeda et al "Toll-Like Receptors" Annu Rev Immunol 2003 vol. 21 pp. 355-376.

De Clercq Erik "(S)-9-(2,3-Dihydroxypropyl)Adenine: An Aliphatic Nucleoside Analog With Broad-Spectrum Antiviral Activity" Science 1978 vol. 200 pp. 563-565.

Fried et al "Peginterferon Alpha-$2_A$ Plus Ribavirin for Chronic Hepatitis C Virus Infection" N Engl J Med 2002 vol. 347(13) pp. 975-982.

Grimm et al "Toll-Like Receptor (TLR) 7 and TLR8 Expression on CD133+Cells in Colorectal Cancer Points to a Specific Role for Inflammation-Induced TLRS in Tumourigenesis and Tumour Progression" European Journal of Cancer 2010 vol. 46 pp. 2849-2857.

Hoffmann Jules A. "The Immune Response of *Drosophila*" Nature 2003 vol. 226 pp. 33-38.

Krieger et al "Enhancement of Hepatitis C Virus RNA Replication by Cell Culture-Adaptive Mutations" Journal of Virology 2001 vol. 75(10) pp. 4614-4624.

Lohmann et al "Replication of Subgenomic Hepatitis C. Virus RNAS in a Hepatoma Cell Line" Science 1999 vol. 285 pp. 110-113.

Lohmann et al "Viral and Cellular Determinants of Hepatitis C Virus RNA Replication in Cell Culture" Journal of Virology 2003 vol. 77(5) pp. 3007-3019.

Organic Syntheses Coll vol. 4 p. 590 1963 and vol. 33 p. 43 1953 Organic Syntheses Inc. Copyright 1921-2005.

Tomonori et al "Tri-Crossed-Claisen Condensation Between Carboxylic Esters and Acid Chlorides or Acids: A Highly Selective and General Method for the Preparation of Various β-Keto Esters" J Am Chem Soc 2005 vol. 127 pp. 2854-2855.

Ulevitch et al "Therapeutics Targeting the Innate Immune System" Nature 2004 vol. 4 pp. 512-520.

Vedantham et al "Mechanism of Interferon Action in Hairy Cell Leukemia: A Model of Effective Cancer Biotherapy" Cancer Research 1992 vol. 52 pp. 1056-1066.

Warshakoon et al "Potential Adjuvantic Properties of Innate Immune Stimuli" Human Vaccines 2009 vol. 5:6 pp. 381-394.

Hood et al "Immunoprofiling Toll-Like Receptor Ligands—Comparison of Immunostimulatory and Proinflammatory Profiles in Ex Vivo Human Blood Models" Human Vaccines 2010 vol. 6 (4) pp. 322-335.

Abdillahi, et al., "Synthesis of a Novel Series of Thieno[3,2-d]pyrimidin-4-(3H)-ones", Synthesis, vol. 9: pp. 1428-1430 (2010).

Banker (Editor), "Prodrugs", Modern Pharmaceutics, Third Edition: pp. 596 (1976).

Baraldi, et al., "New Strategies for the Synthesis of A3 Adenosine Receptor Antagonists", Bioorganic & Medicinal Chemistry, vol. 11: pp. 4161-4169 (2003).

Barker, et al., "A Rapid Conversion of 3-Oxothiolanes into 3-Aminothiophenes", Synthetic Communications, vol. 32(16): pp. 2565-2568 (2002).

Bell, et al., "Chemistry of 5-Pyrimidinecarboxaldehydes", Journal of Heterocyclic Chemistry, vol. 29: pp. 41-44 (Jan.-Feb. 1983).

Bennet, et al. (Editor), "Part XIV Oncology", Cecil Textbook Medicine, vol. 1, 20th Edition: pp. 1004-1010 (1996).

Brittain, et al., "Effects of Pharmaceutical Processing on Drug Polymorphs and Solvates", Polymorphism in Pharmaceutical Solids, 1999, pp. 331-360, Chapter 8.

Bruns, et al, "Solubilities of Adenosine Antagonists Determined by Radioreceptor Assay", Journal of Pharmacy and Pharmacology; vol. 41: pp. 590-594 (1989).

Chawla, et al., "Challenges in Polymorphism of Pharmaceuticals", Current Research & Information on Pharmaceutical Sciences, vol. 5(1): pp. 9-12 (Jan.-Mar. 2004).

(56) References Cited

OTHER PUBLICATIONS

De Nardo, "Toll-Like Receptors: Activation, Signalling and Transcriptional Modulation", Cytokine, 2015, pp. 181-189, vol. 74.
Dermer, "Another Anniversary for the War on Cancer", Bio/Technoiogy, vol. 12: pp. 320 (Mar. 1994).
Douglas, Jr., "Introduction of Viral Diseases", Cecil Textbook of Medicine, 20th Edition, vol. 2: pp. 1973-42 (1996).
Freshney, et al., Culture of Animal Cells, Manual of Basic Technique, 1983, pp. 1-6, Chapter 1.
Hackam, et al, "Translation of Research Evidence From animals to Humans", JAMA, vol. 296 (14): pp. 1731-1732 (2006).
Horscroft, et al., "Antiviral applications of toll-like receptor agonists", J. Antimicrob. Chemother., pp. 1-13 (Jan. 18, 2016).
Huddleston, et al., "A Convenient Synthesis of 2-Substituted 3-Hydroxy- and 3-Amino-Thiophens From Derivatives of 2-Choroacrylic Acid", Synthetic Communications, vol. 9(8): pp. 731-734 (1979).
Isobe, et al., "Synthesis and Structure-Activity Relationships of 2-Substituted-8-hydroxyadenine Derivatives as Orally Available Interferon Inducers without Emetic Side Effects", Bioorganic & Medicinal Chemistry, vol. 11: pp. 3641-3647, (2003).
Jiang, et al., "Synthesis of 4-chlorothieno[3,2-d]pyrimidine", Chemical Industry and Engineering Progress, vol. 30: pp. 2532-2535, (2011). [With English Abstract].
Jordan, "Tamoxifen: A Most Unlikely Pioneering Medicine", Nature Reviews, vol. 2: pp. 205-213; (Mar. 2003).
Kanzler, et al., "Therapeutic Targeting of Innate Immunity with Toll-Like Receptor Agonists and Antagonists", Nature Medicine, vol. 13(5): pp. 552-559 (May 2007).
Kurimoto, et al., "Synthesis and Structure—Activity Relationships of 2-Amino-8-hydroxyadenines as Orally Active Interferon Inducing Agents", Bioorganic & Medicinal Chemistry, vol. 11: pp. 5501-5508 (2003).
Liu, et al., "Synthesis and Biological Activity of 3- and 5-Amino Derivatives of Pyridine-2Carboxaldehyde Thiosemicarbazone", J. Med. Chem, Vo. 39: pp. 2586-2593 (1996).
Makkouk et al., "The potential use of Toll-Like Receptors (TLR) agonistd and antagonists as prophylactic and/or therapeutic agents", Immunopharmacology and Immunotoxicology, vol. 31(3): 331-338 (2009).
Mesguiche, et al., "4-Alkoxy-2,6-diaminopyrimidine Derivatives: Inhibitors of Cyclin Dependent Kinases 1 and 2", Bioorganic & Medicinal Chemistry Letters, vol. 13: pp. 217-222 (2003).
Moreau, et al., "Synthesis of cyclic adenosine 5'-diphosphate ribose analogues: a C2' endo/syn "southern" ribose conformation underlies activity at the sea urchin cADPR receptor", Organic & Biomolecular Chemistry, vol. 9: pp. 278-290 (2011).
Musmuca, et al, "Small-Molecule Interferon Inducers. Toward the Comprehension of the Molecular Determinants through Ligand-Based Approaches", J, Chem. Inf, Model., vol. 49: pp. 1777-1786 (2009).
Newman, et al., "Solid-State Analysis of the Active Pharmaceutical Ingredient in Drug Products", Drug Discovery Today, Oct. 19, 2003, 898-905, vol. 8(19).
O'Hara, et al., "Regioselective Synthesis of imidazo[4,5-g] quinazoline Quinone Nucleosides and Quinazoline Amino Nucleosides. Studies of their Xanthine Oxidase and Purine Nucleoside Phosphorylase Substrate Activity", J. Org. Chem. vol. 56: pp. 776-785 (1991).
Ohto, et al., "Structure and Function of Toll-Like Receptor 8", Microbes and Infections, vol. 16: pp. 273-282 (2014).
Thomas, et al., "Investigating Toll-Like Receptor Agonists for Potential To Treat Hepatitis C Virus Infection", Antimicrobial Agents and Chemotherapy, vol. 51(8): pp. 2969-2978 (Aug. 2007).
Tran, et al, "Design and optimization of orally active TLR7 agonists for the treatment of hepatitis C virus infection", Bioorganic & Medicinal Chemistry Letters, vol. 21: 2389-2393 (2011).
Ulrich, et al, "Crystallization", Kirk-Othmer Encyclopedia of Chemical Technology, Chapter 4: pp. 1-63, (Aug. 16, 2002).

Vippagunta, et al., "Crystalline Solids", Advance Drug Delivery Reviews, vol. 48: pp. 3-26 (2001).
Wermuth, "Molecular Variations Based on Isosteric Replacements", The Practice of Medicinal Chemistry, 1996, pp. 203-237, Ch. 13.
Wolff, et al, Burger's Medicinal Chemistry and Drug Discovery, -, 1994, pp. 975-977, 5th Edition, vol. 1.
Yin, et al., "Synthesis of 2,4-Diaminoquinazolines and Tricyclic Quinazolines by Cascade Reductive Cyclization of Methyl N-Cyano-2-nitrobenzimidates", J. Org. Chem., vol. 77: pp. 2649-2658 (2012).
Yu, et al, "Toll-Like Receptor 7 Agonists: Chemical Feature Based"; PLOS ONE, vol. 8 (3): pp. 1-11 e56514, (Mar. 20, 2013).
Yu, et al., "Dual Character of Toll-Like Receptor Signaling: Pro-Tumorigenic Effects and Anti-Tumor Functions", Biochimica et Biophysica Acta, vol. 1835: 144-154 (2013).
Zhao, et al., "Toll-Like Receptors and Prostate Cancer", Frontiers in Immunology, vol. 5 (Article 352): pp. 1-7 (Jul. 2014).
International Search Report for Corresponding Application No. PCT/EP2012/059234, dated Nov. 18, 2013.
Extended European Search Report for Corresponding Application No. EP11166538.6, dated Nov. 22, 2011.
International Search Report for Corresponding Application No. PCT/EP2012/072090, dated Jan. 4, 2013.
International Search Report for Corresponding Application No. PCT/EP2013/052372 , dated Apr. 17, 2013.
International Search Report for Corresponding Application No. PCT/EP2013/064763, dated Aug. 3, 2013.
International Search Report for Corresponding Application No. PCT/EP2013/066673, dated Sep. 6, 2013.
International Search Report for Corresponding Application No. PCT/EP2013/070990, dated Jan. 17, 2014.
International Search Report for Corresponding Application No. PCT/EP2013/070488, dated Nov. 14, 2013.
International Search Report for Corresponding Application No. PCT/EP2013/073901, dated Dec. 16, 2013.
International Search Report for Corresponding Application No. PCT/EP2014/053273, dated Mar. 18, 2014.
International Search Report for Corresponding Application No. PCT/EP2014/056270, dated Jul. 21, 2014.
International Search Report for Corresponding Application No. PCT/EP2014/060603, dated Jul. 15, 2014.
International Search Report for Corresponding Application No. PCT/EP2014/063467, dated Nov. 3, 2014.
International Search Report for Corresponding Application No. PCT/EP2014/066219, dated Nov. 13, 2014.
Bizanek, et al., Isolation and Structure of an Intrastrand Cross-Link Adduct of Mitomycin C nd DNA', Biochemistry, 1992, pp. 3084-3091, vol. 31.
McGowan et al., "Novel Pyrimidine Toll-Like Receptor 7 and 8 Dual Agonists to Treat Hepatitis B Virus", Journal of Medicinal Chemistry, 2016, pp. 7936-7949, vol. 59 No. 17.
Isobe, et al., "Synthesis and Biological Evaluation of Novel 9-Substituted-8-Hydroxyadenine Derivatives as Potent Inferferon Inducers", J. Med. Chem., vol. 49; pp. 2088-2095 (2006).
Jurk, et al., "Human TLR7 or TLR8 Independently Confer Responsiveness to the Antiviral Compound R-848", Nature Immunology, Jun. 2002, p. 499, vol. 3 (6).
Kurimoto, et al., "Synthesis and Evaluation of 2-Substituted 8-Hydroxyadenines as Potent Interferon Inducers with Improved Oral Bioavailabilities", Bioorganic & Medicinal Chemistry, vol. 12; pp. 1091-1099 (2004).
Lee, et al., "Activation of Anti-Hepatitis C Virus Responses via Toll-Like Receptor 7", PNAS, vol. 3 (6); pp. 1828-1833 (Feb. 7, 2006).
Roethle, et al., "Identification and Optimization of Pteridinone Toll-Like Receptor 7 (TLR7) Agonists for the Oral Treatment of Viral Hepatitis", Journal of Medicinal Chemistry, vol. 56; pp. 7324-73333 (2013).

* cited by examiner

SEQUENCE LISTING

<160> NUMBER OF SEQ ID NOS: 1

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gaaactgaaa ct                                                          12

PYRIMIDINE DERIVATIVES FOR THE TREATMENT OF VIRAL INFECTIONS

CROSS-REFERENCE TO RELATED APPLICATIONS

This application is a divisional of U.S. patent application Ser. No. 14/110,054 filed on Oct. 4, 2013, which is a national phase entry of International Application No. PCT/EP2012/056388 filed on Apr. 10, 2012, which claims priority from European Patent Application No. 11161595.1 filed on Apr. 8, 2011, the entire contents of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Sep. 13, 2016, is named TIP0249USDIV1_SL.txt and is 623 bytes in size.

This invention relates to pyrimidine derivatives, processes for their preparation, pharmaceutical compositions, and their use in treating viral infections, like HBV or HCV.

The present invention relates to the use of pyrimidine derivatives in the treatment of viral infections, immune or inflammatory disorders, whereby the modulation, or agonism, of toll-like-receptors (TLRs) is involved. Toll-Like Receptors are primary transmembrane proteins characterized by an extracellular leucine rich domain and a cytoplasmic extension that contains a conserved region. The innate immune system can recognize pathogen-associated molecular patterns via these TLRs expressed on the cell surface of certain types of immune cells. Recognition of foreign pathogens activates the production of cytokines and upregulation of co-stimulatory molecules on phagocytes. This leads to the modulation of T cell behaviour.

It has been estimated that most mammalian species have between ten and fifteen types of Toll-like receptors. Thirteen TLRs (named TLR1 to TLR13) have been identified in humans and mice together, and equivalent forms of many of these have been found in other mammalian species. However, equivalents of certain TLR found in humans are not present in all mammals. For example, a gene coding for a protein analogous to TLR10 in humans is present in mice, but appears to have been damaged at some point in the past by a retrovirus. On the other hand, mice express TLRs 11, 12, and 13, none of which are represented in humans. Other mammals may express TLRs which are not found in humans. Other non-mammalian species may have TLRs distinct from mammals, as demonstrated by TLR14, which is found in the Takifugu pufferfish. This may complicate the process of using experimental animals as models of human innate immunity.

For detailed reviews on toll-like receptors see the following journal articles. Hoffmann, J. A., Nature, 426, p33-38, 2003; Akira, S., Takeda, K., and Kaisho, T., Annual Rev. Immunology, 21, p335-376, 2003; Ulevitch, R. J., Nature Reviews: Immunology, 4, p512-520, 2004.

Compounds indicating activity on Toll-Like receptors have been previously described such as purine derivatives in WO 2006/117670, adenine derivatives in WO 98/01448 and WO 99/28321, and pyrimidines in WO 2009/067081.

However, there exists a strong need for novel Toll-Like receptor modulators having preferred selectivity, higher potency, higher metabolic stability, and an improved safety profile compared to the compounds of the prior art.

In the treatment of certain viral infections, regular injections of interferon (IFNα) can be administered, as is the case for hepatitis C virus (HCV), (Fried et. al. Peginterferon-alfa plus ribavirin for chronic hepatitis C virus infection, *N Engl J Med* 2002; 347: 975-82). Orally available small molecule IFN inducers offer the potential advantages of reduced immunogenicity and convenience of administration. Thus, novel IFN inducers are potentially effective new class of drugs for treating virus infections. For an example in the literature of a small molecule IFN inducer having antiviral effect see De Clercq, E.; Descamps, J.; De Somer, P. Science 1978, 200, 563-565.

IFNα$_L$ is also given in combination with other drugs in the treatment of certain types of cancer (Eur. J. Cancer 46, 2849-57, and Cancer Res. 1992, 52, 1056). TLR 7/8 agonists are also of interest as vaccine adjuvants because of their ability to induce pronounced Th1 response (Hum. Vaccines 2010, 6, 1-14; Hum. Vaccines 2009, 5, 381-394).

In accordance with the present invention a compound of formula (I) is provided

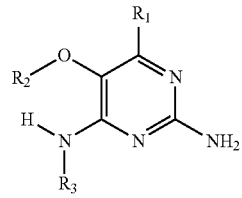

(I)

or a pharmaceutically acceptable salt, tautomer(s), solvate or polymorph thereof, wherein $R_1$ is hydrogen, methyl, $C_{1-2}$alkyl, cyclopropyl, methoxy, halogen, hydroxyl, trifluoromethyl, or difluoromethyl, $R_2$ is $(C_{1-4})$alkoxy-$(C_{1-4})$alkyl, $C_{3-7}$cycloalkyl, $C_{4-7}$heterocycle, aromatic, bicyclic heterocycle, arylalkyl, heteroaryl, heteroarylalkyl each of which is optionally substituted by one or more substituents independently selected from halogen, hydroxyl, amino, $C_{1-6}$alkyl, di-$(C_{1-6})$alkylamino, $C_{1-6}$alkylamino, $C_{1-6}$alkyl, $C_{1-6}$ alkoxy, $C_{3-6}$ cycloalkyl, carboxylic acid, carboxylic ester, carboxylic amide, heterocycle, aryl, alkenyl, alkynyl, arylalkyl, heteroaryl, heteroarylalkyl, nitrile, and $R_3$ is $C_{4-8}$alkyl, $C_{4-8}$alkoxy, $C_{2-6}$ alkenyl or $C_{2-6}$alkynyl, each of which is optionally substituted by one or more substituents independently selected from halogen, hydroxyl, amino, $C_{1-3}$alkyl, $C_{1-3}$alkoxy or $C_{3-6}$ cycloalkyl, nitrile.

In a first embodiment the present invention provides compounds of formula (I) wherein $R_3$ is butyl or pentyl and wherein $R_2$ and $R_1$ are as specified above.

In a further embodiment the invention concerns compounds of formula (I) wherein $R_3$ is $C_{4-8}$alkyl substituted with hydroxyl, and wherein $R_2$ and $R_1$ are as specified above.

Another embodiment relates to compounds of formula (I) wherein $R_3$, when being $C_{4-8}$alkyl substituted with hydroxyl, is one of the following

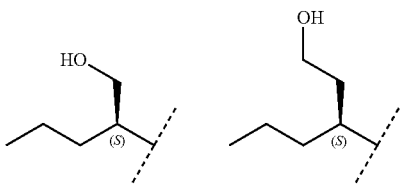

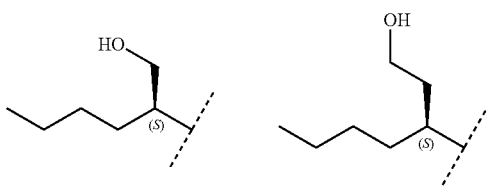

Furthermore the present invention also provides compounds of formula (I) wherein $R_1$ is hydrogen or —$CH_3$ and wherein $R_2$ and $R_3$ are as specified above.

In another embodiment the present invention provides compounds of formula (I) wherein $R_2$ is arylalkyl or heteroarylalkyl, substituted with $C_{1-3}$alkyl, hydroxyl, alkoxy, nitrile, heterocycle or ester and wherein $R_1$ and $R_3$ are as specified above.

In a further embodiment the current invention concerns compounds of formula (I) wherein $R_2$ is $C_{1-3}$alkyl substituted by aryl, heterocycle, or heteroaryl which is further substituted by $C_{1-3}$alkyl, alkoxy, carboxylic ester or carboxylic amide and wherein $R_1$ and $R_3$ are as specified above Furthermore the invention relates to compounds of formula (I) wherein $R_2$ is one of the following examples that can be further substituted with $C_{1-3}$alkyl, hydroxyl, alkoxy, nitrile, heterocycle or ester.

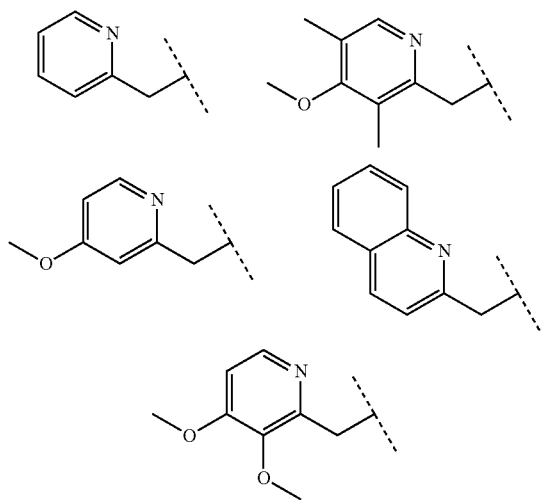

The preferred compounds according to the invention are:

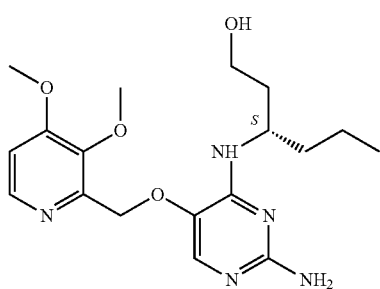

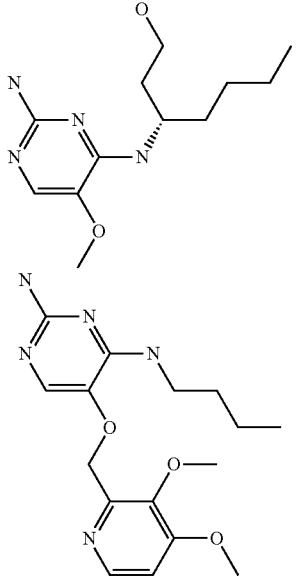

The compounds of formula (I) and their pharmaceutically acceptable salt, tautomer(s), solvate or polymorph thereof have activity as pharmaceuticals, in particular as modulators of Toll-Like Receptors (especially TLR7 and/or TLR8) activity.

In a further aspect the present invention provides a pharmaceutical composition comprising a compound of formula (I) or a pharmaceutically acceptable salt, solvate or polymorph thereof together with one or more pharmaceutically acceptable excipients, diluents or carriers.

Furthermore a compound of formula (I) or a pharmaceutically acceptable salt, solvate or polymorph thereof according to the current invention, or a pharmaceutical composition comprising said compound of formula (I) or a pharmaceutically acceptable salt, solvate or polymorph thereof can be used as a medicament.

Another aspect of the invention is that a compound of formula (I) or a pharmaceutically acceptable salt, solvate or polymorph thereof, or said pharmaceutical composition comprising said compound of formula (I) or a pharmaceutically acceptable salt, solvate or polymorph thereof can be used accordingly in the treatment of a disorder or disease in which the modulation of TLR7 and/or TLR8 is involved.

The term "alkyl" refers to a straight-chain or branched-chain saturated aliphatic hydrocarbon containing the specified number of carbon atoms.

The term "halogen" refers to fluorine, chlorine, bromine or iodine.

The term "alkenyl" refers to an alkyl as defined above consisting of at least two carbon atoms and at least one carbon-carbon double bond.

The term " alkynyl" refers to an alkyl as defined above consisting of at least two carbon atoms and at least one carbon-carbon triple bond.

The term "cycloalkyl" refers to a carbocyclic ring containing the specified number of carbon atoms.

The term "heteroaryl" means an aromatic ring structure as defined for the term "aryl" comprising at least 1 heteroatom selected from N, O and S, in particular from N and O.

The term "aryl" means an aromatic ring structure optionally comprising one or two heteroatoms selected from N, O and S, in particular from N and O. Said aromatic ring structure may have 4, 5, 6 or 7 ring atoms. In particular, said aromatic ring structure may have 5 or 6 ring atoms.

The term "bicyclic heterocycle" means an aromatic ring structure, as defined for the term "aryl" comprised of two fused aromatic rings. Each ring is optionally comprised of heteroatoms selected from N, O and S, in particular from N and O.

The term arylalkyl" means an aromatic ring structure as defined for the term "aryl" optionally substituted with an alkyl group.

The term "heteroarylalkyl" means an aromatic ring structure as defined for the term "heteroaryl" optionally substituted by an alkyl group.

The term "alkoxy" refers to an alkyl (carbon and hydrogen chain) group singular bonded to oxygen like for instance a methoxy group or ethoxy group.

Heterocycle refers to molecules that are saturated or partially saturated and include ethyloxide, tetrahydrofuran, dioxane or other cyclic ethers. Heterocycles containing nitrogen include, for example azetidine, morpholine, piperidine, piperazine, pyrrolidine, and the like. Other heterocycles include, for example, thiomorpholine, dioxolinyl, and cyclic sulfones.

Heteroaryl groups are heterocyclic groups which are aromatic in nature. These are monocyclic, bicyclic, or polycyclic containing one or more heteroatoms selected from N, O or S. Heteroaryl groups can be, for example, imidazolyl, isoxazolyl, furyl, oxazolyl, pyrrolyl, pyridonyl, pyridyl, pyridazinyl, or pyrazinyl.

Pharmaceutically acceptable salts of the compounds of formula (I) include the acid addition and base salts thereof. Suitable acid addition salts are formed from acids which form non-toxic salts. Suitable base salts are formed from bases which form non-toxic salts.

The compounds of the invention may also exist in unsolvated and solvated forms. The term "solvate" is used herein to describe a molecular complex comprising the compound of the invention and one or more pharmaceutically acceptable solvent molecules, for example, ethanol.

The term "polymorph" refers to the ability of the compound of the invention to exist in more than one form or crystal structure.

The compounds of the present invention may be administered as crystalline or amorphous products. They may be obtained for example as solid plugs, powders, or films by methods such as precipitation, crystallization, freeze drying, spray drying, or evaporative drying. They may be administered alone or in combination with one or more other compounds of the invention or in combination with one or more other drugs. Generally, they will be administered as a formulation in association with one or more pharmaceutically acceptable excipients. The term "excipient" is used herein to describe any ingredient other than the compound(s) of the invention. The choice of excipient depends largely on factors such as the particular mode of administration, the effect of the excipient on solubility and stability, and the nature of the dosage form.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, for example, for oral, rectal, or percutaneous administration. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. Also included are solid form preparations that can be converted, shortly before use, to liquid forms. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. The compounds of the present invention may also be administered via inhalation or insufflation by means of methods and formulations employed in the art for administration via this way. Thus, in general the compounds of the present invention may be administered to the lungs in the form of a solution, a suspension or a dry powder.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of infectious diseases will be able to determine the effective amount from the test results presented hereinafter. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that the effective amount may be lowered or increased depending on the response of the treated subject and/or depending on the evaluation of the physician prescribing the compounds of the instant invention. The effective amount ranges mentioned above are therefore only guidelines and are not intended to limit the scope or use of the invention to any extent.

Preparation of Compounds.

Compounds of formula (I), where $R_1$ is hydrogen atom are prepared according to scheme 1.

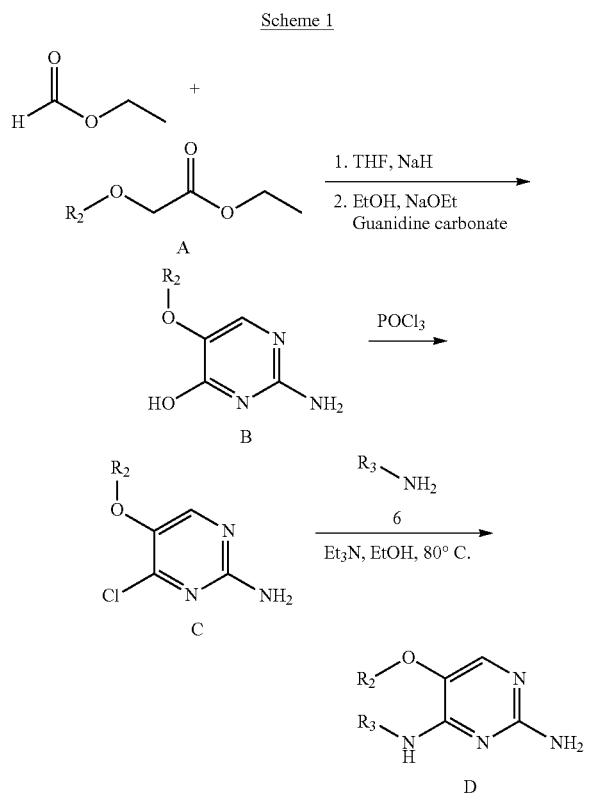

Compounds of type A, in scheme 1 are made by either
(i) Reaction of a heterocyclic alcohol with a halogenated ester and an suitable base, for example potassium carbonate, cesium carbonate, or sodium hydride. Example shown in scheme 2a.
(ii) Reaction of an alcohol, or hydroxy ester, for example 2-hydroxy ethyl acetate, with an alkyl halide using an appropriate base, for example sodium hydride. Example shown in scheme 2b.

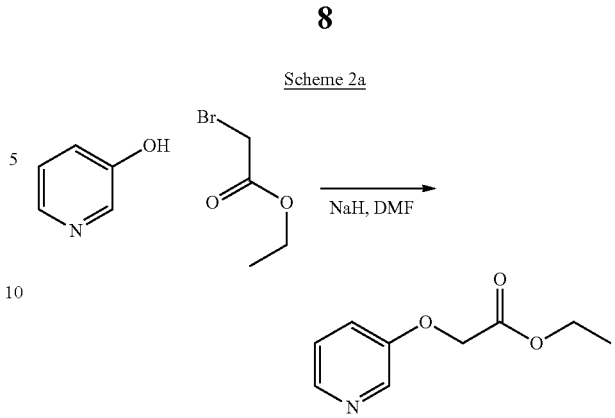

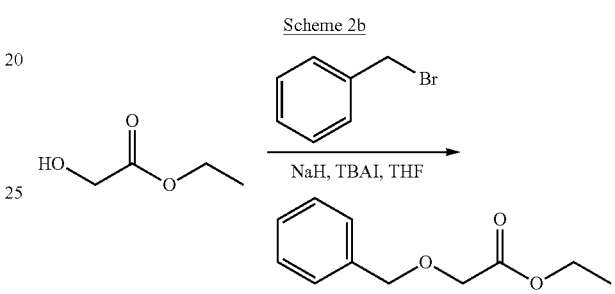

Compounds of formula (I), when $R_1$ is alkyl, cycloalkyl, trifluoromethyl, or alkoxy and where $R_2$ is aryl or heteroaryl, are prepared as in scheme 3 below. The betaketoester (E) can be chlorinated using, for example, thionyl chloride to provide the 2-chloro-beta-ketoester intermediate (F). The phenol or hetero-aromatic alcohol (R2OH) is combined with an equimolar ratio of aqueous sodium hydroxide. The solvents are then removed under reduced pressure to afford the phenol or heteroaromatic alcohol salt of R2. This salt is combined with the 2-chloro-β-ketoester intermediate (F) to afford intermediate G according to literature procedure. Intermediate G is then combined, with or without base, with guanidine carbonate in an appropriate solvent, for example, ethanol. Intermediate H is then reacted with phosphorous oxychloride to form the chloropyrimidine intermediate (J). The products are then formed as a result of heating (J) in the presence of excess amine and optionally excess organic base, for example triethylamine, at elevated temperature. This is a general scheme using methods known to a skilled person, see for instance Organic Syntheses volume 33, p.43 (1953).

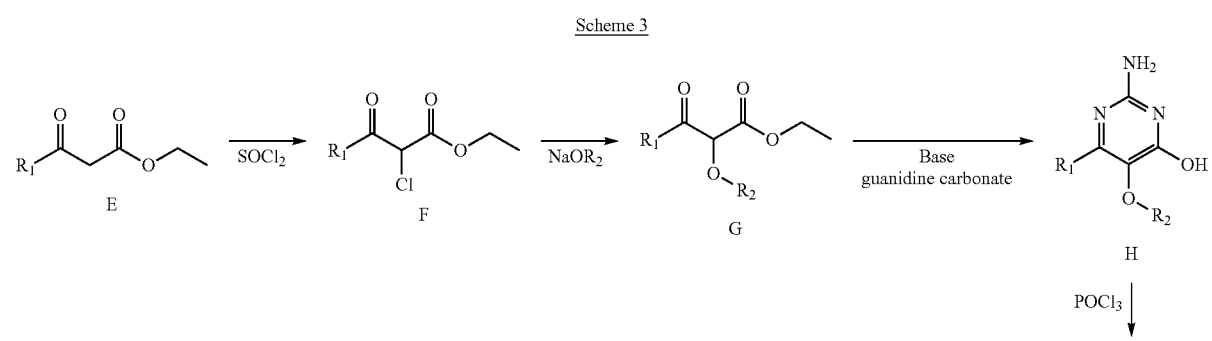

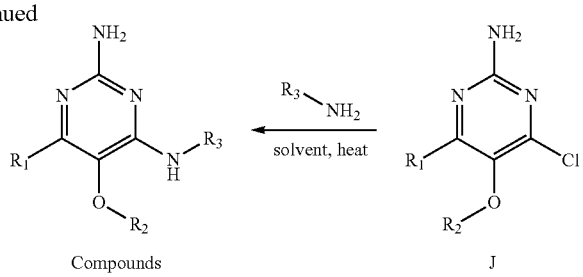

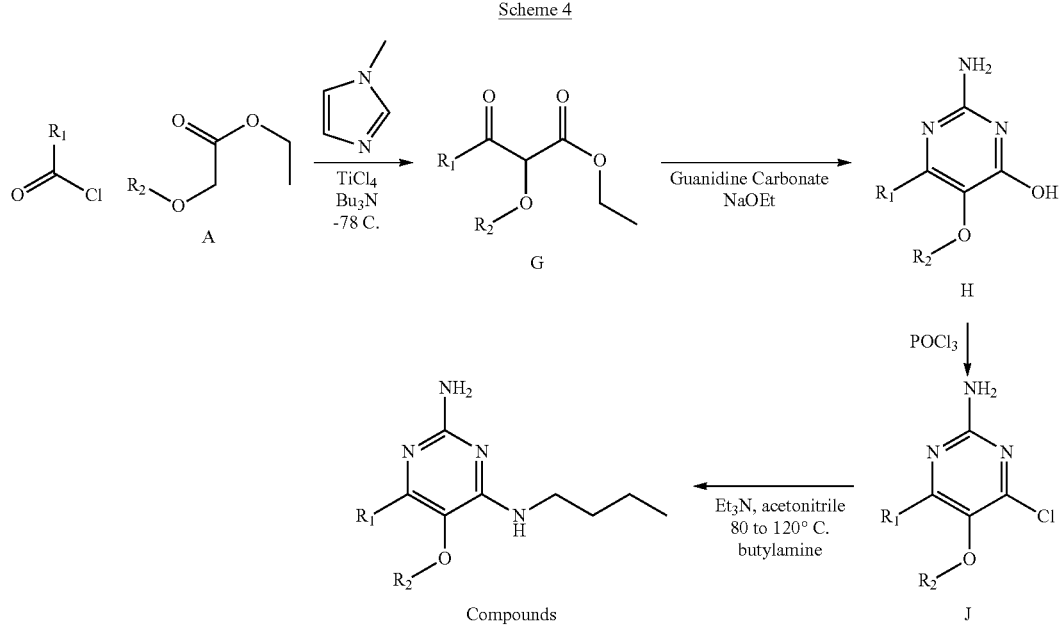

Compounds of formula (I), when $R_1$ is alkyl, cycloalkyl, trifluoromethyl, or alkoxy and where $R_2$ is aromatic or aliphatic, can be prepared according scheme 4. This reaction scheme begins with a crossed-Claisen reaction where an acyl chloride reacts with ester intermediate A (shown in scheme 1) to form intermediates (G) as in scheme 3. From intermediate G, the reaction scheme follows the same pathway to the products as in scheme 3. This is a general scheme using methods known to a skilled person, see for instance The Journal of American Chemical Society volume 127, page 2854 (2005).

EXPERIMENTAL SECTION

Synthesis of Intermediate A-1.

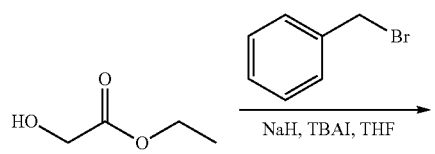

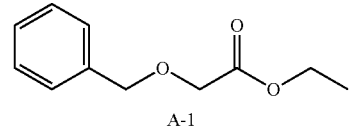

To a mixture of ethyl glycolate [623-50-7] (250.00 g, 2.40 mol), NaH (105.65 g, 2.64 mol), tetrabutylammonium iodide (TBAI) (88.70 g, 240.14 mmol) in anhydrous THF (2 L) was added benzyl bromide (451.80 g, 2.64 mol) dropwise at 0° C. The resulting mixture was stirred at 25° C. for 16 hours. The reaction mixture was quenched with saturated, aqueous ammonium chloride (14 and the aqueous layer was extracted with ethyl acetate (3×1L). The combined organic layers were washed with brine (1 L), dried over magnesium sulfate, the solids were removed via filtration, and the solvents of the filtrate were concentrated under reduced pressure. The residue was purified by silica gel column chromatography (petroleum ether: ethyl acetate=6:1) to obtain intermediate A-1 (200 g).

$^1$H NMR (CDCl$_3$ 400MHz) δ ppm 7.37-7.27 (m, 5H); 4.62 (s, 2H), 4.24-4.19 (q, J=6.8 Hz, 2H); 4.07 (s, 2H); 1.29-1.25 (t, J=6.8 Hz, 3H).

Procedure for Preparation of Intermediate B-1.

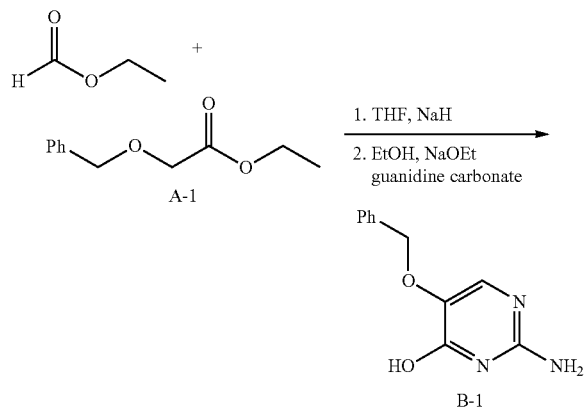

To a stirred suspension of NaH (45.30 g, 1.13 mol) in anhydrous THF (1.2 L) was added ethyl formate (114.42 g, 1.54 mol). The suspension was cooled in an ice bath, and then compound A-1 (200 g, 1.03 mol) in anhydrous THF (300 mL) was added dropwise via an addition funnel. The white mixture was stirred at 0° C. to room temperature for 5 hours. During this time, the reaction was exothermic and turned yellow. In a separate flask, guanidine carbonate [593-85-1] (111.31 g, 0.618 mol) was treated with a sodium ethoxide solution, freshly prepared by the careful addition of Na (28.41 g, 1.24 mol) to anhydrous ethanol (750 mL) at room temperature. The off-white slurry obtained after stirring for 1 hour, was then added to the yellow solution prepared above. The resulting pale yellow reaction mixture was heated to reflux for 15 hours. The solvent was removed, and then the crude residue was dissolved in water (1.5 L). The mixture was adjusted to pH=5 with acetic acid. The solid was collected, washed extensively with water and ethanol to give intermediate B-1 (160 g).

$^1$H NMR (400 MHz, DMSO-d$_6$) δ ppm 4.90 (s, 2 H), 6.33 (br. s., 2 H), 7.25 (s, 1 H), 7.29-7.42 (m, 5 H), 11.21 (br. s., 1 H)

Procedure for Preparation of Intermediate C-1.

Reaction Scheme:

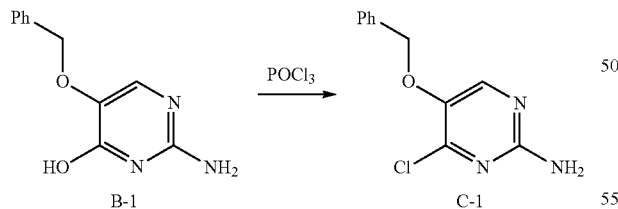

A suspension of intermediate B-1 (160 g, 0.74 mol) in POCl$_3$ (900 mL) was heated to 100° C. under N$_2$ with stirring for 5 hours. The reaction mixture was cooled to room temperature. The excess POCl$_3$ was removed under reduced pressure, the oil residue was poured into cold, sat. aq. NaHCO$_3$ (2 L) that was stirred for 30 minutes. The mixture was extracted with ethyl acetate (3×1.5 L). The combined organic layers were separated and washed with brine (1 L), dried over sodium sulfate, the solids were removed via filtration, and the solvents of the filtrate were concentrated to afford intermediate C-1 (70 g) as a yellow solid. The product was used in the next step without further purification.

Procedure for preparation of compound 1.

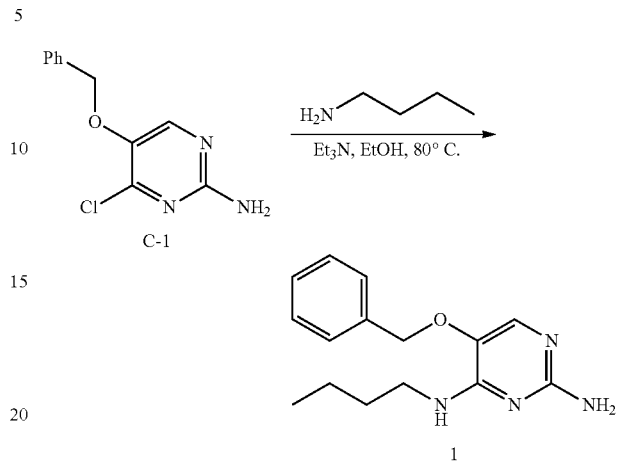

To a suspension of C-1 (70.00 g, 297.03 mmol) in ethanol (1.4 L) was added n-butylamine (217.24 g, 2.97 mol) and triethylamine (60.11 g, 594.05 mmol). The reaction mixture was heated to reflux for 16 hours. The reaction mixture was cooled to room temperature and the solvents were removed under reduced pressure. The residue was purified by silica gel flash chromatography using a petroleum ether to ethyl acetate gradient to obtain 1 (26 g) as a pale yellow solid.

$^1$H NMR (400 MHz, METHANOL-d$_4$) δ ppm 0.96 (t, J=7.3 Hz, 3 H), 1.32-1.43 (m, 2 H), 1.52-1.61 (m, 2 H), 3.38 (t, J=7.2 Hz, 2 H), 5.01 (s, 2 H), 7.28 (s, 1 H), 7.31-7.46 (m, 5H)

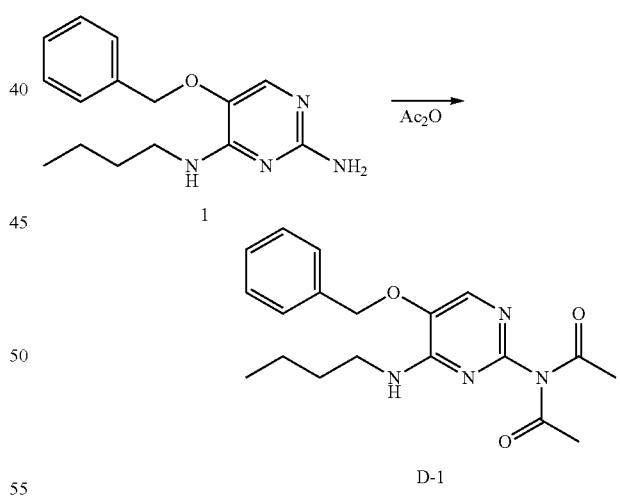

Preparation of intermediate D-1.

Into a 100 mL round bottom flask equipped with a magnetic stir bar was placed 1 (1g, 3.67 mmol) in acetic anhydride (40 mL). The yellow solution was allowed to stir at reflux for 15 hours. The solvents were removed under reduced pressure. The crude was purified via silica gel chromatography using a heptane to ethyl acetate gradient. The best fractions were collected and the solvents were removed under reduced pressure to afford a white solid, D-1.

LC-MS: Anal. Calcd. For C$_{19}$H$_{24}$N$_4$O$_3$: 356.19; found 357[M+H]$^+$

¹H NMR (400 MHz, CHLOROFORM-d) δ ppm 0.94 (t, J=7.4 Hz, 3 H), 1.31-1.45 (m, 2 H), 1.50-1.67 (m, 2 H), 2.31 (s, 6 H), 3.44 (m, J=6.0 Hz, 2 H), 5.12 (s, 2 H), 5.41-5.52 (m, 1 H), 7.43 (m, J=1.5 Hz, 5 H), 7.79 (s, 1 H)

Preparation of Intermediate D-2.

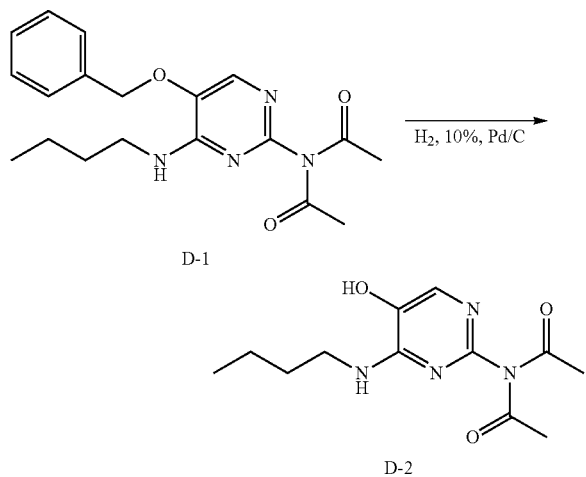

Method A. Into a 250 mL erlenmeyer flask equipped with a magnetic stir bar was placed intermediate D-1 (1 g), and ethanol (100 mL). The flask is sparged with nitrogen, followed by the addition of 10% Pd on carbon (100 mg). The flask was sealed and the atmosphere removed and replaced with hydrogen. The reaction was allowed to stir at room temperature for 15 hours. The heterogeneous mixture was filtered through packed celite and the solvents of the filtrate were removed under reduced pressure to afford D-2 in quantitative yield.

Method B. A 0.1 M solution of starting material in methanol was run through the H-cube, equipped with a 10% Pd/C cartridge, at 0.5 mL/min and 30 bar pressure of hydrogen. LC-MS shows complete conversion. The solvents were removed under reduced pressure. The crude was purified via silica gel chromatography using a dichloromethane to 10% methanol in dichloromethane gradient. The best fractions were pooled; the solvents were removed under reduced pressure to afford a white solid, D-2.

LC-MS: Anal. Calcd. For $C_{12}H_{18}N_4O_3$: 266.14; found 267[M+H]$^+$

¹H NMR (400 MHz, DMSO-d$_6$) δ ppm 0.87 (t, J=7.4 Hz, 3 H), 1.28 (dd, J=14.9, 7.4 Hz, 2 H), 1.49 (t, J=7.2 Hz, 2 H), 2.15 (s, 6 H), 3.20-3.37 (m, 2 H), 7.02-7.12 (m, 1 H), 7.58 (s, 1 H), 10.27 (br. s, 1 H)

Preparation of Intermediate D-3.

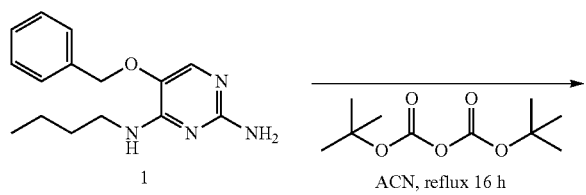

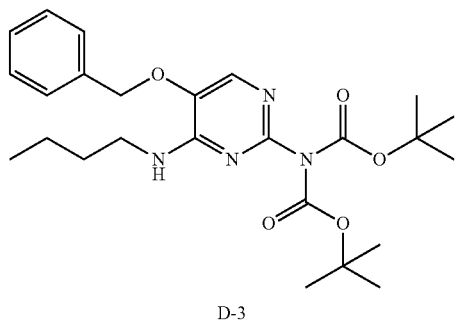

Into a 100 mL round bottom flask was placed 1 (1 g, 3.67 mmol), di-tent-butyl dicarbonate (7.5 g), and acetonitrile (50 mL). The yellow solution was stirred at reflux for 16 hours. The solvents were removed under reduced pressure. The residue was purified via silica chromatography using a prepacked 80 g silica column and a heptane to ethyl acetate gradient autocollecting at 254 nm. The best fractions were pooled to afford a yellow oil, D-3.

LC-MS: Anal. Calcd. For $C_{25}H_{36}N_4O_5$: 472.269; found 473[M+H]$^+$

¹H NMR (400 MHz, CHLOROFORM-d) δ ppm 0.94 (t, J=7.4 Hz, 3 H), 1.33-1.42 (m, 2 H), 1.46 (s, 18 H), 1.50-1.65 (m, 2 H), 3.35-3.51 (m, 2 H), 5.09 (s, 2 H), 5.31-5.38 (m, 1 H), 7.36-7.48 (m, 5 H), 7.75 (s, 1 H)

Preparation of Intermediate D-4.

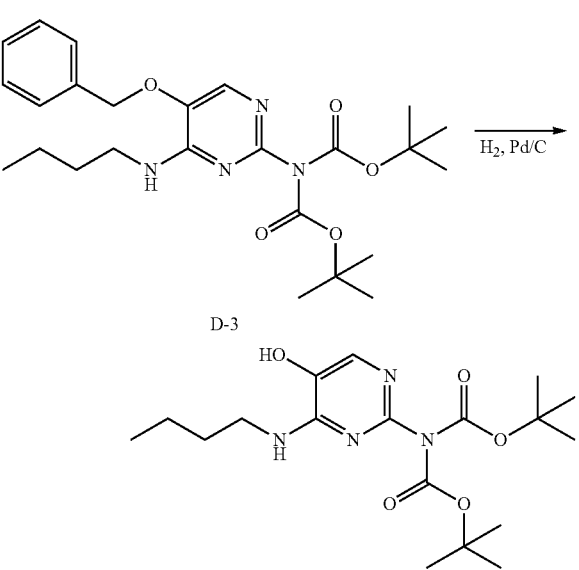

Intermediate D-4 is prepared according to the procedure to prepare intermediate D-2, employing either method A or B.

LC-MS: Anal. Calcd. For $C_{18}H_{30}N_4O_5$: 382.222; found 383[M+H]$^+$

¹H NMR (400 MHz, CHLOROFORM-d) δ ppm 0.95 (t, J=7.3 Hz, 3 H), 1.39 (s, 18 H), 1.40-1.45 (m, 2 H), 1.53-1.64 (m, 2 H), 3.42-3.51 (m, 2 H), 5.66 (s, 1 H), 7.43 (s, 1 H)

Preparation of Compound 2.

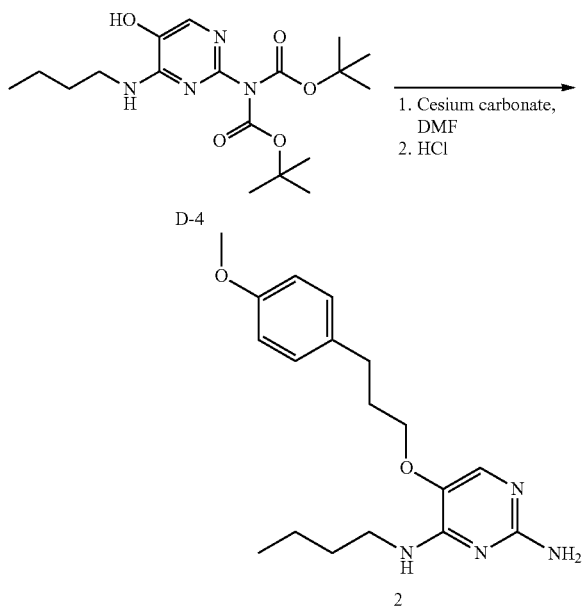

Into a 30 mL vial was placed intermediate D-4 (200 mg, 0.52 mmol), DMF (5 mL), 1-(3-bromopropyl)-4-methoxybenzene (130 mg, 0.57 mmol), and cesium carbonate (508 mg, 1.56 mmol). The reaction was allowed to stir for 15 hours at room temperature. The solids were removed via filtration. The solvents of the filtrate were removed under reduced pressure and the crude was reconstituted in methanol and to it was added HCl (6M in isopropanol) and the reaction was allowed to stir 15 hours at room temperature. The solvents were removed under reduced pressure and the crude was purified via reverse phase separation to afford 2 as the free base.

Preparation of Intermediate G-1.

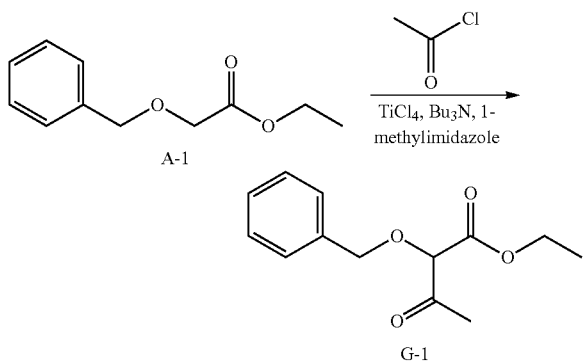

To a stirred solution of A-1 (60 g, 309 mmol, 1 eq) and 1-methylimidazole (30.4 g, 370 mmol, 1.2 eq) in CH$_2$Cl$_2$ (1 L) was added acetyl chloride (24.3 g, 309 mmol, 1 eq) at −45° C. under N$_2$. After stirring for 20 min, TiCl$_4$ (210 g, 1.08 mol, 3.5 eq) and tributylamine (230 g, 1.24 mol, 4 eq) were added to the mixture at −45° C. under N$_2$, and continues to stir for 50 minutes at −45° C. under N$_2$. After completion, water and ethyl acetate were added. The organic layer was separated and the aqueous layer was extracted with ethyl acetate twice. The organic layer was washed with brine and dried over sodium sulfate. The solids were removed by filtration and the solvents of the filtrate were removed under reduced pressure. The crude was purified via silica column chromato-graphy using a heptane to ethyl acetate gradient to afford a pale yellow oil, G-1.

$^1$H NMR (400 MHz, CHLOROFORM-d) δ ppm 1.30 (t, J=7.2 Hz, 3 H), 2.28 (s, 3 H), 4.27 (q, J=7.2 Hz, 2 H), 4.41 (s, 1 H), 4.58 (d, J=11.8 Hz, 1 H), 4.75 (d, J=11.8 Hz, 1 H), 7.32-7.43 (m, 5 H)

Preparation of Intermediate H-1.

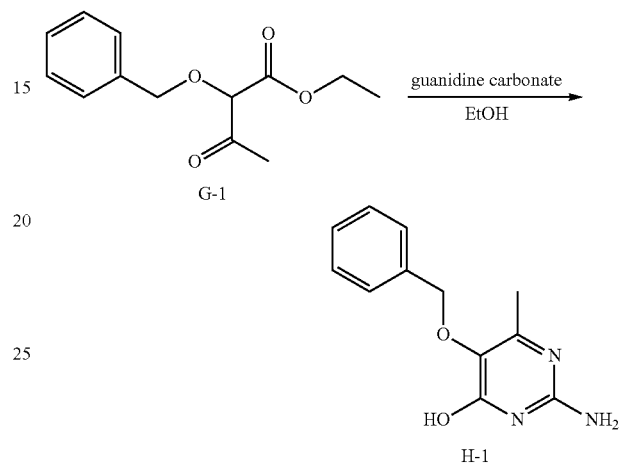

Into a 20 mL microwave vial was placed intermediate G-1 (500 mg, 2.12 mmol), ethanol (5 mL), and guanidine carbonate (200 mg, 2.22 mmol). The vial was sealed and allowed to react at 120° C. with stirring for 4 hours. The solvents were removed under reduced pressure. Water (25 mL) was added. The mixture was brought to pH=5 via careful addition of acetic acid. The precipitate was isolated via filtration to afford a white solid, H-1.

$^1$H NMR (400 MHz, CHLOROFORM-d) δ ppm 1.88 (s, 3 H), 4.85 (s, 2 H), 6.38 (br. s., 2 H), 7.24-7.49 (m, 5 H), 11.16 (s, 1 H)

Preparation of Intermediate G-2.

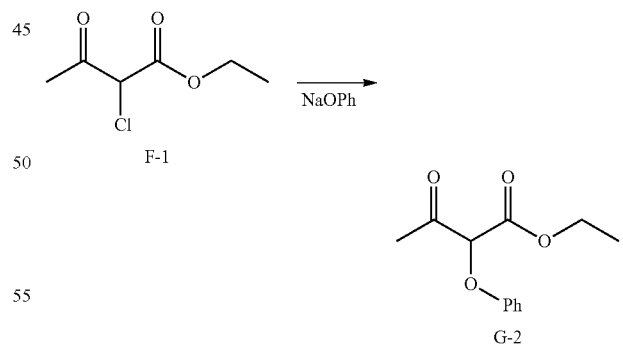

Step 1. Sodium phenolate was prepared by evaporating equimolar portions of phenol and sodium hydroxide in a 1 L round bottom flask on the rotary evaporator. Toluene is used in the azeotropic removal of water.

Step 2. Sodium phenolate (116 g, 1 mol) prepared in step 1 and toluene (1 L) were placed in a 2 L three-necked flask fitted with mechanical stirrer, addition funnel, and reflux condenser with drying tube. The suspension was heated to reflux, then ethyl α-chloroacetoacetate (165 g, 1 mol) was added with stirring through the addition funnel where the reaction continues heating at reflux for 4 hours. The light brown suspension is cooled to room temperature, extracted with water (2×500 mL), and dried (anhydrous magnesium sulfate). The solids were removed via filtration and the solvents of the filtrate were removed under reduced pressure. The crude is used in the next step without purification.

Preparation of Intermediate H-2.

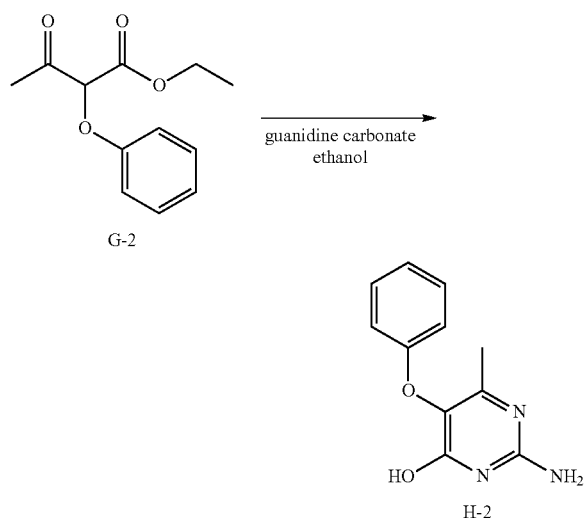

Into a 100 mL round bottom flask equipped with a magnetic stir bar and reflux condenser was added intermediate G-2 (1 g, 4.5 mmol), ethanol (50 mL), and guanidine carbonate [593-85-1](203 mg, 2.25 mmol). The reaction mixture is brought to reflux for 15 hours. The solvent was removed under reduced pressure. Water (25 mL) was added. The mixture was brought to pH=5 via careful addition of acetic acid. The precipitate was isolated via filtration to afford a white solid, H-2. This is used without further purification in the next step.

Preparation of intermediate J-1.

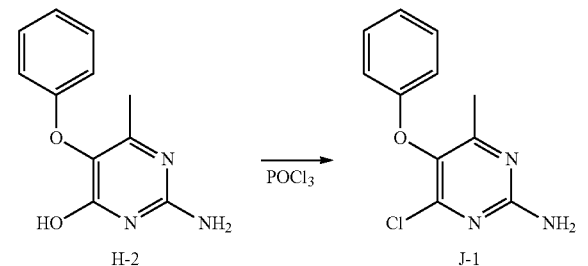

Into a 50 mL round bottom flask equipped with a magnetic stir bar and reflux condenser was added intermediate H-2 (500 mg, 2.3 mmol) and POCl$_3$ (20 mL). The suspension was heated to reflux with stirring for 6 hours. The solvents were removed under reduced pressure to afford a crude brown oil, J-1. No further purification was done. The compound was used as such in the subsequent step.

Preparation of 3.

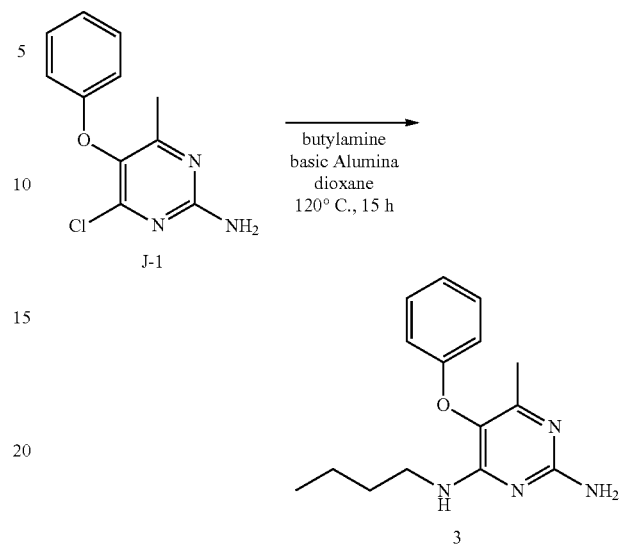

Into a 50 mL sealed tube equipped with a magnetic stir bar was placed intermediate J-1 (150 mg, 0.64 mmol), n-butylamine (70 mg, 0.96 mmol), basic alumina (100 mg), and dioxane (10 mL). The tube was sealed, placed in an oil bath at 120° C., and the reaction was heated with stirring for 15 hours. The vessel was cooled to room temperature and the cap was carefully removed. The contents were poured into a round bottom flask where the solvents were removed under reduced pressure. The crude was purified via silica gel column chromatography using a dichloromethane to 5% methanol in dichloromethane gradient. The best fractions were pooled, and the solvents were removed under reduced pressure to afford 3.

LC-MS: Anal. Calcd. For $C_{15}H_{20}N_4O$: 272.16; found 273 [M+H]$^+$ $^1$H NMR (300 MHz, CHLOROFORM-d) δ ppm 0.80 (t, J=7.3 Hz, 3 H), 1.20 (dq, J=15.0, 7.3 Hz, 2 H), 1.33-1.47 (m, 2 H), 1.98 (s, 3 H), 3.20-3.34 (m, 2 H), 4.74 (br. s., 2 H), 4.79 (br. s., 1 H), 6.78-6.84 (m, 2 H), 6.91-7.01 (m, 1 H), 7.18-7.28 (m, 2 H)

Preparation of 4

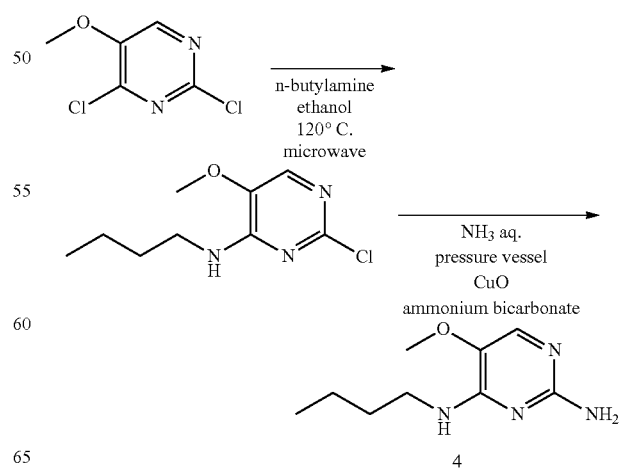

Step 1.

Into a 20 mL microwave vial was added commercially available 2,4-dichloro-5-methoxy pyrimidine (300 mg, 1.68 mmol), ethanol (5 mL), and n-butylamine (0.166 mL, 1.68 mmol). The vial is sealed then heated in the microwave for 10 minutes at 120° C. LC-MS shows complete conversion. The solvents were removed under reduced pressure. The crude is used as such in step 2.

Step 2.

Compound from step 1 was placed into a 20 mL pressure vessel with aqueous ammonia (10 mL) and to this was added ammonium bicarbonate (200 mg, 2.6 mmol), and CuO (24 mg, 0.17 mmol, 0.1 eq). The vessel was sealed and the mixture was heated to 120° C. with stirring for 24 hours. The reaction mixture was extracted 3 times with 5 mL dichloromethane:methanol 9:1 and the volatiles were removed under reduced pressure. The compound was filtered through silica eluting with dichloromethane:methanol 9:1 and the volatiles were removed under reduced pressure. The residue was purified by reversed phase chromatography.

LC/MS: Anal. Calcd. For $C_9H_{16}N_4O$: 196.13; found 197$[M+H]^+$ $^1$H NMR (400 MHz, CHLOROFORM-d) δ ppm 0.97 (t, J=7.3 Hz, 3 H), 1.35-1.48 (m, 2 H), 1.56-1.68 (m, 2 H), 3.44-3.52 (m, 2 H), 3.80 (s, 3 H), 5.86 (s, 1 H), 5.97 (s, 2 H), 7.07-7.14 (m, 1 H)

Preparation of 5.

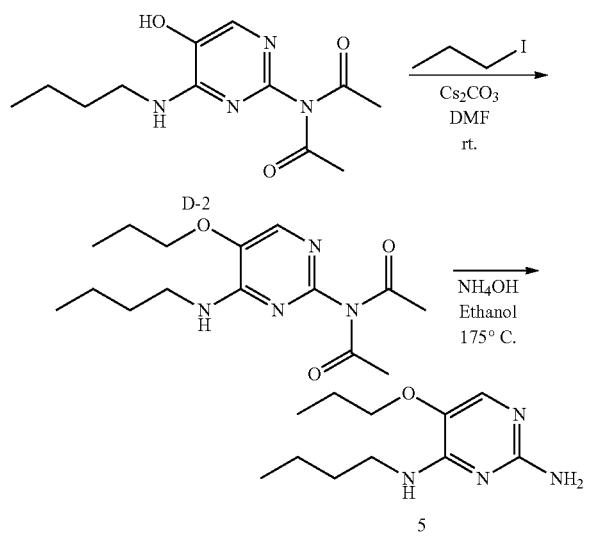

Step 1.

Into a 16×100 test tube was placed intermediate D-2 (180 mg, 0.66 mmol), DMF (5 mL), propyl iodide (111 mg, 0.656 mmol), and cesium carbonate (320 mg, 0.98 mmol). The reaction was allowed to stir at room temperature for 15 hours. The solids were removed by filtration, and the solvents of the filtrate were removed under reduced pressure. The crude was purified via silica gel chromatography using a dichloromethane to 10% methanol in dichloromethane gradient. The best fractions were pooled, the solvents were removed under reduced pressure to afford a white solid.

Step 2.

Into a 10 mL microwave vial was placed the above white solid (100 mg), ammonium hydroxide (1 mL) and ethanol (1 mL). The vial was sealed and heated with stirring to 175° C. for 10 minutes. LC-MS shows complete conversion to product. The solvents were removed under reduced pressure. The crude was purified via silica gel chromatography using a dichloromethane to 10% methanol in dichloromethane gradient. The best fractions were pooled, the solvents were removed under reduced pressure to afford a colorless oil. Addition of one equivalent of HCl (using 5 to 6N HCl in isopropanol) affords a white solid, 5.

LC/MS: Anal. Calcd. For $C_{11}H_{20}N_4O$: 224.16; found 225$[M+H]^+$ $^1$H NMR (400 MHz, DMSO-$d_6$) δ ppm 0.90 (t, J=7.3 Hz, 3H), 0.98 (t, J=7.4 Hz, 3 H), 1.20-1.35 (m, 2 H), 1.54 (t, J=7.2 Hz, 2 H), 1.69-1.75 (m, 2 H), 3.40 (d, J=7.0 Hz, 2 H), 3.87 (t, J=6.5 Hz, 2 H), 7.39 (d, J=5.5 Hz, 1 H), 7.46 (br. s., 2 H), 8.28-8.37 (m, 1 H)

Synthetic Scheme for the preparation of AA-9

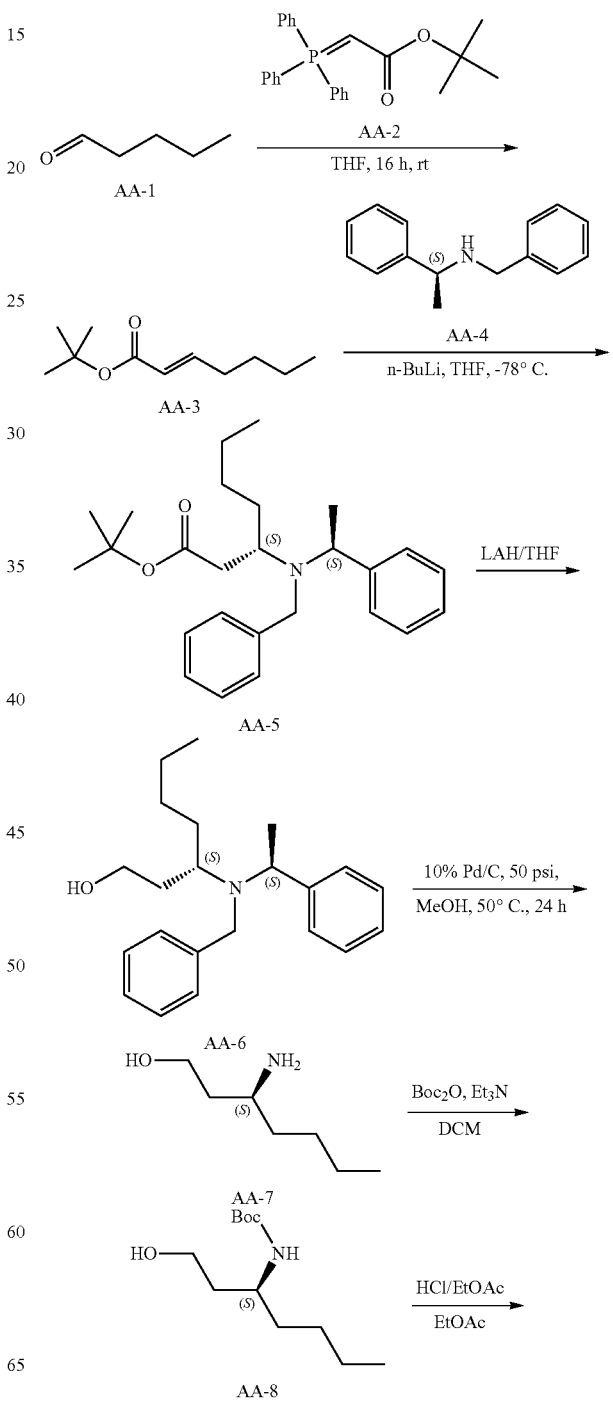

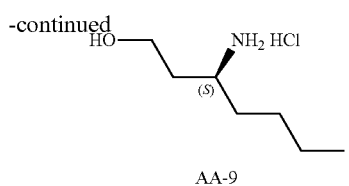

Synthesis of Intermediate AA-3

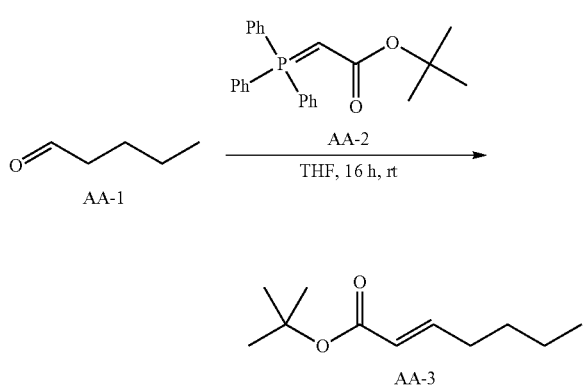

To a solution of valeraldehyde (43 g, 500 mmol) in THF (1 L) was added AA-2 (200 g, 532 mmol) and the reaction mixture was stirred for 16 hours at room temperature. The solvents were evaporated and the residue was diluted in petroleum ether and filtered. The solvents of the filtrate were removed under reduced pressure and the residue was purified by silica chromatography using a petroleum ether to 3% ethyl acetate in petroleum ether gradient to give AA-3 (90 g) as a colorless oil.

$^1$H NMR (400 MHz, CDCl$_3$): δ ppm 6.81-6.77 (m, 1H), 5.68-5.64 (td, J=1.2Hz, 15.6 Hz, 1H), 2.11-2.09 (m, 2H), 1.406 (s, 9H), 1.38-1.26(m, 4H), 0.85-0.81(t, J=7.2Hz, 3H).

Synthesis of Compound AA-5

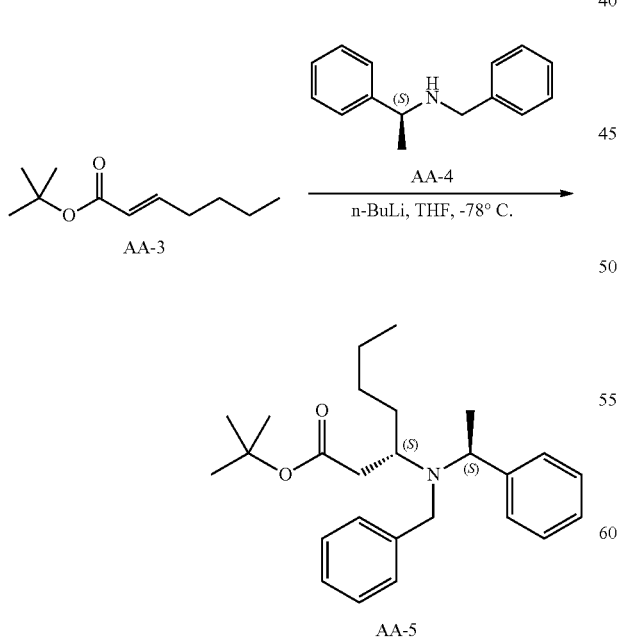

n-butyl lithium (290 mL, 725 mmol, 1.5 eq.) was added to a stirred solution of AA-4 (165 g, 781 mmol) in THF (800 mL) at −78° C. The reaction mixture was stirred for 30 minutes then AA-3 (90 g, 488.4 mmol) in THF (400 mL) was added and the reaction was stirred for 2 hours at −78° C. The mixture was quenched with sat., aq. NH$_4$Cl solution and warmed to room temperature. The product was partitioned between ethyl acetate and water. The organic phase was washed with brine, dried and evaporated. The residue was purified by column chromatography eluting with 5% ethyl acetate in petroleum ether to afford a colorless oil, AA-5 (132 g).

$^1$H NMR (400 MHz, CDCl$_3$): δ ppm 7.36-7.16 (m, 10H), 3.75-3.70 (m, 2H), 3.43-3.39 (d, J=15.2Hz, 1H), 3.33-3.15 (m, 1H), 1.86-1.80 (m, 2H), 1.47-1.37 (m, 2H), 1.32 (s, 9H), 1.26-1.17 (m, 7H), 0.83-0.79 (t, J=7.2Hz, 3H).

Synthesis of AA-6

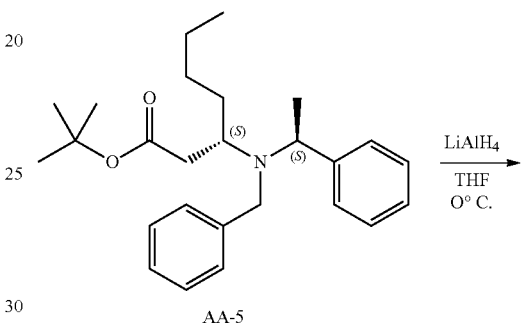

AA-5 (130 g, 328 mmol) was dissolved in THF (1.5 L) and LAH (20 g, 526 mmol) was added at 0° C. in small portions. The resulting mixture was stirred at the same temperature for 2 hours and then allowed to warm to room temperature. The mixture was quenched with a sat. aq. NH$_4$Cl solution. The product was partitioned between ethyl acetate and water. The organic phase was washed with brine, dried and evaporated. The combined organic layers were dried over sodium sulfate, the solids were removed via filtration and concentrated to afford crude AA-6 (100 g), which was used in the next step without further purification.

$^1$H NMR (400 MHz, CDCl$_3$): δ ppm 7.33-7.14 (m, 10H), 3.91-3.86 (m, 1H), 3.80-3.77 (d, J=13.6Hz, 1H), 3.63-3.60 (d, J=13.6Hz, 1H), 3.43-3.42 (m, 1H), 3.15-3.10 (m, 1H), 2.70-2.63 (m, 2H), 1.65-1.28 (m, 10H), 0.89-0.81 (m, 3H).

Synthesis of AA-9

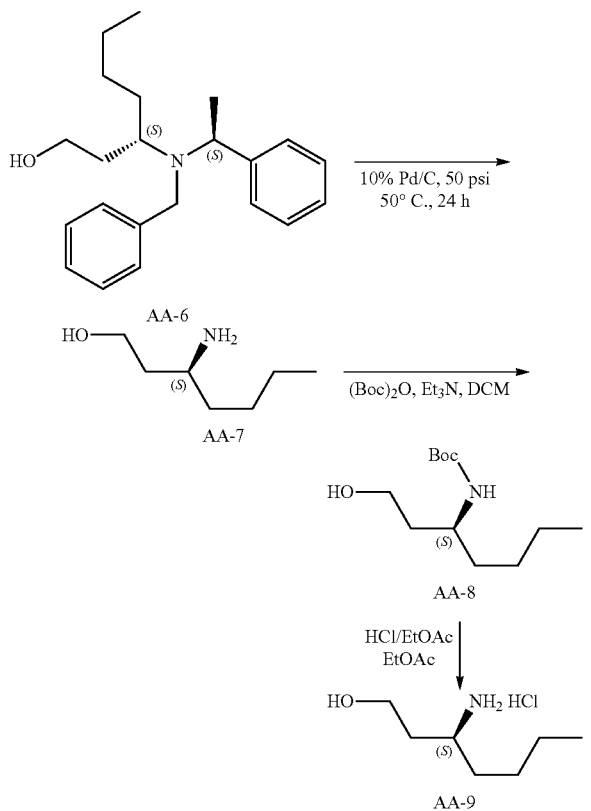

A solution of AA-6 (38 g, 116.75 mmol) and 10% Pd/C in methanol (200 mL) was hydrogenated under 50 PSI hydrogen at 50° C. for 24 hours. The reaction mixture was filtered and the solvent was evaporated to give crude product AA-7 (17 g).

The crude product was dissolved in dichloromethane (200 mL), triethylamine (26.17 g, 259.1 mmol) and di-tert-butyl dicarbonate (84.7 g, 194.4 mmol) was added at 0° C. The resulting mixture was stirred at room temperature for 16 hours. The mixture was partitioned between dichloromethane and water. The organic phase was washed with brine, dried and evaporated. The residue was purified by silica gel chromatography eluting with 20% ethyl acetate in petroleum ether to give AA-8 (13 g) as colorless oil.

$^1$H NMR (400 MHz, CDCl$_3$): δ ppm 4.08-4.03 (br, 1H), 3.68 (m, 1H), 3.58-3.55 (m, 2H), 3.20-2.90(br, 1H), 1.80-1.73 (m, 1H), 1.42-1.17 (m, 15 H), 0.85-0.82(t, J=6.8Hz, 3H).

AA-8 (42 g, 0.182 mol) was dissolved in dioxane (200 mL) and dioxane/HCl (4M, 200 mL) was added at 0° C. The resulting mixture was stirred at room temperature for 2 h. The solvent was evaporated to afford the crude product. A dichloromethane/petroleum ether mixture (50 mL, 1:1, v/v) was added to the crude product, and the supernatant was decanted. This procedure was repeated two times to obtain an oil, AA-9 (26.6 g).

$^1$H NMR (400 MHz, DMSO-d$_6$): δ ppm 8.04 (s, 3H), 3.60-3.49 (m, 2H), 3.16-3.15 (m, 1H), 1.71-1.67 (m, 2H), 1.60-1.55(m, 2H), 1.33-1.26 (m, 4H), 0.90-0.87 (t, J=6.8Hz, 3H).

Preparation of AA-10

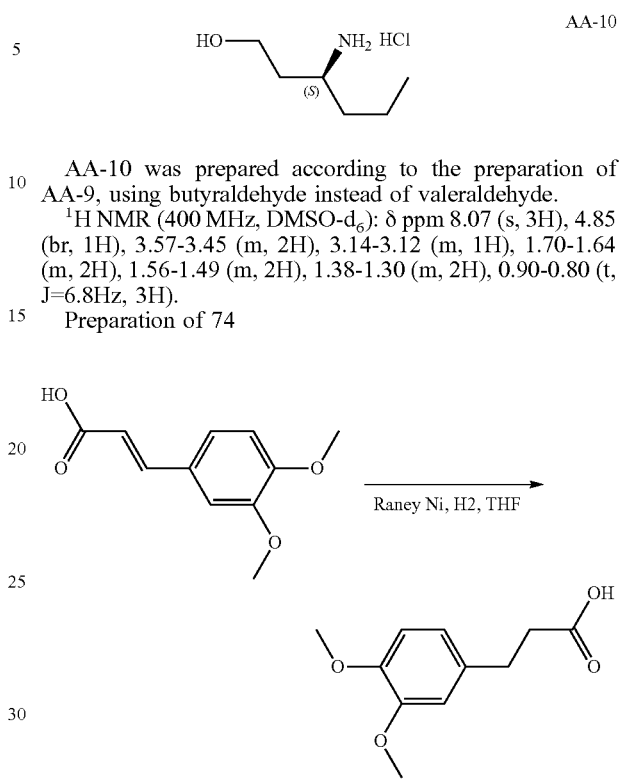

AA-10 was prepared according to the preparation of AA-9, using butyraldehyde instead of valeraldehyde.

$^1$H NMR (400 MHz, DMSO-d$_6$): δ ppm 8.07 (s, 3H), 4.85 (br, 1H), 3.57-3.45 (m, 2H), 3.14-3.12 (m, 1H), 1.70-1.64 (m, 2H), 1.56-1.49 (m, 2H), 1.38-1.30 (m, 2H), 0.90-0.80 (t, J=6.8Hz, 3H).

Preparation of 74

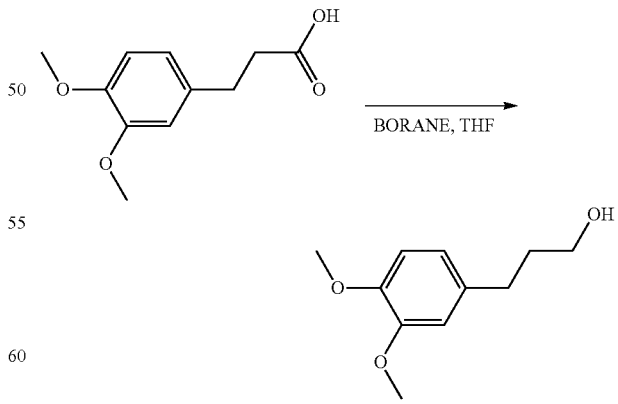

Step 1. 3,4-dimethoxycinnamic acid (5 g, 24 mmol) was dissolved in THF (100 mL). Raney Nickel was added to this solution under a N$_2$ atmosphere.

The reaction mixture was exposed to a hydrogen atmosphere and stirred 15 hours at room temperature. The reaction mixture was filtered over a cartridge packed with diatomateous earth and the solvent of the filtrate was removed under reduced pressure. The residue was used as such in the next step.

LC-MS: Anal. Calcd. For C$_{11}$H$_{14}$O$_4$: 210.09; found 209 [M−H]

Step 2. 3-(3,4-dimethoxyphenyl)propanoic acid was dissolved in THF (100 mL). Borane-dimethyl sulfide complex (2M in diethyl ether, 20 mL, 40 mmol) was added. The reaction mixture was stirred overnight at room temperature. Methanol was added slowly to quench the reaction mixture, then silica was added and the volatiles were removed under reduced pressure. The residue was purified on silica using a heptane to ethyl acetate gradient yielding the product as an oil. This was used as such in the next step.

LC-MS: Anal. Calcd. For $C_{11}H_{16}O_3$: 196.11; found 195 [M–H]

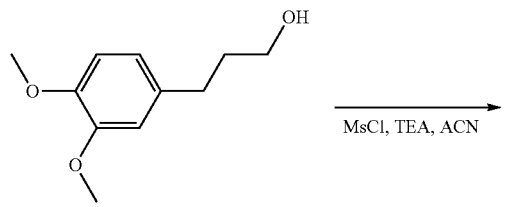

Step 3. 3-(3,4-dimethoxyphenyl)propan-1-ol (3.8 g, 19.5 mmol) and triethylamine (3.8 mL, 27.3 mmol) were dissolved in acetonitrile (15 mL) and then methanesulfonyl chloride (1.5 mL, 19.5 mmol) was added. The reaction mixture was shaken overnight at room temperature. The volatiles were removed under reduced pressure and the residue was purified via silica gel chromatography using a heptane to ethyl acetate gradient yielding the product as a clear oil.

$^1$H NMR (400 MHz, DMSO-$d_6$) δ ppm 1.91-2.01 (m, 2 H), 2.58-2.64 (m, 2 H), 3.17 (s, 3 H), 3.72 (s, 3 H), 3.75 (s, 3 H), 4.19 (t, J=6.4 Hz, 2 H), 6.71-6.76 (m, 1 H), 6.81-6.89 (m, 2 H)

Step 4. A solution of D-4 (400 mg, 1 mmol), cesium carbonate (511 mg, 1.6 mmol) and 3-(3,4-dimethoxyphenyl) propyl methanesulfonate (430 mg, 1.6 mmol) in acetone (50 mL) was heated to 50° C. for 15 hours. The reaction mixture was placed in the centrifuge and the supernatant was decanted then evaporated to dryness. The residue was purified via silica column chromato-graphy using a gradient from heptane to ethyl acetate. The fractions containing the product were pooled and the solvents were removed under reduced pressure to afford D-5.

LC-MS: Anal. Calcd. For $C_{29}H_{44}N_4O_7$: 560.32; found 561 [M+H]$^+$

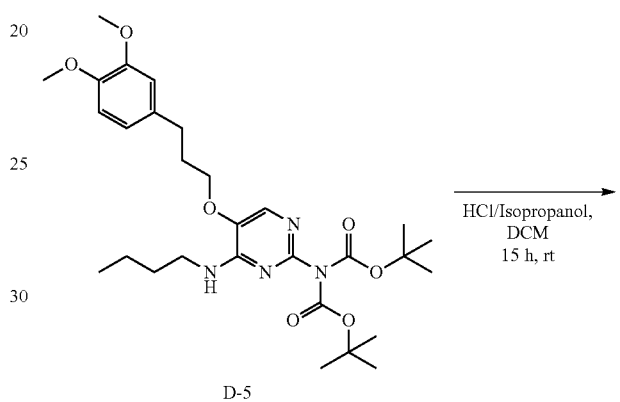

D-5

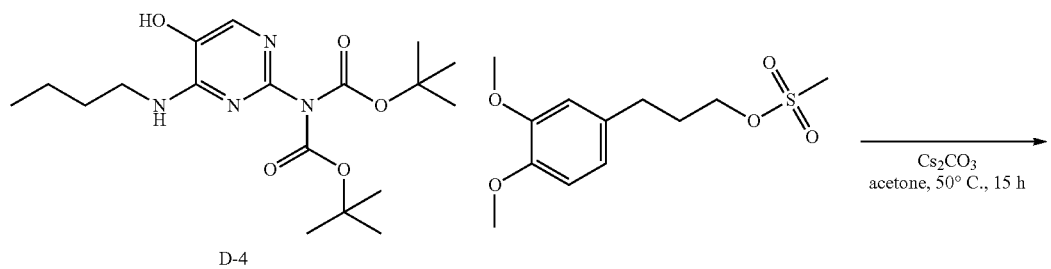

D-4

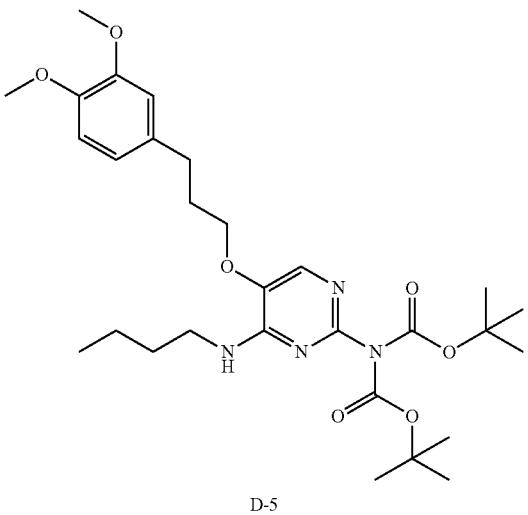

D-5

-continued

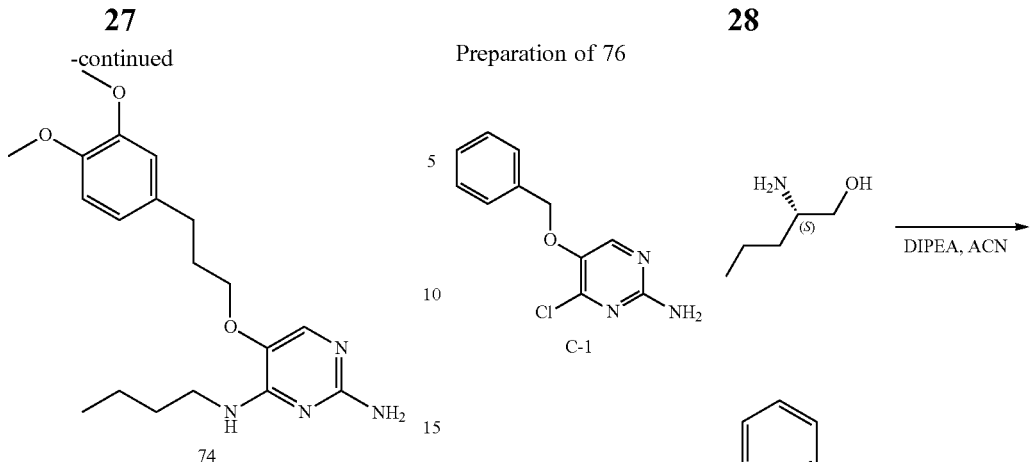

74

Step 5. The boc-protected compound was dissolved in dichloromethane (5 mL) and 6M HCL in isopropanol (3 mL) was added. The reaction mixture was stirred 15 hours at room temperature. The volatiles were removed under reduced pressure. Ether (5 mL) was added and a precipitate formed, 74 was isolated by filtration then dried in the vacuum oven for 15 hours.

Preparation of 75

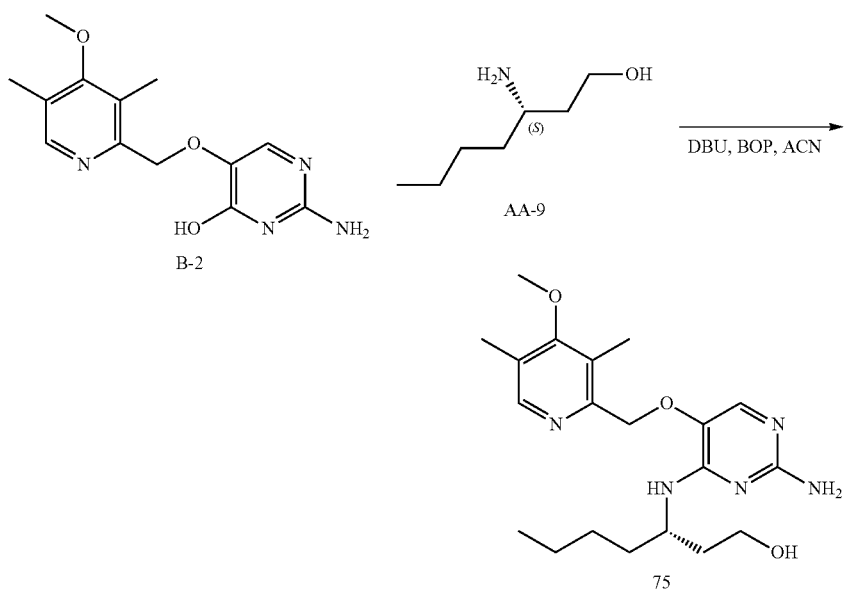

Preparation of 76

Step 1. C-1 (2 g, 8.49 mmol), L-norvalinol (1.75 g, 17 mmol) and diisopropylethylamine (5.85 mL, 34 mmol) were dissolved in acetonitrile (200 mL) in a 500 mL teflon coated pressure vessel and heated to 130° C. for 15 hours. The mixture was allowed to cool to room temperature, the volatiles were removed under reduced pressure and the crude was purified via silica gel column chromatography using a gradient from dichloromethane to 10% methanol in dichloromethane. The best fractions were pooled and the solvents were removed under reduced pressure to afford intermediate D-6.

LC-MS: Anal. Calcd. For $C_{16}H_{22}N_4O_2$: 302.17; found 303 [M+H]$^+$

Step 1. Intermediate B-2 was prepared according to the method described for the preparation of intermediate B-1.

Step 2. To a solution of B-2 (1 g, 3.62 mmol) and DBU (5.4 mL, 36 mmol) in acetonitrile (20 mL) was added BOP (2.08 g, 4.71 mmol) and the reaction mixture became transparent and was stirred for 15 minutes at room temperature. AA-9 (910 mg, 5.43 mmol) was added and the reaction mixture was stirred for 2 days at 50° C. The volatiles were removed under reduced pressure and the residue was purified on silica using a dichloromethane to 10% methanol in dichloromethane gradient. The best fractions were pooled and the solvents were removed under reduced pressure. The crude was reconstituted in dichloromethane (2 mL) then HCl in diethylether was added to form the HCl salt. The precipitate was isolated by filtration and dried in the vacuum oven to afford compound 75.

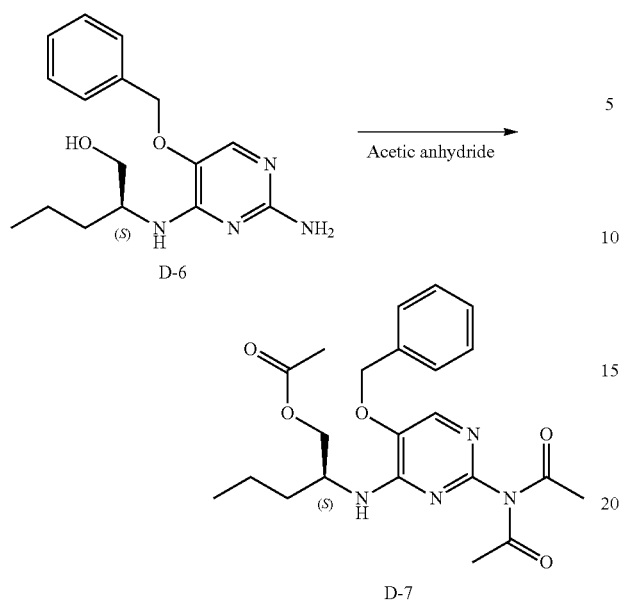

Step 2. D-6 (2 g, 6.61 mmol) was heated to reflux in acetic anhydride (100 mL) in a 250 mL round bottom flask for 4 hours. The volatiles were removed under reduced pressure and the residue was purified via silica gel column chromatography using a heptane to ethyl acetate gradient yielding a yellow oil, D-7.

LC-MS: Anal. Calcd. For $C_{22}H_{28}N_4O_5$: 428.21; found 429 $[M+H]^+$

Step 3. D-8 was prepared according to the method to prepare intermediate D-2.

LC-MS: Anal. Calcd. For $C_{15}H_{22}N_4O_5$: 338.16; found 339 $[M+H]^+$

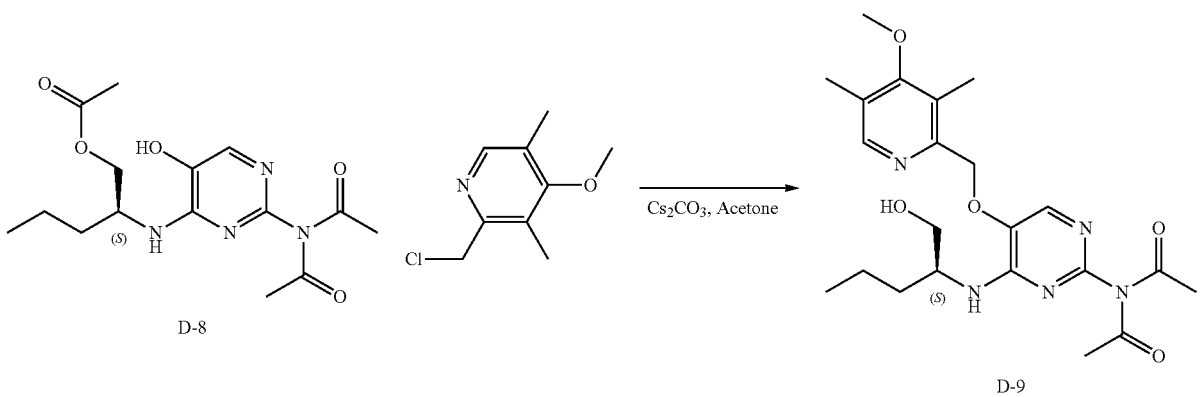

Step 4. Intermediate D-9 was prepared according to the method described in example 75 from intermediate D-4.

LC-MS: Anal. Calcd. For $C_{15}H_{22}N_4O_5$: 338.16; found 339 $[M+H]^+$

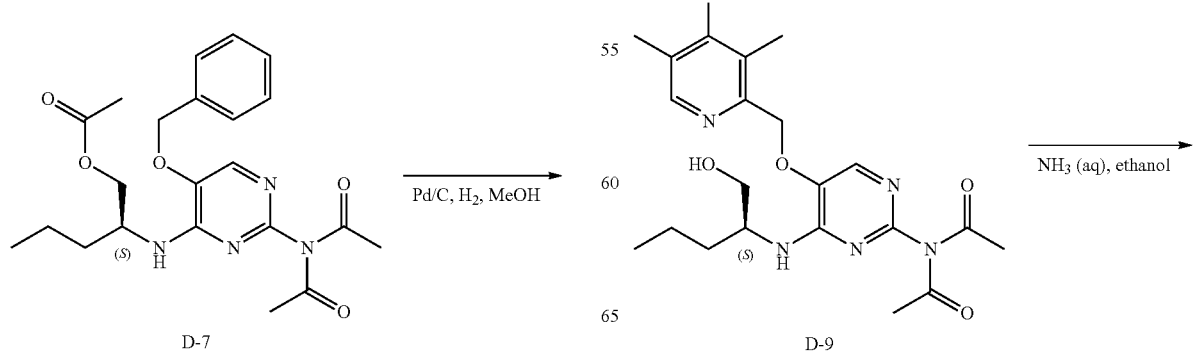

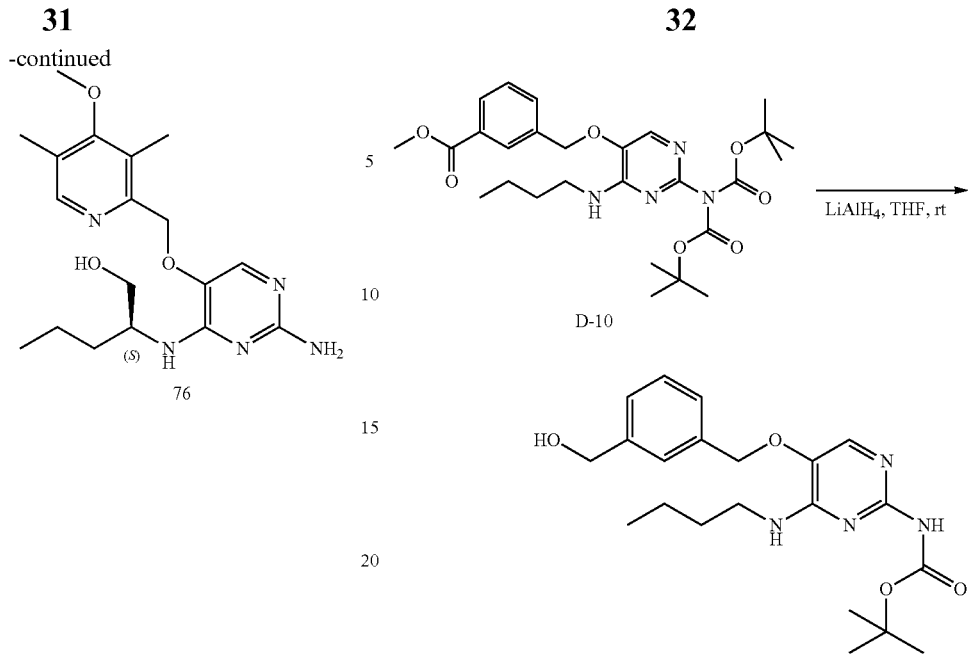

76

Step 5. Deprotection of D-9 was performed according to the method described in step 2 of compound 5 to afford 76.

Preparation of compound 77

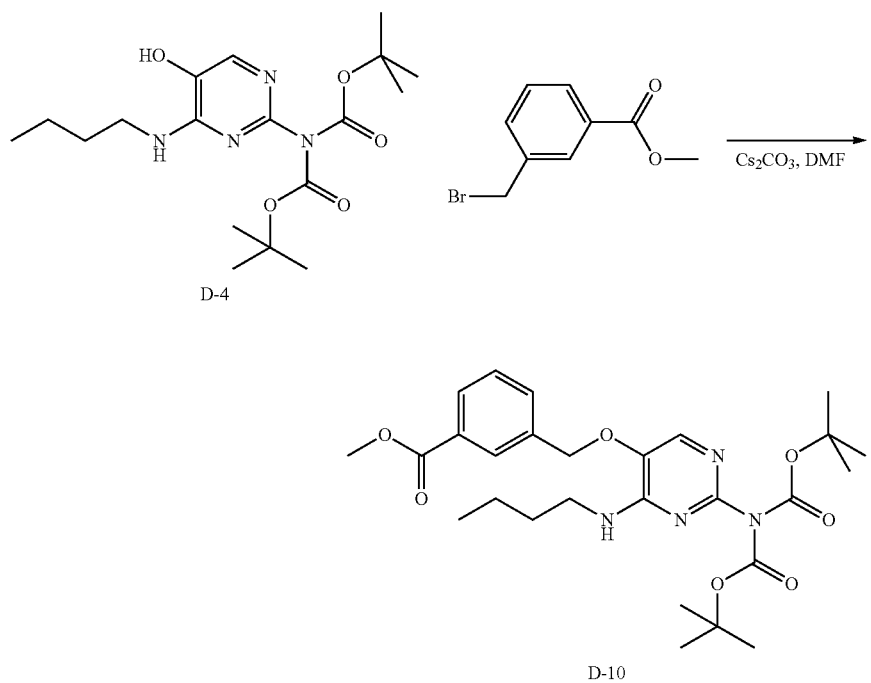

Step 1. D-10 was prepared from D-4 according to the method to prepare example 5, purification via silica column with heptane to ethyl acetate gradient.

LC-MS: Anal. Calcd. For $C_{27}H_{38}N_4O_7$: 530.27; found 531 [M+H]$^+$ $^1$H NMR (400 MHz, CHLOROFORM-d) δ ppm 0.93 (t, J=7.3 Hz, 3 H), 1.37 (dd, J=14.9, 7.4 Hz, 2 H), 1.53-1.62 (m, 2 H), 3.40-3.50 (m, 2 H), 3.92-3.95 (m, 3 H), 5.13 (s, 2 H), 5.33 (s, 1 H), 7.46-7.52 (m, 1 H), 7.56-7.62 (m, 1 H), 7.73 (s, 1 H), 8.05 (dt, J=7.7, 1.4 Hz, 1 H), 8.09 (d, J=1.5 Hz, 1 H)

Step 2. D-10 (2.14 g, 3.91 mmol) was dissolved in anhydrous THF (250 mL). Lithium aluminum hydride (1M in THF, 5.87 mL, 5.87 mmol) was added dropwise and the reaction mixture was stirred for 3 hours at room temperature. NH$_4$Cl (sat., aq.) was added drop wise to the reaction mixture and the precipitated salts were removed by filtration and washed with THF. The filtrate was evaporated to dryness and crude D-11 was used as such in the next step.

LC-MS: Anal. Calcd. For $C_{21}H_{30}N_4O_4$: 402.23; found 403 [M+H]$^+$

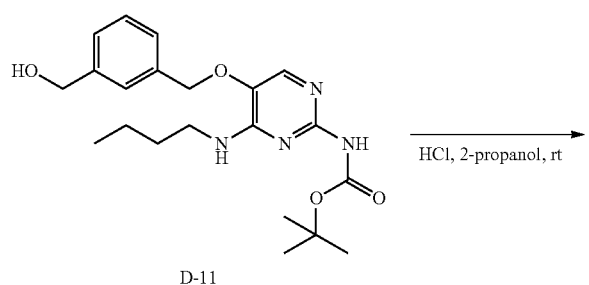

D-11

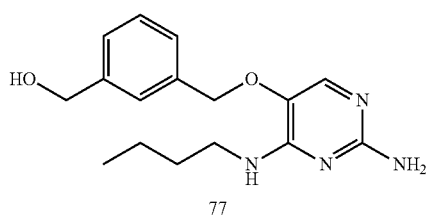

77

Step 3. D-11 (1.57 g, 3.91 mmol) was dissolved in dichloromethane (20 mL) and to it was added HCI (6 M in isopropanol, 50 mL). The reaction mixture stirred for 16 hours at room temperature. The volatiles were removed under reduced pressure and the crude was purified via silica column using a dichloromethane to 10% dichloromethane in methanol gradient yielding 77 as an oil which solidified on standing.

Preparation of 78

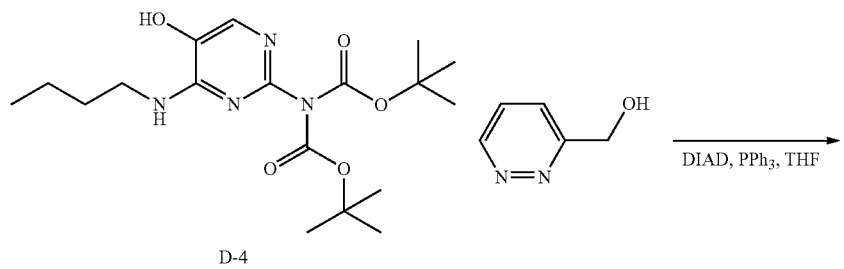

D-4

Step 1. A solution of D-4 (0.5 g, 1.31 mmol), 3-pyridazinylmethanol (158 mg, 1.44 mmol) and triphenylphosphine (377 mg, 1.44 mmol) in anhydrous THF (4 mL) was cooled to 0° C. and a solution of DIAD (0.28 mL, 1.44 mmol) was added dropwise at 0° C. After addition, the reaction mixture was stirred for 3 hours at ambient temperature. The solvent was quenched with water (10 mL), stirred for 10 minutes and the volatiles were removed under reduced pressure. The water layer was extracted with dichloromethane, the organic layers were combined, and the solvent was removed under reduced pressure. The crude was purified via silica gel column chromatography using a heptane to ethyl acetate gradient. The best fractions were combined, the solvents were removed under reduced pressure to afford D-12.

LC-MS: Anal. Calcd. For $C_{23}H_{34}N_6O_5$: 474.26; found 475 $[M+H]^+$

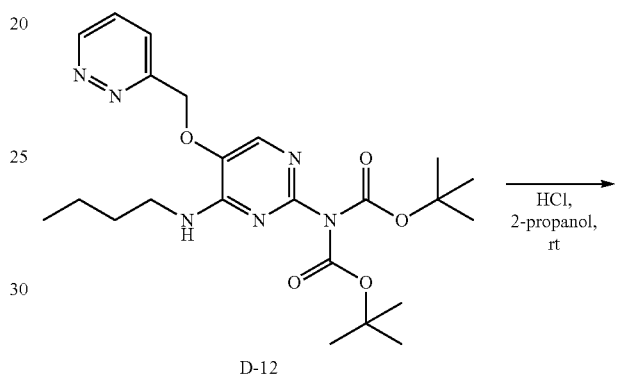

D-12

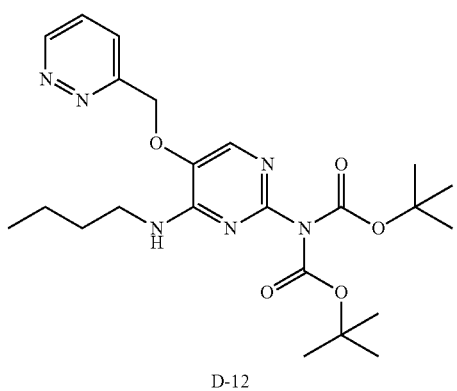

D-12

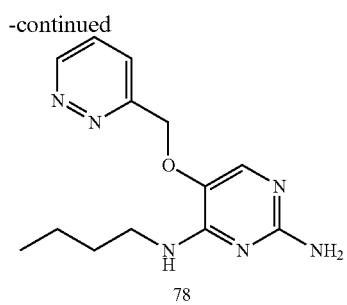

78

Step 2. D-11 (620 mg, 1.31 mmol) was dissolved in dichloromethane (10 mL) and to it was added HCl (6 M in isopropanol, 10 mL). The reaction mixture stirred for 15 hours at room temperature. The volatiles were removed under reduced pressure and the residue was purified by reversed phase chromatography to afford 78.

Preparation of 79

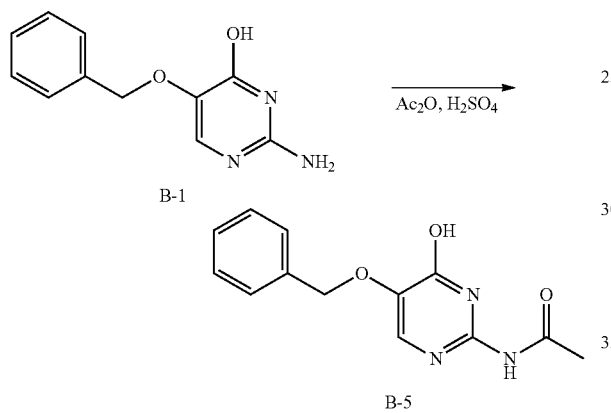

Step 1. In a 500 mL flask a mixture of B-1 (30 g, 138 mmol) and sulfuric acid (3 mL) in acetic anhydride (300 mL) was heated to 90° C. for 3 hours. The reaction cooled to room temperature and the precipitate was isolated by filtration, washed with diisopropylether and dried in vacuo at 50° C. to obtain a white solid, B-5.

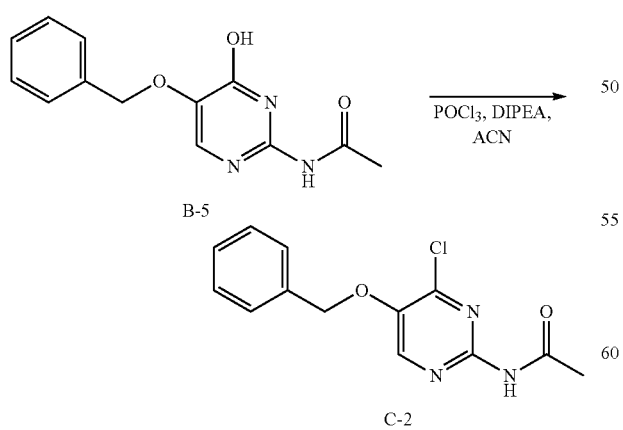

Step 2. In a 400 mL multimax reactor a mixture of B-5 (21.8 g, 84 mmol) in acetonitrile (244 mL) was stirred at 30° C. under a gentle stream of nitrogen. Phosphoryl chloride (18.14 mL, 195 mmol) was added dropwise over a period of 5 minutes. After addition, the reaction mixture was heated to 45° C. and the mixture was stirred for 15 minutes, then DIPEA (33 mL, 195 mmol) was added slowly over a period of 1.5 hours. The reaction was stirred at 45° C. until completion (monitored by LC-MS). A solution of sodium ethanoate (65 g) in water (732 mL) was heated in a 2 L flask to 35° C. and the reaction mixture was portioned into this solution over a period of 5 minutes. The temperature is kept between 35-40° C. via an external cooling bath. The mixture was allowed to reach ambient temperature and stirring was continued for 1 hour. The precipitate was isolated by filtration, washed with water and dried in vacuo at 50° C. to obtain C-2 as a solid.

LC-MS: Anal. Calcd. For $C_{13}H_{12}ClN_3O_2$: 277.06; found 278 $[M+H]^+$ $^1$H NMR (400 MHz, DMSO-$d_6$) δ ppm 2.11 (s, 3 H), 5.31 (s, 2 H), 7.33-7.39 (m, 1 H), 7.43 (t, J=7.2 Hz, 2 H), 7.46-7.51 (m, 2 H), 8.59 (s, 1 H), 10.65 (s, 1 H)

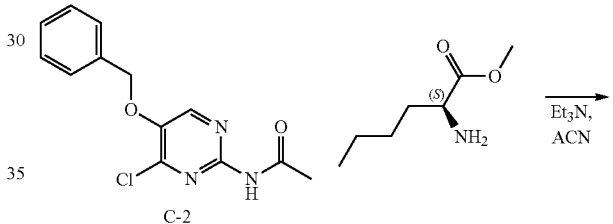

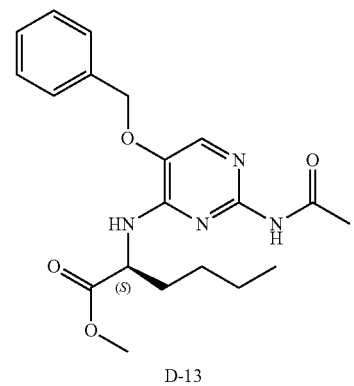

D-13

Step 3. A solution of intermediate C-2 (5.9 g, 21.2 mmol), methyl (2S)-2-aminohexanoate (5.79 g, 31.9 mmol) and triethylamine (14.8 mL, 106 mmol) in acetonitrile (100 mL) was heated to reflux for 4 days. The reaction mixture was cooled to room temperature and the solvent was removed under reduced pressure. The residue was dissolved in dichloromethane and washed with brine. The organic layer was dried (magnesium sulfate) then purified directly via silica column using a gradient of dichloromethane to 10% methanol in dichloromethane. The best fractions were pooled and the solvents were removed under reduced pressure to afford D-13.

LC-MS: Anal. Calcd. For $C_{20}H_{26}N_4O_4$: 386.20; found 387 $[M+H]^+$

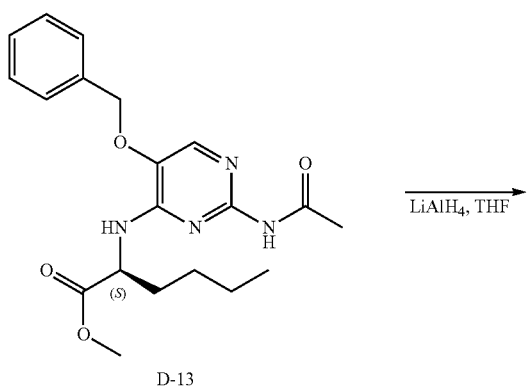

D-13

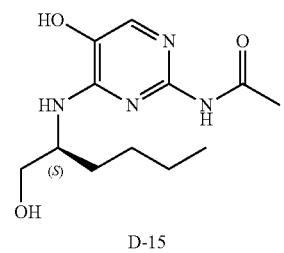

LiAlH₄, THF

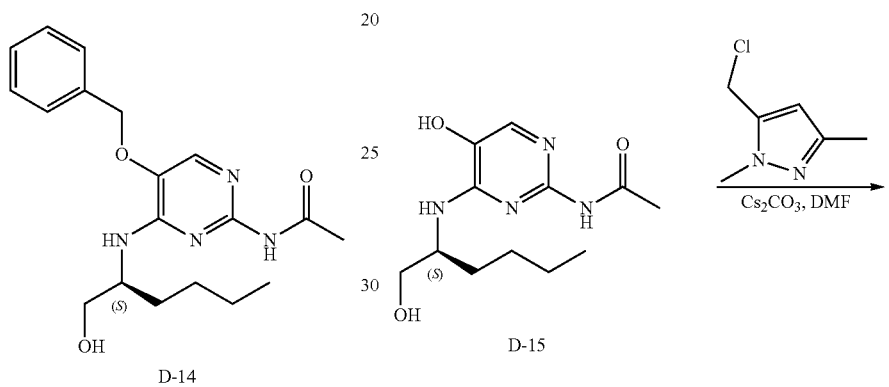

Step 3. D-15 was prepared according to the method described for intermediate D-2. Used without purification in the next step.

LC-MS: Anal. Calcd. For $C_{12}H_{20}H_4O_3$: 268.15; found 269 [M+H]⁺

Step 2. D-13 (3.7 g, 9.57 mmol) was dissolved in anhydrous THF (100 mL). Lithium aluminum hydride (1M in THF, 9.6 mL, 9.6 mmol) was added dropwise and the reaction mixture stirred for 3 hours at room temperature. NH₄Cl (sat., aq.) was added drop wise to the reaction mixture and the precipitated salts were removed via filtration and washed with THF. The filtrate was evaporated to dryness and the residue was purified via silica gel column chromatography using a dichloromethane to 10% methanol in dichloromethane gradient. The best fractions were combined and the solvents were removed under reduced pressure to afford D-14.

LC-MS: Anal. Calcd. For $C_{19}H_{26}N_4O_3$: 358.20; found 359 [M+H]⁺

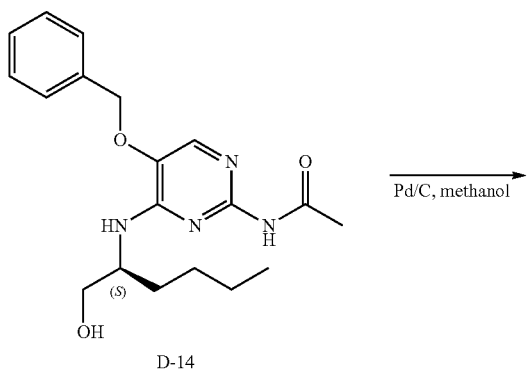

D-14

Pd/C, methanol

Step 4. A mixture of D-15 (210 mg, 0.78 mmol) and cesium carbonate (765 mg, 2.35 mmol) in DMF (25 mL) was heated to 60° C. with stirring then a solution of 5-(chloromethyl)-1,3-dimethyl-1H-pyrazole (113 mg, 0.78 mmol) in DMF(10 mL) was added drop wise. The reaction mixture was stirred for 1 hour at 60° C. The solids were removed by filtration and the solvent was removed under reduced pressure. Crude D-16 was used as such in the next step.

LC-MS: Anal. Calcd. For $C_{18}H_{28}N_6O_3$: 376.22; found 377 [M+H]⁺

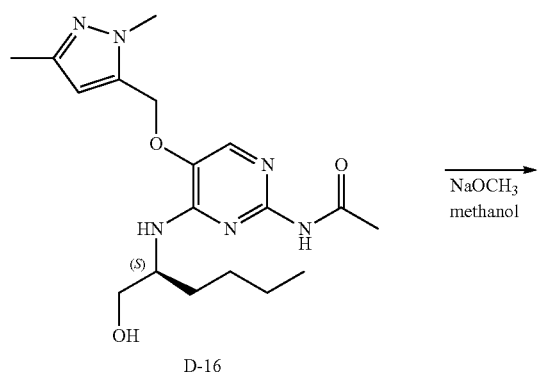

D-16

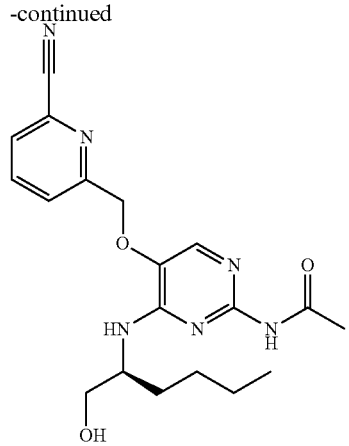

D-17

Step 1. Intermediate D-17 was prepared according to the method used for D-16 via alkylation of D-15.

LC-MS: Anal. Calcd. For $C_{19}H_{24}N_6O_3$: 384.19; found 385 [M+H]$^+$

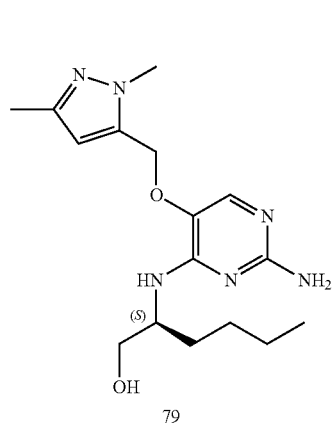

79

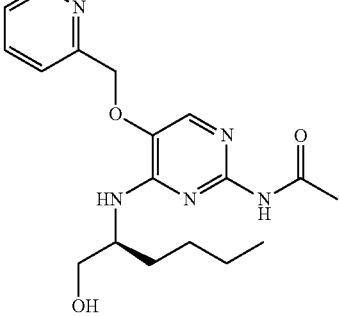

D-17

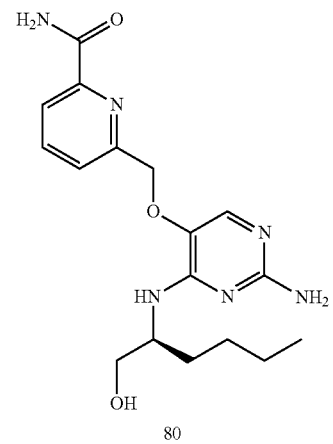

80

Step 5. Into a 30 mL glass tube was placed D-16 (295 mg, 0.78 mmol) and NaOCH$_3$ (30% in methanol, 2 mL) and methanol (20 mL) and the mixture was stirred at 60° C. overnight. The reaction mixture was purified via reverse phase liquid chromatography (Sunfire Prep C18 OBD 10 mm, 30×150 mm. Mobile phase 0.25% NH$_4$OAc solution in water, methanol) to afford 79 as the free base.

Preparation of 80

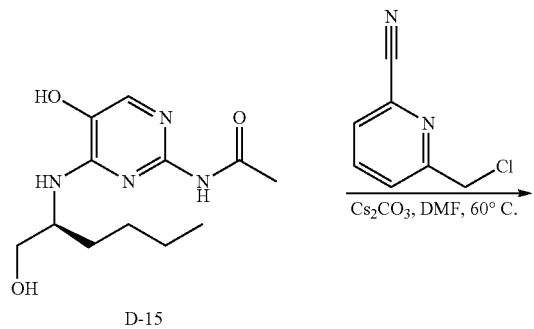

D-15

Step 2. In a 30 mL glass tube D-17 (301 mg, 0.78 mmol) and NaOCH$_3$ (30% in methanol, 2 mL) were dissolved in methanol (20 mL) and stirred at 60° C. overnight. 10 mL of water was added to the reaction mixture and it was stirred for 2 hours at 60° C. The reaction mixture was purified via reverse phase liquid chromatography (Sunfire Prep C18

OBD 10 mm, 30×150 mm. Mobile phase 0.25% NH₄OAc solution in water, methanol) yielding 80 as a powder.

Preparation of 81

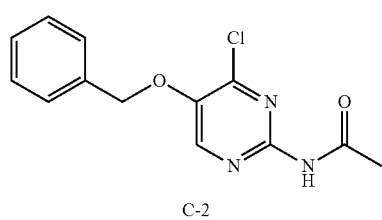 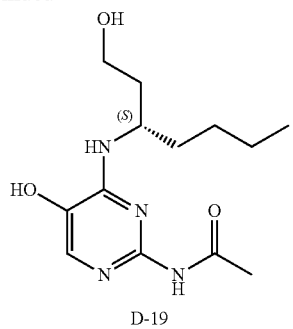

D-19 was prepared from D-18 according to the method employed for intermediate D-2.

LC-MS: Anal. Calcd. For $C_{13}H_{22}N_4O_3$: 282.1; found 283 $[M+H]^+$

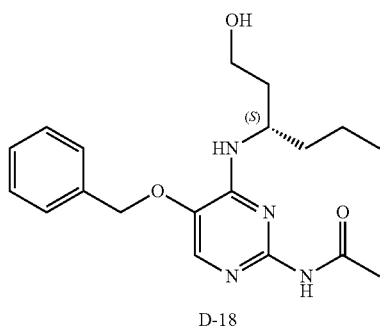 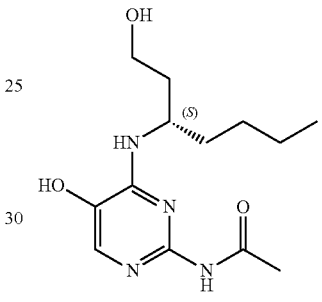

A solution of intermediate C-2 (2 g, 7.2 mmol), AA-9 (3.02 g, 18 mmol) and triethylamine (5 mL, 36 mmol) in acetonitrile (75 mL) was heated to reflux for 6 hours. The reaction mixture was cooled down and the solvent was removed under reduced pressure. The residue was dissolved in dichloromethane and washed with brine. The organic layer was loaded on a silica cartridge and a gradient of dichloromethane to 10% methanol in dichloromethane was applied. The fractions containing the product were evaporated to dryness yielding a white powder, D-18.

LC-MS: Anal. Calcd. For $C_{20}H_{28}N_4O_3$: 372.22; found 373 $[M+H]^+$

¹H NMR (400 MHz, DMSO-d₆) δ ppm 0.77-0.92 (m, 3 H) 1.15-1.36 (m, 4 H) 1.42-1.72 (m, 4 H) 2.12 (s, 3 H) 3.35-3.42 (m, 2 H) 4.11-4.24 (m, 1 H) 4.35-4.52 (m, 1 H) 6.42 (d, J=8.80 Hz, 1 H) 7.42 (s, 1 H) 9.63 (br. s., 1 H)

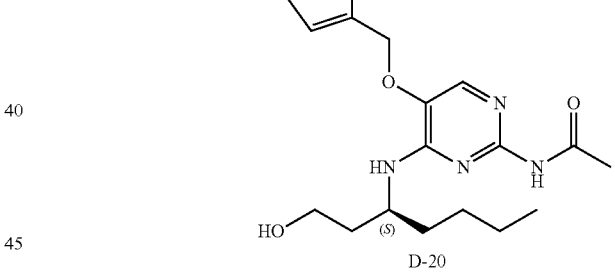

D-20 was prepared from D-19 according to the method to prepare D-17.

LC-MS: Anal. Calcd. For $C_{19}H_{30}N_6O_3$: 390.24; found 391 $[M+H]^+$

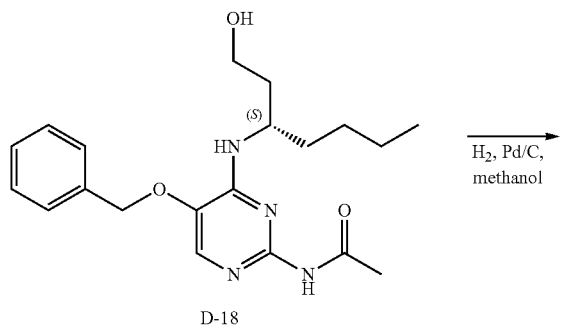 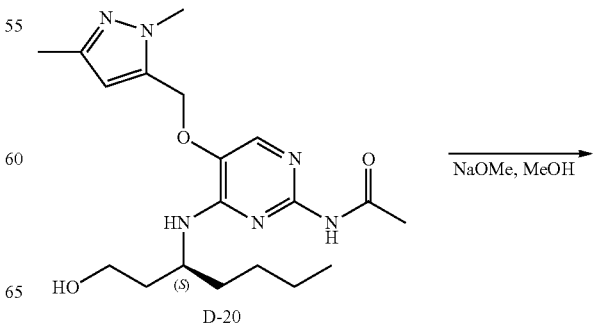

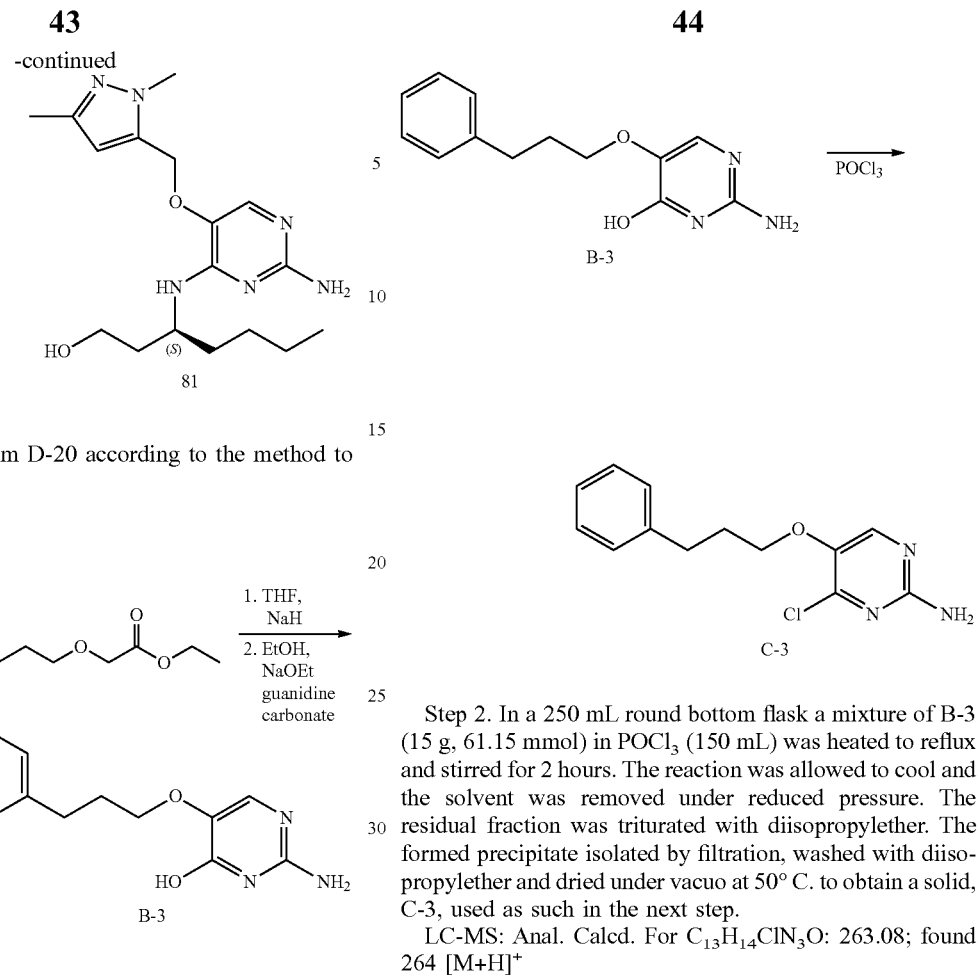

81 was prepared from D-20 according to the method to prepare compound 79.

Preparation of 82

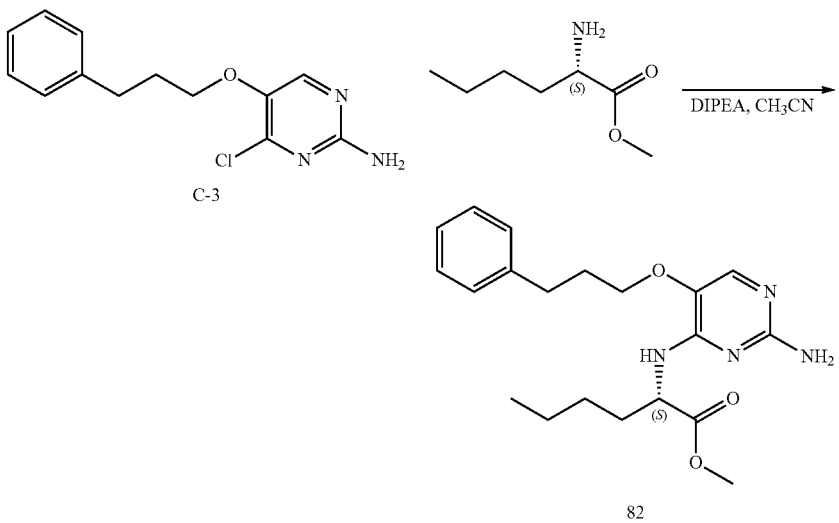

Step 1. Intermediate B-3 was prepared according to the method described for B-1.

LC-MS: Anal. Calcd. For $C_{13}H_{15}N_3O_2$: 245.12; found 246 [M+H]$^+$

1H NMR (400 MHz, DMSO-d$_6$) δ ppm 1.79-1.93 (m, 2 H), 2.66 (t, J=7.8 Hz, 2 H), 3.76 (t, J=6.4 Hz, 2 H), 6.54 (br. s., 2 H), 7.11-7.21 (m, 3H), 7.22-7.29 (m, 3 H), 11.46 (br. s, 1 H)

Step 2. In a 250 mL round bottom flask a mixture of B-3 (15 g, 61.15 mmol) in POCl$_3$ (150 mL) was heated to reflux and stirred for 2 hours. The reaction was allowed to cool and the solvent was removed under reduced pressure. The residual fraction was triturated with diisopropylether. The formed precipitate isolated by filtration, washed with diisopropylether and dried under vacuo at 50° C. to obtain a solid, C-3, used as such in the next step.

LC-MS: Anal. Calcd. For $C_{13}H_{14}ClN_3O$: 263.08; found 264 [M+H]$^+$

Step 3. Into a 20 mL tube was placed C-3 (0.45 g, 1.05 mmol), L-2-aminohexanoic acid-methyl ester HCl (0.48 g, 2.62 mmol), DIPEA (1.18 mL, 6.82 mmol), and acetonitrile (5 mL). The tube was sealed and heated in the microwave for 1.5 hours at 120° C. The reaction was allowed to cool and the solvent was removed under reduced pressure.

The crude mixture was purified by Prep HPLC on (RP Vydac Denali C18-10 μm, 250 g, 5 cm). Mobile phase (0.25% NH₄OAc solution in water, methanol), the desired fractions were collected and evaporated to dryness. The residual fraction was dissolved in a mixture of dichloromethane/methanol and poured over a acid modified solid phase extraction cartridge (SCX). The product was released using with NH₃ 7N in methanol. The collected solution was concentrated under reduced pressure to obtain the desired solid, 82.

Preparation of 83

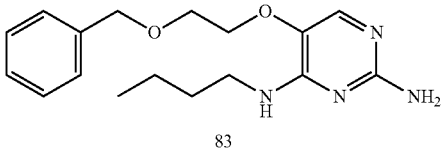

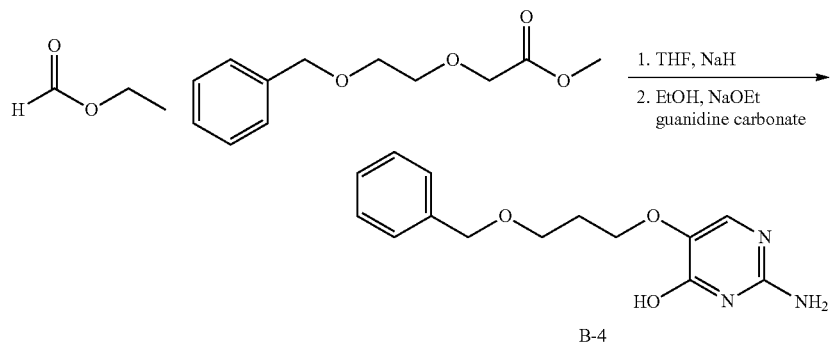

Step 1. Intermediate B-4 was prepared according to the method to prepare B-1.

LC-MS: Anal. Calcd. For $C_{14}H_{17}N_3O_3$: 275.13; found 276 [M+H]⁺

¹H NMR (400 MHz, DMSO-d₆) δ ppm 3.63 (dd, J=5.4, 3.9 Hz, 2 H), 3.95 (dd, J=5.4, 3.6 Hz, 2 H), 4.50 (s, 2 H), 6.33 (br. s., 2 H), 7.22-7.29 (m, 2 H), 7.30-7.36 (m, 4 H), 10.71-11.58 (m, 1 H)

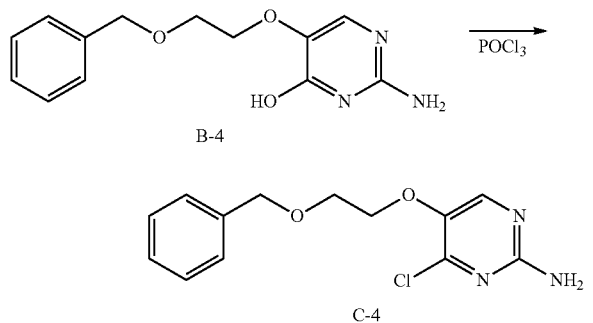

Step 2. Into a 250 mL round bottom flask was placed B-4 (10 g, 38.27 mmol) and POCl₃ (75 mL). The mixture was heated to reflux and stirred for 5 hours. The reaction mixture was allowed to reach room temperature and stirred for 15 hours. The solvent was removed under reduced pressure. Crude C-4 was used as such in the next step.

LC-MS: Anal. Calcd. For $C_{12}H_{12}ClN_3O_2$: 265.06; found 266 [M+H]⁺

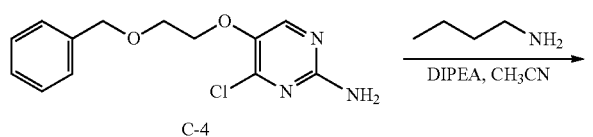

Step 3. Into a 50 mL tubes was placed C-4 (10 g, 35.75 mmol), n-butylamine (10.6 mL, 107.25 mmol) and DIPEA (30.8 mL, 178.75 mmol) in acetonitrile (40 mL). The mixture was heated to 120° C. under microwave irradiation for 3 hours. The combined reaction mixtures were concentrated under reduced pressure and the residual oil was dissolved in dichloromethane and washed with 1N HCl and water. The organic layer was dried (magnesium sulfate), the solids were removed by filtration and the solvent of the filtrate were removed under reduced pressure to obtain an red-brown foam, 83.

Preparation of 84

Step 1. Into a 500 mL round bottom flask was placed 83 (13.5 g, 25.6 mmol), Boc-anhydride (27.94 g, 128 mmol) and acetonitrile (150 mL). The yellow solution was stirred at reflux for 16 hours. The solvent was removed under reduced pressure. The residual fraction was dissolved in dichloromethane and washed with a saturated aqueous NaHCO₃ solution and water. The organic layer was dried (magnesium sulfate), the solids were removed via filtration, and the solvents of the filtrate were removed under reduced pressure to obtain an oil, D-20.

LC-MS: Anal. Calcd. For $C_{22}H_{32}N_4O_4$: 416.24; found 417 [M+H]⁺

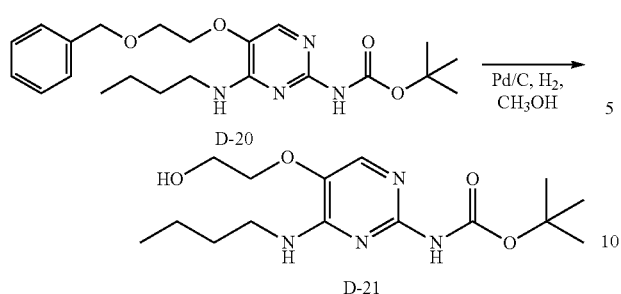

Step 2. Into a 1L erlenmeyer was suspended 10% Pd/C (4 g) in methanol (350 mL) under N₂ gas flow, then D-20 (14.3 g, 34.33 mmol) was added. The mixture was stirred at 50° C. under a hydrogen atmosphere until 1 equivalent of hydrogen was absorbed. The catalyst was removed by filtration over packed decalite. The solvent of the filtrate was removed under reduced pressure to obtain an oil, D-21. The residue was used as such in the next step.

LC-MS: Anal. Calcd. For $C_{15}H_{26}N_4O_4$: 326.20; found 327 [M+H]⁺

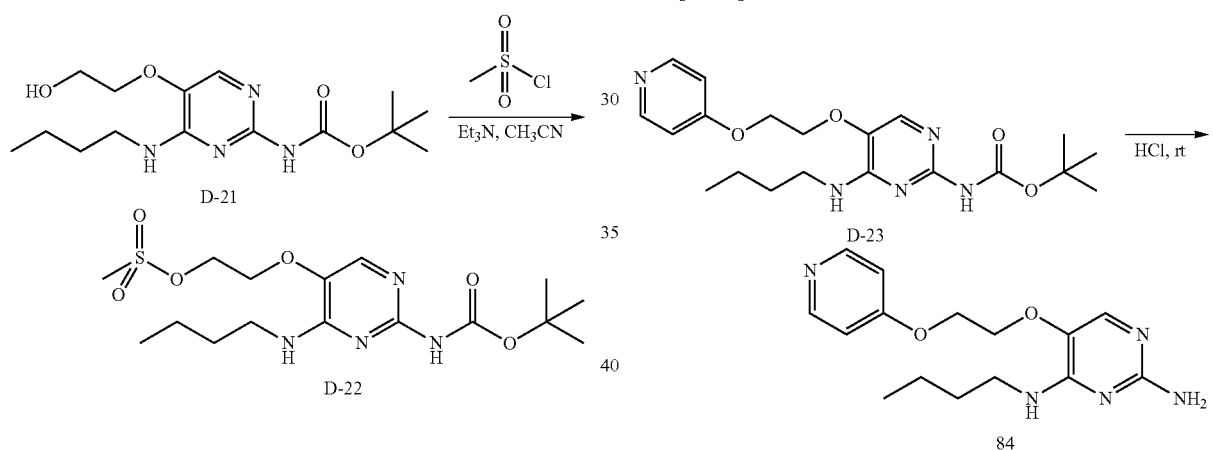

Step 3. Into a 1L round bottom flask a solution of D-21 (8.7 g, 26.66 mmol) and triethylamine (7.41 mL, 53.31 mmol) in acetonitrile (300 mL) was stirred at ambient temperature and methanesulfonyl chloride (3.1 mL, 40 mmol) was added. After addition, the reaction mixture was stirred for 1.5 hours at room temperature. The solvent was removed under reduced pressure. The crude was dissolved in ethyl acetate and washed with saturated aqueous NaHCO₃. The organic layers were combined, dried (magnesium sulfate), the solids were removed by filtration and the solvent of the filtrate were evaporated to dryness to obtain D-22 as an oil.

LC-MS: Anal. Calcd. For $C_{16}H_{28}N_4O_6S$: 404.17; found 405 [M+H]⁺

Step 4. Into a 30 mL glass tube was placed a mixture of 4-hydroxypiridine (94 mg, 0.99 mmol) and Cs₂CO₃ (0.8 g, 2.47 mmol) in acetonitrile (10 mL). The vial was sealed and shaken at ambient temperature for 1 hour. D-22 (400 mg, 0.99 mmol) as a solution in acetonitrile (10 mL) was added to the reaction mixture and shaken for an additional 18 hours at room temperature. Cesium carbonate (320 mg, 1 mmol) was added and the mixture was shaken for 1 day at room temperature. The solvent was removed under reduced pressure and the crude was treated with a mixture of dichloromethane/methanol, 95/5 and shaken for 1 h, then filtered over 2 g of packed silica. The filtrate was concentrated under reduced pressure and D-23 was used as such in the next step.

LC-MS: Anal. Calcd. For $C_{20}H_{29}N_5O_4$: 403.22; found 404 [M+H]⁺

Step 5. D-23 was deprotected to afford 84 using the method applied to deprotect 78.

Preparation of 85

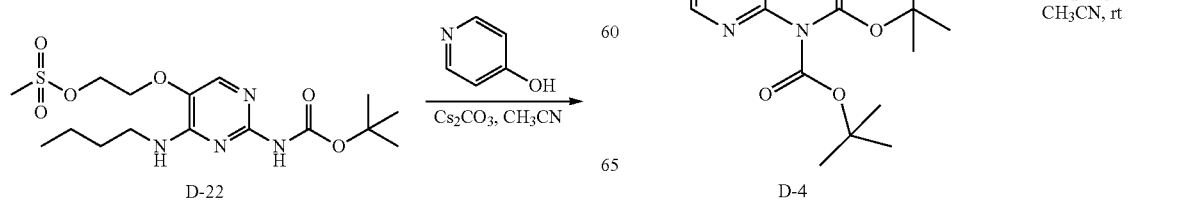

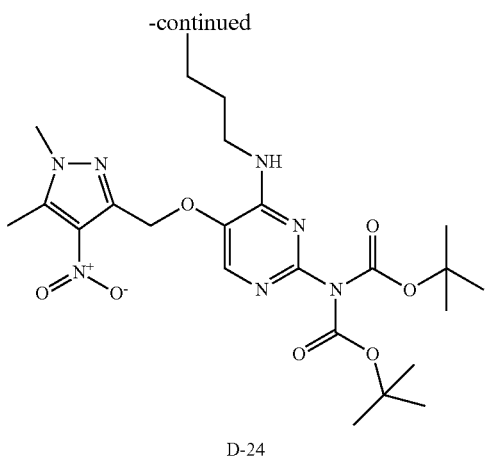

D-24

Step 1. Into a 250 mL round bottem flask equipped with a magnetic stir bar was placed D-4 (0.35 g, 5.23 mmol) and cesium carbonate (0.89 g, 2.75 mmol) in acetonitrile (20 mL). The mixture was stirred at ambient temperature for 30 minutes. A solution of the alkyl halide (0.19 g, 1 mmol) in acetonitrile (5 mL) was added and the reaction mixture was stirred for 1 day at room temperature. The reaction was completed and the salts were removed by filtration. The filtrate was concentrated under reduced pressure and the crude was purified by silica column chromatography using a heptane to ethyl acetate gradient to afford intermediate D-24.

LC-MS: Anal. Calcd. For $C_{24}H_{37}N_7O_7$: 535.28; found 536 $[M+H]^+$

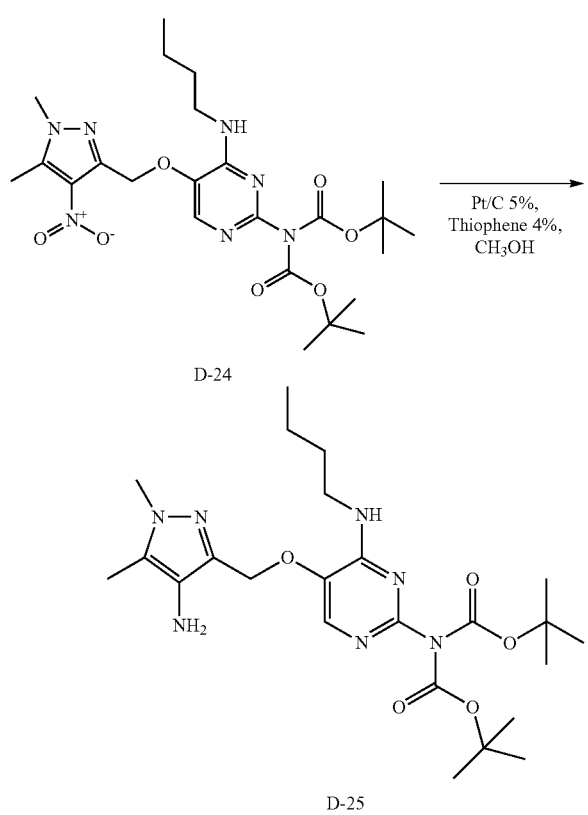

D-24

D-25

Step 2. Into a 100 mL erlenmeyer flask was suspended Pt/C, 5% (100 mg) in thiophene (0.25 mL) and methanol (20 mL) under a blanket of nitrogen gas, then D-24 (130 mg, 0.24 mmol) was added. The reaction mixture was stirred at 50° C. under a hydrogen atmosphere. The catalyst was removed by filtration over packed decalite. The solvents of the filtrate were removed under reduce pressure to obtain D-25 as an oil, that was used as such in the next step.

LC-MS: Anal. Calcd. For $C_{24}H_{39}N_7O_5$: 505.30; found 506 $[M+H]^+$

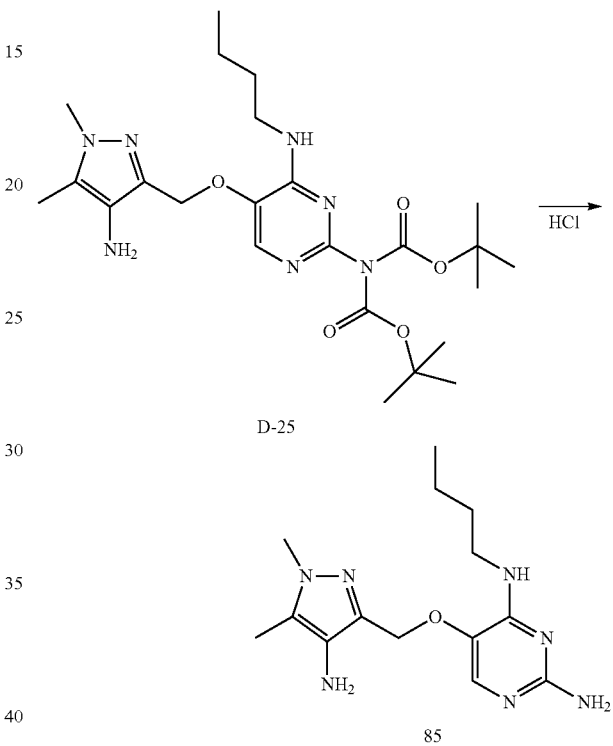

D-25

85

Step 3. Intermediate D-25 is deprotected to afford 85 according to the method used to prepare 78.

Preparation of 86

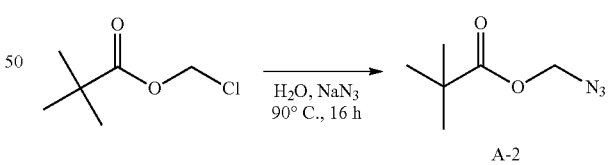

A-2

Step 1. Into a 100 mL round bottom flask was placed sodium azide (6.85 g, 103.76 mmol) in water (12.5 mL) then chloromethyl pivalate (10.6 g, 70.38 mmol) and stirred vigorously at 90° C. for 16 hours. The reaction mixture was allowed to cool to room temperature and dichloromethane (20 mL) was added. The organic layer was separated, dried over anhydrous sodium sulfate, the solids were removed by filtration and the solvent of the filtrate was removed under reduced pressure to obtain A-2 as an oil.

LC-MS: Anal. Calcd. For $C_6H_{11}N_3O_2$: 157.09; found 158 $[M+H]^+$

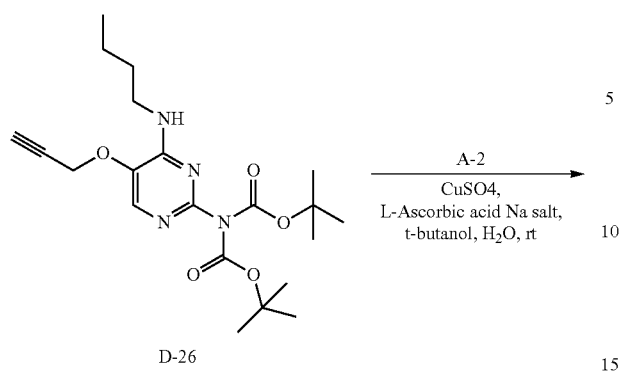

D-26

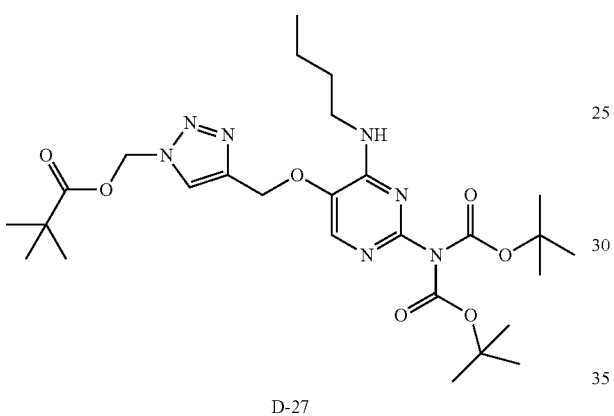

D-27

Step 2. Into a 25 mL tube was placed of D-26 (100 mg, 0.238 mmol), A-2 (37.9 mg, 0.238 mmol), t-butanol (2.5 mL) and water (2.5 mL). The tube was sealed and the mixture was stirred at ambient temperature. Copper(II) sulfate pentahydrate (3 mg, 0.012 mmol) and L-ascorbic acid sodium salt (15.5 mg, 0.079 mmol) were added. The reaction mixture was stirred for 18 hours at room temperature, then water (2.5 mL) was added. The precipitate was isolated by filtration, washed with water and dried in vacuo at 60° C. to obtain a white powder, D-27.

LC-MS: Anal. Calcd. For $C_{27}H_{43}N_7O_7$: 577.32; found 578 [M+H]$^+$

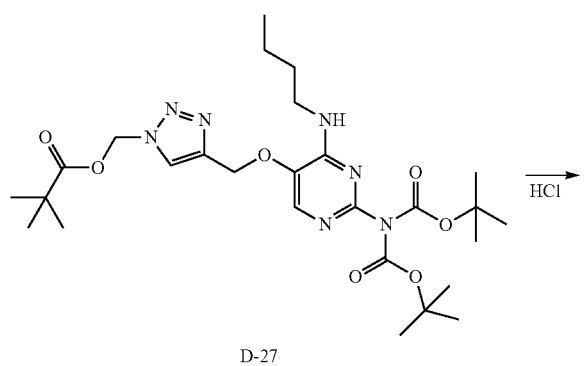

D-27

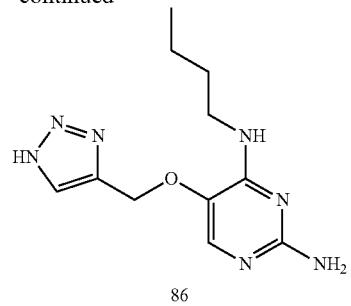

86

Step 3. In a 100 mL round bottom flask a mixture of D-27 (0.1 g, 0.17 mmol) in HCl (5 mL 6M in isopropanol) and dichloromethane (5 mL) was stirred at ambient temperature for 16 hours. The reaction was heated to 65° C. and stirred for an additional 16 hours. The solvent was removed under reduced pressure.

The crude product was purified by reverse phase liquid chromatography (RP Vydac Denali C18-10 µm, 250 g, 5 cm). Mobile phase (0.25% NH$_4$HCO$_3$ solution in water, methanol), the desired fractions were collected, evaporated, dissolved in methanol and treated with 2M HCl in ether. The solid was isolated by filtration to afford 86 as the HCl salt.

Preparation of 87

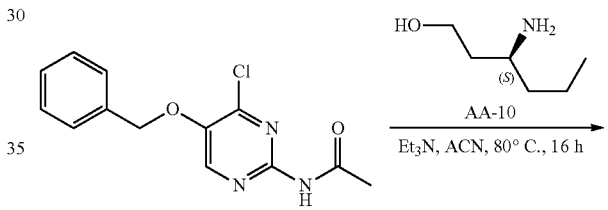

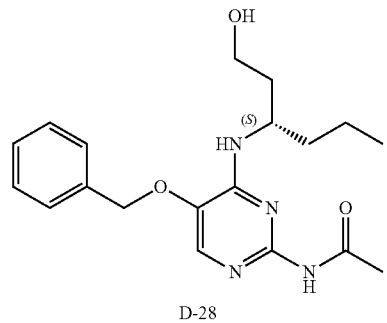

D-28

Step 1. Into a 100 mL round bottom flask was placed a solution of C-2 (500 mg, 1.8 mmol), AA-10 (692 mg, 4.5 mmol) and triethylamine (0.75 mL, 5.4 mmol) in acetonitrile (30 mL). The mixture was heated to 80° C. for 16 hours with stirring. The reaction was allowed to cool and the solvent was removed under reduced pressure. The crude was dissolved in dichloromethane and washed with brine. The organic layer was dried (magnesium sulfate), the solids were removed by filtration and the solvent of the filtrate was removed to obtain an oil, D-28.

LC-MS: Anal. Calcd. For $C_{19}H_{26}N_4O_3$: 358.20; found 359 [M+H]$^+$ $^1$H NMR (360 MHz, DMSO-d$_6$) δ ppm 0.85 (t, J=7.32 Hz, 3 H) 1.19-1.37 (m, 2 H) 1.38-1.53 (m, 1 H) 1.53-1.75 (m, 3 H) 2.13 (s, 3 H) 3.38-3.48 (m, 2 H) 4.19-4.31 (m, 1 H) 5.16

(s, 2 H) 6.69 (d, J=9.15 Hz, 1 H) 7.29-7.41 (m, 3 H) 7.45-7.53 (m, 2 H) 7.66 (s, 1 H) 9.77 (s, 1 H)

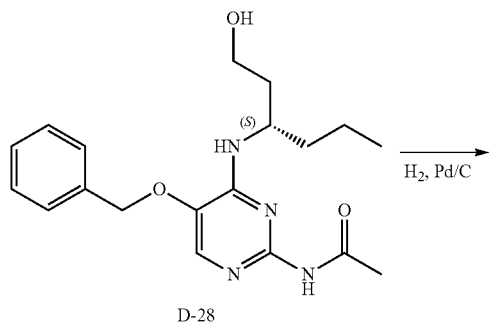

Step2. D-29 was prepared according to the method used to prepare D-21. THF was added to increase the solubility of D-29.

LC-MS: Anal. Calcd. For $C_{12}H_{20}N_4O_3$: 268.15; found 269 $[M+H]^+$

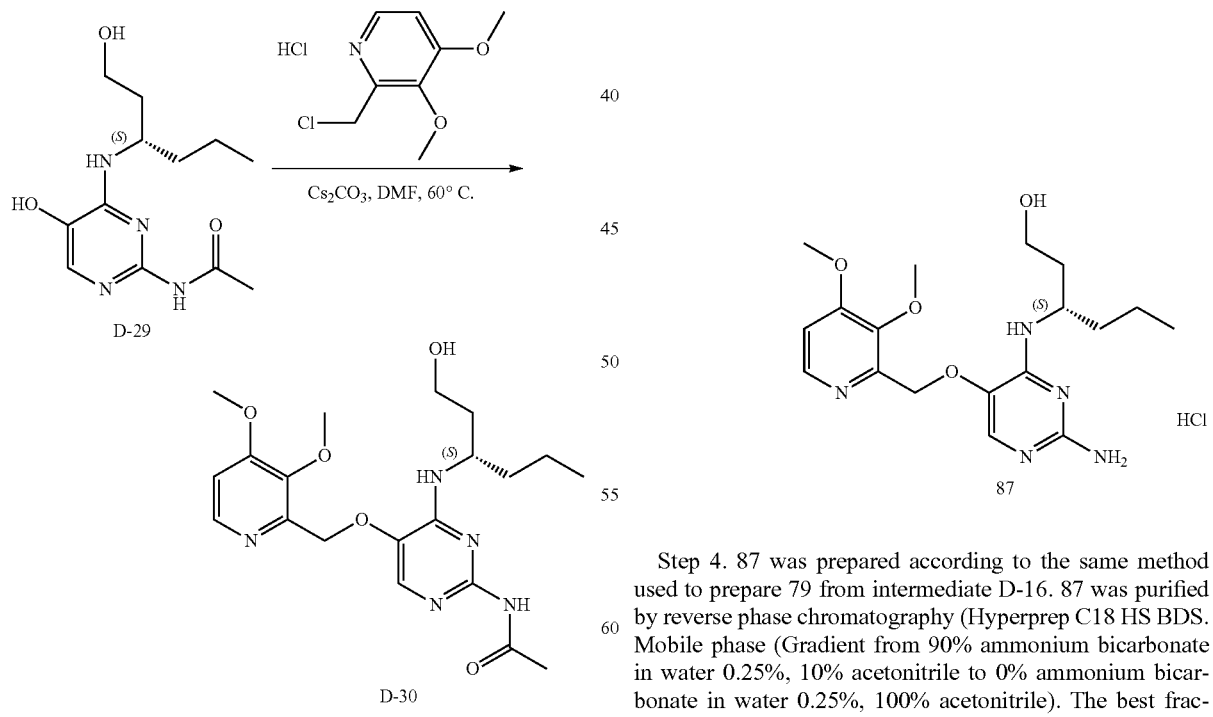

Step 3. In a 250 mL round bottom flask a mixture of D-29 (5 g, 18.6 mmol) and cesium carbonate (18.2 g, 55.9 mmol) in DMF (80 mL) was stirred at ambient temperature for 30 minutes. The mixture was heated to 60° C. and a solution of 2-chloromethyl-3,4-dimethoxy pyridine hydrochloride (3.97 g, 17.7 mmol) in DMF (60 mL) was added dropwise. The reaction mixture was stirred for 2 hours at 60° C. The reaction was allowed to cool and the salts were removed by filtration. The reaction mixture was concentrated under reduced pressure and D-30 was used as such in the next step.

LC-MS: Anal. Calcd. For $C_{20}H_{29}N_5O_5$: 419.22; found 420 $[M+H]^+$ $^1$H NMR (400 MHz, DMSO-$d_6$) δ ppm 0.83 (t, J=7.4 Hz, 3 H), 1.18-1.32 (m, 2 H), 1.41-1.71 (m, 4 H), 2.14 (s, 3 H), 3.34-3.40 (m, 2 H), 3.78 (s, 3 H), 3.91 (s, 3 H), 4.17-4.29 (m, 1 H), 4.41 (t, J=5.3 Hz, 1 H), 5.09 (s, 2 H), 6.79 (d, J=8.8 Hz, 1 H), 7.15 (d, J=5.7 Hz, 1 H), 7.75 (s, 1 H), 8.24 (d, J=5.5 Hz, 1 H), 9.75 (s, 1 H)

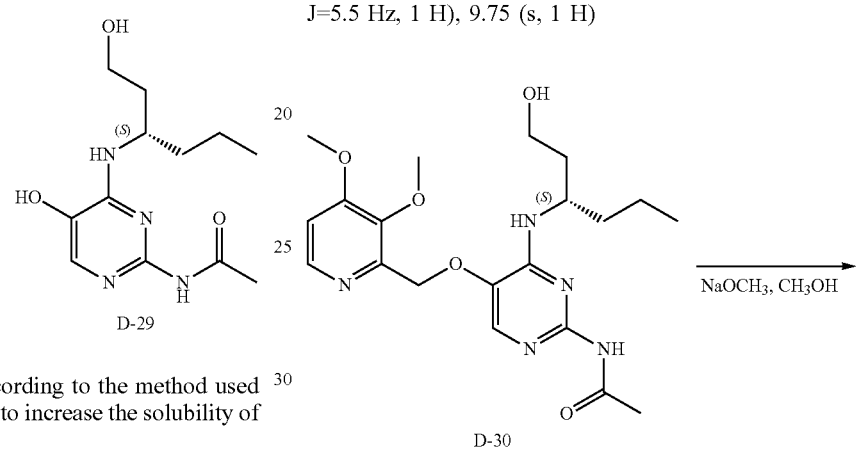

Step 4. 87 was prepared according to the same method used to prepare 79 from intermediate D-16. 87 was purified by reverse phase chromatography (Hyperprep C18 HS BDS. Mobile phase (Gradient from 90% ammonium bicarbonate in water 0.25%, 10% acetonitrile to 0% ammonium bicarbonate in water 0.25%, 100% acetonitrile). The best fractions were pooled, the solvents were removed under reduced pressure, reconstituted in methanol and treated with 2M HCl in ether and then concentrated under reduced pressure to obtain a white solid, the HCl salt of 87.

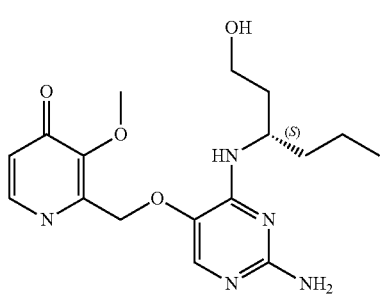

Isolation of the HCl salt of 87 via reverse phase liquid chromatography led to the concomitant isolation of 88 in low yield. The best fractions were pooled, and the solvents were removed under reduced pressure to afford a white solid, 88.

Preparation of 89

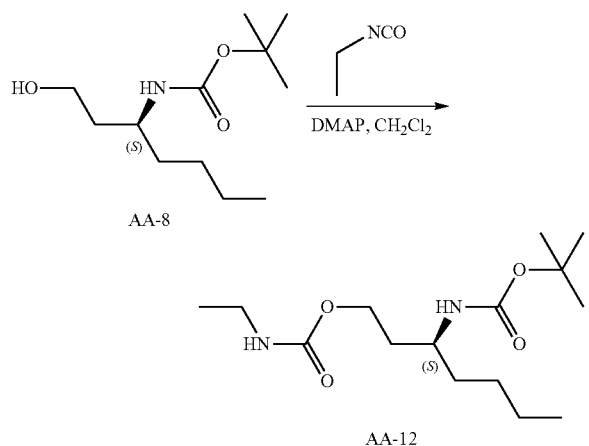

Step 1. Into a 100 mL round bottom flask was placed AA-8 (2 g, 8.65 mmol), dichloromethane (6 mL), ethyl isocyanate (1.6 mL, 10.38 mmol), and DMAP (21 mg, 0.173 mmol). The reaction mixture was allowed to stir for 16 hours at room temperature. The solvent was removed under reduced pressure and AA-12 was used in the subsequent step without further purification.

LC-MS: Anal. Calcd. For $C_{15}H_{30}N_2O_4$: 302.22; found 303 $[M+H]^+$

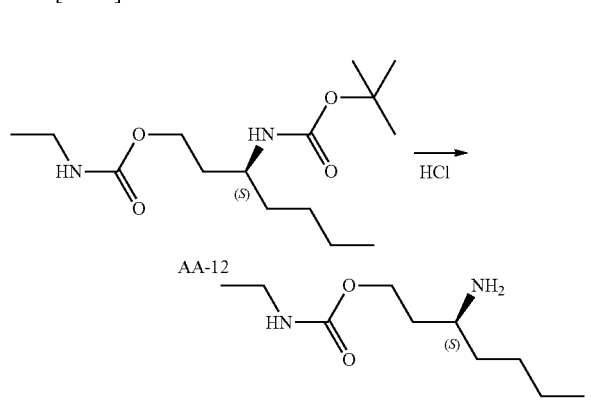

Step 2. Into a 100 mL round bottom flask was placed crude AA-12 (2.61 g, 8.65 mmol), and dichloromethane (30 mL). To this solution was added HCl (20 mL, 4M in dioxane). The reation was allowed to stir 3 hours at room temperature.

LC-MS: Anal. Calcd. For $C_{10}H_{22}N_2O_2$: 202.17; found 203 $[M+H]^+$

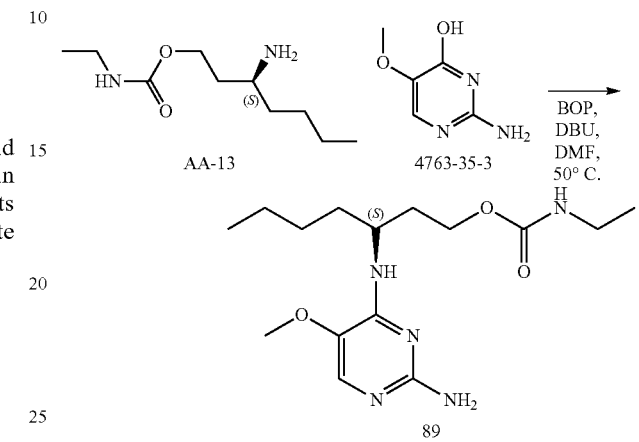

Step 3. Into a 100 mL round bottom flask equipped with a magnetic stir bar was placed 2-Amino-4-hydroxy-5-methoxy-pyrimidine (500 mg, 3.54 mmol), anhydrous DMF (30 mL), AA-13 (1.27 g, 5.31 mmol), DBU (2.12 mL, 14.17 mmol), and BOP (1.96 g, 4.43 mmol). The reaction mixture was allowed to stir at room temperature for 30 minutes then at 50° C. for 16 hours. The solvent was removed under reduced pressure and the residue was partitioned between brine and ethyl acetate. The organic layers were combined, dried (magnesium sulfate), the solids were removed via filtration, and the solvents of the filtrate were removed under reduced pressure. The crude was purified via reverse phase liquid chromatography (RP Vydac Denali C18-10 μm, 250 g, 5 cm. Mobile phase 0.25% $NH_4HCO_3$ solution in water, methanol), the best fractions were pooled, the solvents were removed under reduced pressure to afford 89.

Preparation of 264

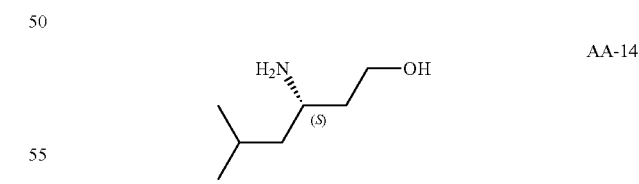

Step 1. AA-14 was prepared according to the procedure to prepare AA-10, employing the appropriate starting aldehyde.

LC-MS: Anal. Calcd. For $C_7H_{17}NO$: 131.13; found 132 $[M+H]^+$ $^1$H NMR (400 MHz, CHLOROFORM-d) δ ppm 0.81-0.89 (m, 6 H), 1.15-1.25 (m, 2 H), 1.33-1.47 (m, 1 H), 1.54-1.69 (m, 2 H), 2.71 (br. s., 3 H), 2.88-2.98 (m, 1 H), 3.69-3.80 (m, 2 H)

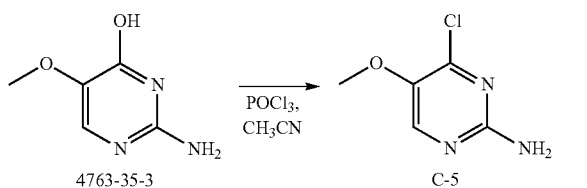

Step 2. C-5 was prepared according to the method used to prepare C-2 from the available starting material. The crude was used without further purification. LC-MS: Anal. Calcd. For $C_5H_6ClN_3O$: 159.02; found 160 $[M+H]^+$

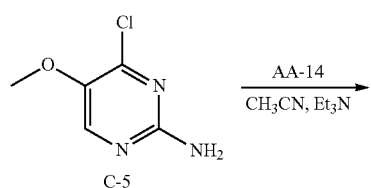

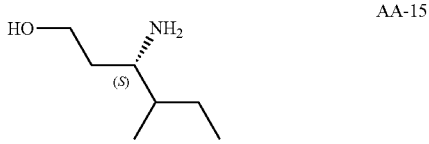

Step 3. C-5 was combined with AA-14 according to the method used to prepare compound 1, except that acetonitrile was used as a solvent, to afford 264.

Preparation of 278

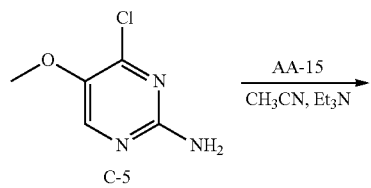

Step 1. AA-15 was prepared according to the procedure to prepare AA-10, employing the appropriate starting aldehyde.

LC-MS: Anal. Calcd. For $C_7H_{17}NO$: 131.13; found 132 $[M+H]^+$ $^1$H NMR (400 MHz, DMSO-d$_6$) δ ppm 0.81-0.89 (m, 6 H), 1.05-1.20 (m, 1 H), 1.27-1.40 (m, 1 H), 1.43-1.77 (m, 3 H), 3.05-3.19 (m, 1 H), 3.44-3.57 (m, 2 H), 4.82 (br. s., 1 H), 7.94 (d, J=18.6 Hz, 2 H)

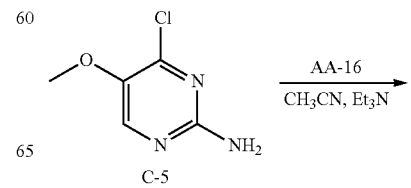

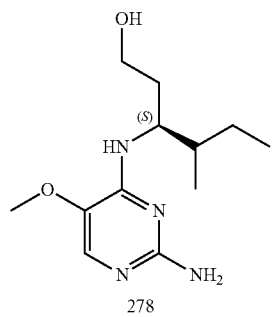

Step 2. C-5 was combined with AA-15 according to the method used to prepare compound 1, except that acetonitrile was used as a solvent, to afford 278.

Preparation of 295

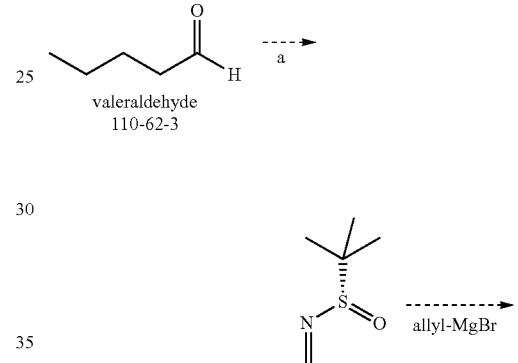

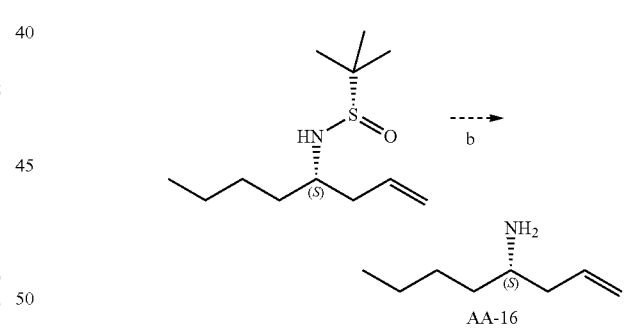

Step 1. AA-16 was prepared according to the procedures outlined in Chem. Rev., 2010, Vol. 110, No. 6, 3600-3740.

LC-MS: Anal. Calcd. For $C_8H_{17}N$: 127.14; found 128 $[M+H]^+$

-continued

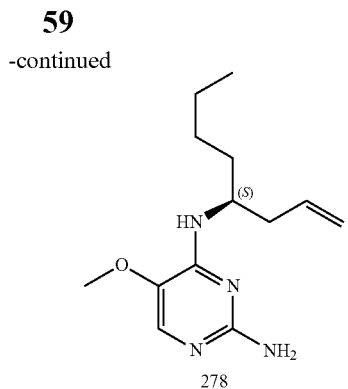
278

Step 2. C-5 was combined with AA-16 according to the method used to prepare compound 1, except that acetonitrile was used as a solvent, to afford 295.

Preparation of 304

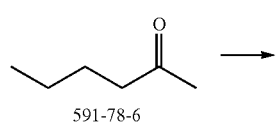
591-78-6

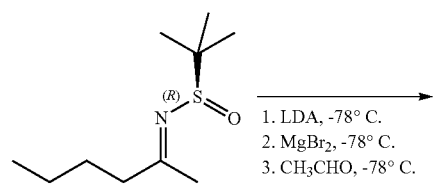
1. LDA, -78° C.
2. MgBr$_2$, -78° C.
3. CH$_3$CHO, -78° C.

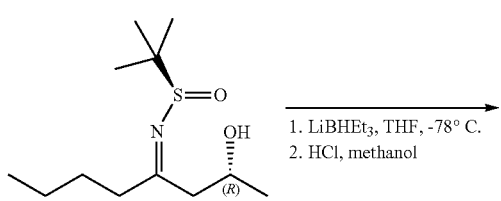
1. LiBHEt$_3$, THF, -78° C.
2. HCl, methanol

-continued

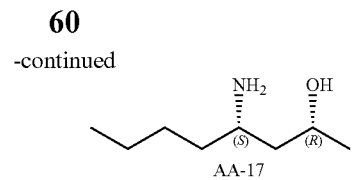
AA-17

Step 1. AA-17 was prepared according to the procedures outlined in Chem. Rev., 2010, Vol. 110, No. 6, 3600-3740.

LC-MS: Anal. Calcd. For $C_8H_{19}NO$: 145.15; found 146 $[M+H]^+$

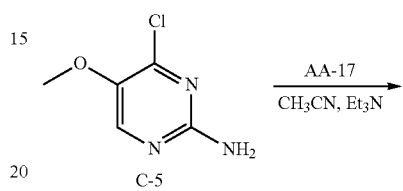
C-5

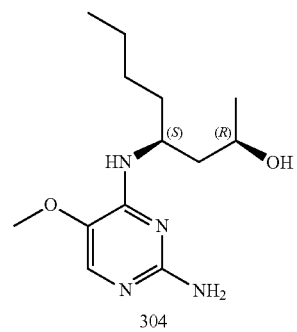
304

Step 2. C-5 was combined with AA-17 according to the method used to prepare compound 1, except that acetonitrile was used as a solvent, to afford 304.

TABLE I

| | STRUCTURE | Exact Mass | Mass Found [M + H] | LCMS Ret Time, Method | 1H NMR |
|---|---|---|---|---|---|
| 1 | 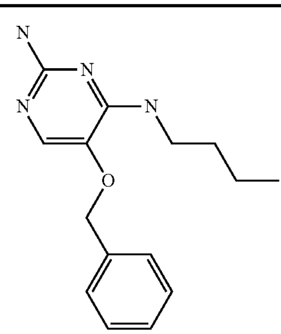 | 272.16 | 273 | 4.51, B | $^1$H NMR (400 MHz, METHANOL-d$_4$) δ ppm 0.96 (t, J = 7.3 Hz, 3 H), 1.32-1.43 (m, 2 H), 1.52-1.61 (m, 2 H), 3.38 (t, J = 7.2 Hz, 2 H), 5.01 (s, 2 H), 7.28 (s, 1 H), 7.31-7.46 (m, 5 H) |

TABLE I-continued

| | STRUCTURE | Exact Mass | Mass Found [M + H] | LCMS Ret Time, Method | 1H NMR |
|---|---|---|---|---|---|
| 2 | 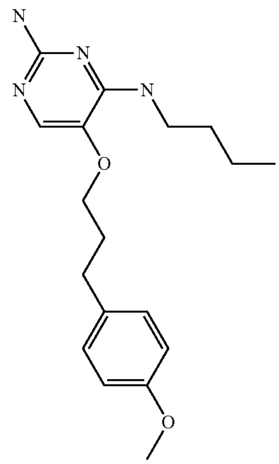 [SMILES: CCCCNc1nc(N)ncc1OCCCc1ccc(OC)cc1] | 330.21 | 331 | 2.46, E | $^1$H NMR (300 MHz, CHLOROFORM-d) δ ppm 0.89 (t, J = 7.3 Hz, 3 H), 1.24-1.40 (m, 2 H), 1.43-1.59 (m, 2 H), 1.88-2.07 (m, 2 H), 2.65 (t, J = 7.4 Hz, 2 H), 3.24-3.37 (m, 2 H), 3.72 (s, 3 H), 3.82 (t, J = 6.3 Hz, 2 H), 4.54 (br. s., 2 H), 4.99-5.14 (m, 1 H), 6.72-6.82 (m, 2 H), 7.04 (d, J = 8.5 Hz, 2 H), 7.19 (s, 1 H) |
| 3 | 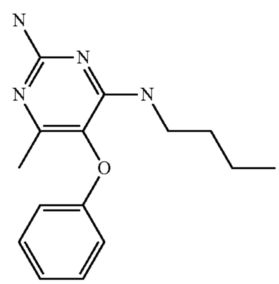 [SMILES: CCCCNc1nc(N)nc(C)c1Oc1ccccc1] | 272.16 | 273 | 1.54, E | $^1$H NMR (300 MHz, CHLOROFORM-d) δ ppm 0.80 (t, J = 7.3 Hz, 3 H), 1.20 (dq, J = 15.0, 7.3 Hz, 2 H), 1.33-1.47 (m, 2 H), 1.98 (s, 3 H), 3.20-3.34 (m, 2 H), 4.74 (br s, 2 H), 4.79 (br. s., 1 H), 6.78-6.84 (m, 2 H), 6.91-7.01 (m, 1 H), 7.18-7.28 (m, 2 H) |
| 4 | 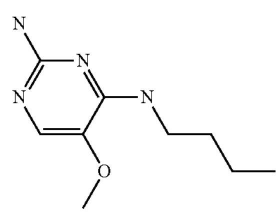 | 196.13 | 197 | 0.49, A | $^1$H NMR (400 MHz, CHLOROFORM-d) δ ppm 0.97 (t, J = 7.3 Hz, 3 H), 1.35-1.48 (m, 2 H), 1.56-1.68 (m, 2 H), 3.44-3.52 (m, 2 H), 3.80 (s, 3 H), 5.86 (s, 1 H), 5.97 (s, 2 H), 7.07-7.14 (m, 1 H) |
| 5 | 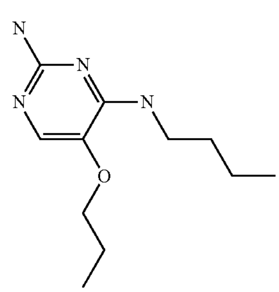 [SMILES: CCCCNc1nc(N)ncc1OCCC] | 224.16 | 225 | 0.83, A | $^1$H NMR (400 MHz, CHLOROFORM-d) δ ppm 0.92 (t, J = 7.3 Hz, 3 H), 1.03 (t, J = 7.4 Hz, 3 H), 1.30-1.40 (m, 2 H), 1.50-1.62 (m, 2 H), 1.83 (m, J = 7.5 Hz, 2 H), 2.27 (s, 6 H), 3.34-3.48 (m, 2 H), 3.99 (t, J = 6.4 Hz, 2 H), 5.39-5.52 (m, 1 H), 7.63 (s, 1 H) |

TABLE I-continued

| | STRUCTURE | Exact Mass | Mass Found [M + H] | LCMS Ret Time, Method | 1H NMR |
|---|---|---|---|---|---|
| 6 | 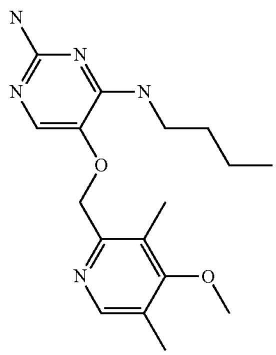 [SMILES: CCCCNc1nc(N)ncc1OCc1ncc(C)c(OC)c1C] | 331.20 | 332 | 0.88, D | $^1$H NMR (360 MHz, DMSO-$d_6$) δ ppm 0.88 (t, J = 7.3 Hz, 3 H), 1.21-1.34 (m, 2 H), 1.48 (t, J = 7.3 Hz, 2 H), 2.22 (s, 3 H), 2.24 (s, 3 H), 3.26 (q, J = 7.0 Hz, 2 H), 3.74 (s, 3 H), 4.96 (s, 2 H), 5.54 (s, 2 H), 6.62 (s, 1 H), 7.39 (s, 1 H), 8.21 (s, 1 H) |
| 7 | 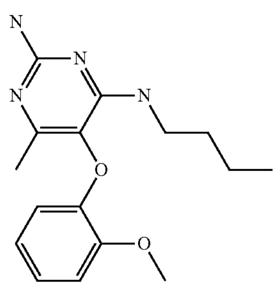 [SMILES: CCCCNc1nc(N)nc(C)c1Oc1ccccc1OC] | 302.17 | 303 | 1.55, E | $^1$H NMR (300 MHz, CHLOROFORM-d) δ ppm 0.80 (t, J = 7.2 Hz, 3 H), 1.12-1.29 (m, 2 H), 1.34-1.47 (m, 2 H), 2.03 (s, 3 H), 3.21-3.31 (m, 2 H), 3.89 (s, 3 H), 4.67 (br. s., 2 H), 4.93-5.04 (m, 1 H), 6.55-6.62 (m, 1 H), 6.76 (td, J = 7.4, 2.3 Hz, 1 H), 6.90-6.96 (m, 2 H) |
| 8 | 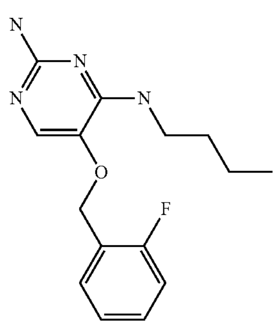 [SMILES: CCCCNc1nc(N)ncc1OCc1ccccc1F] | 290.15 | 291 | 1.64, E | $^1$H NMR (300 MHz, CHLOROFORM-d) δ ppm 0.82-0.94 (m, 3 H), 1.22-1.39 (m, 2 H), 1.41-1.56 (m, 2 H), 3.24-3.38 (m, 2 H), 4.51 (br. s., 2 H), 4.92 (s, 2 H), 5.16 (br. s., 1 H), 6.97-7.15 (m, 2 H), 7.23-7.37 (m, 2 H), 7.40 (s, 1 H) |
| 9 | 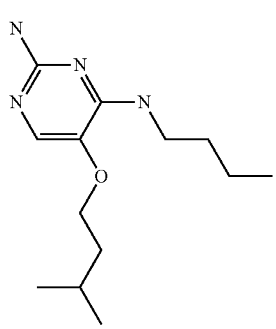 [SMILES: CCCCNc1nc(N)ncc1OCCC(C)C] | 252.20 | 253 | 2.33, E | $^1$H NMR (300 MHz, CHLOROFORM-d) δ ppm 0.84-0.93 (m, 9 H), 1.24-1.39 (m, 2 H), 1.45-1.55 (m, 2 H), 1.53-1.62 (m, 2 H), 1.70 (dd, J = 13.5, 6.7 Hz, 1 H), 3.28-3.38 (m, 2 H), 3.84 (t, J = 6.6 Hz, 2 H), 4.47 (br. s., 2 H), 5.04-5.16 (m, 1 H), 7.20 (s, 1 H) |

TABLE I-continued

| | STRUCTURE | Exact Mass | Mass Found [M + H] | LCMS Ret Time, Method | 1H NMR |
|---|---|---|---|---|---|
| 10 | 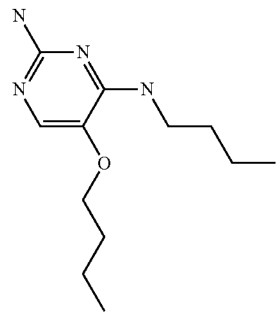 [SMILES: CCCCNc1nc(N)ncc1OCCCC] | 238.18 | 239 | 2.15, E | ¹H NMR (300 MHz, CHLOROFORM-d) δ ppm 0.85-0.90 (m, 3 H), 0.89-0.95 (m, 3 H), 1.25-1.44 (m, 4 H), 1.45-1.58 (m, 2 H), 1.61-1.73 (m, 2 H), 3.27-3.39 (m, 2 H), 3.82 (t, J = 6.5 Hz, 2 H), 4.57 (br. s., 2 H), 5.05-5.21 (m, 1 H), 7.25 (s, 1 H) |
| 11 | 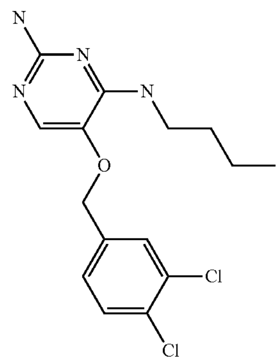 [SMILES: CCCCNc1nc(N)ncc1OCc1ccc(Cl)c(Cl)c1] | 340.09 | 341 | 1.98, E | ¹H NMR (300 MHz, CHLOROFORM-d) δ ppm 0.85 (t, J = 7.3 Hz, 3 H), 1.20-1.36 (m, 2 H), 1.40-1.54 (m, 2 H), 3.24-3.36 (m, 2 H), 4.55 (br. s., 2 H), 4.80 (s, 2 H), 5.00-5.11 (m, 1 H), 7.11 (dd, J = 8.2, 1.9 Hz, 1 H), 7.35 (s, 1 H), 7.38 (d, J = 2.5 Hz, 2 H) |
| 12 | 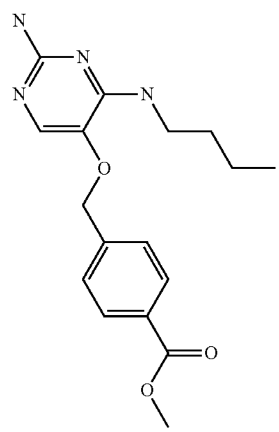 [SMILES: CCCCNc1nc(N)ncc1OCc1ccc(C(=O)OC)cc1] | 330.17 | 331 | 1.66, E | ¹H NMR (300 MHz, CHLOROFORM-d) δ ppm 0.85 (t, J = 7.3 Hz, 3 H), 1.28 (dd, J = 15.2, 7.2 Hz, 2 H), 1.39-1.54 (m, 2 H), 3.25-3.35 (m, 2 H), 3.84 (s, 3 H), 4.61 (br. s., 2 H), 4.91 (s, 2 H), 5.07-5.17 (m, 1 H), 7.17 (s, 1 H), 7.35 (d, J = 8.1 Hz, 2 H), 7.97 (d, J = 8.2 Hz, 2 H) |
| 13 | 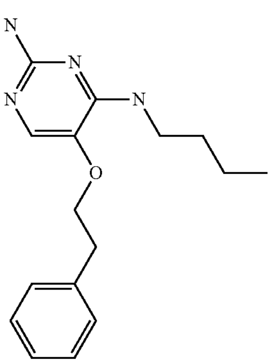 [SMILES: CCCCNc1nc(N)ncc1OCCc1ccccc1] | 286.18 | 287 | 2.29, E | ¹H NMR (300 MHz, CHLOROFORM-d) δ ppm 0.86 (t, J = 1.0 Hz, 3 H), 1.17-1.31 (m, 2 H), 1.33-1.46 (m, 2 H), 2.98 (t, J = 6.5 Hz, 2 H), 3.17-3.27 (m, 2 H), 4.03 (t, J = 6.6 Hz, 2 H), 4.61 (br. s., 2 H), 4.83-4.97 (m, 1 H), 7.15-7.22 (m, 3 H), 7.23-7.31 (m, 3 H) |

TABLE I-continued

| | STRUCTURE | Exact Mass | Mass Found [M + H] | LCMS Ret Time, Method | 1H NMR |
|---|---|---|---|---|---|
| 14 | 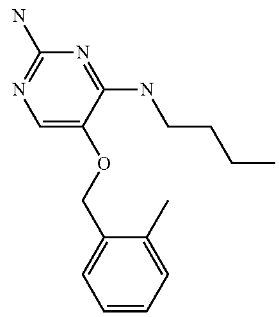 [SMILES: CCCCNc1nc(N)ncc1OCc1ccccc1C] | 286.18 | 287 | 1.75, E | ¹H NMR (300 MHz, CHLOROFORM-d) δ ppm 0.86 (t, J = 7.3 Hz, 3 H), 1.28 (dd, J = 15.3, 7.3 Hz, 2 H), 1.41-1.54 (m, 2 H), 2.29 (s, 3 H), 3.26-3.37 (m, 2 H), 4.79-4.84 (m, 1 H), 4.87 (s, 2 H), 7.11-7.27 (m, 4 H), 7.31 (s, 1 H) |
| 15 | 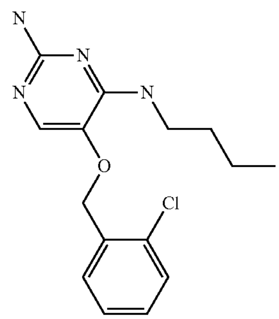 | 306.12 | 307 | 1.79, E | ¹H NMR (300 MHz, CHLOROFORM-d) δ ppm 0.87 (t, J = 7.3 Hz, 3 H), 1.24-1.37 (m, 2 H), 1.42-1.57 (m, 2 H), 3.24-3.38 (m, 2 H), 4.54 (br. s., 2 H), 4.97 (s, 2 H), 5.14-5.24 (m, 1 H), 7.17-7.27 (m, 2 H), 7.31-7.39 (m, 3 H) |
| 16 | 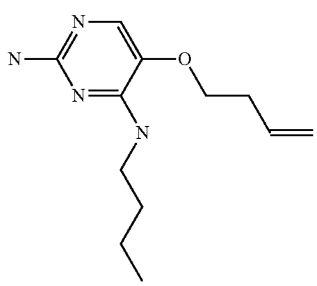 [SMILES: C=CCCOc1cnc(N)nc1NCCCC] | 236.16 | 237 | 1.98, E | ¹H NMR (300 MHz, CHLOROFORM-d) δ ppm 0.88 (t, J = 7.3 Hz, 3 H), 1.25-1.39 (m, 2 H), 1.44-1.57 (m, 2 H), 2.43 (q, J = 6.6 Hz, 2 H), 3.27-3.37 (m, 2 H), 3.87 (t, J = 6.5 Hz, 2 H), 4.51 (br. s., 2 H), 5.02-5.09 (m, 2 H), 5.10-5.18 (m, 1 H), 5.79 (ddt, J = 17.1, 10.3, 6.7, 6.7 Hz, 1 H), 7.20 (s, 1 H) |
| 17 | 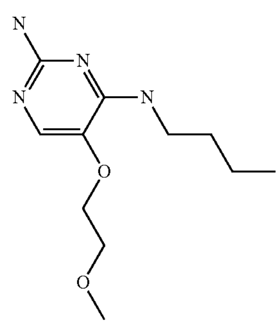 | 240.16 | 241 | 1.52, E | ¹H NMR (300 MHz, CHLOROFORM-d) δ ppm 0.88 (t, J = 7.3 Hz, 3 H), 1.33 (dq, J = 15.0, 7.2 Hz, 2 H), 1.44-1.57 (m, 2 H), 3.32 (m, J = 7.1, 7.1, 5.7 Hz, 2 H), 3.36 (s, 3 H), 3.54-3.62 (m, 2 H), 3.90-3.96 (m, 2 H), 4.57 (br. s., 2 H), 5.55-5.69 (m, 1 H), 7.38 (s, 1 H) |
| 18 | 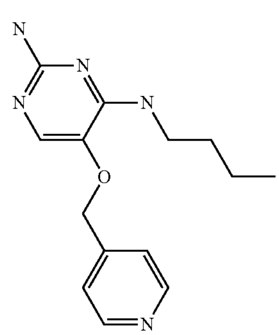 [SMILES: CCCCNc1nc(N)ncc1OCc1ccncc1] | 273.16 | 274 | 0.58, E | ¹H NMR (300 MHz, CHLOROFORM-d) δ ppm 0.89 (t, J = 7.3 Hz, 3 H), 1.32 (dq, J = 15.0, 7.3 Hz, 2 H), 1.45-1.59 (m, 2 H), 3.35 (td, J = 7.0, 6.0 Hz, 2 H), 4.59 (br. s., 2 H), 4.92 (s, 2 H), 5.11-5.19 (m, 1 H), 7.20 (s, 1 H), 7.23 (s, 2 H), 8.54-8.59 (m, 2 H) |

TABLE I-continued

| | STRUCTURE | Exact Mass | Mass Found [M + H] | LCMS Ret Time, Method | 1H NMR |
|---|---|---|---|---|---|
| 19 | 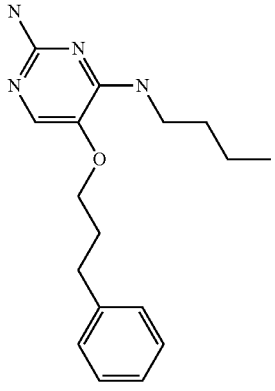 [SMILES: CCCCNc1nc(N)ncc1OCCCc1ccccc1] | 300.20 | 301 | 2.46, E | $^{1}$H NMR (300 MHz, CHLOROFORM-d) δ ppm 0.90 (t, J = 7.1 Hz, 3 H), 1.25-1.39 (m, 2 H), 1.50 (m, J = 6.7 Hz, 2 H), 2.04-2.19 (m, 2 H), 2.66-2.79 (m, 2 H), 3.37 (d, J = 4.5 Hz, 2 H), 3.70-3.94 (m, 2 H), 5.68-5.88 (m, 1 H), 7.05-7.37 (m, 6 H) |
| 20 | 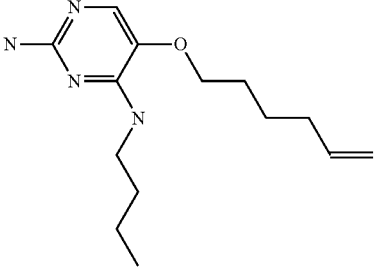 [SMILES: C=CCCCCOc1cnc(N)nc1NCCCC] | 264.20 | 265 | 2.38, E | $^{1}$H NMR (300 MHz, CHLOROFORM-d) δ ppm 0.91 (t, J = 7.3 Hz, 3 H), 1.27-1.42 (m, 2 H), 1.44-1.61 (m, 3 H), 1.65-1.80 (m, 2 H), 2.07 (q, J = 7.2 Hz, 2 H), 3.36 (td, J = 7.0, 5.9 Hz, 2 H), 3.84 (t, J = 6.5 Hz, 2 H), 4.60 (br. s., 2 H), 4.90-4.98 (m, 1 H), 5.02 (q, J = 1.6 Hz, 1 H), 5.09-5.21 (m, 1 H), 5.77 (ddt, J = 17.0, 10.3, 6.6, 6.6 Hz, 1 H), 7.27 (s, 1 H) |
| 21 | 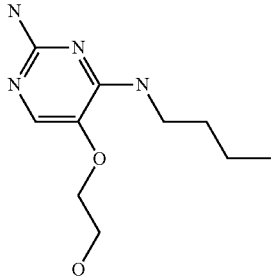 [SMILES: CCCCNc1nc(N)ncc1OCCO] | 226.14 | 227 | 0.82, E | $^{1}$H NMR (300 MHz, CHLOROFORM-d) δ ppm 0.93 (t, J = 7.3 Hz, 3 H), 1.30-1.46 (m, 2 H), 1.49-1.62 (m, 2 H), 3.20 (br. s., 1 H), 3.32-3.43 (m, 2 H), 3.88-3.94 (m, 2 H), 3.95-4.00 (m, 2 H), 4.62 (br. s., 2 H), 5.68 (t, J = 5.2 Hz, 1 H), 7.39 (s, 1 H) |
| 22 | 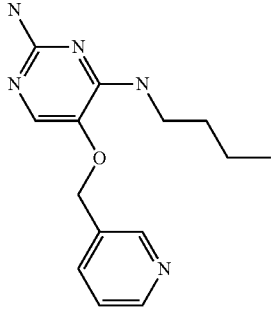 [SMILES: CCCCNc1nc(N)ncc1OCc1cccnc1] | 273.16 | 274 | 0.807, E | $^{1}$H NMR (300 MHz, CHLOROFORM-d) δ ppm 0.94 (t, J = 7.3 Hz, 3 H), 1.29-1.45 (m, 2 H), 1.55 (quin, J = 7.3 Hz, 2 H), 3.39 (q, J = 6.8 Hz, 2 H), 4.57 (br. s., 2 H), 4.97 (s, 2 H), 5.08-5.19 (m, 1 H), 7.34 (dd, J = 7.8, 4.9 Hz, 1 H), 7.44 (s, 1 H), 7.71 (m, J = 7.8 Hz, 1 H), 8.62 (dd, J = 4.7, 1.3 Hz, 1 H), 8.67 (d, J = 1.5 Hz, 1 H) |

TABLE I-continued

| | STRUCTURE | Exact Mass | Mass Found [M + H] | LCMS Ret Time, Method | 1H NMR |
|---|---|---|---|---|---|
| 23 | 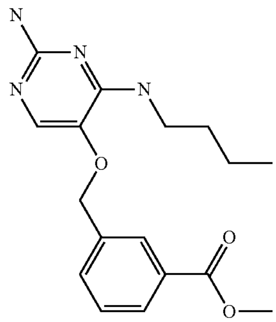 [SMILES: CCCCNc1nc(N)ncc1OCc1cccc(C(=O)OC)c1] | 330.17 | 331 | 1.65, E | ¹H NMR (300 MHz, CHLOROFORM-d) δ ppm 0.94 (t, J = 7.3 Hz, 3 H), 1.30-1.47 (m, 2 H), 1.56 (quin, J = 7.3 Hz, 2 H), 3.35-3.45 (m, 2 H), 3.94 (s, 3 H), 4.62 (br. s., 2 H), 5.00 (s, 2 H), 5.15-5.25 (m, 1 H), 7.40 (s, 1 H), 7.49 (d, J = 7.6 Hz, 1 H), 7.55-7.63 (m, 1 H), 7.99-8.13 (m, 2 H) |
| 24 | 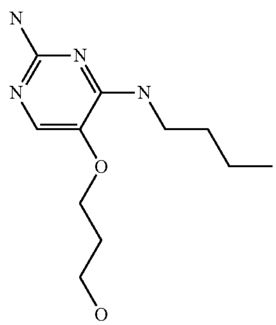 [SMILES: CCCCNc1nc(N)ncc1OCCCO] | 240.16 | 241 | 0.97, E | ¹H NMR (300 MHz, CHLOROFORM-d) δ ppm 0.95 (t, J = 7.2 Hz, 3 H), 1.31-1.46 (m, 2 H), 1.51-1.65 (m, 2 H), 2.01 (quin, J = 6.0 Hz, 2 H), 2.61 (br. s., 1 H), 3.30-3.45 (m, 2 H), 3.84 (t, J = 5.9 Hz, 2 H), 4.01 (t, J = 6.0 Hz, 2 H), 4.55 (br. s., 2 H), 5.31-5.42 (m, 1 H), 7.35 (s, 1 H) |
| 25 | 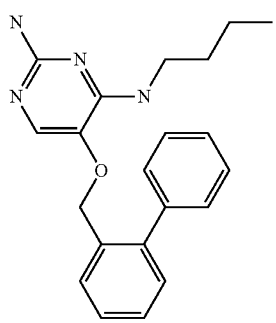 [SMILES: CCCCNc1nc(N)ncc1OCc1ccccc1-c1ccccc1] | 348.20 | 349 | 2.02, E | ¹H NMR (300 MHz, CHLOROFORM-d) δ ppm 0.95 (t, J = 7.3 Hz, 3 H), 1.28-1.45 (m, 2 H), 1.47-1.60 (m, 2 H), 3.30-3.40 (m, 2 H), 4.60 (br. s., 2 H), 4.87 (s, 2 H), 5.10 (m, J = 5.2 Hz, 1 H), 7.20 (s, 1 H), 7.31-7.47 (m, 8 H), 7.49-7.56 (m, 1 H) |
| 26 | 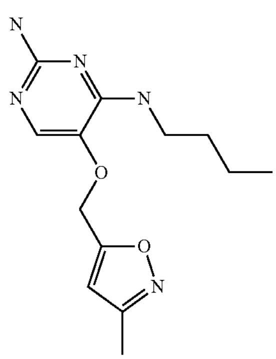 [SMILES: CCCCNc1nc(N)ncc1OCc1cc(C)no1] | 277.15 | 278 | 1.69, E | ¹H NMR (300 MHz, CHLOROFORM-d) δ ppm 0.96 (t, J = 7.3 Hz, 3 H), 1.28-1.46 (m, 2 H), 1.50-1.63 (m, 2 H), 2.32 (s, 3 H), 3.39 (td, J = 7.1, 5.9 Hz, 2 H), 4.70 (br. s., 2 H), 5.00 (s, 2 H), 5.18-5.27 (m, 1 H), 6.15 (s, 1 H), 7.45 (s, 1 H) |

TABLE I-continued

| | STRUCTURE | Exact Mass | Mass Found [M + H] | LCMS Ret Time, Method | 1H NMR |
|---|---|---|---|---|---|
| 27 | 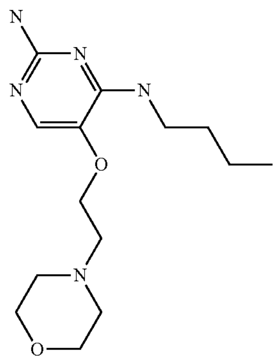 [SMILES: CCCCNc1nc(N)ncc1OCCN1CCOCC1] | 295.20 | 296 | 0.67, E | ¹H NMR (300 MHz, CHLOROFORM-d) δ ppm 0.96 (t, J = 7.3 Hz, 3 H), 1.34-1.47 (m, 2 H), 1.52-1.67 (m, 2 H), 2.51-2.60 (m, 4 H), 2.69 (t, J = 5.4 Hz, 2 H), 3.41 (td, J = 7.1, 5.9 Hz, 2 H), 3.71-3.81 (m, 4 H), 3.98 (t, J = 5.4 Hz, 2 H), 4.60 (br. s., 2 H), 5.85-5.98 (m, 1 H), 7.44 (s, 1 H) |
| 28 | 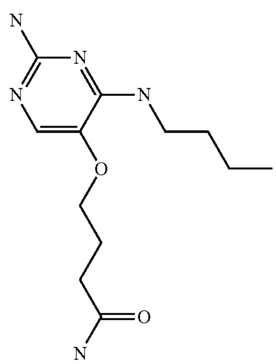 [SMILES: CCCCNc1nc(N)ncc1OCCCC(N)=O] | 267.17 | 268 | 0.94, E | ¹H NMR (300 MHz, CHLOROFORM-d) δ ppm 0.98 (t, J = 7.3 Hz, 3 H), 1.34-1.50 (m, 2 H), 1.55-1.70 (m, 2 H), 2.06 (d, J = 3.4 Hz, 2 H), 2.15 (dt, J = 13.0, 6.4 Hz, 2 H), 2.37-2.47 (m, 2 H), 3.42 (td, J = 7.1, 5.8 Hz, 2 H), 3.96 (t, J = 6.0 Hz, 2 H), 4.70 (br. s., 2 H), 5.34-5.44 (m, 1 H), 7.32 (s, 1 H) |
| 29 | 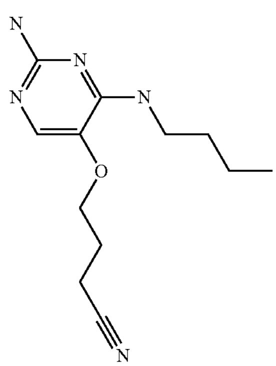 [SMILES: CCCCNc1nc(N)ncc1OCCCC#N] | 249.16 | 250 | 1.18, E | ¹H NMR (300 MHz, CHLOROFORM-d) δ ppm 0.98 (t, J = 7.3 Hz, 3 H), 1.34-1.50 (m, 2 H), 1.56-1.69 (m, 2 H), 2.15 (dt, J = 13.0, 6.4 Hz, 2 H), 2.39-2.47 (m, 2 H), 3.42 (td, J = 7.1, 5.8 Hz, 2 H), 3.96 (t, J = 6.0 Hz, 2 H), 4.70 (br. s., 2 H), 5.45-5.59 (m, 1 H), 7.32 (s, 1 H) |
| 30 | 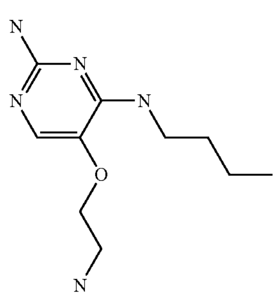 [SMILES: CCCCNc1nc(N)ncc1OCCN] | 225.16 | 226 | 0.20, E | ¹H NMR (300 MHz, METHANOL-d₄) δ ppm 0.86 (t, J = 7.4 Hz, 3 H), 1.22-1.37 (m, 2 H), 1.49 (t, J = 7.5 Hz, 2 H), 2.89 (t, J = 5.0 Hz, 2 H), 3.29 (t, J = 7.2 Hz, 2 H), 3.81 (t, J = 5.1 Hz, 2 H), 7.16 (s, 1 H) |

TABLE I-continued

| | STRUCTURE | Exact Mass | Mass Found [M + H] | LCMS Ret Time, Method | 1H NMR |
|---|---|---|---|---|---|
| 31 | 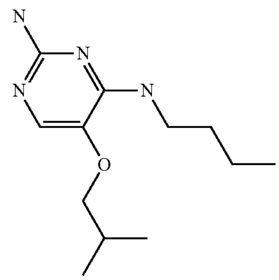 [SMILES: CCCCNc1nc(N)ncc1OCC(C)C] | 238.18 | 239 | 2.16, E | ¹H NMR (300 MHz, METHANOL-d₄) δ ppm 0.97 (t, J = 1.0 Hz, 3 H), 1.05 (d, J = 6.7 Hz, 6 H), 1.27-1.48 (m, 2 H), 1.54-1.73 (m, 2 H), 1.99-2.22 (m, 1 H), 3.45-3.60 (m, 2 H), 3.68-3.79 (m, 2 H), 7.15-7.22 (m, 1 H) |
| 32 | 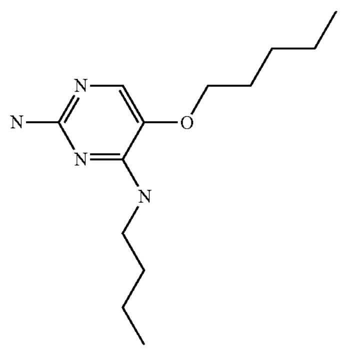 [SMILES: CCCCCOc1cnc(N)nc1NCCCC] | 252.20 | 253 | 2.36, E | ¹H NMR (300 MHz, METHANOL-d₄) δ ppm 1.00-1.13 (m, 6 H), 1.38-1.60 (m, 6 H), 1.65-1.78 (m, 2 H), 1.87-1.97 (m, 2 H), 3.56-3.64 (m, 2 H), 3.66-3.78 (m, 1 H), 4.00-4.09 (m, 2 H) |
| 33 | 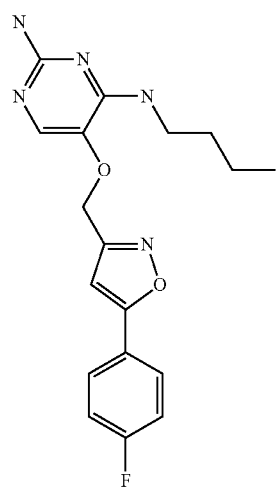 [SMILES: CCCCNc1nc(N)ncc1OCc1cc(-c2ccc(F)cc2)on1] | 357.16 | 358 | 1.01, D | ¹H NMR (360 MHz, DMSO-d₆) δ ppm 0.85 (t, J = 7.3 Hz, 3 H), 1.19-1.33 (m, 2 H), 1.41-1.53 (m, 2 H), 3.28 (q, J = 6.6 Hz, 2 H), 5.04 (s, 2 H), 5.63 (s, 2 H), 6.52 (t, J = 5.9 Hz, 1 H), 7.23 (s, 1 H), 7.37-7.45 (m, 2 H), 7.50 (s, 1 H), 7.91-7.98 (m, 2 H) |
| 34 | 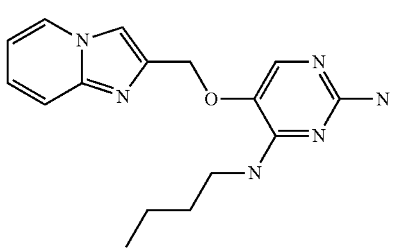 [SMILES: CCCCNc1nc(N)ncc1OCc1cn2ccccc2n1] | 312.17 | 313 | 0.71, D | ¹H NMR (360 MHz, DMSO-d₆) δ ppm 0.87 (t, J = 7.3 Hz, 3 H), 1.19-1.35 (m, 2 H), 1.40-1.53 (m, 2 H), 3.26 (q, J = 7.0 Hz, 2 H), 5.00 (s, 2 H), 5.58 (s, 2 H), 6.62 (t, J = 5.7 Hz, 1 H), 6.90 (t, J = 6.6 Hz, 1 H), 7.21-7.30 (m, 1 H), 7.46-7.57 (m, 2 H), 8.00 (s, 1 H), 8.53 (d, J = 7.0 Hz, 1 H) |

TABLE I-continued

| | STRUCTURE | Exact Mass | Mass Found [M + H] | LCMS Ret Time, Method | 1H NMR |
|---|---|---|---|---|---|
| 35 | 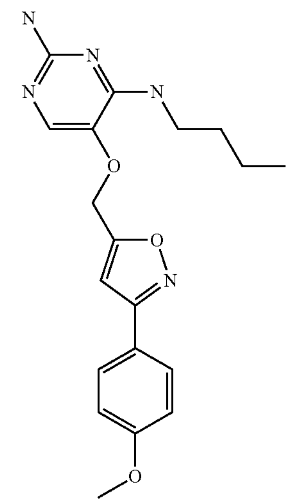 [SMILES: CCCCNc1nc(N)ncc1OCc1cc(-c2ccc(OC)cc2)no1] | 369.18 | 370 | 0.98, D | ¹H NMR (360 MHz, DMSO-d₆) δ ppm 0.87 (t, J = 7.5 Hz, 3 H), 1.23-1.32 (m, 2 H), 1.42-1.53 (m, 2 H), 3.23-3.31 (m, 2 H), 3.82 (s, 3 H), 5.09 (s, 2 H), 5.63 (s, 2 H), 6.48-6.56 (m, 1 H), 7.07 (d, J = 8.4 Hz, 2 H), 7.15 (s, 1 H), 7.46 (s, 1 H), 7.81 (d, J = 8.4 Hz, 2 H) |
| 36 | 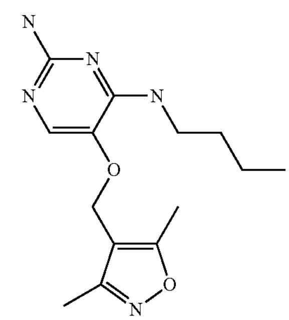 [SMILES: CCCCNc1nc(N)ncc1OCc1c(C)noc1C] | 291.17 | 292 | 0.78, D | ¹H NMR (360 MHz, DMSO-d₆) δ ppm 0.88 (t, J = 7.3 Hz, 3 H), 1.18-1.31 (m, 2 H), 1.38-1.51 (m, 2 H), 2.20 (s, 3 H), 2.33 (s, 3 H), 3.18-3.29 (m, 2 H), 4.72 (s, 2 H), 5.57 (s, 2 H), 6.40 (t, J = 5.9 Hz, 1 H), 7.38 (s, 1 H) |
| 37 | 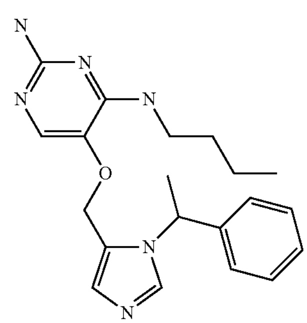 [SMILES: CCCCNc1nc(N)ncc1OCc1cncn1C(C)c1ccccc1] | 366.22 | 367 | 0.84, D | ¹H NMR (360 MHz, DMSO-d₆) δ ppm 0.88 (t, J = 7.3 Hz, 3 H), 1.20-1.32 (m, 2 H), 1.38-1.49 (m, 2 H), 1.81 (d, J = 7.0 Hz, 3 H), 3.21 (dt, J = 13.4, 6.9 Hz, 2 H), 4.62 (d, J = 12.8 Hz, 1 H), 4.87 (d, J = 12.4 Hz, 1 H), 5.52-5.61 (m, 3 H), 6.12 (t, J = 5.9 Hz, 1 H), 7.00 (s, 1 H), 7.15 (d, J = 7.0 Hz, 2 H), 7.25-7.37 (m, 4 H), 7.99 (s, 1 H) |
| 38 | 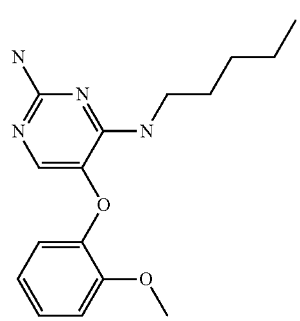 [SMILES: CCCCCNc1nc(N)ncc1Oc1ccccc1OC] | 302.17 | 303 | 0.99, D | ¹H NMR (400 MHz, CHLOROFORM-d) δ ppm 0.86-0.94 (m, 3 H), 1.26 (s, 1 H), 1.29-1.39 (m, 4 H), 1.60 (t, J = 7.2 Hz, 2 H), 3.40-3.49 (m, 2 H), 3.87 (s, 3 H), 5.50-5.64 (m, 1 H), 5.74-5.84 (m, 1 H), 6.92 (dd, J = 7.3, 1.3 Hz, 1 H), 6.95-7.01 (m, 2 H), 7.11-7.17 (m, 1 H), 7.26 (s, 1 H) |

TABLE I-continued

| | STRUCTURE | Exact Mass | Mass Found [M + H] | LCMS Ret Time, Method | 1H NMR |
|---|---|---|---|---|---|
| 39 | 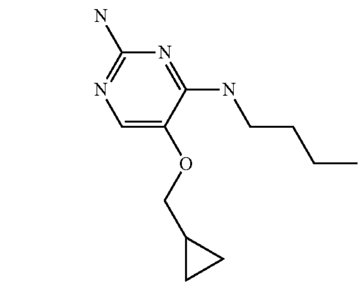 [SMILES: CCCCNc1nc(N)ncc1OCC1CC1] | 236.16 | 237 | 1.91, E | ¹H NMR (300 MHz, CHLOROFORM-d) δ ppm 0.31-0.43 (m, 2 H), 0.63-0.78 (m, 2 H), 0.99 (t, J = 7.3 Hz, 3 H), 1.16-1.31 (m, 1 H), 1.35-1.49 (m, 2 H), 1.65 (quin, J = 7.4 Hz, 2 H), 3.43-3.59 (m, 2 H), 3.72 (d, J = 7.0 Hz, 2 H), 6.02-6.18 (m, 1 H), 7.01 (s, 1 H) |
| 40 | 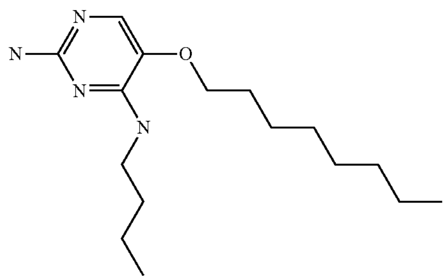 [SMILES: CCCCCCCCOc1cnc(N)nc1NCCCC] | 294.24 | 295 | 2.83, E | ¹H NMR (300 MHz, CHLOROFORM-d) δ ppm 0.77-0.85 (m, 3 H), 0.88 (t, J = 7.3 Hz, 3 H), 1.15-1.40 (m, 8 H), 1.45-1.58 (m, 2 H), 1.62-1.73 (m, 2 H), 1.77 (m, J = 13.3 Hz, 2 H), 3.33 (td, J = 7.0, 5.9 Hz, 2 H), 3.53-3.62 (m, 1 H), 3.66-3.74 (m, 1 H), 3.81 (t, J = 6.6 Hz, 2 H), 4.41 (br. s., 2 H), 5.03-5.14 (m, 1 H), 7.27 (s, 1 H) |
| 41 | 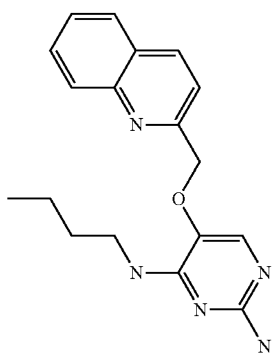 [SMILES: CCCCNc1nc(N)ncc1OCc1ccc2ccccc2n1] | 323.17 | 324 | 0.90, D | ¹H NMR (360 MHz, DMSO-d₆) δ ppm 0.89 (t, J = 7.3 Hz, 3 H), 1.23-1.36 (m, 2 H), 1.52 (t, J = 7.1 Hz, 2 H), 3.27-3.33 (m, 2 H), 5.20 (s, 2 H), 5.57 (s, 2 H), 6.78 (s, 1 H), 7.43 (s, 1 H), 7.59-7.66 (m, 1 H), 7.74-7.82 (m, 2 H), 8.01 (d, J = 8.4 Hz, 2 H), 8.43 (d, J = 8.4 Hz, 1 H) |
| 42 | 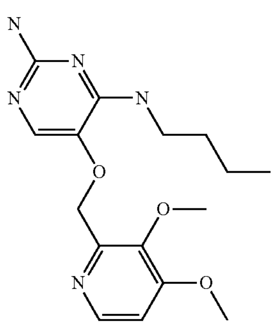 [SMILES: CCCCNc1nc(N)ncc1OCc1nccc(OC)c1OC] | 333.18 | 334 | 0.76, D | ¹H NMR (360 MHz, DMSO-d₆) δ ppm 0.89 (t, J = 7.5 Hz, 3 H), 1.21-1.36 (m, 2 H), 1.42-1.54 (m, 2 H), 3.23-3.30 (m, 2 H), 3.75 (s, 3 H), 3.90 (s, 3 H), 4.90 (s, 2 H), 5.59 (s, 2 H), 6.72 (t, J = 5.5 Hz, 1 H), 7.14 (d, J = 5.9 Hz, 1 H), 7.44 (s, 1 H), 8.23 (d, J = 5.5 Hz, 1 H) |
| 43 | 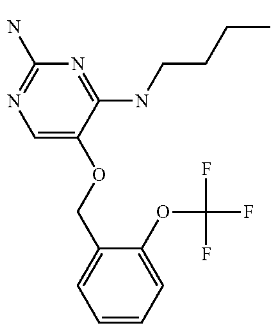 [SMILES: CCCCNc1nc(N)ncc1OCc1ccccc1OC(F)(F)F] | 356.15 | 357 | 1.07, D | ¹H NMR (360 MHz, DMSO-d₆) δ ppm 0.89 (t, J = 7.3 Hz, 3 H), 1.28 (dq, J = 14.9, 7.3 Hz, 2 H), 1.49 (quin, J = 7.2 Hz, 2 H), 3.28 (q, J = 6.6 Hz, 2 H), 4.98 (s, 2 H), 5.60 (s, 2 H), 6.40 (t, J = 5.9 Hz, 1 H), 7.35 (s, 1 H), 7.37-7.54 (m, 3 H), 7.70 (dd, J = 7.3, 1.5 Hz, 1 H) |

TABLE I-continued

| | STRUCTURE | Exact Mass | Mass Found [M + H] | LCMS Ret Time, Method | 1H NMR |
|---|---|---|---|---|---|
| 44 | 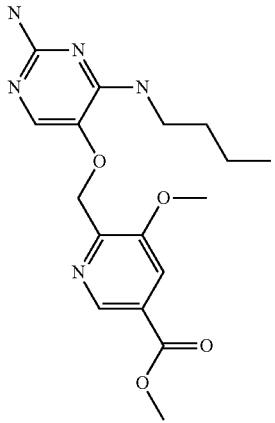 [SMILES: CCCCNc1nc(N)ncc1OCc1ncc(C(=O)OC)cc1OC] | 360.18 | 361 | 0.95, D | $^1$H NMR (400 MHz, CHLOROFORM-d) δ ppm 0.95 (t, J = 7.3 Hz, 3 H), 1.38 (dq, J = 15.1, 7.4 Hz, 2 H), 1.57 (quin, J = 7.3 Hz, 2 H), 3.36-3.44 (m, 2 H), 3.92 (s, 3 H), 3.93 (s, 3 H), 4.63-4.72 (m, 2 H), 5.00 (s, 2 H), 5.32 (br. s., 1 H), 7.40 (d, J = 7.8 Hz, 1 H), 7.43 (s, 1 H), 7.57 (d, J = 1.0 Hz, 1 H), 7.66 (dd, J = 7.8, 1.5 Hz, 1 H) |
| 45 | 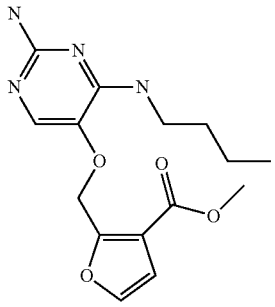 [SMILES: CCCCNc1nc(N)ncc1OCc1occc1C(=O)OC] | 320.15 | 321 | 0.83, D | $^1$H NMR (360 MHz, DMSO-d$_6$) δ ppm 0.89 (t, J = 7.3 Hz, 3 H), 1.22-1.36 (m, 2 H), 1.49 (s, 2 H), 3.22-3.31 (m, 2 H), 3.82 (s, 3 H), 5.09 (s, 2 H), 5.57 (s, 2 H), 6.52 (t, J = 5.9 Hz, 1 H), 6.94 (d, J = 1.5 Hz, 1 H), 7.36 (s, 1 H), 7.95 (d, J = 1.8 Hz, 1 H) |
| 46 | 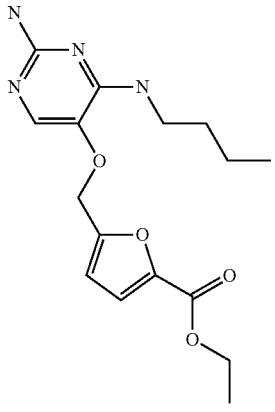 [SMILES: CCCCNc1nc(N)ncc1OCc1ccc(C(=O)OCC)o1] | 334.16 | 335 | 0.89, D | $^1$H NMR (360 MHz, DMSO-d$_6$) δ ppm 0.88 (t, J = 7.5 Hz, 3 H), 1.21-1.29 (m, 2 H), 1.29 (t, J = 7.0 Hz, 3 H), 1.47 (quin, J = 7.4 Hz, 2 H), 3.25 (q, J = 6.8 Hz, 2 H), 4.29 (q, J = 7.1 Hz, 2 H), 4.95 (s, 2 H), 5.60 (s, 2 H), 6.41 (t, J = 5.9 Hz, 1 H), 6.76 (d, J = 3.7 Hz, 1 H), 7.28 (d, J = 3.3 Hz, 1 H), 7.39 (s, 1 H) |
| 47 | 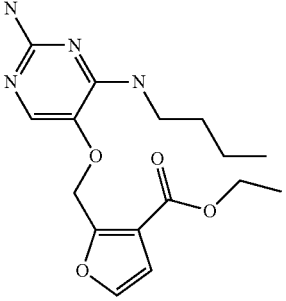 [SMILES: CCCCNc1nc(N)ncc1OCc1occc1C(=O)OCC] | 334.16 | 335 | 0.93, D | $^1$H NMR (360 MHz, DMSO-d$_6$) δ ppm 0.89 (t, J = 7.3 Hz, 3 H), 1.24 (t, J = 7.0 Hz, 3 H), 1.26-1.34 (m, 2 H), 1.43-1.54 (m, 2 H), 3.21-3.30 (m, 2 H), 4.21 (q, J = 7.0 Hz, 2 H), 5.11 (s, 2 H), 5.62 (s, 2 H), 6.42 (t, J = 5.9 Hz, 1 H), 6.78 (d, J = 1.5 Hz, 1 H), 7.29 (s, 1 H), 7.78-7.86 (m, 1 H) |

TABLE I-continued

| | STRUCTURE | Exact Mass | Mass Found [M + H] | LCMS Ret Time, Method | 1H NMR |
|---|---|---|---|---|---|
| 48 | 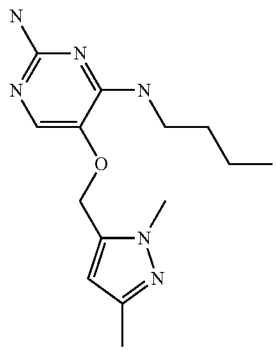 [SMILES: CCCCNc1nc(N)ncc1OCc1cc(C)nn1C] | 290.19 | 291 | 0.73, D | ¹H NMR (360 MHz, DMSO-d₆) δ ppm 0.88 (t, J = 7.3 Hz, 3 H), 1.26 (dd, J = 15.2, 7.5 Hz, 2 H), 1.41-1.53 (m, 2 H), 2.10 (s, 3 H), 3.21-3.29 (m, 2 H), 3.73 (s, 3 H), 4.91 (s, 2 H), 5.55 (s, 2 H), 6.11 (s, 1 H), 6.44 (t, J = 5.9 Hz, 1 H), 7.39 (s, 1 H) |
| 49 | 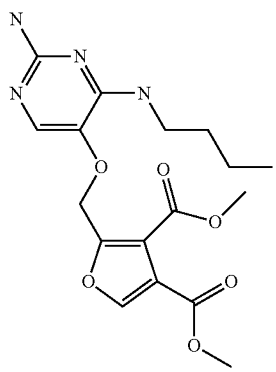 [SMILES: CCCCNc1nc(N)ncc1OCc1occ(C(=O)OC)c1C(=O)OC] | 378.15 | 379 | 0.83, D | ¹H NMR (360 MHz, DMSO-d₆) δ ppm 0.88 (t, J = 7.3 Hz, 3 H), 1.27 (dd, J = 15.2, 7.5 Hz, 2 H), 1.46 (t, J = 7.1 Hz, 2 H), 3.20-3.29 (m, 2 H), 3.74 (s, 3 H), 3.77 (s, 3 H), 5.00 (s, 2 H), 5.68 (s, 2 H), 6.38-6.48 (m, 1 H), 7.29 (s, 1 H), 8.46 (s, 1 H) |
| 50 | 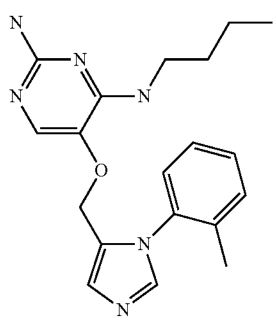 [SMILES: CCCCNc1nc(N)ncc1OCc1cncn1-c1ccccc1C] | 352.20 | 353 | 0.82, D | ¹H NMR (360 MHz, DMSO-d₆) δ ppm 0.89 (t, J = 7.3 Hz, 3 H), 1.18-1.31 (m, 2 H), 1.37-1.49 (m, 2 H), 2.00 (s, 3 H), 3.19 (q, J = 6.8 Hz, 2 H), 4.61 (br. s., 2 H), 5.53 (s, 2 H), 5.93 (t, J = 5.9 Hz, 1 H), 7.01 (s, 1 H), 7.21 (s, 1 H), 7.32 (dd, J = 8.6, 3.5 Hz, 1 H), 7.40-7.45 (m, 3 H), 7.82 (s, 1 H) |
| 51 | 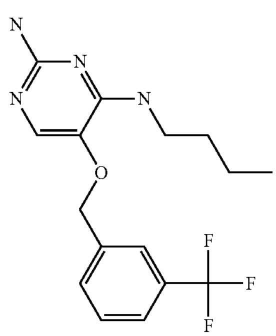 [SMILES: CCCCNc1nc(N)ncc1OCc1cccc(C(F)(F)F)c1] | 340.15 | 341 | 1.06, D | ¹H NMR (360 MHz, DMSO-d₆) δ ppm 0.89 (t, J = 7.3 Hz, 3 H), 1.23-1.34 (m, 2 H), 1.49 (t, J = 7.3 Hz, 2 H), 3.23-3.31 (m, 2 H), 5.05 (s, 2 H), 5.54 (s, 2 H), 6.57 (s, 1 H), 7.42 (s, 1 H), 7.63 (m, J = 7.7 Hz, 1 H), 7.66-7.71 (m, 1 H), 7.75-7.84 (m, 2 H) |

TABLE I-continued

| | STRUCTURE | Exact Mass | Mass Found [M + H] | LCMS Ret Time, Method | 1H NMR |
|---|---|---|---|---|---|
| 52 | 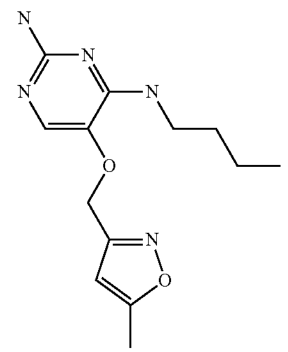 [SMILES: CCCCNc1nc(N)ncc1OCc1cc(C)on1] | 277.15 | 278 | 0.78, D | ¹H NMR (360 MHz, DMSO-d₆) δ ppm 0.89 (t, J = 7.3 Hz, 3 H), 1.21-1.35 (m, 2 H), 1.42-1.54 (m, 2 H), 2.41 (s, 3 H), 3.27 (q, J = 6.7 Hz, 2 H), 4.95 (s, 2 H), 5.61 (s, 2 H), 6.41 (s, 1 H), 6.50 (t, J = 5.7 Hz, 1 H), 7.42 (s, 1 H) |
| 53 | 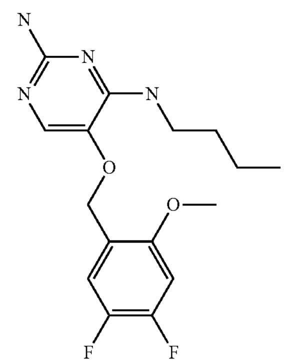 [SMILES: CCCCNc1nc(N)ncc1OCc1cc(F)c(F)cc1OC] | 338.16 | 339 | 1.00, D | ¹H NMR (360 MHz, DMSO-d₆) δ ppm 0.89 (t, J = 7.3 Hz, 3 H), 1.21-1.35 (m, 2 H), 1.49 (quin, J = 7.3 Hz, 2 H), 3.29 (q, J = 6.6 Hz, 2 H), 3.81 (s, 3 H), 4.83 (s, 2 H), 5.56 (s, 2 H), 6.45 (t, J = 5.9 Hz, 1 H), 7.20 (dd, J = 12.8, 6.6 Hz, 1 H), 7.38 (s, 1 H), 7.60 (dd, J = 11.0, 9.5 Hz, 1 H) |
| 54 | 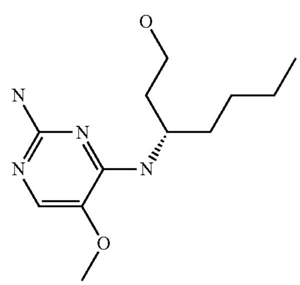 [SMILES: CCCC[C@@H](CCO)Nc1nc(N)ncc1OC] | 254.17 | 255 | 0.68, D | ¹H NMR (400 MHz, DMSO-d₆) δ ppm 0.84 (t, J = 6.9 Hz, 3 H), 1.14-1.33 (m, 4 H), 1.44-1.54 (m, 2 H), 1.56-1.72 (m, 2 H), 3.40 (t, J = 6.4 Hz, 2 H), 3.67 (s, 3 H), 4.05-4.18 (m, 1 H), 4.39 (br. s., 1 H), 5.45 (s, 2 H), 6.13 (d, J = 9.0 Hz, 1 H), 7.34 (s, 1 H) |
| 55 | 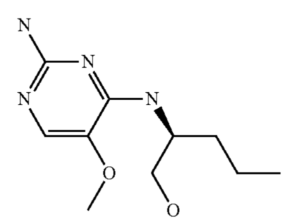 [SMILES: CCC[C@@H](CO)Nc1nc(N)ncc1OC] | 226.14 | 227 | 0.52, D | ¹H NMR (400 MHz, DMSO-d₆) δ ppm 0.86 (t, J = 7.4 Hz, 3 H), 1.19-1.35 (m, 2 H), 1.45 (dt, J = 13.5, 4.4 Hz, 1 H), 1.50-1.62 (m, 1 H), 3.30-3.49 (m, 2 H), 3.67 (s, 3 H), 4.05 (td, J = 8.8, 5.0 Hz, 1 H), 4.36-4.96 (m, 1 H), 5.46 (s, 2 H), 5.89 (d, J = 9.0 Hz, 1 H), 7.35 (s, 1 H) |
| 56 | 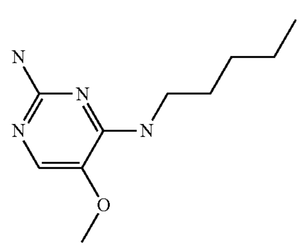 | 210.15 | 211 | 0.75, D | ¹H NMR (400 MHz, CHLOROFORM-d) δ ppm 0.86-0.98 (m, 3 H), 1.29-1.43 (m, 4 H), 1.55-1.65 (m, 2 H), 3.39 (td, J = 7.2, 5.8 Hz, 2 H), 3.78 (s, 3 H), 4.42 (br. s., 2 H), 5.14 (br. s., 1 H), 7.37 (s, 1 H) |

TABLE I-continued

| | STRUCTURE | Exact Mass | Mass Found [M + H] | LCMS Ret Time, Method | 1H NMR |
|---|---|---|---|---|---|
| 57 | 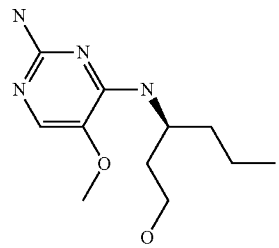 [SMILES: CCC[C@@H](CCO)Nc1nc(N)ncc1OC] | 240.16 | 241 | 0.58, D | $^1$H NMR (400 MHz, DMSO-d$_6$) δ ppm 0.85 (t, J = 7.4 Hz, 3 H), 1.15-1.34 (m, 2 H), 1.37-1.54 (m, 2 H), 1.56-1.73 (m, 2 H), 3.40 (t, J = 6.4 Hz, 2 H), 3.67 (s, 3 H), 4.04-4.22 (m, 1 H), 4.40 (br. s., 1 H), 5.46 (s, 2 H), 6.13 (d, J = 8.8 Hz, 1 H), 7.35 (br. s., 1 H) |
| 58 | 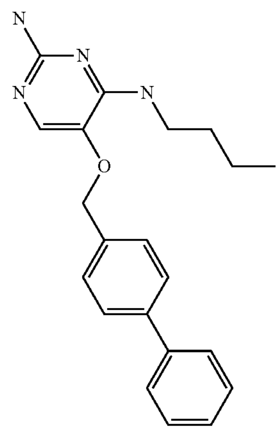 [SMILES: CCCCNc1nc(N)ncc1OCc1ccc(-c2ccccc2)cc1] | 348.20 | 349 | 1.16, D | $^1$H NMR (400 MHz, DMSO-d$_6$) δ ppm 0.84-0.93 (m, 3 H), 1.20-1.36 (m, 2 H), 1.53 (t, J = 7.4 Hz, 2 H), 3.33-3.45 (m, 2 H), 5.11 (s, 2 H), 7.33-7.40 (m, 1 H), 7.43-7.50 (m, 2 H), 7.51-7.60 (m, 4 H), 7.64-7.73 (m, 3 H), 8.42-8.50 (m, 1 H), 12.15 (d, J = 4.8 Hz, 0 H) |
| 59 | 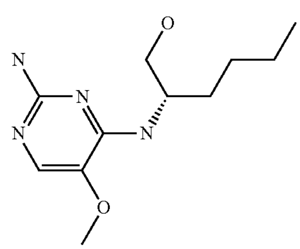 [SMILES: CCCC[C@@H](CO)Nc1nc(N)ncc1OC] | 240.16 | 241 | 0.62, D | $^1$H NMR (400 MHz, DMSO-d$_6$) δ ppm 0.79-0.90 (m, 3 H), 1.16-1.34 (m, 4 H), 1.37-1.49 (m, 1 H), 1.53-1.67 (m, 1 H), 3.17-3.51 (m, 2 H), 3.68 (s, 3 H), 3.95-4.11 (m, 1 H), 4.67 (br. s., 1 H), 5.45 (s, 2 H), 5.89 (d, J = 9.0 Hz, 1 H), 7.36 (s, 1 H) |
| 60 | 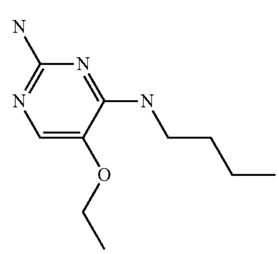 | 210.15 | 211 | 3.93, B | $^1$H NMR (400 MHz, DMSO-d$_6$) δ ppm 0.83-0.92 (m, 3 H), 1.22-1.29 (m, 2 H), 1.32 (t, J = 7.0 Hz, 3 H), 1.52 (quin, J = 7.3 Hz, 2 H), 3.36-3.42 (m, 2 H), 3.96 (q, J = 6.9 Hz, 2 H), 7.41 (s, 1 H), 7.48 (br. s., 2 H), 8.36 (t, J = 5.9 Hz, 1 H) |

TABLE I-continued

| | STRUCTURE | Exact Mass | Mass Found [M + H] | LCMS Ret Time, Method | 1H NMR |
|---|---|---|---|---|---|
| 61 | 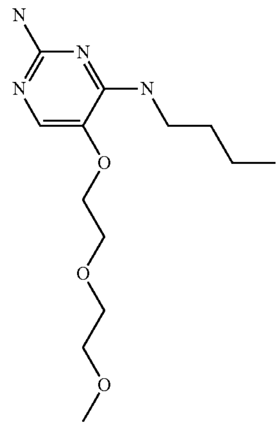 [SMILES: CCCCNc1nc(N)ncc1OCCOCCOC] | 284.18 | 285 | 0.68, D | ¹H NMR (360 MHz, DMSO-d₆) δ ppm 0.89 (t, J = 7.3 Hz, 3 H), 1.23-1.37 (m, 2 H), 1.44-1.55 (m, 2 H), 3.26 (s, 3 H), 3.26-3.31 (m, 2 H), 3.47 (dd, J = 5.5, 3.7 Hz, 2 H), 3.56-3.60 (m, 2 H), 3.65 (dd, J = 5.5, 3.7 Hz, 2 H), 3.90 (dd, J = 5.3, 3.8 Hz, 2 H), 5.60 (s, 2 H), 6.28 (t, J = 5.9 Hz, 1 H), 7.41 (s, 1 H) |
| 62 | 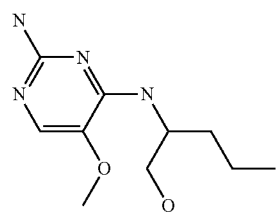 [SMILES: CCCC(CO)Nc1nc(N)ncc1OC] | 226.14 | 227 | 0.52, D | ¹H NMR (400 MHz, CHLOROFORM-d) δ ppm 0.96 (t, J = 7.3 Hz, 3 H), 1.33-1.48 (m, 2 H), 1.50-1.67 (m, 2 H), 3.61 (dd, J = 10.9, 6.9 Hz, 1 H), 3.76 (d, J = 3.0 Hz, 1 H), 3.79 (s, 3 H), 3.87-4.00 (m, 1 H), 4.01-4.13 (m, 1 H), 4.45 (br. s., 2 H), 5.22 (d, J = 6.8 Hz, 1 H), 7.39 (s, 1 H) |
| 63 | 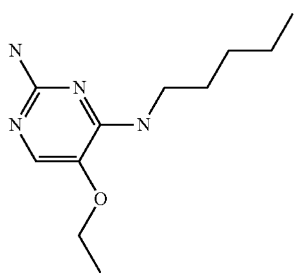 [SMILES: CCCCCNc1nc(N)ncc1OCC] | 224.16 | 225 | 3.23, C | ¹H NMR (400 MHz, DMSO-d₆) δ ppm 0.89 (t, J = 7.0 Hz, 3 H), 1.29 (dd, J = 15.3, 7.5 Hz, 2 H), 1.24 (m, J = 3.0 Hz, 2 H), 1.32-1.38 (m, 3 H), 1.51-1.62 (m, 2 H), 3.40-3.44 (m, 2 H), 3.98 (q, J = 6.9 Hz, 2 H), 7.42 (s, 1 H), 7.49 (br. s., 2 H), 8.39 (t, J = 5.8 Hz, 1 H) |
| 64 | 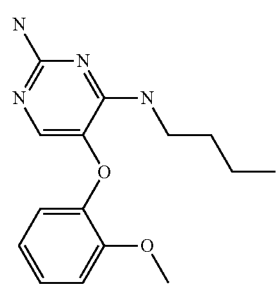 [SMILES: CCCCNc1nc(N)ncc1Oc1ccccc1OC] | 288.16 | 289 | 0.91, D | ¹H NMR (400 MHz, CHLOROFORM-d) δ ppm 0.94 (t, J = 7.3 Hz, 3 H), 1.26 (s, 1 H), 1.37 (dd, J = 15.1, 7.5 Hz, 2 H), 1.52-1.63 (m, 2 H), 3.39-3.50 (m, 2 H), 3.88 (s, 3 H), 5.31-5.44 (m, 1 H), 5.60-5.71 (m, 1 H), 6.87-7.01 (m, 3 H), 7.08-7.15 (m, 1 H), 7.33 (s, 1 H). |
| 65 | 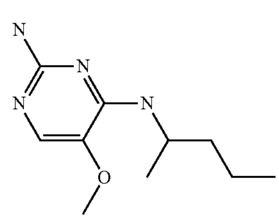 | 210.15 | 211 | 0.73, D | ¹H NMR (400 MHz, CHLOROFORM-d) δ 0.86-0.99 (m, 3 H), 1.18 (d, J = 6.5 Hz, 3 H), 1.28-1.39 (m, 2 H), 1.44-1.55 (m, 2 H), 3.76 (s, 3 H), 4.08-4.22 (m, 1 H), 4.40 (br. s., 2 H), 4.94 (d, J = 7.8 Hz, 1 H), 7.34 (s, 1 H) |

TABLE I-continued

| | STRUCTURE | Exact Mass | Mass Found [M + H] | LCMS Ret Time, Method | 1H NMR |
|---|---|---|---|---|---|
| 66 | 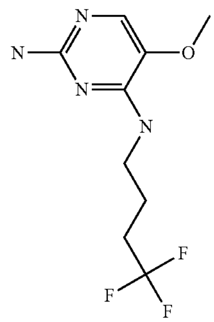 [SMILES: COc1cnc(N)nc1NCCCC(F)(F)F] | 250.10 | 251 | 0.66, D | $^1$H NMR (400 MHz, CHLOROFORM-d) δ ppm 1.82-1.93 (m, 2 H), 2.07-2.25 (m, 2 H), 3.50 (q, J = 6.6 Hz, 2 H), 3.77 (s, 3 H), 4.54 (br. s., 2 H), 5.21-5.31 (m, 1 H), 7.39 (s, 1 H) |
| 67 | 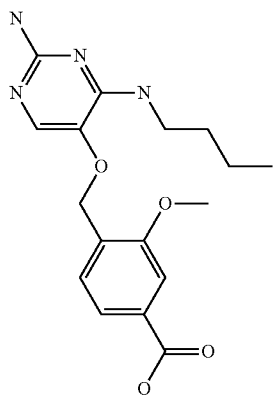 [SMILES: CCCCNc1nc(N)ncc1OCc1ccc(C(=O)O)cc1OC] | 346.16 | 347 | 0.56, D | $^1$H NMR (400 MHz, DMSO-d$_6$) δ ppm 0.89 (t, J = 7.3 Hz, 3 H), 1.24-1.35 (m, 2 H), 1.50 (t, J = 7.2 Hz, 2 H), 3.25-3.33 (m, 2 H), 3.83 (s, 3 H), 4.88 (s, 2 H), 5.57 (s, 1 H), 6.32 (s, 1 H), 7.33 (d, J = 7.8 Hz, 1 H), 7.36 (s, 1 H), 7.48 (dd, J = 7.7, 1.1 Hz, 1 H), 7.54 (d, J = 1.0 Hz, 1 H) |
| 68 | 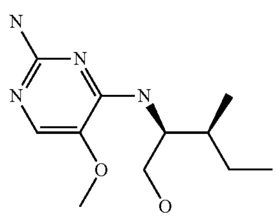 [SMILES: CC[C@H](C)[C@@H](CO)Nc1nc(N)ncc1OC] | 240.16 | 241 | 0.61, D | $^1$H NMR (400 MHz, CHLOROFORM-d) δ ppm 0.91 (t, J = 7.4 Hz, 3 H), 0.96 (d, J = 7.0 Hz, 3 H), 1.19 (ddd, J = 13.6, 8.8, 7.3 Hz, 1 H), 1.53 (ddd, J = 13.5, 7.5, 4.1 Hz, 1 H), 1.75 (ddd, J = 6.6, 4.2, 2.3 Hz, 1 H), 3.65-3.71 (m, 1 H), 3.75 (s, 3 H), 3.77 (d, J = 3.0 Hz, 1 H), 3.80 (d, J = 3.3 Hz, 1 H), 3.90-4.00 (m, 1 H), 4.64 (br. s., 2 H), 5.39 (d, J = 7.8 Hz, 1 H), 7.32 (s, 1 H) |
| 69 | 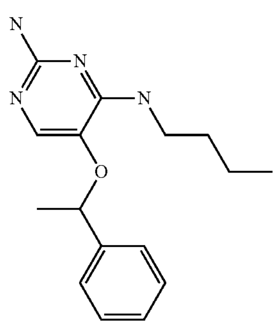 [SMILES: CCCCNc1nc(N)ncc1OC(C)c1ccccc1] | 286.18 | 287 | 1.00, D | $^1$H NMR (400 MHz, CHLOROFORM-d) δ ppm 0.91 (t, J = 7.4 Hz, 3 H), 1.23-1.36 (m, 2 H), 1.49-1.57 (m, 2 H), 1.58 (d, J = 6.5 Hz, 3 H), 3.37-3.47 (m, 2 H), 5.39 (d, J = 6.5 Hz, 1 H), 7.21 (s, 1 H), 7.27-7.33 (m, 2 H), 7.34-7.40 (m, 2 H), 7.41-7.46 (m, 1 H), 8.43 (s, 1 H), 11.05-11.32 (m, 1 H) |
| 70 | 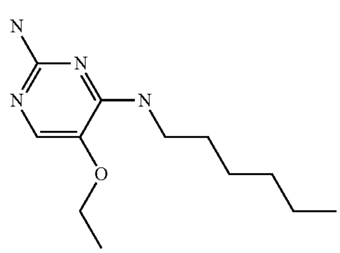 [SMILES: CCCCCCNc1nc(N)ncc1OCC] | 238.18 | 239 | 3.56, C | $^1$H NMR (400 MHz, DMSO-d$_6$) δ ppm 0.83-0.92 (m, 3 H), 1.22-1.31 (m, 7 H), 1.35 (t, J = 6.9 Hz, 3 H), 1.49-1.63 (m, 2 H), 3.40-3.44 (m, 2 H), 3.99 (q, J = 6.9 Hz, 2 H), 7.47 (br. s., 2 H), 8.39 (t, J = 5.8 Hz, 1 H) |

TABLE I-continued

| | STRUCTURE | Exact Mass | Mass Found [M + H] | LCMS Ret Time, Method | 1H NMR |
|---|---|---|---|---|---|
| 71 | 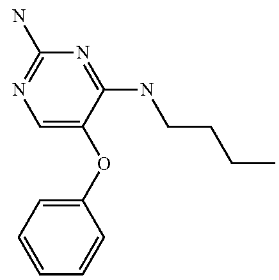 [SMILES: CCCCNc1nc(N)ncc1Oc1ccccc1] | 258.15 | 259 | 0.94, A | ¹H NMR (400 MHz, CHLOROFORM-d) δ ppm 0.86-0.91 (m, 3 H), 1.24-1.30 (m, 2 H), 1.44-1.54 (m, 2 H), 3.37 (td, J = 7.1, 5.9 Hz, 2 H), 4.97 (br. s., 3 H), 6.92-6.97 (m, 2 H), 7.01-7.06 (m, 1 H), 7.25-7.31 (m, 2 H), 7.58 (s, 1 H) |
| 72 | 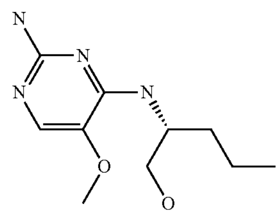 | 226.14 | 227 | 0.52, D | ¹H NMR (400 MHz, DMSO-d₆) δ ppm 0.86 (t, J = 7.3 Hz, 3 H), 1.18-1.36 (m, 2 H), 1.45 (dd, J = 8.9, 4.9 Hz, 1 H), 1.51-1.62 (m, 1 H), 3.40 (d, J = 16.6 Hz, 2 H), 3.67 (s, 3 H), 3.95-4.13 (m, 1 H), 4.65 (br. s., 1 H), 5.44 (s, 2 H), 5.88 (d, J = 9.0 Hz, 1 H), 7.35 (s, 1 H) |
| 73 | 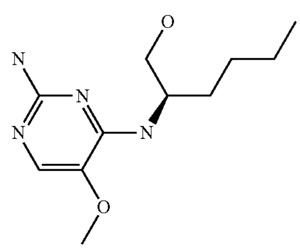 [SMILES: CCCC[C@H](CO)Nc1nc(N)ncc1OC] | 240.16 | 241 | 0.63, D | ¹H NMR (400 MHz, DMSO-d₆) δ ppm 0.81-0.90 (m, 3 H), 1.17-1.37 (m, 3 H), 1.39-1.51 (m, 1 H), 1.54-1.66 (m, 1 H), 2.51 (dt, J = 3.7, 1.8 Hz, 1 H), 3.34-3.41 (m, 1 H), 3.41-3.48 (m, 1 H), 3.68 (s, 3 H), 4.04 (td, J = 8.7, 5.0 Hz, 1 H), 4.43-4.91 (m, 1 H), 5.47 (s, 2 H), 5.90 (d, J = 9.0 Hz, 1 H), 7.36 (s, 1 H) |
| 74 | 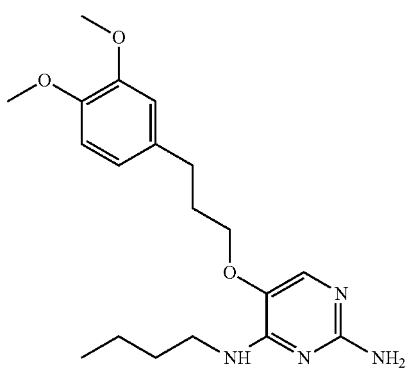 [SMILES: CCCCNc1nc(N)ncc1OCCCc1ccc(OC)c(OC)c1] | 360.22 | 361 | 0.94, D | ¹H NMR (400 MHz, DMSO-d₆) δ ppm 0.91 (t, J = 7.4 Hz, 3 H), 1.30 (dq, J = 14.9, 7.4 Hz, 2 H), 1.49-1.61 (m, 2 H), 1.95-2.09 (m, 2 H), 2.70 (t, J = 7.7 Hz, 2 6 H), 3.42 (q, J = 6.8 Hz, 2 H), 3.71 (s, 3 H), 3.72 (s, 3 H), 3.89 (t, J = 6.3 Hz, 2 H), 6.72 (dd, J = 8.2, 1.9 Hz, 1 H), 6.81 (d, J = 1.8 Hz, 1 H), 6.86 (d, J = 8.3 Hz, 1 H), 7.36 (d, J = 5.8 Hz, 1 H), 7.43 (br. s., 2 H), 8.32 (t, J = 6.0 Hz, 1 H), 11.77 (d, J = 5.3 Hz, 1 H) |
| 75 | 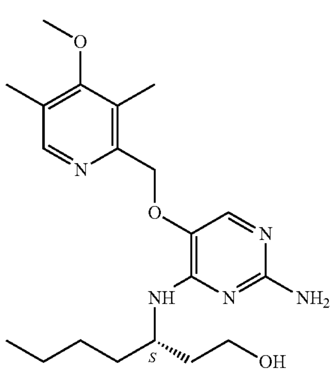 | 389.24 | 390 | 0.88, D | ¹H NMR (400 MHz, DMSO-d₆) δ ppm 0.84 (t, J = 6.9 Hz, 3 H), 1.15-1.38 (m, 4 H), 1.58 (m, J = 13.3, 13.3, 7.0 Hz, 1 H), 1.67-1.83 (m, 2 H), 1.84-1.99 (m, 6 1 H), 2.27 (s, 3 H), 2.38 (s, 3 H), 3.41 (t, J = 6.4 Hz, 2 H), 3.97 (s, 3 H), 4.38 (dt, J = 9.0, 4.7 Hz, 1 H), 5.35 (s, 2 H), 7.51 (br. s., 2 H), 7.77 (s, 1 H), 8.53 (s, 1 H), 8.96 (br. s., 1 H), 12.20 (br. s., 1 H) |

TABLE I-continued

| | STRUCTURE | Exact Mass | Mass Found [M + H] | LCMS Ret Time, Method | 1H NMR |
|---|---|---|---|---|---|
| 76 | 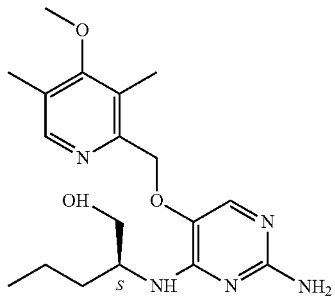 | 361.21 | 362 | 0.75, D | ¹H NMR (400 MHz, DMSO-d₆) δ ppm 0.86 (t, J = 7.3 Hz, 3 H), 1.18-1.36 (m, 2 H), 1.36-1.50 (m, 1 H), 1.50-1.63 (m, 1 H), 2.22 (s, 3 H), 2.24 (s, 3 H), 6 3.29-3.48 (m, 2 H), 3.74 (s, 3 H), 4.03 (td, J = 8.7, 4.6 Hz, 1 H), 4.68 (br. s., 1 H), 4.91-5.05 (m, 2 H), 5.53 (s, 2 H), 6.19 (d, J = 8.8 Hz, 1 H), 7.44 (s, 1 H), 8.21 (s, 1 H) |
| 77 | 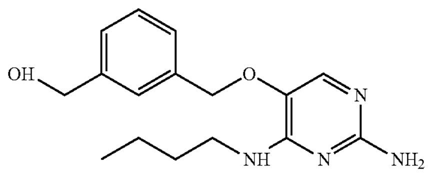 [SMILES: CCCCNc1nc(N)ncc1OCc1cccc(CO)c1] | 302.17 | 303 | 0.75, D | ¹H NMR (400 MHz, DMSO-d₆) δ ppm 0.89 (t, J = 7.3, Hz, 3 H), 1.22-1.35 (m, 2 H), 1.50 (quin, J = 7.3 Hz, 2 H), 3.24-3.30 (m, 2 H), 4.51 (d, J = 5.3 Hz, 2 H), 6 4.95 (s, 2 H), 5.19 (t, J = 5.6 Hz, 1 H), 5.52 (s, 2 H), 6.42 (t, J = 5.8 Hz, 1 H), 7.24-7.29 (m, 1 H), 7.29-7.34 (m, 2 H), 7.35-7.40 (m, 2 H) |
| 78 | 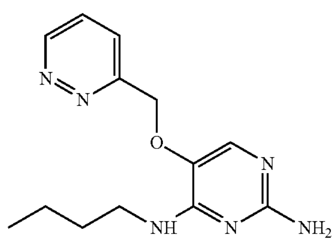 [SMILES: CCCCNc1nc(N)ncc1OCc1cccnn1] | 274.15 | 275 | 0.59, D | ¹H NMR (400 MHz, DMSO-d₆) δ ppm 0.90 (t, J = 7.3 Hz, 3 H), 1.30 (dq, J = 14.9, 7.3 Hz, 2 H), 1.51 (quin, J = 7.3 Hz, 2 H), 3.26-3.32 (m, 2 H), 5.24 (s, 2 H), 6 5.68 (s, 2 H), 6.78 (t, J = 5.8 Hz, 1 H), 7.46 (s, 1 H), 7.76 (dd, J = 8.4, 4.9 Hz, 1 H), 7.93 (dd, J = 8.5, 1.5 Hz, 1 H), 9.21 (dd, J = 5.0, 1.5 Hz, 1 H) |
| 79 | 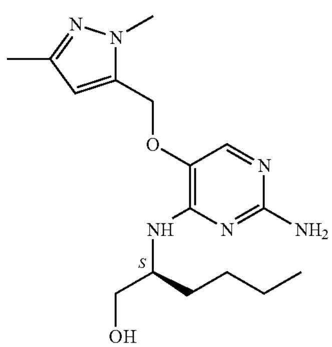 | 334.21 | 335 | 0.7, D | ¹H NMR (400 MHz, DMSO-d₆) δ ppm 0.85 (t, J = 7.0 Hz, 3 H), 1.15-1.34 (m, 4 H), 1.36-1.50 (m, 1 H), 1.51-1.64 (m, 1 H), 2.11 (s, 3 H), 3.39-3.46 (m, 2 6 H), 3.73 (s, 3 H), 4.02 (td, J = 8.8, 4.8 Hz, 1 H), 4.66 (br. s., 1 H), 4.94 (s, 2 H), 5.56 (s, 2 H), 5.85 (d, J = 8.8 Hz, 1 H), 6.09 (s, 1 H), 7.43 (s, 1 H) |
| 80 | 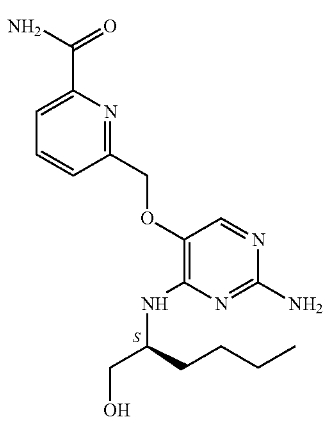 | 360.19 | 361 | 0.63, D | ¹H NMR (400 MHz, DMSO-d₆) δ ppm 0.84 (t, J = 6.9 Hz, 3 H), 1.14-1.34 (m, 4 H), 1.37-1.51 (m, 1 H), 1.52-1.67 (m, 1 H), 3.36-3.48 (m, 2 H), 3.99-6 4.11 (m, 1 H), 4.69 (br. s., 1 H), 5.10 (s, 2 H), 5.54 (s, 2 H), 6.00 (d, J = 8.8 Hz, 1 H), 7.46 (s, 1 H), 7.68 (br. s., 1 H), 7.72 (dd, J = 7.3, 1.3 Hz, 1 H), 7.93-8.02 (m, 2 H), 8.03 (s, 1 H) |

TABLE I-continued

| | STRUCTURE | Exact Mass | Mass Found [M + H] | LCMS Ret Time, Method | 1H NMR |
|---|---|---|---|---|---|
| 81 | 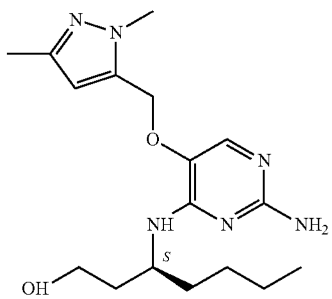 | 348.23 | 349 | 0.73, D | ¹H NMR (400 MHz, DMSO-d₆) δ ppm 0.84 (t, J = 7.2 Hz, 3 H), 1.11-1.37 (m, 4 H), 1.47-1.63 (m, 2 H), 1.63-1.79 (m, 2 H), 2.13 (s, 2 H), 3.40 (t, J = 6.3 Hz, 6 2 H), 3.75 (s, 3 H), 4.30 (m, J = 8.0 Hz, 1 H), 5.08 (s, 2 H), 6.21 (s, 1 H), 7.48 (br. s., 2 H), 7.55 (d, J = 5.3 Hz, 1 H), 8.11 (d, J = 8.8 Hz, 1 H), 11.96 (d, J = 5.3 Hz, 1 H) |
| 82 | 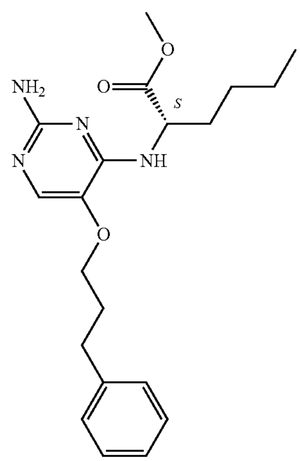 | 372.22 | 373 | 1.15, D | ¹H NMR (400 MHz, DMSO-d₆) δ ppm 0.77-0.91 (m, 3 H) 1.17-1.37 (m, 4 H) 1.75-1.91 (m, 2 H) 1.93-2.09 (m, 2 H) 2.74 (t, J = 7.65 Hz, 2 H) 3.63 (s, 3 H) 3.87 (q, J = 6.02 Hz, 2 H) 4.58 (q, J = 7.28 Hz, 1 H) 5.71 (br. s., 2 H) 6.53 (d, J = 8.28 Hz, 1 H) 7.15-7.35 (m, 5 H) 7.43 (br. s., 1 H) |
| 83 | 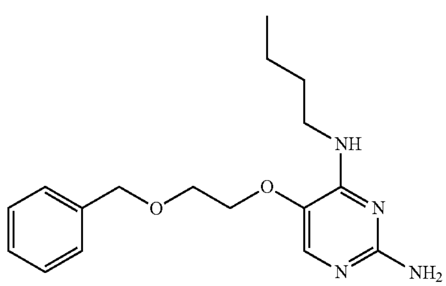 [SMILES: CCCCNc1nc(N)ncc1OCCOCc1ccccc1] | 316.19 | 317 | 0.95, D | ¹H NMR (360 MHz, DMSO-d₆) δ ppm 0.85 (t, J = 7.3 Hz, 3 H), 1.17-1.31 (m, 2 H), 1.33-1.46 (m, 2 H), 3.16-3.25 (m, 2 H), 3.71 (dd, J = 5.5, 3.7 Hz, 2 H), 3.96 (dd, J = 5.5, 3.7 Hz, 2 H), 4.55 (s, 2 H), 5.60 (s, 2 H), 6.26 (t, J = 5.5 Hz, 1 H), 7.26-7.37 (m, 5 H), 7.41 (s, 1 H) |
| 84 | 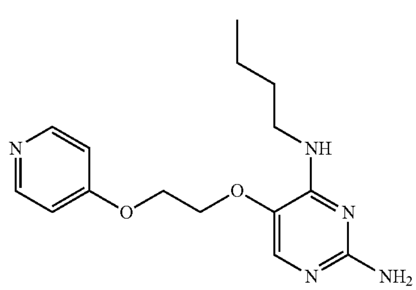 [SMILES: CCCCNc1nc(N)ncc1OCCOc1ccncc1] | 303.17 | 304 | 0.65, D | ¹H NMR (400 MHz, DMSO-d₆) δ ppm 0.86 (t, J = 7.28 Hz, 3 H) 1.20-1.31 (m, 2 H) 1.36-1.49 (m, 2 H) 3.17-3.27 (m, 2 H) 4.16 (dd, J = 5.27, 3.26 Hz, 2 H) 4.26-4.44 (m, 2 H) 5.57 (s, 2 H) 6.25 (s, 1 H) 6.93-7.09 (m, 2 H) 7.44 (s, 1 H) 8.30-8.52 (m, 2 H) |

TABLE I-continued

| | STRUCTURE | Exact Mass | Mass Found [M + H] | LCMS Ret Time, Method | 1H NMR |
|---|---|---|---|---|---|
| 85 | 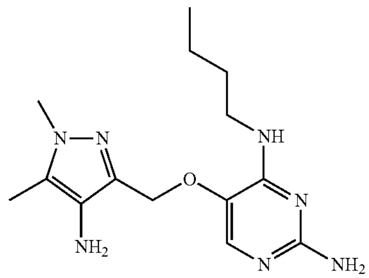 [SMILES: CCCCNc1nc(N)ncc1OCc1nn(C)c(C)c1N] | 305.20 | 306 | 0.45, D | not available |
| 86 | 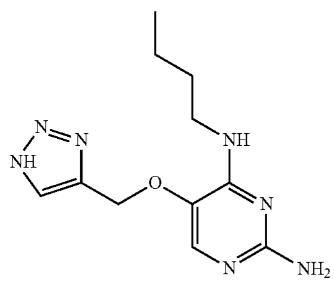 [SMILES: CCCCNc1nc(N)ncc1OCc1c[nH]nn1] | 263.15 | 264 | 0.58, D | ¹H NMR (400 MHz, DMSO-d₆) δ ppm 0.85-0.92 (m, 2 H) 1.18-1.36 (m, 2 H) 1.42-1.57 (m, 2 H) 3.23-3.52 (m, 2 H) 5.16 (s, 2 H) 7.53 (br. s., 2 H) 7.61 (d, J = 5.02 Hz, 1 H), 8.09 (s, 1 H) 8.38 (br. s., 1 H) 12.08 (s, 1 H) |
| 87 | 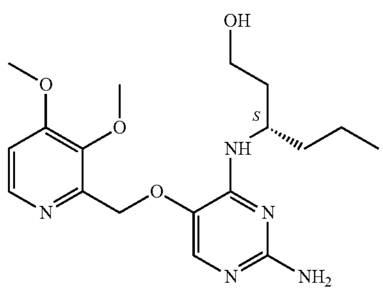 | 377.21 | 378 | 0.7, D | ¹H NMR (400 MHz, DMSO-d₆) δ ppm 0.86 (t, J = 7.40 Hz, 3 H) 1.19-1.32 (m, 2 H) 1.49-1.59 (m, 1 H) 1.66-1.79 (m, 2 H) 1.83-1.93 (m, 1 H) 3.35-3.48 (m, 2 H) 3.90 (s, 3 H) 4.09 (s, 3 H) 4.35-4.51 (m, 1 H) 5.32 (s, 2 H) 7.52 (br. s., 2 H) 7.56 (br. s., 1 H) 7.71 (d, J = 5.27 Hz, 1 H) 8.53 (d, J = 6.27 Hz, 1 H) 8.82 (br. s., 1 H) 12.01 (d, J = 4.27 Hz, 1 H) |
| 88 | 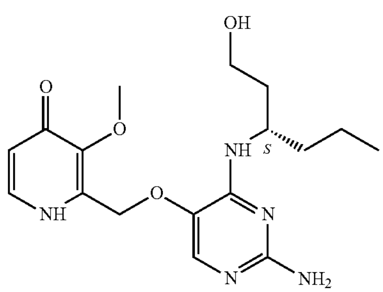 | 395.16 | 396 | 0.48, D | ¹H NMR (400 MHz, DMSO-d₆) δ ppm 0.84-0.91 (m, 3 H), 1.21-1.36 (m, 2 H), 1.47-1.55 (m, 2 H), 1.57-1.78 (m, 2 H), 3.45 (dd, J = 6.9, 6.1 Hz, 4 H), 3.76 (s, 3 H), 4.06-4.22 (m, 1 H), 4.89 (s, 2 H), 5.31 (s, 2 H), 6.07 (br. s., 1 H), 6.40 (d, J = 6.1 Hz, 1 H), 7.47 (s, 1 H), 7.67 (d, J = 6.5 Hz, 1 H) |
| 89 | 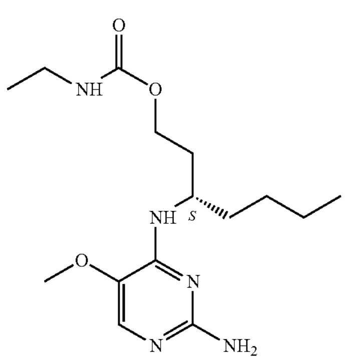 | 325.21 | 326 | 0.87, H | ¹H NMR (400 MHz, DMSO-d₆) δ ppm 0.84 (t, J = 6.78 Hz, 3 H) 0.99 (t, J = 7.15 Hz, 3 H) 1.11-1.36 (m, 4 H) 1.49 (m, J = 5.00 Hz, 2 H) 1.77 (q, J = 6.78 Hz, 2 H) 2.97 (quin, J = 6.78 Hz, 2 H) 3.67 (s, 3 H) 3.90 (m, J = 4.00 Hz, 2 H) 4.05-4.25 (m, 1 H) 5.40 (br. s., 2 H) 6.17 (d, J = 9.03 Hz, 1 H) 6.99 (br. t, J = 1.00, 1.00 Hz, 1 H) 7.35 (s, 1 H) |

TABLE I-continued

| | STRUCTURE | Exact Mass | Mass Found [M + H] | LCMS Ret Time, Method | 1H NMR |
|---|---|---|---|---|---|
| 90 | 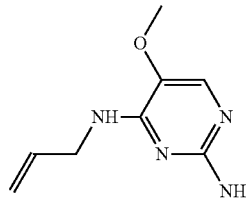 | 180.10 | 181 | 0.47, D | $^1$H NMR (400 MHz, CHLOROFORM-d) δ ppm 3.78 (s, 3 H), 4.06 (tt, J = 5.7, 1.5 Hz, 2 H), 4.44 (br. s., 2 H), 5.15 (dq, J = 10.3, 1.4 Hz, 1 H), 5.23 (br. s, 1 H), 5.23 (dq, J = 17.1, 1.7 Hz, 1 H), 5.94 (ddt, J = 17.2, 10.3, 5.6, 5.6 Hz, 1 H), 7.39 (s, 1 H) |
| 91 | 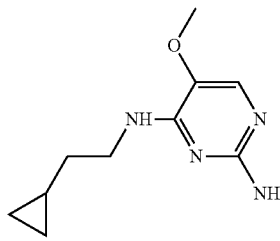 | 208.13 | 209 | 0.65, D | $^1$H NMR (400 MHz, CHLOROFORM-d) δ ppm 0.05-0.13 (m, 2 H), 0.42-0.52 (m, 2 H), 0.65-0.80 (m, 1 H), 1.50 (q, J = 7.0 Hz, 2 H), 3.49 (td, J = 7.0, 5.9 Hz, 2 H), 3.73-3.80 (m, 3 H), 4.42 (br. s., 2 H), 5.27 (br. s., 1 H), 7.36 (s, 1 H) |
| 92 | 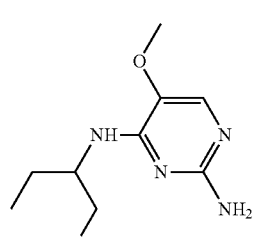 | 212.13 | 213 | 0.42, D | $^1$H NMR (400 MHz, DMSO-d$_6$) δ ppm 0.84 (t, J = 7.5 Hz, 3 H), 1.37-1.54 (m, 1 H), 1.54-1.71 (m, 1 H), 3.38 (dt, J = 10.7, 5.3 Hz, 1 H), 3.45 (dt, J = 10.4, 5.1 Hz, 1 H), 3.68 (s, 3 H), 3.85-4.02 (m, 1 H), 4.66 (t, J = 5.4 Hz, 1 H), 5.45 (br. s., 1 H), 5.88 (d, J = 8.8 Hz, 1 H), 7.36 (s, 1 H) |
| 93 | 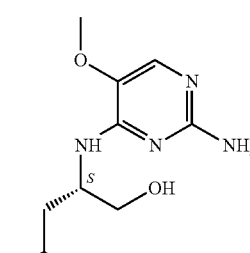 | 240.16 | 241 | 0.61, D | $^1$H NMR (400 MHz, DMSO-d$_6$) δ ppm 0.87 (dd, J = 6.7, 4.9 Hz, 6 H), 1.31-1.49 (m, 2 H), 1.50-1.64 (m, 1 H), 3.37-3.44 (m, 2 H), 3.67 (s, 3 H), 4.15 (tq, 6 J = 9.7, 4.8 Hz, 1 H), 4.65 (br. s., 1 H), 5.42 (s, 2 H), 5.88 (d, J = 9.3 Hz, 1 H), 7.35 (s, 1 H) |
| 94 | 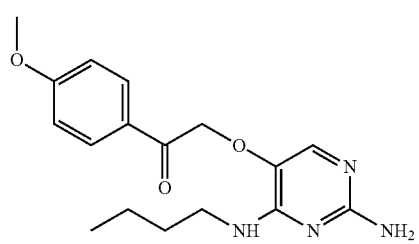 [SMILES: CCCCNc1nc(N)ncc1OCC(=O)c1ccc(OC)cc1] | 330.17 | 331 | 1.65, E | $^1$H NMR (300 MHz, CHLOROFORM-d) δ ppm 0.98 (t, J = 7.3 Hz, 3 H), 1.35-1.49 (m, 2 H), 1.54-1.74 (m, 2 H), 3.36-3.47 (m, 2 H), 3.88-3.96 (m, 3 H), 4.84 (br. s., 2 H), 5.19 (s, 2 H), 6.15 (br. s., 1 H), 6.94-7.05 (m, 2 H), 7.45 (s, 1 H), 7.86-7.98 (m, 2 H) |
| 95 | 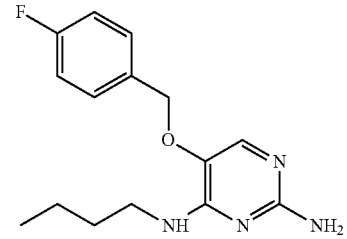 | 290.15 | 291 | 1.67, E | $^1$H NMR (300 MHz, METHANOL-d$_4$) δ ppm 0.84 (t, J = 7.3 Hz, 3 H), 1.17-1.33 (m, 2 H), 1.36-1.52 (m, 2 H), 3.26 (t, J = 7.1 Hz, 2 H), 4.86 (s, 2 H), 6.94-7.05 (m, 2 H), 7.17 (s, 1 H), 7.29-7.40 (m, 2 H), 3 labile protons not seen. |

TABLE I-continued

| | STRUCTURE | Exact Mass | Mass Found [M + H] | LCMS Ret Time, Method | 1H NMR |
|---|---|---|---|---|---|
| 96 | 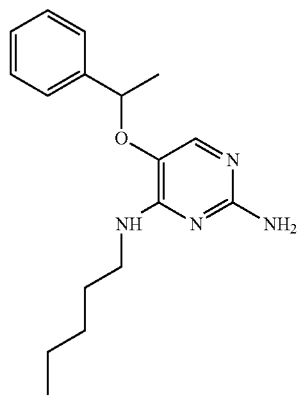 [SMILES: CCCCCNc1nc(N)ncc1OC(C)c1ccccc1] | 300.20 | 301 | 1.09, D | $^1$H NMR (400 MHz, DMSO-d$_6$) δ ppm 0.88 (t, J = 7.0 Hz, 3 H), 1.21-1.36 (m, 4 H), 1.46-1.51 (m, 2 H), 1.52 (d, J = 6.5 Hz, 3 H), 3.22-3.29 (m, 2 H), 5.17 (q, J = 6.3 Hz, 1 H), 5.41 (s, 2 H), 6.34 (t, J = 5.9 Hz, 1 H), 7.20 (s, 1 H), 7.23-7.29 (m, 1 H), 7.29-7.36 (m, 2 H), 7.38-7.44 (m, 2 H) |
| 97 | 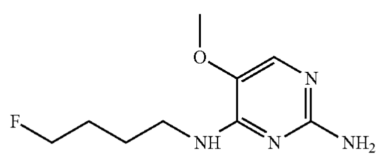 | 214.12 | 215 | 0.53, D | $^1$H NMR (400 MHz, CHLOROFORM-d) δ ppm 1.68-1.87 (m, 4 H), 3.46 (q, J = 6.5 Hz, 2 H), 3.77 (s, 2 H), 4.43 (br. s, 2 H), 4.38-4.48 (m, 1 H), 4.55 (t, J = 5.9 Hz, 1 H), 5.19 (br. s, 1 H), 7.37 (s, 1 H) |
| 98 | 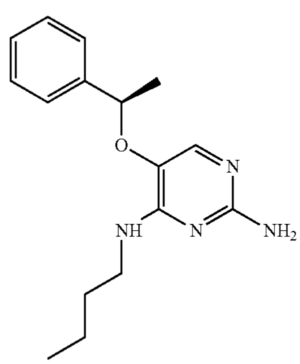 [SMILES: CCCCNc1nc(N)ncc1O[C@H](C)c1ccccc1] | 286.18 | 287 | 0.96, D | $^1$H NMR (400 MHz, DMSO-d$_6$) δ ppm 0.90 (t, J = 7.4 Hz, 3 H), 1.29 (dq, J = 14.9, 7.3 Hz, 2 H), 1.45-1.50 (m, 2 H), 1.52 (d, J = 6.5 Hz, 3 H), 3.23-3.30 (m, 2 H), 5.16 (q, J = 6.4 Hz, 1 H), 5.41 (s, 2 H), 6.33 (t, J = 5.9 Hz, 1 H), 7.20 (s, 1 H), 7.23-7.29 (m, 1 H), 7.29-7.36 (m, 2 H), 7.37-7.44 (m, 2 H) |
| 99 | 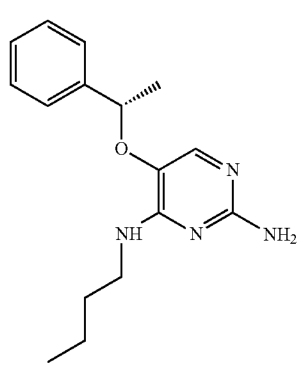 [SMILES: CCCCNc1nc(N)ncc1O[C@@H](C)c1ccccc1] | 286.18 | 287 | 0.97, D | $^1$H NMR (400 MHz, DMSO-d$_6$) δ ppm 0.90 (t, J = 7.4 Hz, 3 H), 1.29 (dq, J = 15.0, 7.3 Hz, 2 H), 1.44-1.50 (m, 2 H), 1.52 (d, J = 6.3 Hz, 3 H), 3.23-3.29 (m, 2 H), 5.17 (q, J = 6.3 Hz, 1 H), 5.42 (s, 2 H), 6.35 (t, J = 5.9 Hz, 1 H), 7.20 (s, 1 H), 7.22-7.29 (m, 1 H), 7.29-7.36 (m, 2 H), 7.38-7.44 (m, 2 H) |
| 100 | 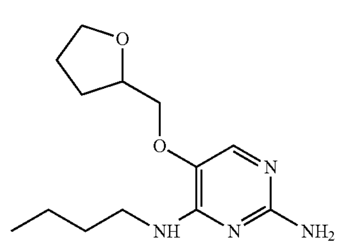 [SMILES: CCCCNc1nc(N)ncc1OCC1CCCO1] | 266.17 | 267 | 1.4, E | $^1$H NMR (300 MHz, CHLOROFORM-d) δ ppm 0.95 (t, J = 7.3 Hz, 3 H), 1.32-1.48 (m, 2 H), 1.51-1.61 (m, 2 H), 1.62-1.73 (m, 1 H), 1.88-1.98 (m, 2 H), 1.98-2.10 (m, 1 H), 3.38 (td, J = 7.0, 5.8 Hz, 2 H), 3.73-3.81 (m, 1 H), 3.82-3.95 (m, 3 H), 4.13-4.27 (m, 1 H), 4.73 (br. s, 2 H), 5.84 (br. s, 1 H), 7.42 (s, 1 H) |

TABLE I-continued

| | STRUCTURE | Exact Mass | Mass Found [M + H] | LCMS Ret Time, Method | 1H NMR |
|---|---|---|---|---|---|
| 101 | 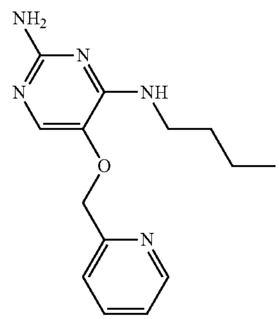 [SMILES: CCCCNc1nc(N)ncc1OCc1ccccn1] | 273.16 | 274 | 1.28, F | ¹H NMR (300 MHz, CHLOROFORM-d) δ ppm 0.89 (t, J = 7.4 Hz, 3 H), 1.26-1.43 (m, 2 H), 1.47-1.61 (m, 2 H), 3.35 (td, J = 7.0, 5.8 Hz, 2 H), 4.53 (br. s., 2 H), 4.97 (s, 2 H), 5.91 (br. s., 1 H), 7.16-7.24 (m, 1 H), 7.30 (d, J = 7.8 Hz, 1 H), 7.38 (s, 1 H), 7.66 (td, J = 7.7, 1.6 Hz, 1 H), 8.55 (d, J = 4.7 Hz, 1 H) |
| 102 | 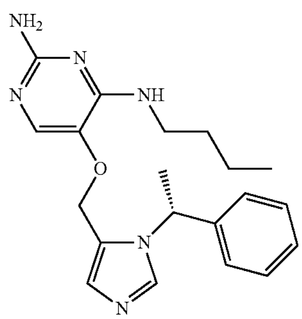 [SMILES: CCCCNc1nc(N)ncc1OCc1cncn1[C@H](C)c1ccccc1] | 366.22 | 367 | 0.83, D | ¹H NMR (400 MHz, DMSO-d₆) δ ppm 0.88 (t, J = 7.3 Hz, 3 H), 1.26 (dq, J = 14.8, 7.3 Hz, 2 H), 1.38-1.50 (m, 2 H), 1.82 (d, J = 7.3 Hz, 3 H), 3.12-3.29 (m, 2 H), 4.63 (d, J = 12.5 Hz, 1 H), 4.87 (d, J = 12.9 Hz, 1 H), 5.51 (s, 2 H), 5.58 (q, J = 6.9 Hz, 1 H), 6.08 (t, J = 5.9 Hz, 1 H), 7.01 (s, 1 H), 7.12-7.18 (m, 2 H), 7.25-7.30 (m, 1 H), 7.27 (s, 1 H), 7.30-7.37 (m, 2 H), 7.97 (s, 1 H) |
| 103 | 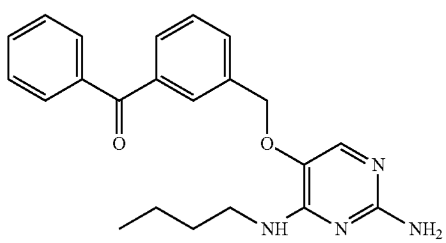 [SMILES: CCCCNc1nc(N)ncc1OCc1cccc(C(=O)c2ccccc2)c1] | 376.19 | 377 | 2.52, F | ¹H NMR (300 MHz, CHLOROFORM-d) δ ppm 0.82 (t, J = 7.3 Hz, 3 H), 1.18-1.33 (m, 2 H), 1.38-1.51 (m, 2 H), 3.22-3.34 (m, 2 H), 4.50 (br. s., 2 H), 4.92 (s, 2 H), 5.05-5.15 (m, 1 H), 7.13 (s, 1 H), 7.32-7.41 (m, 4 H), 7.43-7.52 (m, 1 H), 7.63-7.74 (m, 4 H) |
| 104 | 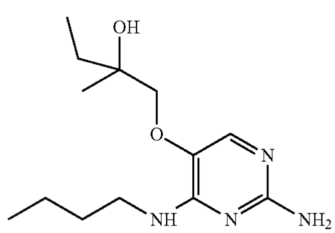 [SMILES: CCCCNc1nc(N)ncc1OCC(C)(O)CC] | 268.19 | 269 | 1.74, F | ¹H NMR (300 MHz, CHLOROFORM-d) δ ppm 0.89 (td, J = 7.4, 5.0 Hz, 6 H), 1.20 (s, 3 H), 1.25-1.39 (m, 2 H), 1.44-1.62 (m, 4 H), 1.81-2.20 (m, 1 H), 3.33 (td, J = 7.0, 5.8 Hz, 2 H), 3.60-3.69 (m, 2 H), 4.55 (br. s., 2 H), 5.40 (br. s., 1 H), 7.19 (s, 1 H) |
| 105 | 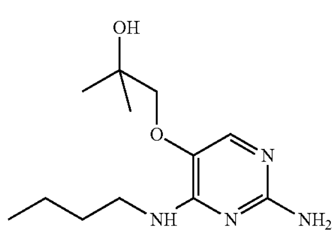 | 254.17 | 255 | 1.56, F | ¹H NMR (300 MHz, CHLOROFORM-d) δ ppm 0.84-0.93 (m, 3 H), 1.27 (s, 6 H), 1.28-1.39 (m, 2 H), 1.45-1.58 (m, 2 H), 3.34 (td, J = 7.0, 5.8 Hz, 2 H), 3.62-3.65 (m, 3 H), 4.62 (br. s., 2 H), 5.37-5.55 (m, 1 H), 7.32 (s, 1 H) |
| 106 | 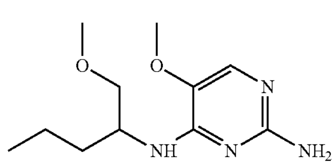 [SMILES: CCCC(COC)Nc1nc(N)ncc1OC] | 240.16 | 241 | 0.64, D | ¹H NMR (400 MHz, DMSO-d₆) δ ppm 0.86 (t, J = 7.3 Hz, 3 H), 1.15-1.35 (m, 2 H), 1.44-1.60 (m, 2 H), 3.23 (s, 2 H), 3.35-3.38 (m, 1 H), 3.40-3.47 (m, 1H), 3.77 (s, 3 H), 4.36-4.49 (m, 1 H), 7.39 (s, 1 H), 7.44 (br. s., 2 H), 8.16 (d, J = 8.8 Hz, 1 H), 11.88 (br. s., 1 H) |

TABLE I-continued

| | STRUCTURE | Exact Mass | Mass Found [M + H] | LCMS Ret Time, Method | 1H NMR |
|---|---|---|---|---|---|
| 107 | 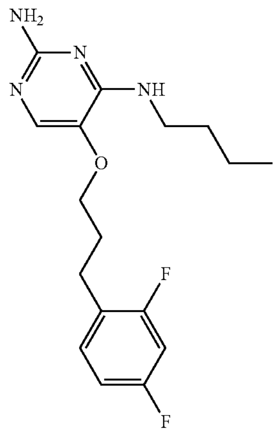 [SMILES: CCCCNc1nc(N)ncc1OCCCc1ccc(F)cc1F] | 336.18 | 337 | 2.57, F | ¹H NMR (300 MHz, CHLOROFORM-d) δ ppm 0.97 (t, J = 7.2 Hz, 3 H), 1.32-1.48 (m, 2 H), 1.52-1.66 (m, 2 H), 2.01-2.14 (m, 2 H), 2.78 (t, J = 7.5 Hz, 2 H), 3.33-3.47 (m, 2 H), 3.91 (t, J = 6.1 Hz, 2 H), 4.55 (br. s., 2 H), 5.12 (br. s., 1 H), 6.74-6.88 (m, 2 H), 7.07-7.22 (m, 1 H), 7.31 (s, 1 H) |
| 108 | 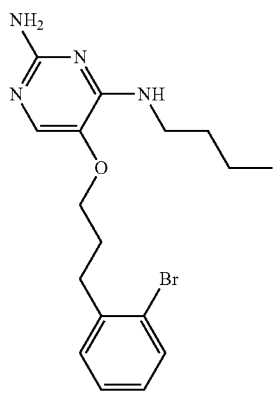 [SMILES: CCCCNc1nc(N)ncc1OCCCc1ccccc1Br] | 378.11 | 379 | 2.62, F | ¹H NMR (300 MHz, CHLOROFORM-d) δ ppm 0.89 (t, J = 7.3 Hz, 3 H), 1.24-1.40 (m, 2 H), 1.44-1.58 (m, 2 H), 1.96-2.09 (m, 2 H), 2.73-2.90 (m, 2 H), 3.26-3.43 (m, 2 H), 3.87 (t, J = 6.1 Hz, 2 H), 4.43 (br. s., 2 H), 5.09 (br. s., 1 H), 6.93-7.06 (m, 1 H), 7.11-7.22 (m, 3 H), 7.48 (d, J = 8.2 Hz, 1 H) |
| 109 | 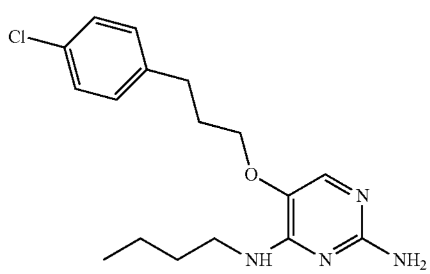 [SMILES: CCCCNc1nc(N)ncc1OCCCc1ccc(Cl)cc1] | 334.16 | 335 | 2.68, F | ¹H NMR (300 MHz, CHLOROFORM-d) δ ppm 0.83-0.97 (m, 3 H), 1.25-1.41 (m, 2 H), 1.50 (dt, J = 14.6, 7.3 Hz, 2 H), 1.93-2.05 (m, 2 H), 2.68 (t, J = 7.5 Hz, 2 H), 3.24-3.40 (m, 2 H), 3.82 (t, J = 6.2 Hz, 2 H), 4.42 (br. s., 2 H), 4.95 (br. s., 1 H), 7.01-7.12 (m, 2 H), 7.16-7.22 (m, 3 H) |
| 110 | 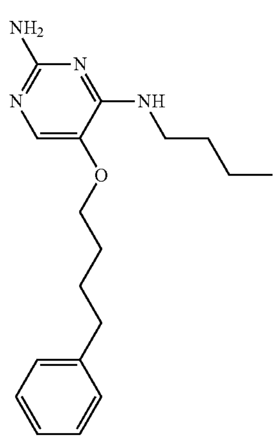 [SMILES: CCCCNc1nc(N)ncc1OCCCCc1ccccc1] | 314.21 | 315 | 2.64, F | ¹H NMR (300 MHz, CHLOROFORM-d) δ ppm 0.88 (t, J = 7.3 Hz, 3 H), 1.31 (dq, J = 15.0, 7.3 Hz, 2 H), 1.43-1.57 (m, 2 H), 1.65-1.78 (m, 4 H), 2.61 (t, J = 6.9 Hz, 2 H), 3.27-3.38 (m, 2 H), 3.77-3.89 (m, 2 H), 4.48 (br. s., 2 H), 5.09 (br. s., 1 H), 7.09-7.16 (m, 3 H), 7.18-7.23 (m, 3 H) |

TABLE I-continued

| | STRUCTURE | Exact Mass | Mass Found [M + H] | LCMS Ret Time, Method | 1H NMR |
|---|---|---|---|---|---|
| 111 | 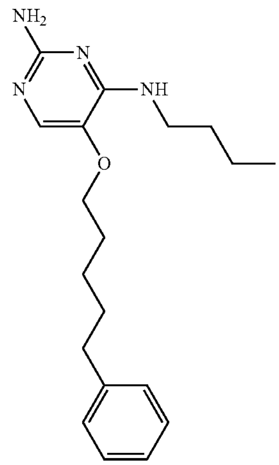 [SMILES: CCCCNc1nc(N)ncc1OCCCCCc1ccccc1] | 328.23 | 329 | 2.75, F | $^1$H NMR (300 MHz, CHLOROFORM-d) δ ppm 0.88 (t, J = 7.3 Hz, 3 H), 1.24-1.43 (m, 4 H), 1.44-1.55 (m, 2 H), 1.55-1.65 (m, 2 H), 1.66-1.77 (m, 2 H), 2.57 (t, J = 7.6 Hz, 2 H), 3.25-3.37 (m, 2 H), 3.80 (t, J = 6.5 Hz, 2 H), 4.45 (br. s., 2 H), 5.07 (br. s., 1 H), 7.07-7.15 (m, 3 H), 7.17-7.24 (m, 3 H) |
| 112 | 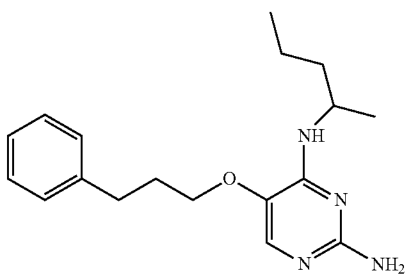 [SMILES: CCCC(C)Nc1nc(N)ncc1OCCCc1ccccc1] | 314.21 | 315 | 1.12, D | $^1$H NMR (400 MHz, DMSO-d$_6$) δ ppm 0.86 (t, J = 7.28 Hz, 3 H) 1.11 (d, J = 6.53 Hz, 3 H) 1.20-1.35 (m, 2 H) 1.36-1.59 (m, 2 H) 1.94-2.05 (m, 2 H) 2.65-2.78 (m, 2 H) 3.83 (t, J = 6.40 Hz, 2 H) 4.07-4.18 (m, 1 H) 5.60 (s, 2 H) 5.99 (d, J = 8.53 Hz, 1 H) 7.14-7.32 (m, 5 H) 7.33 (s, 1 H) |
| 113 | 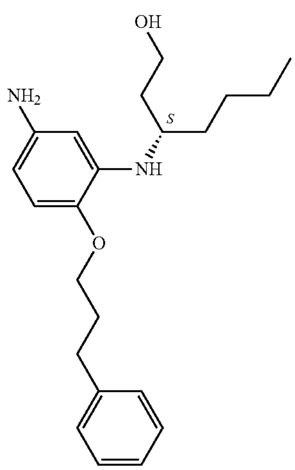 | 358.24 | 359 | 1.04, D | $^1$H NMR (400 MHz, DMSO-d$_6$) δ ppm 0.79-0.87 (m, 3 H) 1.18-1.31 (m, 4 H) 1.42-1.59 (m, 2 H) 1.59-1.75 (m, 2 H) 1.94-2.02 (m, 2 H) 2.66-2.75 (m, 2 H) 3.41-3.50 (m, 2 H) 3.79-3.87 (m, 2 H) 4.10-4.18 (m, 1 H) 4.44-4.49 (m, 1 H) 5.71 (br. s., 2 H) 6.25 (br. s., 1 H) 7.12-7.31 (m, 5 H) 7.33 (s, 1 H) |
| 114 | 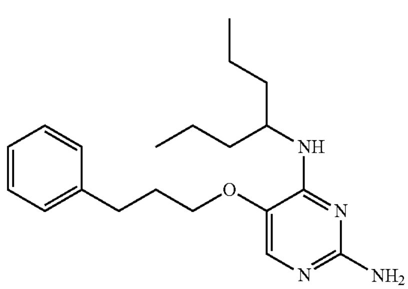 [SMILES: CCCC(CCC)Nc1nc(N)ncc1OCCCc1ccccc1] | 342.24 | 343 | 1.25, D | $^1$H NMR (400 MHz, DMSO-d$_6$) δ ppm 0.85 (t, J = 7.28 Hz, 6 H) 1.13-1.38 (m, 4 H) 1.38-1.54 (m, 4 H) 1.95-2.09 (m, 2 H) 2.72 (t, J = 7.15 Hz, 2 H) 3.71-3.85 (m, 2 H) 4.01-4.21 (m, 1 H) 5.59 (br. s., 2 H) 5.92 (d, J = 9.03 Hz, 1 H) 7.29 (s, 1 H) 7.15-7.43 (m, 5 H) |

TABLE I-continued

| | STRUCTURE | Exact Mass | Mass Found [M + H] | LCMS Ret Time, Method | 1H NMR |
|---|---|---|---|---|---|
| 115 | 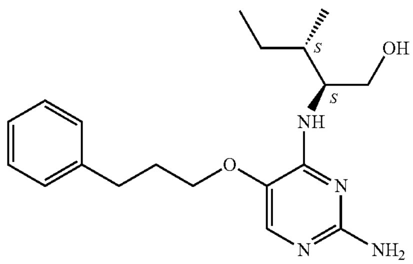 | 344.22 | 345 | 0.98, D | ¹H NMR (400 MHz, DMSO-d₆) δ ppm 0.82-0.88 (m, 3 H) 0.89 (d, J = 6.86 Hz, 3 H) 1.06-1.17 (m, 1 H) 1.44-1.53 (m, 1 H) 1.71-1.78 (m, 1 H) 1.95-2.04 (m, 2 H) 2.72 (t, J = 7.67 Hz, 2 H) 3.48-3.60 (m, 2 H) 3.84-3.90 (m, 2 H) 3.90-3.96 (m, 1 H) 4.38 (t, J = 5.25 Hz, 1 H), 5.21 (br. s., 2 H) 5.55 (d, J = 8.88 Hz, 1 H) 7.14-7.31 (m, 5 H) 7.37 (s, 1 H) |
| 116 | 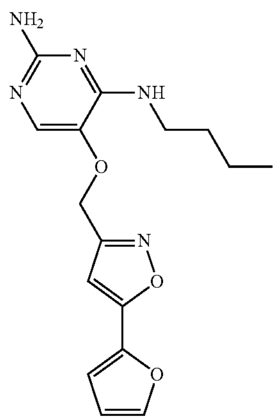 [SMILES: CCCCNc1nc(N)ncc1OCc1cc(-c2ccco2)on1] | 329.15 | 330 | 0.9, D | ¹H NMR (400 MHz, DMSO-d₆) δ ppm 0.86 (t, J = 7.40 Hz, 3 H) 1.21-1.33 (m, 2 H) 1.42-1.53 (m, 2 H) 3.24-3.31 (m, 2 H) 5.04 (s, 2 H) 5.58 (s, 2 H) 6.52 (t, J = 5.90 Hz, 1 H) 6.73 (dd, J = 3.51, 1.76 Hz, 1 H) 6.99 (s, 1 H) 7.14 (d, J = 3.26 Hz, 1 H) 7.49 (s, 1 H) 7.96 (dd, J = 1.76, 0.50 Hz, 1 H) |
| 117 | 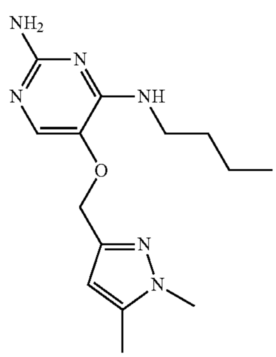 [SMILES: CCCCNc1nc(N)ncc1OCc1cc(C)n(C)n1] | 290.19 | 291 | 0.75, D | ¹H NMR (400 MHz, DMSO-d₆) δ ppm 0.89 (t, J = 7.40 Hz, 3 H) 1.28 (quin, J = 1.00 Hz, 2 H) 1.43-1.52 (m, 2 H) 2.22 (s, 3 H) 3.21-3.27 (m, 2 H) 3.68 (s, 3 H) 4.76 (s, 2 H) 5.48 (s, 2 H) 6.10 (s, 1 H) 6.26 (t, J = 5.65 Hz, 1 H) 7.40 (s, 1 H) |
| 118 | 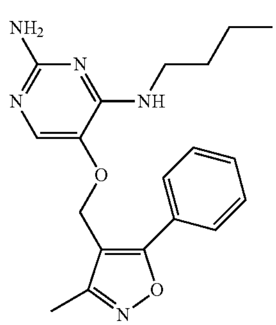 [SMILES: CCCCNc1nc(N)ncc1OCc1c(C)noc1-c1ccccc1] | 353.19 | 354 | 0.97, D | ¹H NMR (400 MHz, DMSO-d₆) δ ppm 0.86 (t, J = 7.40 Hz, 3 H) 1.20-1.30 (m, 2 H) 1.40-1.49 (m, 2 H) 2.27 (s, 3 H) 3.21-3.29 (m, 2 H) 4.87 (s, 2 H) 5.56 (s, 2 H) 6.40 (t, J = 5.77 Hz, 1 H) 7.37 (s, 1 H) 7.53-7.60 (m, 3 H) 7.71-7.77 (m, 2 H) |

TABLE I-continued

| | STRUCTURE | Exact Mass | Mass Found [M + H] | LCMS Ret Time, Method | 1H NMR |
|---|---|---|---|---|---|
| 119 | 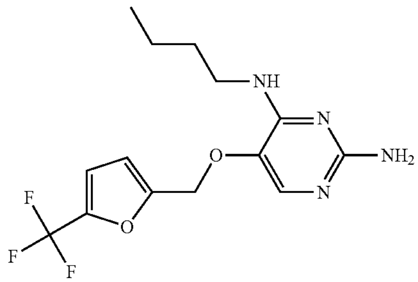 [SMILES: CCCCNc1nc(N)ncc1OCc1ccc(C(F)(F)F)o1] | 330.13 | 331 | 0.99, D | $^1$H NMR (400 MHz, DMSO-d$_6$) δ ppm 0.88 (t, J = 7.28 Hz, 3 H) 1.21-1.33 (m, 2 H) 1.41-1.52 (m, 2 H) 3.16-3.29 (m, 2 H) 4.95 (s, 2 H) 5.58 (s, 2 H) 6.39 (t, J = 5.77 Hz, 1 H) 6.78 (d, J = 3.01 Hz, 1 H) 7.21 (dd, J = 3.51, 1.25 Hz, 1 H) 7.38 (s, 1 H) |
| 120 | 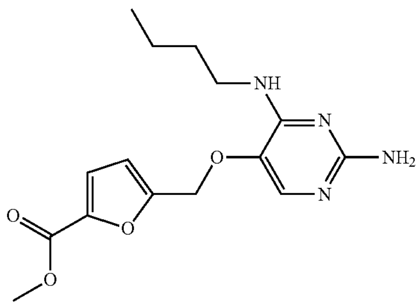 [SMILES: CCCCNc1nc(N)ncc1OCc1ccc(C(=O)OC)o1] | 320.15 | 321 | 0.79, D | $^1$H NMR (400 MHz, DMSO-d$_6$) δ ppm 0.88 (t, J = 7.40 Hz, 3 H) 1.22-1.32 (m, 2 H) 1.42-1.52 (m, 2 H) 3.21-3.28 (m, 2 H) 3.81 (s, 3 H) 4.94 (s, 2 H) 5.57 (s, 2 H) 6.38 (t, J = 5.65 Hz, 1 H) 6.75 (d, J = 3.51 Hz, 1 H) 7.29 (d, J = 3.51 Hz, 1 H) 7.39 (s, 1 H) |
| 121 | 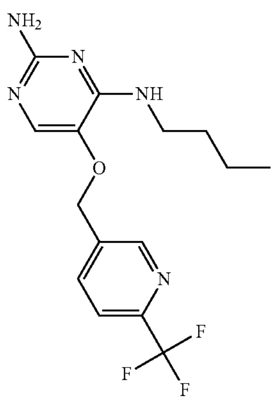 [SMILES: CCCCNc1nc(N)ncc1OCc1ccc(C(F)(F)F)nc1] | 341.15 | 342 | 0.89, D | $^1$H NMR (400 MHz, DMSO-d$_6$) δ ppm 0.89 (t, J = 7.28 Hz, 3 H) 1.20-1.35 (m, 2 H) 1.39-1.55 (m, 2 H) 3.21-3.30 (m, 2 H) 5.11 (s, 2 H) 5.54 (s, 2 H) 6.58 (s, 1 H) 7.47 (s, 1 H) 7.93 (d, J = 8.03 Hz, 1 H) 8.14-8.22 (m, 1 H) 8.85-8.93 (m, 1 H) |
| 122 | 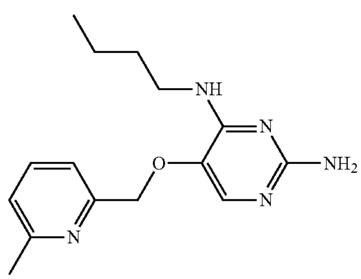 [SMILES: CCCCNc1nc(N)ncc1OCc1cccc(C)n1] | 287.17 | 288 | 0.79, D | $^1$H NMR (400 MHz, DMSO-d$_6$) δ ppm 0.90 (t, J = 7.28 Hz, 3 H) 1.23-1.37 (m, 2 H) 1.45-1.58 (m, 2 H) 2.48 (s, 3 H) 3.29-3.33 (m 2 H) 4.93 (s, 2 H) 5.54 (s, 2 H) 6.75 (s, 1 H) 7.20 (d, J = 7.78 Hz, 1 H) 7.37 (d, J = 7.53 Hz, 1 H) 7.40 (s, 1 H) 7.71 (t, J = 7.65 Hz, 1 H) |
| 123 | 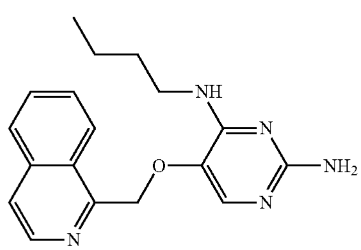 [SMILES: CCCCNc1nc(N)ncc1OCc1nccc2ccccc12] | 323.17 | 324 | 0.87, D | $^1$H NMR (400 MHz, DMSO-d$_6$) δ ppm 0.82-0.91 (m, 3 H) 1.18-1.28 (m, 2 H) 1.38-1.47 (m, 2H) 3.19-3.27 (m, 2 H) 5.50 (s, 2 H) 5.52 (s, 2 H) 6.49 (s, 1 H) 7.44 (s, 1 H) 7.71 (ddd, J = 8.41, 7.03, 1.13 Hz, 1 H) 7.81 (ddd, J = 8.09, 6.96, 1.25 Hz, 1 H) 7.85 (d, J = 5.52 Hz, 1 H) 8.02 (d, J = 8.03 Hz, 1 H) 8.38-8.42 (m, 1 H) 8.48 (d, J = 5.77 Hz, 1 H) |

TABLE I-continued

| | STRUCTURE | Exact Mass | Mass Found [M + H] | LCMS Ret Time, Method | 1H NMR |
|---|---|---|---|---|---|
| 124 | 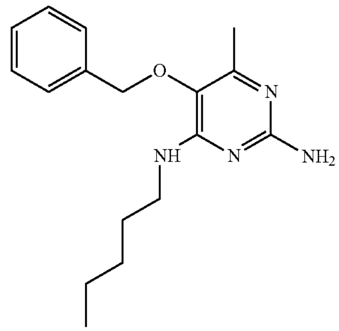 [SMILES: CCCCCNc1nc(N)nc(C)c1OCc1ccccc1] | 300.20 | 301 | 1.08, D | $^1$H NMR (400 MHz, DMSO-d$_6$) δ ppm 0.88 (t, J = 7.2 Hz, 3 H), 1.16-1.37 (m, 4 H), 1.53 (quin, J = 7.3 Hz, 2 H), 2.03 (s, 3 H), 3.37 (q, J = 6.6 Hz, 2 H), 4.36 (br. s., 2 H), 4.83 (s, 2 H), 7.29-7.58 (m, 5 H), 8.30 (t, J = 5.9 Hz, 1 H), 12.68 (br. s., 1 H) |
| 125 | 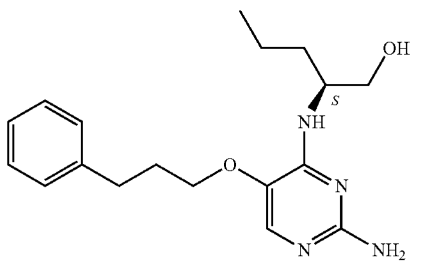 | 330.21 | 331 | 0.9, D | $^1$H NMR (400 MHz, DMSO-d$_6$) δ ppm 0.87 (t, J = 7.28 Hz, 3 H) 1.19-1.38 (m, 2 H) 1.40-1.51 (m, 1 H) 1.51-1.62 (m, 1 H) 1.94-2.02 (m, 2 H) 2.66-2.76 (m, 2 H) 3.38-3.48 (m, 2 H) 3.83 (td, J = 6.34, 2.64 Hz, 2 H) 4.00-4.10 (m, 1 H) 4.69 (br. s., 1 H) 5.48 (s, 2 H) 5.72-5.79 (m, 1 H) 7.05-7.33 (m, 5 H) 7.35 (s, 1 H) |
| 126 | 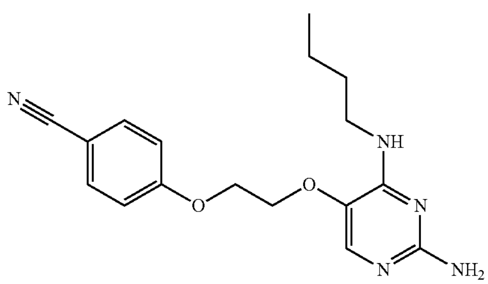 [SMILES: CCCCNc1nc(N)ncc1OCCOc1ccc(C#N)cc1] | 327.17 | 328 | 0.84, D | $^1$H NMR (400 MHz, DMSO-d$_6$) δ ppm 0.86 (t, J = 7.40 Hz, 3 H) 1.19-1.31 (m, 2 H) 1.37-1.48 (m, 2 H) 3.20-3.27 (m, 2 H) 4.13-4.23 (m, 2 H) 4.30-4.42 (m, 2 H) 5.57 (s, 2 H) 6.22 (s, 1 H) 7.12-7.20 (m, 2 H) 7.45 (s, 1 H) 7.75-7.83 (m, 2 H) |
| 127 | 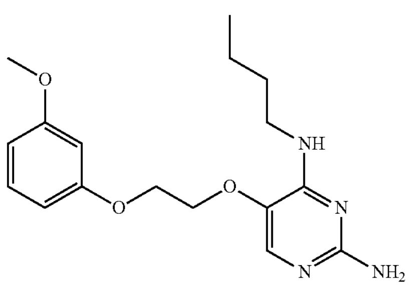 [SMILES: CCCCNc1nc(N)ncc1OCCOc1cccc(OC)c1] | 332.18 | 333 | 0.94, D | $^1$H NMR (400 MHz, DMSO-d$_6$) δ ppm 0.80-0.91 (m, 3 H) 1.20-1.32 (m, 2 H) 1.37-1.50 (m, 2 H) 3.17-3.28 (m, 2 H) 3.73 (s, 3 H) 4.13 (dd, J = 5.52, 3.26 Hz, 2 H) 4.23 (dd, J = 5.52, 3.26 Hz, 2 H) 5.56 (s, 2 H) 6.20 (s, 1 H) 6.49-6.59 (m, 3 H) 7.16-7.22 (m, 1 H) 7.45 (s, 1 H) |
| 128 | 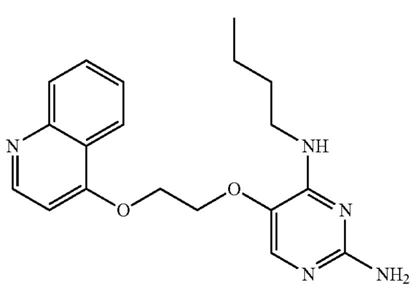 [SMILES: CCCCNc1nc(N)ncc1OCCOc1ccnc2ccccc12] | 353.19 | 354 | 0.79, D | $^1$H NMR (400 MHz, DMSO-d$_6$) δ ppm 0.76 (t, J = 7.28 Hz, 3 H) 1.11-1.21 (m, 2 H) 1.32 (t, J = 7.15 Hz, 2 H) 3.15-3.22 (m, 2 H) 4.32-4.36 (m, 2 H) 4.52-4.56 (m, 2 H) 5.57 (s, 2 H) 6.24 (s, 1 H) 7.07 (d, J = 5.27 Hz, 1 H) 7.55 (s, 1 H) 7.52-7.58 (m, 1 H) 7.74 (ddd, J = 8.41, 6.90, 1.25 Hz, 1 H) 7.95 (d, J = 8.03 Hz, 1 H) 8.12 (dd, J = 8.28, 1.00 Hz, 1 H) 8.73 (d, J = 5.27 Hz, 1 H) |

TABLE I-continued

| | STRUCTURE | Exact Mass | Mass Found [M + H] | LCMS Ret Time, Method | 1H NMR |
|---|---|---|---|---|---|
| 129 | 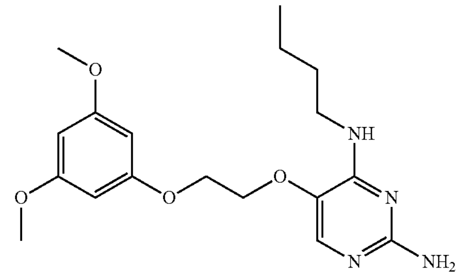 [SMILES: CCCCNc1nc(N)ncc1OCCOc1cc(OC)cc(OC)c1] | 362.20 | 363 | 0.92, D | ¹H NMR (400 MHz, DMSO-d₆) δ ppm 0.78-0.93 (m, 3 H) 1.12-1.35 (m, 2 H) 1.39-1.54 (m, 2 H) 3.18-3.28 (m, 2 H) 4.07-4.17 (m, 2 H) 4.21 (dd, J = 5.52, 3.01 Hz, 2 H) 5.58 (br. s., 2 H) 6.09-6.12 (m, 1 H) 6.14 (d, J = 2.26 Hz, 2 H) 6.21 (s, 1 H) 7.45 (s, 1 H) |
| 130 | 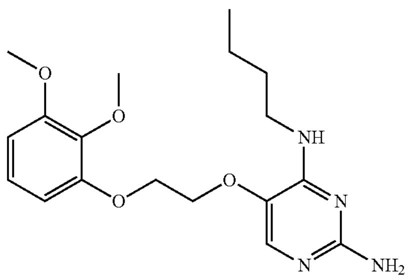 [SMILES: CCCCNc1nc(N)ncc1OCCOc1cccc(OC)c1OC] | 362.20 | 363 | 0.87, D | ¹H NMR (400 MHz, DMSO-d₆) δ ppm 0.86 (t, J = 7.28 Hz, 3 H) 1.20-1.31 (m, 2 H) 1.39-1.48 (m, 2 H) 3.21-3.28 (m, 2 H) 3.67 (s, 3 H) 3.77 (s, 3 H) 4.11-4.18 (m, 2 H) 4.22-4.29 (m, 2 H) 5.56 (s, 2 H) 6.18 (t, J = 5.90 Hz, 1 H) 6.66-6.74 (m, 2 H) 6.96-7.01 (m, 1 H) 7.47 (s, 1 H) |
| 131 | 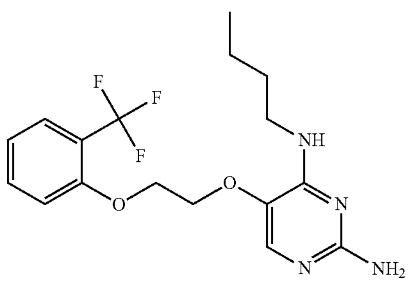 [SMILES: CCCCNc1nc(N)ncc1OCCOc1ccccc1C(F)(F)F] | 370.16 | 371 | 1.05, D | ¹H NMR (400 MHz, DMSO-d₆) δ ppm 0.85 (t, J = 7.28 Hz, 3 H) 1.18-1.30 (m, 2 H) 1.36-1.47 (m, 2 H) 3.17-3.28 (m, 2 H) 4.12-4.22 (m, 2 H) 4.33-4.43 (m, 2 H) 5.61 (s, 2 H) 5.98 (s, 1 H) 7.09-7.15 (m, 1 H) 7.33 (d, J = 8.53 Hz, 1 H) 7.47 (s, 1 H) 7.63 (d, J = 7.78 Hz, 2 H) |
| 132 | 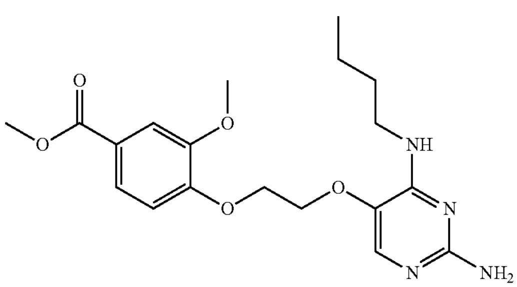 [SMILES: CCCCNc1nc(N)ncc1OCCOc1ccc(C(=O)OC)cc1OC] | 390.19 | 391 | 0.86, D | ¹H NMR (400 MHz, DMSO-d₆) δ ppm 0.85 (t, J = 7.28 Hz, 3 H) 1.19-1.32 (m, 2 H) 1.37-1.49 (m, 2 H) 3.17-3.28 (m, 2 H) 3.83 (s, 3 H) 3.82 (s, 3 H) 4.16 (dd, J = 5.27, 3.26 Hz, 2 H) 4.32 (dd, J = 5.27, 3.26 Hz, 2 H) 5.59 (s, 2 H) 6.18 (s, 1 H) 7.14 (d, J = 8.53 Hz, 1 H) 7.45-7.53 (m, 2 H) 7.59 (dd, J = 8.53-2.01 Hz, 1 H) |
| 133 | 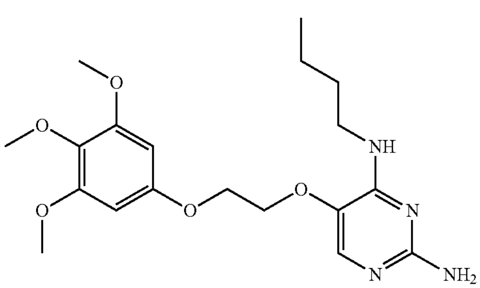 [SMILES: CCCCNc1nc(N)ncc1OCCOc1cc(OC)c(OC)c(OC)c1] | 392.21 | 393 | 0.84, D | ¹H NMR (400 MHz, DMSO-d₆) δ ppm 0.86 (t, J = 7.40 Hz, 3 H) 1.20-1.34 (m, 2 H) 1.40-1.52 (m, 2 H) 3.14-3.28 (m, 2 H) 3.58 (s, 3 H) 3.75 (s, 6 H) 4.13 (dd, J = 5.52, 3.26 Hz, 2 H) 4.23 (dd, J = 5.52, 3.01 Hz, 2 H) 5.58 (s, 2 H) 6.22 (s, 1 H) 6.28 (s, 2 H) 7.46 (s, 1 H) |

TABLE I-continued

| | STRUCTURE | Exact Mass | Mass Found [M + H] | LCMS Ret Time, Method | 1H NMR |
|---|---|---|---|---|---|
| 134 | 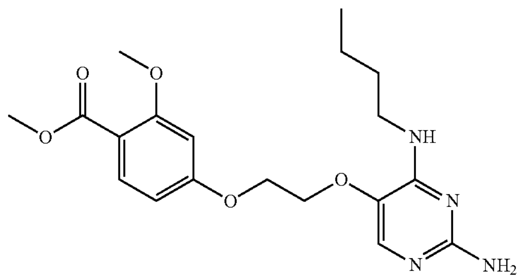 [SMILES: CCCCNc1nc(N)ncc1OCCOc1ccc(C(=O)OC)c(OC)c1] | 390.19 | 391 | 0.83, D | $^1$H NMR (400 MHz, DMSO-d$_6$) δ ppm 0.85 (t, J = 7.40 Hz, 3 H) 1.20-1.30 (m, 2 H) 1.39-1.48 (m, 2 H) 3.20-3.28 (m, 2 H) 3.73 (s, 3 H) 3.81 (s, 3 H) 4.13-4.19 (m, 2 H) 4.34 (dd, J = 5.27, 3.26 Hz, 2 H) 5.56 (s, 2 H) 6.20 (s, 1 H) 6.63 (dd, J = 8.66, 2.38 Hz, 1 H) 6.68 (d, J = 2.26 Hz, 1 H) 7.46 (s, 1 H) 7.71 (d, J = 8.53 Hz, 1 H) |
| 135 | 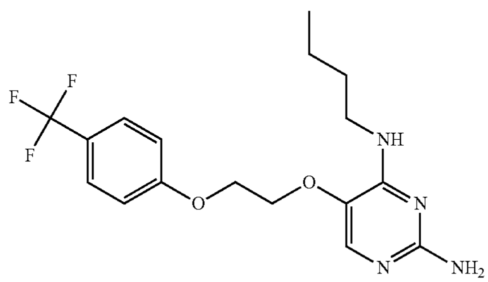 [SMILES: CCCCNc1nc(N)ncc1OCCOc1ccc(C(F)(F)F)cc1] | 370.16 | 371 | 1.06, D | $^1$H NMR (400 MHz, DMSO-d$_6$) δ ppm 0.85 (t, J = 7.40 Hz, 3 H) 1.18-1.34 (m, 2 H) 1.36-1.47 (m, 2 H) 3.17-3.27 (m, 2 H) 4.13-4.23 (m, 2 H) 4.29-4.41 (m, 2 H) 5.57 (s, 2 H) 6.21 (s, 1 H) 7.17 (m, J = 8.53 Hz, 2 H) 7.46 (s, 1 H) 7.67 (m, J = 8.53 Hz, 2 H) |
| 136 | 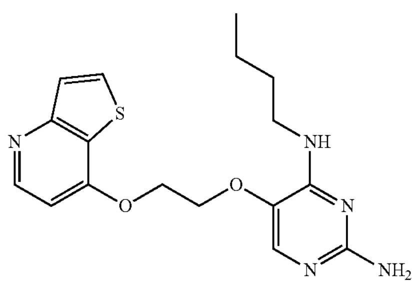 [SMILES: CCCCNc1nc(N)ncc1OCCOc1ccnc2ccsc12] | 359.14 | 360 | 0.77, D | $^1$H NMR (400 MHz, DMSO-d$_6$) δ ppm 0.81 (t, J = 7.40 Hz, 3 H) 1.16-1.25 (m, 2 H) 1.34-1.42 (m, 2 H) 3.19-3.25 (m, 2 H) 4.24-4.28 (m, 2 H) 4.55-4.60 (m, 2 H) 5.57 (s, 2 H) 6.16 (s, 1 H) 7.07 (d, J = 5.27 Hz, 1 H) 7.50 (s, 1 H) 7.53 (d, J = 5.52 Hz, 1 H) 8.07 (d, J = 5.52 Hz, 1 H) 8.55 (d, J = 5.52 Hz, 1 H) |
| 137 | 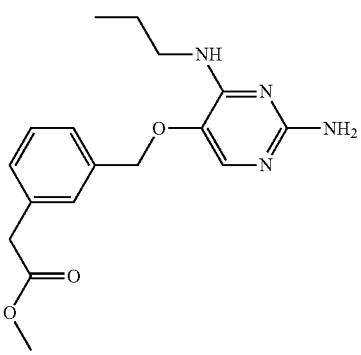 [SMILES: CCCNc1nc(N)ncc1OCc1cccc(CC(=O)OC)c1] | 344.18 | 345 | 0.88, D | $^1$H NMR (400 MHz, DMSO-d$_6$) δ ppm 0.89 (t, J = 7.40 Hz, 3 H) 1.22-1.34 (m, 2 H) 1.44-1.54 (m, 2 H) 3.25-3.30 (m, 2 H) 3.61 (s, 3 H) 3.69 (s, 2 H) 4.93 (s, 2 H) 5.50 (s, 2 H) 6.39 (s, 1 H) 7.22 (d, J = 6.00 Hz, 1 H) 7.33 (s, 1 H) 7.28-7.37 (m, 2 H) 7.38 (s, 1 H) |
| 138 | 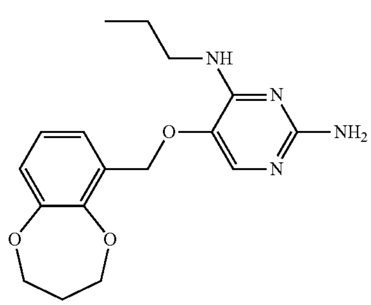 [SMILES: CCCNc1nc(N)ncc1OCc1cccc2c1OCCCO2] | 344.18 | 345 | 0.94, D | $^1$H NMR (400 MHz, DMSO-d$_6$) δ ppm 0.89 (t, J = 7.40 Hz, 3 H) 1.20-1.37 (m, 2 H) 1.42-1.57 (m, 2 H) 2.02-2.19 (m, 2 H) 3.26-3.32 (m, 2 H) 4.07-4.18 (m, 4 H) 4.89 (s, 2 H) 5.52 (s, 2 H) 6.31 (s, 1 H) 6.88-7.04 (m, 2 H) 7.12 (d, J = 6.70 Hz, 1 H) 7.37 (s, 1 H) |

TABLE I-continued

| | STRUCTURE | Exact Mass | Mass Found [M + H] | LCMS Ret Time, Method | 1H NMR |
|---|---|---|---|---|---|
| 139 | 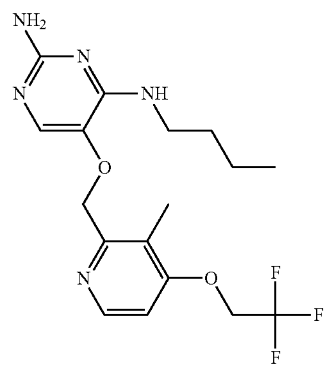 [SMILES: CCCCNc1nc(N)ncc1OCc1nccc(OCC(F)(F)F)c1C] | 385.17 | 386 | 0.93, D | $^1$H NMR (400 MHz, DMSO-d$_6$) δ ppm 0.88 (t, J = 7.28 Hz, 3 H) 1.22-1.36 (m, 2 H) 1.42-1.57 (m, 2 H) 2.20 (s, 3 H) 3.22-3.29 (m, 2 H) 4.84-4.98 (m, 2 H) 5.01 (s, 2 H) 5.50 (s, 2 H) 6.59 (s, 1 H) 7.13 (d, J = 5.77 Hz, 1 H) 7.40 (s, 1 H) 8.34 (d, J = 5.52 Hz, 1 H) |
| 140 | 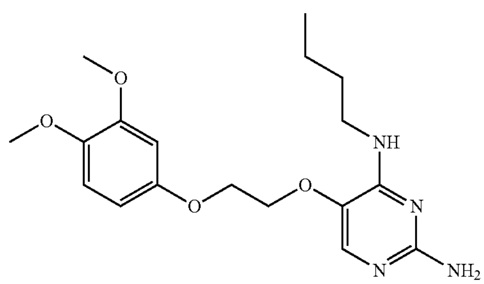 [SMILES: CCCCNc1nc(N)ncc1OCCOc1ccc(OC)c(OC)c1] | 362.20 | 363 | 0.71, D | $^1$H NMR (400 MHz, DMSO-d$_6$) δ ppm 0.86 (t, J = 7.28 Hz, 3 H) 1.18-1.34 (m, 2 H) 1.37-1.52 (m, 2 H), 3.23-3.28 (m, 2 H) 3.69 (s, 3 H) 3.74 (s, 3 H) 4.07-4.15 (m, 2 H) 4.15-4.26 (m, 2 H) 5.56 (s, 2 H) 6.20 (s, 1 H) 6.47 (dd, J = 8.66, 2.89 Hz, 1 H) 6.60 (d, J = 3.01 Hz, 1 H) 6.85 (d, J = 8.78 Hz, 1 H) 7.45 (s, 1 H) |
| 141 | 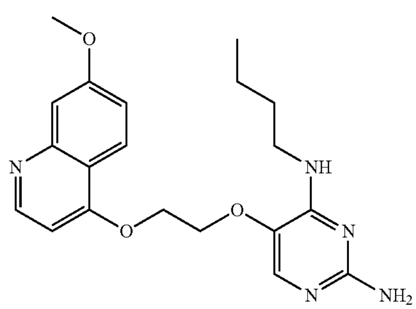 [SMILES: CCCCNc1nc(N)ncc1OCCOc1ccnc2cc(OC)ccc12] | 383.20 | 384 | 0.82, D | $^1$H NMR (400 MHz, DMSO-d$_6$) δ ppm 0.77 (t, J = 7.28 Hz, 3 H) 1.12-1.26 (m, 2 H) 1.28-1.37 (m, 2 H) 3.15-3.25 (m, 2 H) 3.90 (s, 3 H) 4.29-4.34 (m, 2 H) 4.51 (dd, J = 5.14, 3.14 Hz, 2 H) 5.58 (s, 2 H) 6.24 (s, 1 H) 6.93 (d, J = 5.27 Hz, 1 H) 7.17 (dd, J = 9.16, 2.64 Hz, 1 H) 7.32 (d, J = 2.51 Hz, 1 H) 7.52 (s, 1 H) 8.00 (d, J = 9.29 Hz, 1 H) 8.65 (d, J = 5.27 Hz, 1 H) |
| 142 | 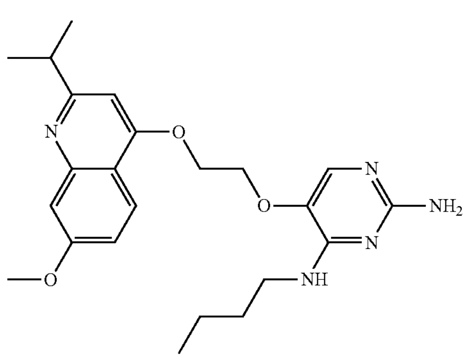 [SMILES: CCCCNc1nc(N)ncc1OCCOc1cc(C(C)C)nc2cc(OC)ccc12] | 425.24 | 426 | 1, D | $^1$H NMR (400 MHz, DMSO-d$_6$) δ ppm 0.77 (t, J = 7.40 Hz, 3 H) 1.13-1.19 (m, 2 H) 1.28-1.35 (m, 6 H) 1.28-1.35 (m, 2 H) 3.05-3.15 (m, 1 H) 3.16-3.21 (m, 2 H) 3.89 (s, 3 H) 4.29-4.32 (m, 2 H) 4.50-4.52 (m, 2 H) 5.57 (s, 2 H) 6.22 (s, 1 H) 6.83 (s, 1 H) 7.08 (dd, J = 9.29, 2.51 Hz, 1 H) 7.25 (d, J = 2.51 Hz, 1 H) 7.52 (s, 1 H) 7.93 (d, J = 9.03 Hz, 1 H) |

TABLE I-continued

| | STRUCTURE | Exact Mass | Mass Found [M + H] | LCMS Ret Time, Method | 1H NMR |
|---|---|---|---|---|---|
| 143 | 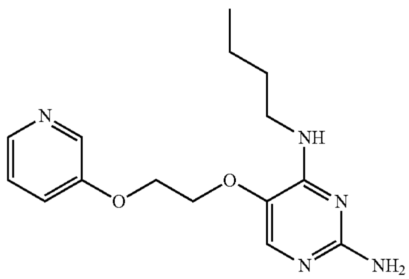 [SMILES: CCCCNc1nc(N)ncc1OCCOc1cccnc1] | 303.17 | 304 | 0.68, D | ¹H NMR (400 MHz, DMSO-d₆) δ ppm 0.86 (t, J = 7.40 Hz, 3 H) 1.20-1.35 (m, 2 H) 1.38-1.51 (m, 2 H) 3.22-3.28 (m, 2 H) 4.09-4.25 (m, 2 H) 4.27-4.40 (m, 2 H) 5.60 (s, 2 H) 6.27 (s, 1 H) 7.31-7.37 (m, 1 H) 7.41-7.45 (m, 1 H) 7.45 (s, 1 H) 8.19 (dd, J = 4.52, 1.25 Hz, 1 H) 8.33 (d, J = 2.76 Hz, 1 H) |
| 144 | 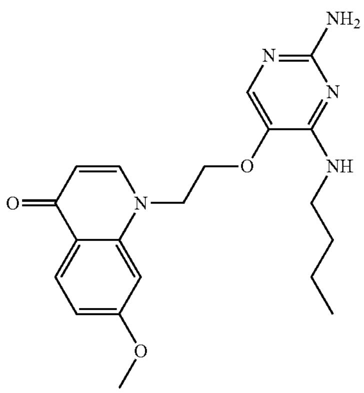 [SMILES: CCCCNc1nc(N)ncc1OCCn1ccc(=O)c2ccc(OC)cc21] | 383.20 | 384 | 0.65, D | ¹H NMR (400 MHz, DMSO-d₆) δ ppm 0.87 (t, J = 7.28 Hz, 3 H) 1.19-1.25 (m, 2 H) 1.39 (t, J = 7.40 Hz, 2 H) 3.17-3.22 (m, 2 H) 3.90 (s, 3 H) 4.11-4.22 (m, 2 H) 4.59 (m, J = 4.90, 4.90 Hz, 2 H) 5.53 (s, 2 H) 5.86 (s, 1 H) 5.97 (d, J = 7.53 Hz, 1 H) 6.99 (d, J = 8.80 Hz, 1 H) 7.11 (d, J = 2.26 Hz, 1 H) 7.32 (s, 1 H) 8.04 (d, J = 7.78 Hz, 1 H) 8.09 (d, J = 9.03 Hz, 1 H) |
| 145 | 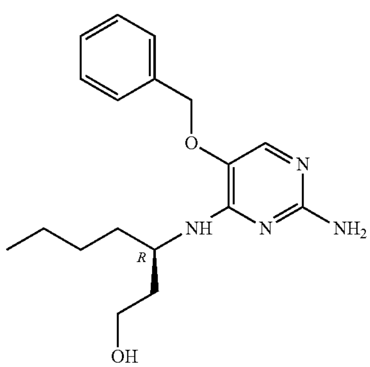 | 330.21 | 331 | 2.18, F | ¹H NMR (300 MHz, CHLOROFORM-d) δ ppm 0.76-0.87 (m, 3 H), 1.14-1.31 (m, 5 H), 1.33-1.57 (m, 3 H), 1.80 (m, J = 11.4, 5.1, 2.7 Hz, 1 H), 3.31-3.43 (m, 1 H), 3.45-3.56 (m, 1 H), 4.03 (d, J = 3.3 Hz, 1 H), 4.44 (s, 2 H), 4.81-4.89 (m, 1 H), 4.91 (s, 2 H), 7.27-7.35 (m, 5 H), 7.39 (s, 1 H) |
| 146 | 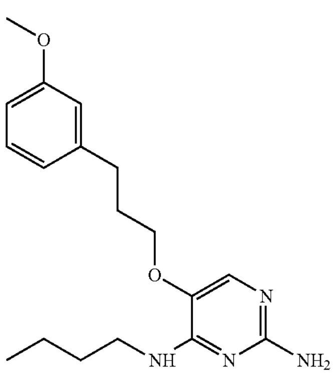 [SMILES: CCCCNc1nc(N)ncc1OCCCc1cccc(OC)c1] | 330.21 | 331 | 1.03, D | ¹H NMR (400 MHz, DMSO-d₆) δ ppm 0.91 (t, J = 7.3 Hz, 3 H), 1.30 (dq, J = 14.9, 7.4 Hz, 2 H), 1.55 (quin, J = 7.3 Hz, 2 H), 1.97-2.08 (m, 2 H), 2.69-2.78 (m, 6 2 H), 3.42 (q, J = 6.8 Hz, 2 H), 3.73 (s, 3 H), 3.90 (t, J = 6.3 Hz, 2 H), 6.73-6.78 (m, 1 H), 6.78-6.83 (m, 2 H), 7.17-7.25 (m, 1 H), 7.37 (s, 1 H), 7.43 (br. s., 2 H), 8.32 (t, J = 6.0 Hz, 1 H), 11.83 (br. s., 1 H) |

TABLE I-continued

| | STRUCTURE | Exact Mass | Mass Found [M + H] | LCMS Ret Time, Method | 1H NMR |
|---|---|---|---|---|---|
| 147 | 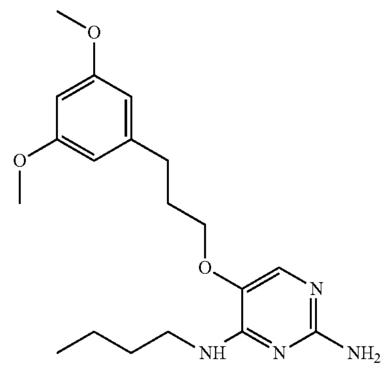 [SMILES: CCCCNc1nc(N)ncc1OCCCc1cc(OC)cc(OC)c1] | 360.22 | 361 | 1.02, D | ¹H NMR (400 MHz, CHLOROFORM-d) δ ppm 0.90 (t, J = 7.4 Hz, 3 H), 1.24-1.37 (m, 2 H), 1.55 (t, J = 7.3 Hz, 2 H), 1.96-2.07 (m, 2 H), 2.65-2.74 (m, 2 H), 3.42 (q, J = 6.9 Hz, 2 H), 3.71 (s, 6 H), 3.89 (t, J = 6.1 Hz, 2 H), 6.31-6.35 (m, 1 H), 6.38 (d, J = 2.3 Hz, 2 H), 7.34 (s, 1 H), 7.39 (br. s., 2 H), 8.31 (s, 1 H) |
| 148 | 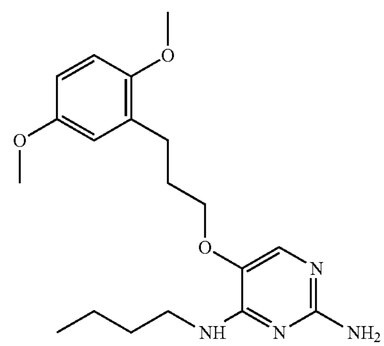 | 360.22 | 361 | 1.03, D | ¹H NMR (400 MHz, DMSO-d₆) δ ppm 0.90 (t, J = 7.4 Hz, 3 H), 1.23-1.36 (m, 2 H), 1.49-1.60 (m, 2 H), 1.92-2.04 (m, 2 H), 2.68 (t, J = 7.5 Hz, 2 H), 3.41 (q, 6 J = 6.8 Hz, 2 H), 3.67 (s, 3 H), 3.71 (s, 3 H), 3.89 (t, J = 6.3 Hz, 2 H), 6.69-6.77 (m, 2 H), 6.84-6.91 (m, 1 H), 7.34 (s, 1 H), 7.41 (br. s., 2 H), 8.31 (t, J = 5.9 Hz, 1 H), 11.70 (s, 1 H) |
| 149 | 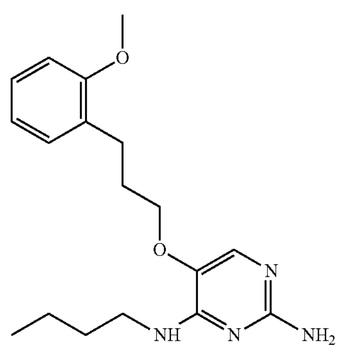 [SMILES: CCCCNc1nc(N)ncc1OCCCc1ccccc1OC] | 330.21 | 331 | 1.06, D | ¹H NMR (400 MHz, DMSO-d₆) δ ppm 0.90 (t, J = 7.4 Hz, 3 H), 1.24-1.37 (m, 2 H), 1.49-1.61 (m, 2 H), 1.92-2.05 (m, 2 H), 2.67-2.76 (m, 2 H), 3.41 (q, 6 J = 6.9 Hz, 2 H), 3.76 (s, 3 H), 3.90 (t, J = 6.3 Hz, 2 H), 6.87 (td, J = 7.4, 1.0 Hz, 1 H), 6.96 (d, J = 7.5 Hz, 1 H), 7.11-7.23 (m, 2 H), 7.33 (s, 1 H), 7.40 (br. s., 2 H), 8.31 (t, J = 5.9 Hz, 1 H), 11.67 (br. s., 1 H) |
| 150 | 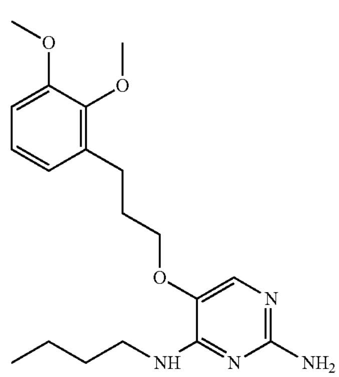 [SMILES: CCCCNc1nc(N)ncc1OCCCc1cccc(OC)c1OC] | 360.22 | 361 | 1.02, D | ¹H NMR (400 MHz, DMSO-d₆) δ ppm 0.90 (t, J = 7.4 Hz, 3 H), 1.24-1.36 (m, 2 H), 1.55 (quin, J = 7.3 Hz, 2 H), 1.93-2.04 (m, 2 H), 2.69-2.76 (m, 2 H), 6 3.41 (q, J = 6.8 Hz, 2 H), 3.70 (s, 3 H), 3.78 (s, 3 H), 3.91 (t, J = 6.4 Hz, 2 H), 6.79 (dd, J = 7.5, 1.5 Hz, 1 H), 6.87-6.92 (m, 1 H), 6.99 (t, J = 7.9 Hz, 1 H), 7.36 (s, 1 H), 7.44 (br. s., 2 H), 8.31 (t, J = 6.0 Hz, 1 H), 11.81 (s, 1 H) |

TABLE I-continued

| | STRUCTURE | Exact Mass | Mass Found [M + H] | LCMS Ret Time, Method | 1H NMR |
|---|---|---|---|---|---|
| 151 | 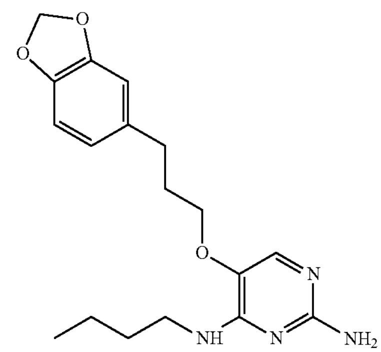 [SMILES: CCCCNc1nc(N)ncc1OCCCc1ccc2c(c1)OCO2] | 344.18 | 345 | 1, D | $^1$H NMR (400 MHz, DMSO-d$_6$) δ ppm 0.91 (t, J = 7.3 Hz, 3 H), 1.30 (dq, J = 14.9, 7.4 Hz, 2 H), 1.55 (quin, J = 7.3 Hz, 2 H), 1.93-2.04 (m, 2 H), 2.68 (t, J = 7.5 6 Hz, 2 H), 3.42 (q, J = 6.8 Hz, 2 H), 3.88 (t, J = 6.1 Hz, 2 H), 5.94-5.99 (m, 2 H), 6.67 (dd, J = 7.9, 1.6 Hz, 1 H), 6.82 (d, J = 6.0 Hz, 1 H), 6.83 (s, 1 H), 7.36 (s, 1 H), 7.42 (br. s., 2 H), 8.31 (t, J = 5.9 Hz, 1 H), 11.77 (br. s., 1 H) |
| 152 | 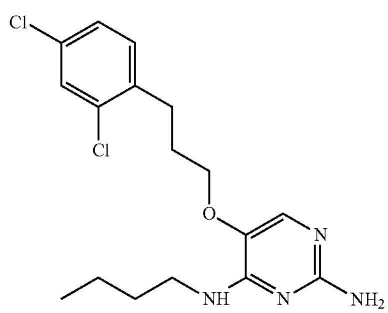 [SMILES: CCCCNc1nc(N)ncc1OCCCc1ccc(Cl)cc1Cl] | 368.12 | 369 | 1.13, D | $^1$H NMR (400 MHz, DMSO-d$_6$) δ ppm 0.86-0.95 (m, 3 H), 1.24-1.36 (m, 2 H), 1.55 (quin, J = 7.3 Hz, 2 H), 1.97-2.07 (m, 2 H), 2.82-2.90 (m, 2 H), 3.42 6 (q, J = 6.8 Hz, 2 H), 3.92 (t, J = 6.1 Hz, 2 H), 7.37 (s, 1 H), 7.38-7.40 (m, 2 H), 7.43 (br. s., 2 H), 7.55-7.61 (m, 1 H), 8.32 (t, J = 5.9 Hz, 1 H), 11.80 (br. s., 1 H) |
| 153 | 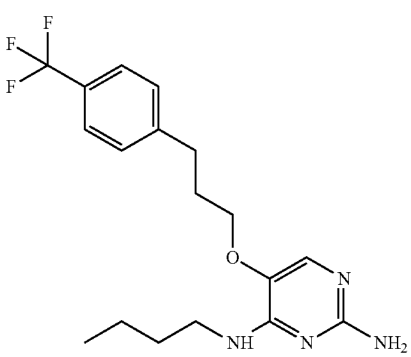 [SMILES: CCCCNc1nc(N)ncc1OCCCc1ccc(C(F)(F)F)cc1] | 368.18 | 369 | 1.15, D | $^1$H NMR (400 MHz, DMSO-d$_6$) δ ppm 0.91 (t, J = 7.3 Hz, 3 H), 1.31 (dq, J = 14.9, 7.4 Hz, 2 H), 1.56 (quin, J = 7.3 Hz, 2 H), 1.99-2.11 (m, 2 H), 2.87 (t, J = 7.8 6 Hz, 2 H), 3.38-3.47 (m, 2 H), 3.92 (t, J = 6.1 Hz, 2 H), 7.38 (s, 1 H), 7.43 (br. s., 1 H), 7.48 (d, J = 8.0 Hz, 2 H), 7.66 (d, J = 8.0 Hz, 2 H), 8.33 (t, J = 6.0 Hz, 1 H), 11.83 (br. s., 1 H) |
| 154 | 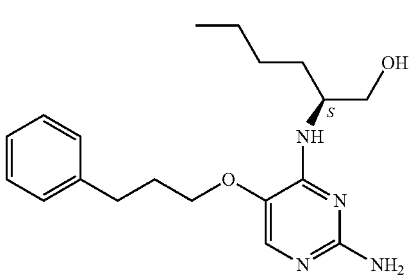 | 344.22 | 345 | 0.98, D | $^1$H NMR (400 MHz, DMSO-d$_6$) δ ppm 0.84 (t, J = 6.90 Hz, 3 H) 1.22-1.36 (m, 4 H) 1.44-1.67 (m, 2 H) 1.95-2.08 (m, 2 H) 2.73 (t, J = 7.65 Hz, 2 H) 3.41-3.64 (m, 2 H) 3.81-3.96 (m, 2 H) 4.05-4.20 (m, 1 H) 4.80 (br. s., 1 H) 6.69 (br. s., 2 H) 6.99 (d, J = 8.53 Hz, 1 H) 7.14-7.34 (m, 5 H) 7.39 (s, 1 H) 7.90 (br. s., 1 H) |

TABLE I-continued

| | STRUCTURE | Exact Mass | Mass Found [M + H] | LCMS Ret Time, Method | 1H NMR |
|---|---|---|---|---|---|
| 155 | 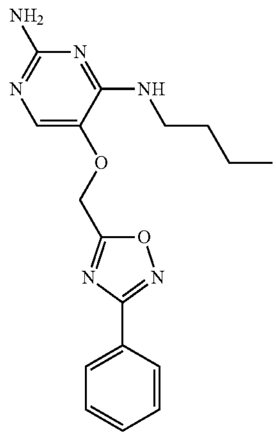 [SMILES: CCCCNc1nc(N)ncc1OCc1nc(-c2ccccc2)no1] | 340.16 | 341 | 0.99, D | ¹H NMR (400 MHz, DMSO-d₆) δ ppm 0.89 (t, J = 1.00 Hz, 3 H) 1.20-1.37 (m, 2 H) 1.47-1.60 (m, 2 H) 3.39-3.47 (m, 2 H) 5.53 (s, 2 H) 7.55-7.67 (m, 5 H) 7.71 (s, 1 H) 7.97-8.08 (m, 2 H) 8.59 (s, 1 H) 12.05 (br. s., 1 H) |
| 156 | 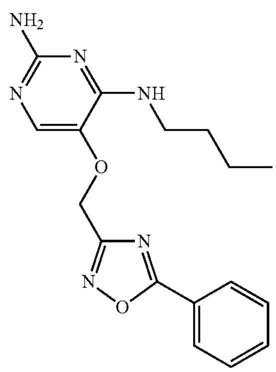 [SMILES: CCCCNc1nc(N)ncc1OCc1noc(-c2ccccc2)n1] | 340.16 | 341 | 0.97, D | ¹H NMR (400 MHz, DMSO-d₆) δ ppm 0.86 (t, J = 7.40 Hz, 3 H) 1.21-1.33 (m, 2 H) 1.44-1.57 (m, 2 H) 3.36-3.46 (m, 2 H) 5.34 (s, 2 H) 7.58 (br. s., 2 H) 7.67 (s, 1 H) 7.63-7.70 (m, 2 H) 7.72-7.78 (m, 1 H) 8.10-8.18 (m, 2 H) 8.50 (s, 1 H) 11.98 (br. s., 1 H) |
| 157 | 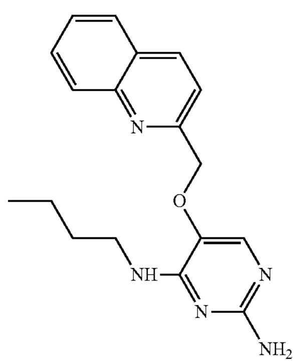 [SMILES: CCCCNc1nc(N)ncc1OCc1ccc2ccccc2n1] | 323.17 | 324 | 0.33, D | ¹H NMR (400 MHz, DMSO-d₆) δ ppm 0.90 (t, J = 7.40 Hz, 3 H) 1.25-1.37 (m, 2 H) 1.50-1.61 (m, 2 H) 3.39-3.50 (m, 2 H) 5.39 (s, 2 H) 7.54 (br. s., 2 H) 7.59 (d, J = 4.77 Hz, 1 H) 7.69 (t, J = 7.40 Hz, 1 H) 7.81-7.91 (m, 2 H) 8.08 (d, J = 8.28 Hz, 1 H) 8.12 (d, J = 8.03 Hz, 1 H) 8.57 (d, J = 8.78 Hz, 1 H) 8.68 (br. s., 1 H) 11.94 (br. s., 1 H) |
| 158 | 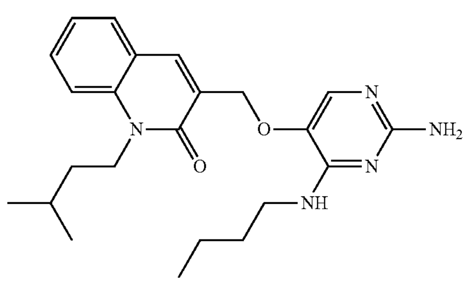 [SMILES: CCCCNc1nc(N)ncc1OCc1cc2ccccc2n(CCC(C)C)c1=O] | 409.25 | 410 | 1.21, D | ¹H NMR (400 MHz, DMSO-d₆) δ ppm 0.91 (t, J = 7.28 Hz, 3 H) 1.00 (d, J = 6.78 Hz, 6 H) 1.31-1.41 (m, 2 H) 1.48-1.63 (m, 4 H) 1.70-1.80 (m, 1 H) 3.33-3.42 (m, 2 H) 4.28-4.37 (m, 2 H) 4.75 (s, 2 H) 5.62 (s, 2 H) 7.08 (t, J = 1.00 Hz, 1 H) 7.31 (t, J = 7.28 Hz, 1 H) 7.49 (s, 1 H) 7.57 (d, J = 8.53 Hz, 1 H) 7.66 (dd, J = 7.15, 1.38 Hz, 1 H) 7.79 (dd, J = 7.78, 1.25 Hz, 1 H) 8.12 (s, 1 H) |

TABLE I-continued

| | STRUCTURE | Exact Mass | Mass Found [M + H] | LCMS Ret Time, Method | 1H NMR |
|---|---|---|---|---|---|
| 159 | 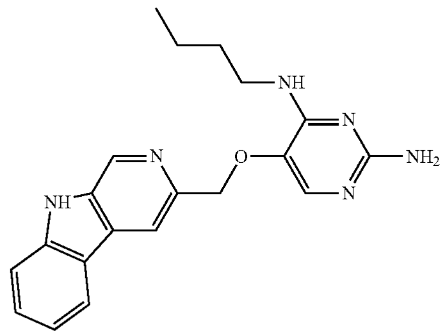 [SMILES: CCCCNc1nc(N)ncc1OCc1cc2c(cn1)[nH]c1ccccc12] | 362.19 | 363 | 0.89, D | ¹H NMR (400 MHz, DMSO-d₆) δ ppm 0.89 (t, J = 7.28 Hz, 3 H) 1.27-1.37 (m, 2 H) 1.49-1.57 (m, 2 H) 3.32-3.39 (m, 2 H) 5.10 (s, 2 H) 5.53 (s, 2 H) 6.83 (s, 1 H) 7.23-7.28 (m, 1 H) 7.48 (s, 1 H) 7.56 (dd, J = 6.90, 1.13 Hz, 1 H) 7.59-7.62 (m, 1 H) 8.25 (d, J = 8.03 Hz, 1 H) 8.28 (s, 1 H) 8.88 (d, J = 1.00 Hz, 1 H) 11.64 (s, 1 H) |
| 160 | 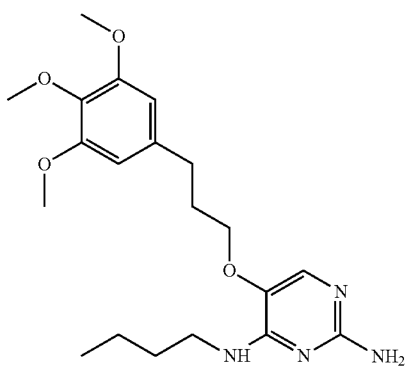 [SMILES: CCCCNc1nc(N)ncc1OCCCc1cc(OC)c(OC)c(OC)c1] | 390.23 | 391 | 0.95, D | ¹H NMR (400 MHz, DMSO-d₆) δ ppm 0.90 (t, J = 7.3 Hz, 3 H), 1.30 (dq, J = 14.9, 7.3 Hz, 2 H), 1.55 (quin, J = 7.3 Hz, 2 H), 1.94-2.12 (m, 2 H), 2.70 (t, J = 7.7 6 Hz, 2 H), 3.37-3.44 (m, 2 H), 3.62 (s, 3 H), 3.70-3.79 (m, 6 H), 3.89 (t, J = 6.3 Hz, 2 H), 6.51 (s, 2 H), 7.27 (br. s., 2 H), 7.39 (s, 1 H), 8.15 (t, J = 5.6 Hz, 1 H) |
| 161 | 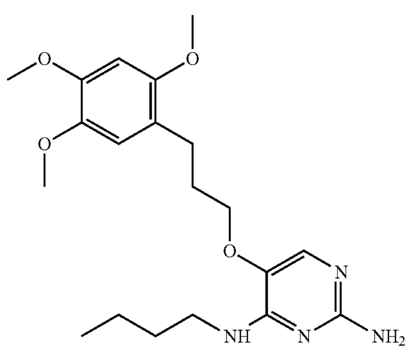 [SMILES: CCCCNc1nc(N)ncc1OCCCc1cc(OC)c(OC)cc1OC] | 390.23 | 391 | 0.97, D | ¹H NMR (400 MHz, DMSO-d₆) δ ppm 0.90 (t, J = 7.3 Hz, 3 H), 1.30 (dq, J = 14.9, 7.4 Hz, 2 H), 1.55 (quin, J = 7.3 Hz, 2 H), 1.89-2.03 (m, 2 H), 2.64 (t, J = 7.3 6 Hz, 2 H), 3.38-3.46 (m, 2 H), 3.65 (s, 3 H), 3.74 (s, 3 H), 3.76 (s, 3 H), 3.87 (t, J = 6.4 Hz, 2 H), 6.66 (s, 1 H), 6.75 (s, 1 H), 7.39 (s, 1 H), 7.48 (br. s., 2 H), 8.30 (t, J = 5.9 Hz, 1 H) |
| 162 | 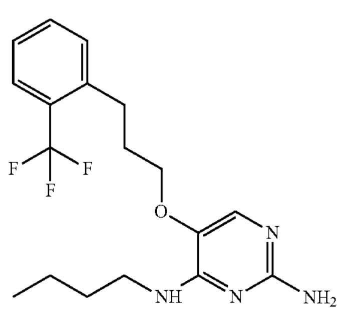 [SMILES: CCCCNc1nc(N)ncc1OCCCc1ccccc1C(F)(F)F] | 368.18 | 369 | 1.15, D | ¹H NMR (400 MHz, DMSO-d₆) δ ppm 0.90 (t, J = 7.4 Hz, 3 H), 1.31 (dq, J = 14.9, 7.4 Hz, 2 H), 1.55 (quin, J = 7.3 Hz, 2 H), 1.98-2.09 (m, 2 H), 2.87-2.96 (m, 6 2 H), 3.36-3.44 (m, 2 H), 3.97 (t, J = 6.3 Hz, 2 H), 7.17 (br. s., 2 H), 7.42 (s, 1 H), 7.43 (t, J = 7.5 Hz, 1 H), 7.55 (d, J = 7.8 Hz, 1 H), 7.63 (t, J = 7.5 Hz, 1 H), 7.69 (d, J = 7.8 Hz, 1 H), 7.97 (t, J = 5.6 Hz, 1 H) |

TABLE I-continued

| | STRUCTURE | Exact Mass | Mass Found [M + H] | LCMS Ret Time, Method | 1H NMR |
|---|---|---|---|---|---|
| 163 | 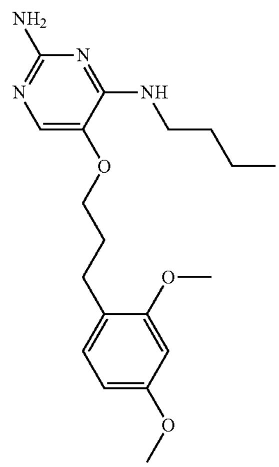 [SMILES: CCCCNc1nc(N)ncc1OCCCc1ccc(OC)cc1OC] | 360.22 | 361 | 1.05, D | $^1$H NMR (400 MHz, DMSO-d$_6$) δ ppm 0.90 (t, J = 7.4 Hz, 3 H), 1.30 (dq, J = 14.9, 7.4 Hz, 2 H), 1.55 (quin, J = 7.3 Hz, 2 H), 1.88-2.01 (m, 2 H), 2.63 (t, J = 7.4 6 Hz, 2 H), 3.37-3.44 (m, 2 H), 3.75 (s, 3 H), 3.73 (s, 3 H), 3.86 (t, J = 6.4 Hz, 2 H), 6.44 (dd, J = 8.3, 2.5 Hz, 1 H), 6.52 (d, J = 2.3 Hz, 1 H), 7.02 (d, J = 8.0 Hz, 1 H), 7.29 (br. s., 2 H), 7.35 (s, 1 H), 8.14 (t, J = 5.9 Hz, 1 H) |
| 164 | 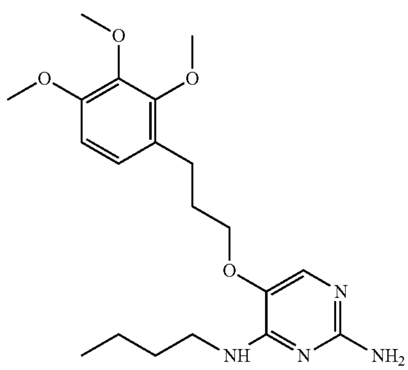 [SMILES: CCCCNc1nc(N)ncc1OCCCc1ccc(OC)c(OC)c1OC] | 390.23 | 391 | 1.02, D | $^1$H NMR (400 MHz, DMSO-d$_6$) δ ppm 0.90 (t, J = 7.3 Hz, 3 H), 1.30 (dq, J = 14.9, 7.3 Hz, 2 H), 1.55 (quin, J = 7.3 Hz, 2 H), 1.90-2.03 (m, 2 H), 2.66 (t, J = 7.5 6 Hz, 2 H), 3.37-3.46 (m, 2 H), 3.73 (s, 3 H), 3.76 (s, 6 H), 3.86-3.95 (m, 2 H), 6.72 (d, J = 8.5 Hz, 1 H), 6.86 (d, J = 8.5 Hz, 1 H), 7.38 (s, 1 H), 7.46 (br. s., 2 H), 8.30 (t, J = 5.9 Hz, 1 H), 11.94 (br. s., 1 H) |
| 165 | 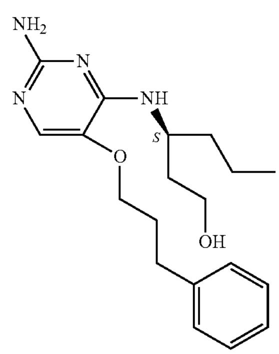 | 344.22 | 345 | 0.97, D | $^1$H NMR (400 MHz, DMSO-d$_6$) δ ppm 0.85 (t, J = 7.40 Hz, 3 H) 1.21-1.34 (m, 2 H) 1.41-1.57 (m, 2 H) 1.57-1.70 (m, 2 H) 1.94-2.01 (m, 2 H) 2.69-2.75 (m, 2 H) 3.38-3.46 (m, 2 H) 3.82 (td, J = 6.34, 1.88 Hz, 2 H) 4.11-4.18 (m, 1 H) 4.45 (t, J = 5.02 Hz, 1 H) 5.48 (s, 2 H) 6.00 (d, J = 8.78 Hz, 1 H) 7.11-7.31 (m, 5 H) 7.33 (s, 1 H) |
| 166 | 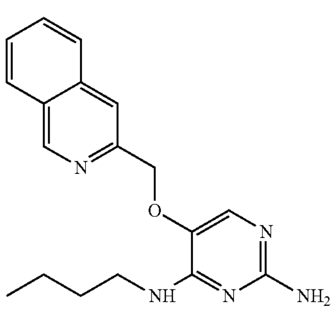 [SMILES: CCCCNc1nc(N)ncc1OCc1cc2ccccc2cn1] | 323.17 | 324 | 5.32, G | $^1$H NMR (400 MHz, DMSO-d$_6$) δ ppm 0.90 (t, J = 7.40 Hz, 3 H) 1.02-1.14 (m, 2 H) 1.23-1.38 (m, 2 H) 1.46-1.59 (m, 2 H) 3.36-3.46 (m, 2 H) 5.13 (s, 2 H) 5.55 (s, 2 H) 6.79 (br. s., 1 H) 7.48 (s, 1 H) 7.70 (ddd, J = 8.16, 6.90, 1.00 Hz, 1 H) 7.78-7.85 (m, 1 H) 8.00 (d, J = 1.00 Hz, 1 H) 7.99 (s, 1 H) 8.16 (d, J = 7.53 Hz, 1 H) 9.34 (s, 1 H) |

TABLE I-continued

| | STRUCTURE | Exact Mass | Mass Found [M + H] | LCMS Ret Time, Method | 1H NMR |
|---|---|---|---|---|---|
| 167 | 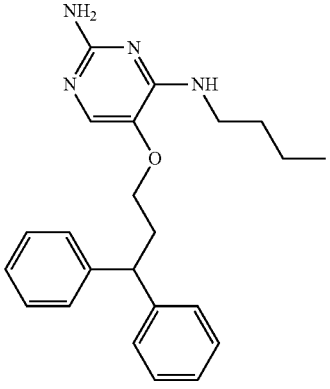 [SMILES: CCCCNc1nc(N)ncc1OCCC(c1ccccc1)c1ccccc1] | 376.23 | 377 | 1.18, D | ¹H NMR (400 MHz, DMSO-d$_6$) δ ppm 0.92 (t, J = 7.3 Hz, 3 H), 1.27-1.38 (m, 2 H), 1.51-1.63 (m, 2 H), 3.40-3.48 (m, 2 H), 3.78 (t, J = 6.1 Hz, 2 H), 4.32 (t, J =8.0 Hz, 1 H), 7.13-7.22 (m, 2 H), 7.25-7.36 (m, 10 H), 7.49 (br. s., 2 H), 8.33 (t, J = 6.0 Hz, 1 H), 12.01 (s, 1 H). 214 |
| 168 | 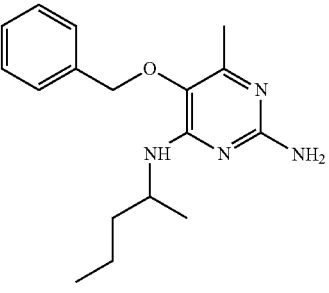 [SMILES: CCCC(C)Nc1nc(N)nc(C)c1OCc1ccccc1] | 300.20 | 301 | 1.06, D | ¹H NMR (400 MHz, DMSO-d$_6$) δ ppm 0.87 (t, J = 7.3 Hz, 3 H), 1.12 (d, J = 6.8 Hz, 3 H), 1.19-1.31 (m, 2 H), 1.39-1.50 (m, 1 H), 1.52-1.64 (m, 1 H), 2.03 (s, 3 H), 4.07 (br. s., 2 H), 4.15-4.27 (m, 1 H), 4.78-4.91 (m, 2 H), 7.35-7.43 (m, 3 H), 7.44-7.48 (m, 2 H), 7.92 (d, J = 8.8 Hz, 1 H) |
| 169 | 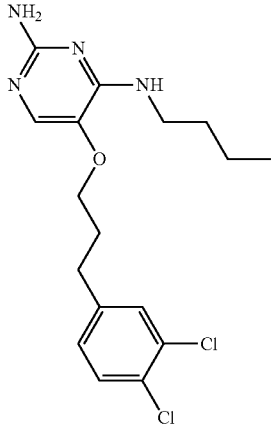 [SMILES: CCCCNc1nc(N)ncc1OCCCc1ccc(Cl)c(Cl)c1] | 368.12 | 369 | 1.19, D | ¹H NMR (400 MHz, DMSO-d$_6$) δ ppm 0.91 (t, J = 7.3 Hz, 3 H), 1.31 (dq, J = 14.9, 7.4 Hz, 2 H), 1.55 (quin, J = 7.3 Hz, 2 H), 1.96-2.09 (m, 2 H), 2.74-2.83 (m, 6 2 H), 3.42 (q, J = 6.8 Hz, 2 H), 3.90 (t, J = 6.1 Hz, 2 H), 7.25 (dd, J = 8.3, 2.0 Hz, 1 H), 7.38 (s, 1 H), 7.44 (br. s., 1 H), 7.53 (d, J = 2.0 Hz, 1 H), 7.55 (d, J = 8.0 Hz, 1 H), 8.31 (t, J = 5.9 Hz, 1 H), 11.84 (br. s., 1 H) |
| 170 | 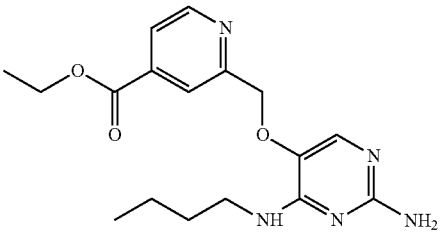 [SMILES: CCCCNc1nc(N)ncc1OCc1cc(C(=O)OCC)ccn1] | 345.18 | 346 | 0.36, D | ¹H NMR (400 MHz, DMSO-d$_6$) δ ppm 0.90 (t, J = 7.3 Hz, 3 H), 1.24-1.33 (m, 2 H), 1.35 (t, J = 7.2 Hz, 3 H), 1.55 (m, J = 7.3, 7.3, 7.3, 7.3 Hz, 2 H), 3.42 (q, 6 J = 6.9 Hz, 2 H), 4.38 (q, J = 7.1 Hz, 1 H), 5.26 (s, 2 H), 7.56 (br. s, 2 H), 7.57 (s, 1 H), 7.85 (dd, J = 5.0, 1.5 Hz, 1 H), 8.04 (s, 1 H), 8.61 (t, J = 5.8 Hz, 1 H), 8.82 (dd, J = 5.0, 0.8 Hz, 1 H), 12.05 (br. s., 1 H) |

TABLE I-continued

| | STRUCTURE | Exact Mass | Mass Found [M + H] | LCMS Ret Time, Method | 1H NMR |
|---|---|---|---|---|---|
| 171 | 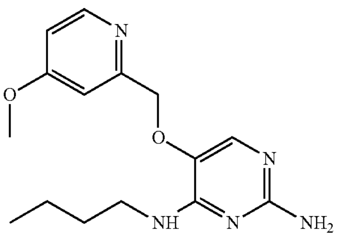 [SMILES: CCCCNc1nc(N)ncc1OCc1cc(OC)ccn1] | 303.17 | 304 | 0.75, D | $^1$H NMR (400 MHz, DMSO-d$_6$) δ ppm 0.90 (t, J = 7.4 Hz, 3 H), 1.31 (dq, J = 14.9, 7.4 Hz, 2 H), 1.59 (quin, J = 7.3 Hz, 2 H), 3.44 (q, J = 6.9 Hz, 2 H), 4.07 (s, 3 6 H), 5.36 (s, 2 H), 7.41-7.51 (m, 1 H), 7.52-7.69 (m, 4 H), 8.71 (d, J = 6.8 Hz, 1 H), 9.06 (br. s., 1 H), 12.08 (br. s., 1 H) |
| 172 | 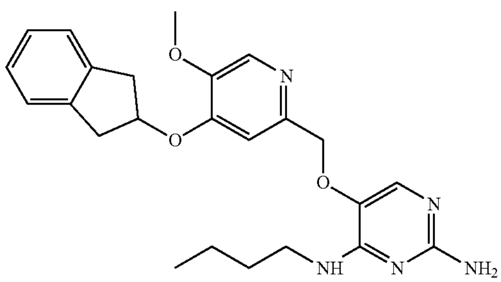 [SMILES: CCCCNc1nc(N)ncc1OCc1cc(OC2Cc3ccccc3C2)c(OC)cn1] | 435.23 | 436 | 1.02, D | $^1$H NMR (400 MHz, DMSO-d$_6$) δ ppm 0.87 (t, J = 7.4 Hz, 3 H), 1.22-1.36 (m, 2 H), 1.52 (quin, J = 7.3 Hz, 2 H), 3.03 (dd, J = 17.1, 2.0 Hz, 2 H), 3.32 (q, J = 6.9 6 Hz, 2 H), 3.40 (dd, J = 17.2, 6.1 Hz, 2 H), 3.77 (s, 3 H), 4.95 (s, 2 H), 5.29-5.37 (m, 1 H), 5.94 (br. s, 2 H), 7.07 (t, J = 5.6 Hz, 1 H), 7.14-7.22 (m, 2 H), 7.22-7.30 (m, 3 H), 7.45 (s, 1 H), 8.12 (s, 1 H) |
| 173 | 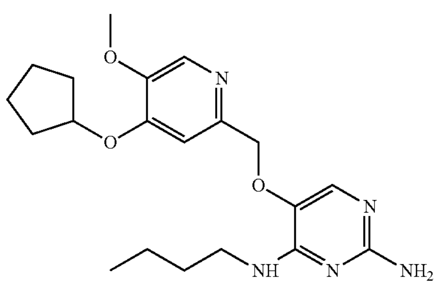 | 387.23 | 388 | 0.96, D | $^1$H NMR (400 MHz, DMSO-d$_6$) δ ppm 0.90 (t, J = 7.3 Hz, 3 H), 1.31 (dq, J = 15.0, 7.4 Hz, 2 H), 1.52-1.62 (m, 2 H), 1.62-1.86 (m, 6 H), 1.97-2.13 (m, 2 H), 6 3.43 (q, J = 6.9 Hz, 2 H), 3.96 (s, 3 H), 5.11-5.20 (m, 1 H), 5.35 (s, 2 H), 7.62 (br. s., 2 H), 7.65 (d, J = 3.5 Hz, 1 H), 7.68 (s, 1 H), 8.30 (s, 1 H), 9.06 (t, J = 5.4 Hz, 1 H), 12.21 (br. s., 1 H) |
| 174 | 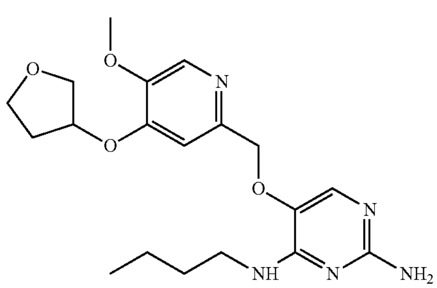 | 389.21 | 390 | 0.73, D | $^1$H NMR (400 MHz, DMSO-d$_6$) δ ppm 0.90 (t, J = 7.3 Hz, 3 H), 1.30 (dq, J = 15.0, 7.4 Hz, 2 H), 1.57 (quin, J = 7.3 Hz, 2 H), 1.98-2.10 (m, 1 H), 2.28-2.43 (m, 6 1 H), 3.42 (q, J = 6.9 Hz, 2 H), 3.79 (td, J = 8.4, 4.8 Hz, 1 H), 3.83-3.94 (m, 3 H), 3.95 (s, 3 H), 5.27 (s, 2 H), 5.30-5.37 (m, 1 H), 7.49-7.69 (m, 4 H), 8.31 (s, 1 H), 8.92 (br. s., 1 H), 11.99-12.13 (m, 1 H) |
| 175 | 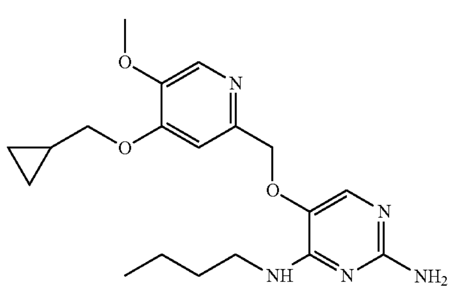 [SMILES: CCCCNc1nc(N)ncc1OCc1cc(OCC2CC2)c(OC)cn1] | 373.21 | 374 | 0.52, D | $^1$H NMR (400 MHz, DMSO-d$_6$) δ ppm 0.35-0.44 (m, 2 H), 0.61-0.69 (m, 2 H), 0.90 (t, J = 7.4 Hz, 3 H), 1.23-1.39 (m, 1 H), 1.23-1.39 (m, 2 H), 1.58 6 (quin, J = 7.3 Hz, 2 H), 3.43 (q, J = 6.9 Hz, 2 H), 4.00 (s, 3 H), 4.18 (d, J = 7.3 Hz, 2 H), 5.33 (s, 2 H), 7.62 (br. s., 2 H), 7.64 (d, J = 5.0 Hz, 1 H), 7.69 (s, 1 H), 8.34 (s, 1 H), 9.04 (t, J = 5.6 Hz, 1 H), 12.16 (d, J = 4.8 Hz, 1 H) |

TABLE I-continued

| | STRUCTURE | Exact Mass | Mass Found [M + H] | LCMS Ret Time, Method | 1H NMR |
|---|---|---|---|---|---|
| 176 | 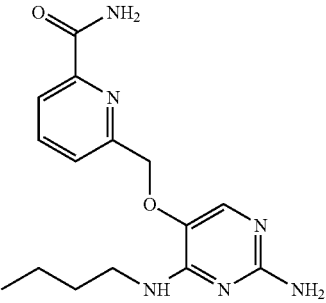 [SMILES: CCCCNc1nc(N)ncc1OCc1cccc(C(N)=O)n1] | 316.16 | 317 | 0.65, D | $^1$H NMR (400 MHz, DMSO-d$_6$) δ ppm 0.89 (t, J = 7.4 Hz, 3 H), 1.28 (dq, J = 15.0, 7.4 Hz, 2 H), 1.44-1.56 (m, 2 H), 3.29 (q, J = 6.9 Hz, 2 H), 5.09 (s, 2 H), 5.52 6 (br. s, 2 H), 6.59 (t, J = 5.9 Hz, 1 H), 7.43 (s, 1 H), 7.68 (br. s., 1 H), 7.79 (dd, J = 7.5, 1.3 Hz, 1 H), 7.96 (dd, J = 7.5, 1.3 Hz, 1 H), 7.98-8.02 (m, 1 H), 8.04 (br. s., 1 H) |
| 177 | 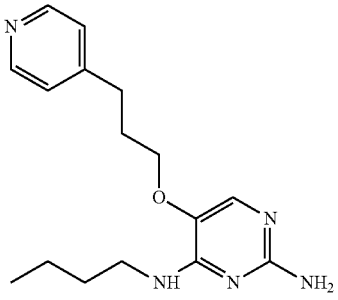 [SMILES: CCCCNc1nc(N)ncc1OCCCc1ccncc1] | 301.19 | 302 | 0.74, D | $^1$H NMR (400 MHz, DMSO-d$_6$) δ ppm 0.89 (t, J = 7.3 Hz, 3 H), 1.20-1.38 (m, 2 H), 1.44-1.56 (m, 2 H), 1.95-2.06 (m, 2 H), 2.73-2.80 (m, 2 H), 3.23-6 3.32 (m, 2 H), 3.82 (t, J = 6.3 Hz, 2 H), 5.49 (s, 2 H), 6.32 (t, J = 5.9 Hz, 1 H), 7.23-7.29 (m, 2 H), 7.34 (s, 1 H), 8.42-8.51 (m, 2 H) |
| 178 | 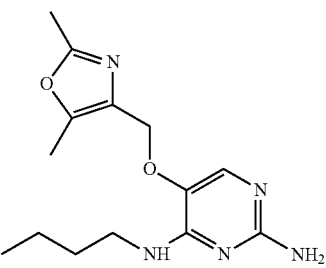 [SMILES: CCCCNc1nc(N)ncc1OCc1nc(C)oc1C] | 291.17 | 292 | 0.77, D | $^1$H NMR (400 MHz, DMSO-d$_6$) δ ppm 0.89 (t, J = 7.3 Hz, 3 H), 1.20-1.34 (m, 2 H), 1.52 (quin, J = 7.3 Hz, 2 H), 2.31 (s, 3 H), 2.36 (s, 3 H), 3.37 (q, J = 6.8 Hz, 6 2 H), 4.85 (s, 2 H), 7.57 (br. s., 3 H), 8.32 (t, J = 5.9 Hz, 1 H), 12.26 (br. s., 1 H) |
| 179 | 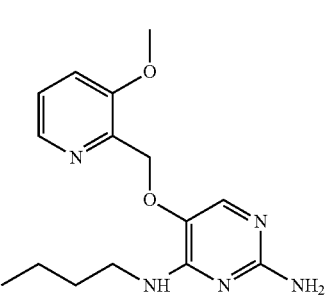 [SMILES: CCCCNc1nc(N)ncc1OCc1ncccc1OC] | 303.17 | 304 | 0.77, D | $^1$H NMR (400 MHz, DMSO-d$_6$) δ ppm 0.89 (t, J = 7.4 Hz, 3 H), 1.24-1.36 (m, 2 H), 1.51-1.59 (m, 2 H), 3.37-3.45 (m, 2 H), 3.92 (s, 3 H), 5.21 (s, 2 H), 7.50 (br. s., 2 H), 7.58-7.66 (m, 2 H), 7.79 (d, J = 7.8 Hz, 1 H), 8.28 (d, J = 4.3 Hz, 1 H), 8.73-8.91 (m, 1 H), 11.86 (d, J = 5.5 Hz, 1 H) |
| 180 | 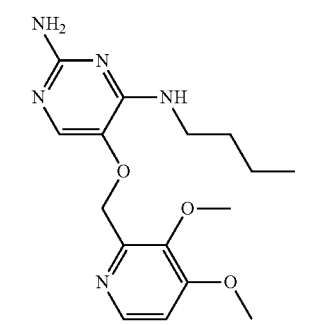 [SMILES: CCCCNc1nc(N)ncc1OCc1nccc(OC)c1OC] | 333.18 | 334 | 0.75, D | $^1$H NMR (400 MHz, DMSO-d$_6$) δ ppm 0.90 (t, J = 7.40 Hz, 3 H) 1.18-1.37 (m, 2 H) 1.51-1.66 (m, 2 H) 3.33-3.53 (m, 2 H) 3.93 (s, 3 H) 4.17 (s, 3 H) 5.44 (s, 2 H) 7.62 (br. s., 2 H) 7.73 (d, J = 7.03 Hz, 1 H) 7.83 (br. s., 1 H) 8.63 (d, J = 6.78 Hz, 1 H) 9.58 (t, J = 5.90 Hz, 1 H) 12.45 (br. s., 1 H) |

TABLE I-continued

| | STRUCTURE | Exact Mass | Mass Found [M + H] | LCMS Ret Time, Method | 1H NMR |
|---|---|---|---|---|---|
| 181 | 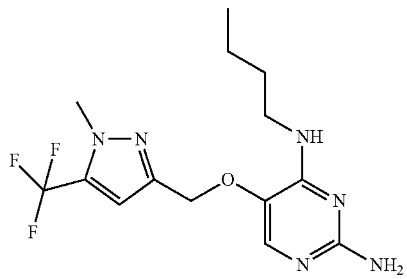 [SMILES: CCCCNc1nc(N)ncc1OCc1cc(C(F)(F)F)n(C)n1] | 344.16 | 345 | 0.93, D | ¹H NMR (400 MHz, DMSO-d₆) δ ppm 0.89 (t, J = 7.28 Hz, 3 H) 1.17-1.32 (m, 2 H) 1.47-1.56 (m, 2 H) 3.35-3.43 (m, 2 H) 3.97 (s, 3 H) 5.02 (s, 2 H) 7.11 (s, 1 H) 7.48 (br. s., 2 H) 7.56 (s, 1 H) 8.35 (t, J = 6.02 Hz, 1 H) 11.85 (br. s., 1 H) |
| 182 | 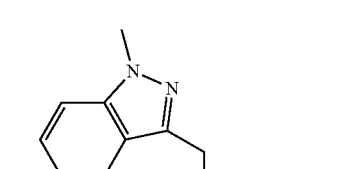 | 326.19 | 327 | 0.75, D | ¹H NMR (400 MHz, DMSO-d₆) δ ppm 0.86 (t, J = 7.28 Hz, 3 H) 1.15-1.31 (m, 2 H) 1.32-1.48 (m, 2 H) 3.15-3.26 (m, 3 H) 4.03 (s, 3 H) 5.26 (s, 2 H) 5.51 (s, 2 H) 6.28 (s, 1 H) 7.15 (td, J = 7.53, 0.75 Hz, 1 H) 7.43 (s, 1 H) 7.36-7.49 (m, 1 H) 7.62 (d, J = 8.53 Hz, 1 H) 7.79-7.89 (m, 1 H) |
| 183 | 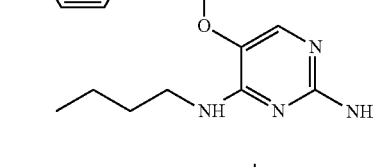 | 386.21 | 387 | 0.79, D | ¹H NMR (400 MHz, DMSO-d₆) δ ppm 0.84 (t, J = 1.00 Hz, 3 H) 1.12-1.27 (m, 2 H) 1.31-1.46 (m, 2 H) 3.13-3.27 (m, 2 H) 3.77 (s, 3 H) 3.85 (s, 3 H) 3.96 (s, 3 H) 5.18 (s, 2 H) 5.48 (s, 2 H) 6.26 (s, 1 H) 7.12 (d, J = 9.29 Hz, 2 H) 7.42 (s, 1 H) |
| 184 | 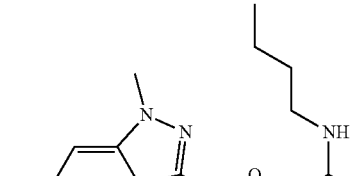 | 323.17 | 324 | 0.93, D | ¹H NMR (400 MHz, DMSO-d₆) δ ppm 0.90 (t, J = 7.4 Hz, 3 H), 1.48-1.60 (m, 2 H), 1.71-1.80 (m, 2 H), 3.43-3.49 (m, 2 H), 5.65 (s, 2 H), 7.56 (br. s., 2 H), 7.67 (d, J = 5.0 Hz, 1 H), 7.71-7.77 (m, 2 H), 8.05-8.14 (m, 2 H), 8.60 (dd, J = 8.3, 1.3 Hz, 1 H), 8.67 (t, J = 5.9 Hz, 1 H), 9.04 (dd, J = 4.3, 1.8 Hz, 1 H), 12.01 (d, J = 4.8 Hz, 1 H) |
| 185 | 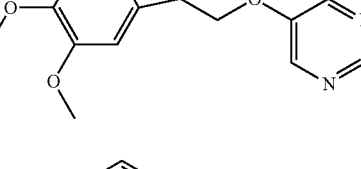 | 337.19 | 338 | 0.95, D | ¹H NMR (400 MHz, CHLOROFORM-d) δ ppm 0.89 (t, J = 7.3 Hz, 3 H), 1.21 (d, J = 6.5 Hz, 3 H), 1.28-1.40 (m, 2 H), 1.43-1.62 (m, 2 H), 3.45 (s, 2 H), 4.23 (dd, J = 7.9, 7.2 Hz, 1 H), 5.29 (s, 2 H), 6.70 (d, J = 8.5 Hz, 1 H), 7.40 (s, 1 H), 7.54 (d, J = 8.5 Hz, 1 H), 7.56-7.60 (m, 1 H), 7.74 (ddd, J = 8.5, 7.0, 1.4 Hz, 1 H), 7.85 (dd, J = 8.0, 1.0 Hz, 1 H), 8.08 (d, J = 8.5 Hz, 1 H), 8.22 (d, J = 8.3 Hz, 1 H) |

TABLE I-continued

| | STRUCTURE | Exact Mass | Mass Found [M + H] | LCMS Ret Time, Method | 1H NMR |
|---|---|---|---|---|---|
| 186 | 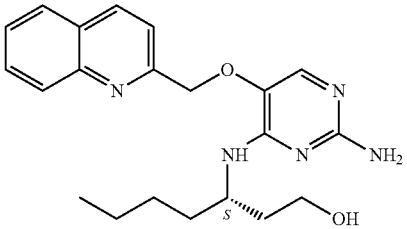 | 381.22 | 382 | 0.9, D | ¹H NMR (400 MHz, CHLOROFORM-d) δ ppm 0.80-0.89 (m, 3 H), 1.20-1.35 (m, 5 H), 1.44 (d, J = 3.5 Hz, 1 H), 1.59 (dd, J = 8.3, 5.8 Hz, 2 H), 1.86-1.98 (m, 1 H), 3.11-3.40 (m, 2 H), 3.55 (dd, J = 10.8, 3.0 Hz, 1 H), 3.59 (dd, J = 5.0, 3.3 Hz, 1 H), 4.14-4.27 (m, 1 H), 5.25 (s, 2 H), 6.32 (d, J = 8.8 Hz, 1 H), 7.46 (s, 1 H), 7.48 (d, J = 8.5 Hz, 1 H), 7.57 (ddd, J = 8.1, 7.0, 1.3 Hz, 1 H), 7.75 (ddd, J = 8.5, 7.0, 1.4 Hz, 1 H), 7.84 (d, J = 8.3 Hz, 1 H), 8.07 (d, J = 8.5 Hz, 1 H), 8.21 (d, J = 8.5 Hz, 1 H) taken on the free base |
| 187 | 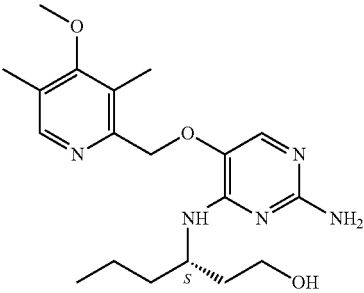 | 375.23 | 376 | 0.81, D | ¹H NMR (400 MHz, DMSO-d₆) δ ppm 0.87 (t, J = 7.3 Hz, 3 H), 1.21-1.36 (m, 2 H), 1.47-1.63 (m, 1 H), 1.69-1.88 (m, 2 H), 1.89-2.04 (m, 1 H), 2.29 (s, 3 H), 2.43 (s, 3 H), 3.41 (t, J = 6.5 Hz, 2 H), 4.03 (s, 3 H), 4.36-4.50 (m, 1 H), 5.41 (s, 2 H), 7.53 (br. s., 2 H), 7.86 (d, J = 5.5 Hz, 1 H), 8.62 (s, 1 H), 9.19 (d, J = 8.8 Hz, 1 H), 12.35 (d, J = 5.3 Hz, 1 H) |
| 188 | 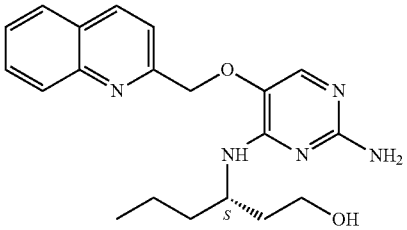 | 367.20 | 368 | 0.78, H | ¹H NMR (400 MHz, CHLOROFORM-d) δ ppm 0.85 (t, J = 7.40 Hz, 3 H), 1.25-1.43 (m, 3 H) 1.50-1.59 (m, 2 H) 1.82-1.94 (m, 1 H) 2.92-3.32 (m, 1 H) 3.42-3.51 (m, 1 H) 3.53-3.60 (m, 1 H) 4.11-4.23 (m, 1 H) 4.83 (s, 2 H) 5.22 (s, 2 H) 5.73 (d, J = 8.78 Hz, 1 H) 7.46 (d, J = 8.53 Hz, 1 H) 7.53 (s, 1 H) 7.55-7.59 (m, 1 H) 7.73 (ddd, J = 8.47, 6.96, 1.38 Hz, 1 H) 7.82 (d, J = 8.03 Hz, 1 H) 8.08 (d, J = 8.28 Hz, 1 H) 8.18 (d, J = 8.53 Hz, 1 H) |
| 189 | 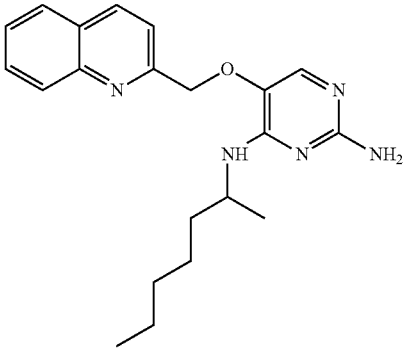 [SMILES: CCCCCC(C)Nc1nc(N)ncc1OCc1ccc2ccccc2n1] | 365.22 | 366 | 1.13, D | ¹H NMR (400 MHz, DMSO-d₆) δ ppm 0.79-0.87 (m, 3 H), 1.15-1.21 (m, 4 H), 1.22-1.28 (m, 6 H), 4.16-4.40 (m, 1 H), 5.35-5.40 (m, 2 H), 7.40-7.48 (m, 2 H), 7.50-7.54 (m, 1 H), 7.62-7.68 (m, 1 H), 7.73-7.77 (m, 1 H), 7.78-7.85 (m, 1 H), 7.99-8.07 (m, 2 H), 8.31-8.38 (m, 1 H), 8.45-8.51 (m, 1 H), 11.47-11.58 (m, 1 H) |

TABLE I-continued

| | STRUCTURE | Exact Mass | Mass Found [M + H] | LCMS Ret Time, Method | 1H NMR |
|---|---|---|---|---|---|
| 190 | 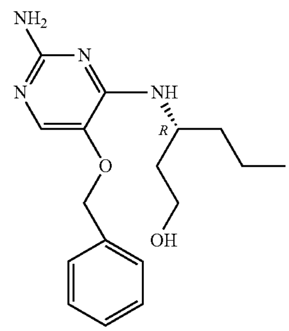 | 316.19 | 317 | 0.84, D | $^1$H NMR (300 MHz, CHLOROFORM-d) δ ppm 0.84 (t, J = 7.4 Hz, 3 H), 1.14-1.55 (m, 6 H), 1.75-1.90 (m, 1 H), 3.30-3.43 (m, 1 H), 3.45-3.57 (m, 1 H), 4.06 (ddd, J = 11.3, 5.2, 3.3 Hz, 1 H), 4.42 (s, 2 H), 4.80-4.86 (m, 1 H), 4.90 (s, 2 H), 7.27-7.34 (m, 5 H), 7.40 (s, 1 H) |
| 191 | 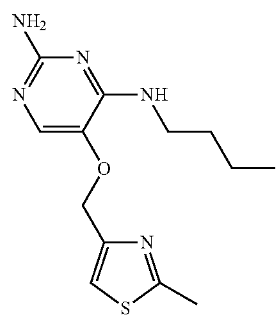 [SMILES: CCCCNc1nc(N)ncc1OCc1csc(C)n1] | 293.13 | 294 | 0.71, D | $^1$H NMR (400 MHz, DMSO-d$_6$) δ ppm 0.89 (t, J = 7.28 Hz, 3 H), 1.12-1.40 (m, 2 H) 1.43-1.60 (m, 2 H) 2.68 (s, 3 H) 3.32-3.48 (m, 2 H) 5.07 (s, 2 H) 7.57 (br. s., 2 H) 7.61 (br. s., 1 H) 7.78 (s, 1 H) 8.45 (t, J = 5.90 Hz, 1 H) 12.21 (br. s., 1 H) |
| 192 | 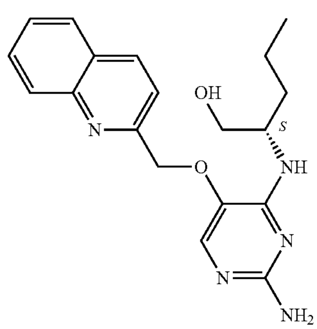 | 353.19 | 354 | 0.78, D | $^1$H NMR (400 MHz, DMSO-d$_6$) δ ppm 0.87 (t, J = 7.4 Hz, 3 H), 1.16-1.35 (m, 2 H), 1.51-1.63 (m, 2 H), 3.48-3.55 (m, 2 H), 4.28 (d, J = 6.0 Hz, 1 H), 5.41 (s, 2 H), 7.51 (br. s., 2 H), 7.58 (d, J = 5.5 Hz, 1 H), 7.68 (td, J = 7.5, 1.0 Hz, 1 H), 7.79 (d, J = 8.5 Hz, 1 H), 7.85 (ddd, J = 8.5, 7.0, 1.4 Hz, 1 H), 8.07 (d, J = 7.3 Hz, 1 H), 8.11 (d, J = 8.5 Hz, 1 H), 8.18 (d, J = 9.0 Hz, 1 H), 8.55 (d, J = 8.5 Hz, 1 H), 11.83 (d, J = 5.5 Hz, 1 H) |
| 193 | 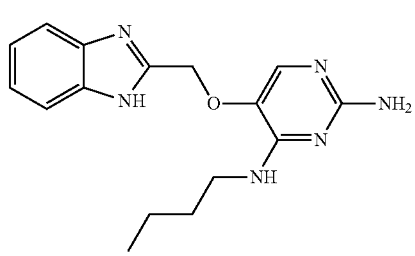 [SMILES: CCCCNc1nc(N)ncc1OCc1nc2ccccc2[nH]1] | 312.17 | 313 | 0.76, D | $^1$H NMR (400 MHz, DMSO-d$_6$) δ ppm 0.89 (t, J = 7.40 Hz, 3 H) 1.25-1.36 (m, 2 H) 1.47-1.55 (m 2 H) 3.25-3.29 (m, 2 H) 5.13 (s, 2 H) 5.58 (s, 2 H) 6.71 (t, J = 5.77 Hz, 1 H) 7.19 (br. s., 2 H) 7.51 (s, 1 H) 7.53 (br. s., 1 H) 7.59 (br. s., 1 H) 12.60 (br. s., 1 H) |

TABLE I-continued

| | STRUCTURE | Exact Mass | Mass Found [M + H] | LCMS Ret Time, Method | 1H NMR |
|---|---|---|---|---|---|
| 194 | 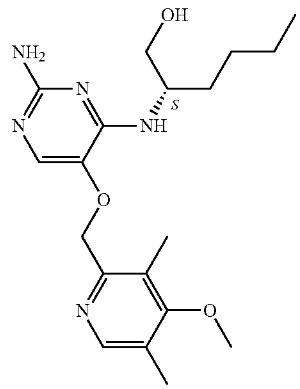 | 375.23 | 376 | 0.82, D | ¹H NMR (400 MHz, DMSO-d₆) δ ppm 0.84 (t, J = 6.9 Hz, 3 H), 1.14-1.35 (m, 4 H), 1.59-1.80 (m, 2 H), 2.29 (s, 3 H), 2.42 (s, 3 H), 3.51-3.61 (m, 2 H), 6 4.02 (s, 3 H), 4.26-4.39 (m, 1 H), 5.41 (s, 2 H), 7.54 (br. s., 2 H), 7.86 (d, J = 3.3 Hz, 1 H), 8.61 (s, 1 H), 9.00 (d, J = 8.0 Hz, 1 H), 12.41 (d, J = 3.3 Hz, 1 H) |
| 195 | 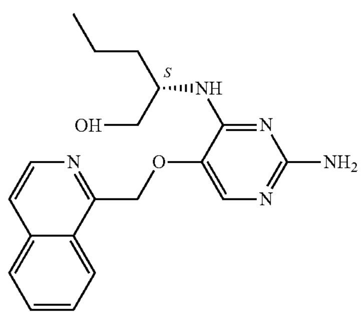 | 353.19 | 354 | 0.76, D | ¹H NMR (400 MHz, DMSO-d₆) δ ppm 0.88 (t, J = 7.6 Hz, 3 H), 1.18-1.39 (m, 2 H), 1.56-1.69 (m, 1 H), 1.69-1.84 (m, 1 H), 3.53-3.68 (m, 2 H), 4.33-6 4.45 (m, 1 H), 6.08 (s, 2 H), 7.55 (br. s., 2 H), 7.96-8.08 (m, 2 H), 8.17 (t, J = 7.5 Hz, 1 H), 8.33 (d, J = 8.3 Hz, 1 H), 8.41 (d, J = 6.3 Hz, 1 H), 8.65 (d, J = 6.5 Hz, 1 H), 8.70 (d, J = 8.5 Hz, 1 H), 9.10-9.28 (m, 1 H), 12.58 (br. s., 1 H) |
| 196 | 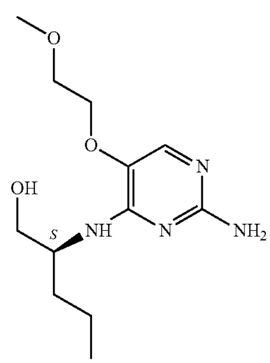 | 270.17 | 271 | 1.37, F | ¹H NMR (300 MHz, CHLOROFORM-d) δ ppm 0.95 (t, J = 7.1 Hz, 3 H), 1.30-1.48 (m, 3 H), 1.49-1.67 (m, 2 H), 3.44 (s, 3 H), 3.55-3.64 (m, 1 H), 3.67 (t, J = 4.4 Hz, 2 H), 3.73-3.80 (m, 1 H), 3.97-4.04 (m, 2 H), 4.09 (d, J = 2.6 Hz, 1 H), 4.80 (br. s., 2 H), 5.91 (d, J = 7.0 Hz, 1 H), 7.47 (s, 1 H) |
| 197 | 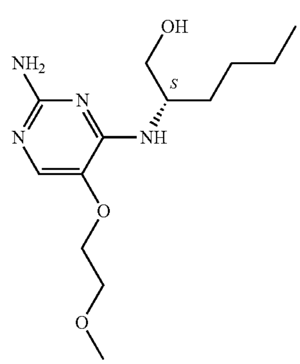 | 284.18 | 285 | 1.62, F | ¹H NMR (300 MHz, CHLOROFORM-d) δ ppm 0.86-0.97 (m, 3 H), 1.24-1.43 (m, 4 H), 1.46-1.72 (m, 2 H), 3.40-3.45 (m, 3 H), 3.48 (br. s., 1 H), 3.60 (dd, J = 11.1, 6.7 Hz, 1 H), 3.67 (t, J = 4.3 Hz, 2 H), 3.72-3.81 (m, 1 H), 4.00 (q, J = 3.9 Hz, 2 H), 4.04-4.14 (m, 1 H), 4.92 (br. s., 2 H), 5.96 (d, J = 7.4 Hz, 1 H), 7.45 (s, 1 H) |

TABLE I-continued

| | STRUCTURE | Exact Mass | Mass Found [M + H] | LCMS Ret Time, Method | 1H NMR |
|---|---|---|---|---|---|
| 198 | 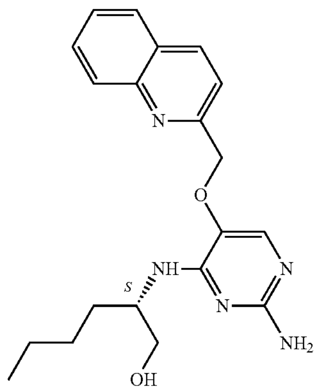 | 367.20 | 368 | 0.85, D | ¹H NMR (400 MHz, DMSO-d₆) δ ppm 0.77-0.84 (m, 3 H), 1.14-1.34 (m, 5 H), 1.48 (d, J = 5.8 Hz, 2 H), 1.56-1.67 (m, 1 H), 3.39-3.51 (m, 2 H), 4.07 (d, J = 5.0 Hz, 1 H), 4.72 (br. s., 1 H), 5.63 (s, 2 H), 6.35 (d, J = 9.0 Hz, 1 H), 7.47 (s, 1 H), 7.62 (ddd, J = 8.1, 6.8, 1.1 Hz, 1 H), 7.69 (d, J = 8.5 Hz, 1 H), 7.79 (ddd, J = 8.4, 6.9, 1.5 Hz, 1 H), 7.98-8.05 (m, 2 H), 8.41 (d, J = 8.5 Hz, 1 H) |
| 199 | 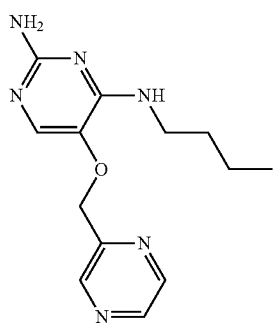 [SMILES: CCCCNc1nc(N)ncc1OCc1cnccn1] | 274.15 | 275 | 0.65, D | ¹H NMR (400 MHz, DMSO-d₆) δ ppm 0.88-0.94 (m, 3 H), 1.20-1.37 (m, 2 H), 1.55 (quin, J = 7.3 Hz, 2 H), 3.42 (q, J = 6.8 Hz, 2 H), 5.22 (s, 2 H), 7.59 (br. s, 2 H), 7.66 (br. s, 1 H), 8.51 (t, J = 5.9 Hz, 1 H), 8.68 (s, 2 H), 9.02 (s, 1 H), 12.24 (br. s., 1 H) |
| 200 | 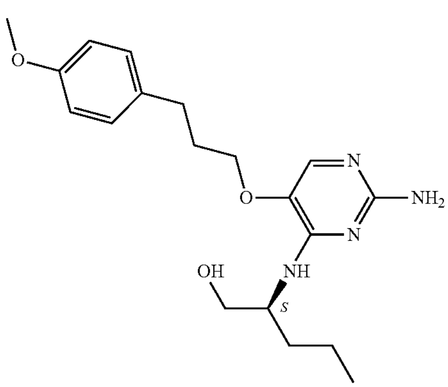 | 360.22 | 361 | 2.21, F | ¹H NMR (300 MHz, CHLOROFORM-d) δ ppm 0.96 (t, J = 7.2 Hz, 3 H), 1.36-1.50 (m, 3 H), 1.50-1.69 (m, 3 H), 2.00-2.14 (m, 2 H), 2.72 (t, J = 7.4 Hz, 2 H), 3.58-3.66 (m, 1 H), 3.80 (s, 3 H), 3.91 (t, J = 6.3 Hz, 2 H), 4.05 (d, J = 5.9 Hz, 1 H), 4.59 (br. s., 2 H), 5.25 (d, J = 6.9 Hz, 1 H), 6.80-6.88 (m, 2 H), 7.11 (d, J = 8.5 Hz, 2 H), 7.34 (s, 1 H) |

TABLE I-continued

| | STRUCTURE | Exact Mass | Mass Found [M + H] | LCMS Ret Time, Method | 1H NMR |
|---|---|---|---|---|---|
| 201 | 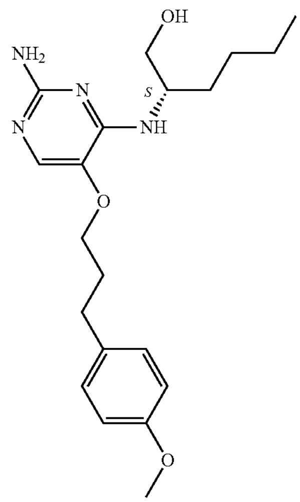 | 374.23 | 375 | 2.43, F | ¹H NMR (300 MHz, CHLOROFORM-d) δ ppm 0.85-0.96 (m, 3 H), 1.23-1.43 (m, 5 H), 1.46-1.71 (m, 2 H), 1.99-2.13 (m, 2 H), 2.71 (t, J = 7.5 Hz, 2 H), 3.57-3.66 (m, 1 H), 3.74 (d, J = 3.2 Hz, 1 H), 3.78 (s, 3 H), 3.90 (t, J = 6.3 Hz, 2 H), 4.03 (t, J = 5.5 Hz, 1 H), 4.63 (br. s., 2 H), 5.26 (d, J = 7.1 Hz, 1 H), 6.80-6.89 (m, 2 H), 7.10 (d, J = 8.5 Hz, 2 H), 7.32 (s, 1 H) |
| 202 | 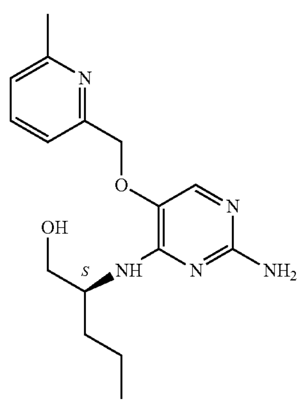 | 317.19 | 318 | 1.35, F | ¹H NMR (300 MHz, CHLOROFORM-d) δ ppm 0.94 (t, J = 7.3 Hz, 3 H), 1.32-1.52 (m, 3 H), 1.53-1.68 (m, 2 H), 2.59 (s, 3 H), 3.58-3.68 (m, 1 H), 3.74-3.84 (m, 1 H), 4.12 (td, J = 6.9, 3.0 Hz, 1 H), 4.61 (br. s., 2 H), 4.99 (s, 2 H), 5.94 (d, J = 7.1 Hz, 1 H), 7.15 (dd, J = 11.7, 7.7 Hz, 2 H), 7.49 (s, 1 H), 7.62 (t, J = 7.7 Hz, 1 H) |
| 203 | 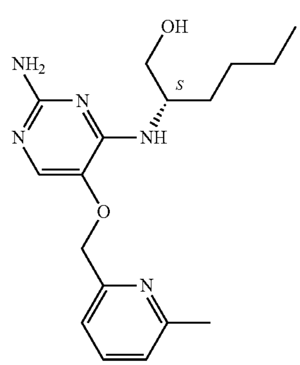 | 331.20 | 332 | 1.63, F | ¹H NMR (300 MHz, CHLOROFORM-d) δ ppm 0.85-0.96 (m, 3 H), 1.18-1.46 (m, 5 H), 1.50-1.72 (m, 2 H), 2.59 (s, 3 H), 3.58-3.69 (m, 1 H), 3.75-3.84 (m, 1 H), 4.09 (td, J = 6.9, 2.6 Hz, 1 H), 4.62 (br. s., 2 H), 5.00 (s, 2 H), 5.95 (d, J = 7.0 Hz, 1 H), 7.15 (dd, J = 12.3, 7.8 Hz, 2 H), 7.49 (s, 1 H), 7.62 (t, J = 7.7 Hz, 1 H) |

TABLE I-continued

| | STRUCTURE | Exact Mass | Mass Found [M + H] | LCMS Ret Time, Method | 1H NMR |
|---|---|---|---|---|---|
| 204 | 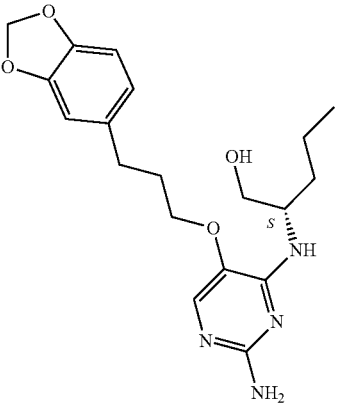 | 374.20 | 375 | 2.26, F | ¹H NMR (300 MHz, CHLOROFORM-d) δ ppm 0.97 (t, J = 7.2 Hz, 3 H), 1.32-1.49 (m, 3 H), 1.51-1.70 (m, 3 H), 1.98-2.14 (m, 2 H), 2.70 (t, J = 7.5 Hz, 1 H), 3.59-3.71 (m, 1 H), 3.74-3.83 (m, 1 H), 3.91 (t, J = 6.4 Hz, 1 H), 3.99-4.15 (m, 1 H), 4.68 (br. s., 2 H), 5.26-5.33 (m, 2 H), 5.92-5.95 (m, 2 H), 6.59-6.66 (m, 1 H), 6.69 (d, J = 1.4 Hz, 1 H), 6.72-6.78 (m, 1 H), 7.33 (s, 1 H) |
| 205 | 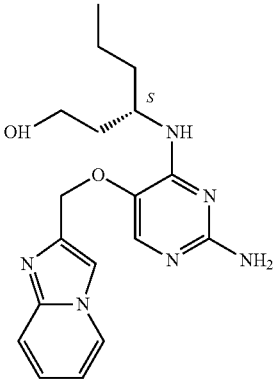 | 356.20 | 357 | 0.66, D | ¹H NMR (400 MHz, DMSO-d₆) δ ppm 0.84 (t, J = 7.28 Hz, 3 H), 1.15-1.30 (m, 2 H) 1.43-1.57 (m, 1 H) 1.57-1.69 (m, 1 H) 1.69-1.87 (m, 2 H) 3.37-3.45 (m, 2 H) 4.24-4.43 (m, 1 H) 5.30 (s, 2 H) 7.28 (t, J = 6.53 Hz, 1 H) 7.55 (br. s., 2 H) 7.70 (s, 1 H) 7.62-7.77 (m, 1 H) 7.81 (d, J = 8.78 Hz, 1 H) 8.31 (s, 1 H) 8.27-8.35 (m, 1 H) 8.81 (d, J = 6.78 Hz, 1 H) 12.15 (br. s., 1 H) |
| 206 | 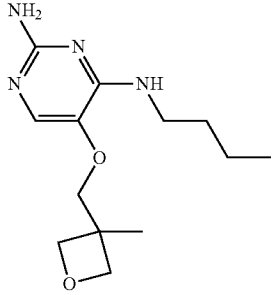 [SMILES: CCCCNc1nc(N)ncc1OCC1(C)COC1] | 266.17 | 267 | 0.72, D | ¹H NMR (400 MHz, DMSO-d₆) δ ppm 0.89 (t, J = 7.40 Hz, 3 H) 1.15-1.33 (m, 2 H) 1.35 (s, 3 H) 1.43-1.56 (m, 2 H) 3.12-3.30 (m, 2 H) 3.91 (s, 2 H) 4.28 (d, J = 5.77 Hz, 2 H) 4.46 (d, J = 5.77 Hz, 2 H) 5.50 (s, 2 H) 6.20 (t, J = 5.90 Hz, 1 H) 7.41 (s, 1 H) |
| 207 | 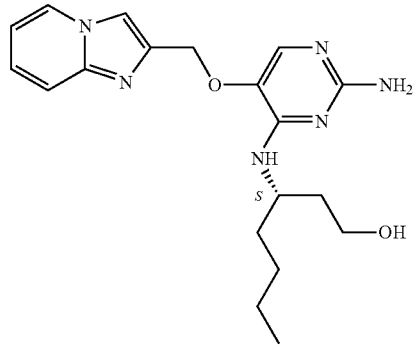 | 370.21 | 371 | 0.71, D | ¹H NMR (400 MHz, DMSO-d₆) δ ppm 0.83 (t, J = 1.00 Hz, 3 H) 1.13-1.33 (m, 4 H) 1.47-1.61 (m, 1 H) 1.61-1.78 (m, 2 H) 1.79-1.89 (m, 1 H) 3.29-3.47 (m, 2 H) 4.27-4.38 (m, 2 H) 5.37 (s, 2 H) 7.47 (br. s., 1 H) 7.57 (br. s., 2 H) 7.73 (br. s., 1 H) 7.86-8.01 (m, 2 H) 8.35 (d, J = 9.03 Hz, 1 H) 8.42 (s, 1 H) 8.94 (d, J = 6.27 Hz, 1 H) 12.19 (br. s., 1 H) |

TABLE I-continued

| | STRUCTURE | Exact Mass | Mass Found [M + H] | LCMS Ret Time, Method | 1H NMR |
|---|---|---|---|---|---|
| 208 | 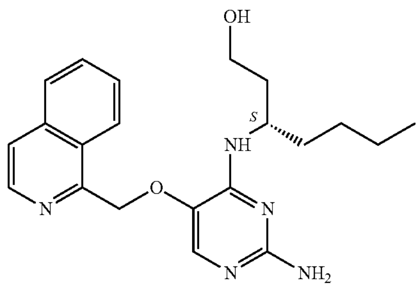 | 381.22 | 382 | 0.86, D | $^1$H NMR (400 MHz, DMSO-d$_6$) δ ppm 0.84 (t, J = 7.03 Hz, 3 H) 1.13-1.36 (m, 4 H) 1.52-1.67 (m 1 H) 1.71-1.84 (m, 2 H) 1.88-2.00 (m, 1 H) 3.33-3.48 (m, 2 H) 4.42 (m, J = 8.0, 4.60, 4.60 Hz, 1 H) 6.02 (s, 2 H) 7.51 (br. s., 2 H) 7.96 (t, J = 1.00 Hz, 1 H) 7.96 (t, J = 1.00 Hz, 1 H) 8.13 (t, J = 7.65 Hz, 1 H) 8.21-8.47 (m, 1 H) 8.32 (d, J = 1.00 Hz, 1 H) 8.65 (s, 1 H) 8.64 (d, J = 1.00 Hz, 1 H) 9.17 (br. s., 1 H) 12.34 (br. s., 1 H)" |
| 209 | 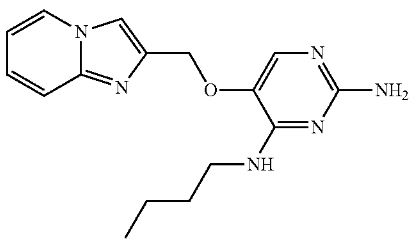 [SMILES: CCCCNc1nc(N)ncc1OCc1cn2ccccc2n1] | 312.17 | 313 | 0.69, D | $^1$H NMR (400 MHz, DMSO-d$_6$) δ ppm 0.89 (t, J = 7.4 Hz, 3 H), 1.29 (dq, J = 14.9, 7.3 Hz, 2 H), 1.57 (quin, J = 7.3 Hz, 2 H), 3.43 (dd, J = 13.6, 6.8 Hz, 2 H), 5.38 6 (s, 2 H), 7.48 (td, J = 6.7, 1.3 Hz, 1 H), 7.62 (br. s., 2 H), 7.72 (s, 1 H), 7.87-8.02 (m, 2 H), 8.46 (s, 1 H), 8.82 (t, J = 5.9 Hz, 1 H), 8.94 (d, J = 6.8 Hz, 1 H), 12.29 (br. s., 1 H) |
| 210 | 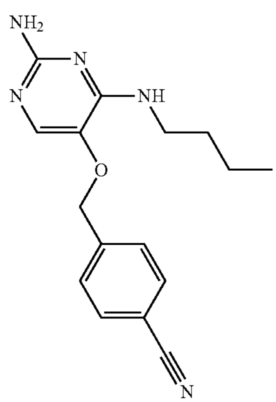 [SMILES: CCCCNc1nc(N)ncc1OCc1ccc(C#N)cc1] | 297.16 | 298 | 0.85, D | $^1$H NMR (400 MHz, DMSO-d$_6$) δ ppm 0.90 (t, J = 7.4 Hz, 3 H), 1.22-1.35 (m, 2 H), 1.49-1.60 (m, 2 H), 3.37-3.47 (m, 2 H), 5.18 (s, 2 H), 7.49-7.62 (m, 3 6 H), 7.71 (m, J = 8.5 Hz, 2 H), 7.86-7.93 (m, 2 H), 8.51 (t, J = 5.9 Hz, 1 H), 12.17-12.31 (m, 1 H) |
| 211 | 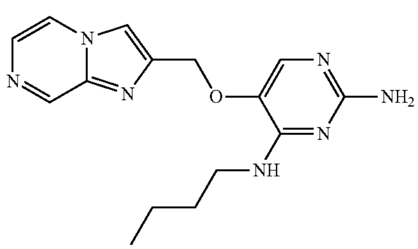 [SMILES: CCCCNc1nc(N)ncc1OCc1cn2ccncc2n1] | 313.17 | 314 | 0.59, D | $^1$H NMR (400 MHz, DMSO-d$_6$) δ ppm 0.89 (t, J = 7.4 Hz, 3 H), 1.21-1.37 (m, 2 H), 1.48-1.62 (m, 2 H), 3.41 (q, J = 6.8 Hz, 2 H), 5.33 (s, 2 H), 7.60 (br. s., 2 6 H), 7.69 (br. s., 1 H), 8.09 (d, J = 4.5 Hz, 1 H), 8.50-8.67 (m, 2 H), 8.85 (d, J = 4.3 Hz, 1 H), 9.32 (s, 1 H), 12.29 (br. s., 1 H) |
| 212 | 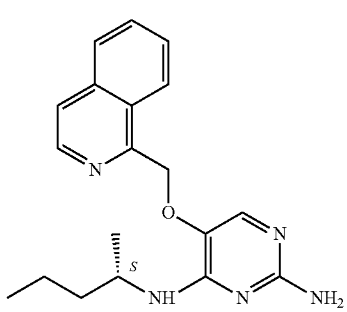 | 337.19 | 338 | 0.94, D | $^1$H NMR (400 MHz, DMSO-d$_6$) δ ppm 0.85 (t, J = 7.3 Hz, 3 H), 1.17 (d, J = 6.5 Hz, 3 H), 1.19-1.29 (m, 2 H), 1.40-1.55 (m, 1 H), 1.57-1.72 (m, 1 H), 4.21-6 4.35 (m, 1 H), 5.81 (s, 2 H), 7.47 (br. s., 2 H), 7.66 (br. s., 1 H), 7.78-7.86 (m, 1 H), 7.95 (t, J = 7.3 Hz, 1 H), 8.08 (br. s., 1 H), 8.15 (d, J = 8.0 Hz, 1 H), 8.48 (d, J = 8.3 Hz, 1 H), 8.56 (d, J = 5.8 Hz, 1 H), 11.73 (br. s., 1 H) |

TABLE I-continued

| | STRUCTURE | Exact Mass | Mass Found [M + H] | LCMS Ret Time, Method | 1H NMR |
|---|---|---|---|---|---|
| 213 | 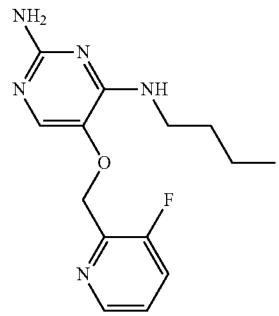 [SMILES: CCCCNc1nc(N)ncc1OCc1ncccc1F] | 291.15 | 292 | 0.75, D | ¹H NMR (400 MHz, DMSO-d₆) δ ppm 0.88 (t, J = 7.4 Hz, 3 H), 1.27 (dq, J = 14.9, 7.4 Hz, 2 H), 1.51 (quin, J = 7.3 Hz, 2 H), 3.38 (q, J = 6.9 Hz, 2 H), 5.20 (d, 6 J = 1.8 Hz, 2 H), 7.51 (br. s., 2 H), 7.54-7.62 (m, 2 H), 7.84 (ddd, J = 9.9, 8.6, 1.1 Hz, 1 H), 8.39-8.53 (m, 2 H), 11.85 (d, J = 5.5 Hz, 1 H) |
| 214 | 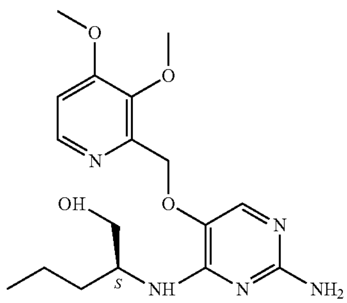 | 363.19 | 364 | 0.65, D | ¹H NMR (400 MHz, DMSO-d₆) δ ppm 0.86 (t, J = 7.3 Hz, 3 H), 1.18-1.35 (m, 2 H), 1.36-1.48 (m, 1 H), 1.51-1.64 (m, 1 H), 3.31-3.49 (m, 2 H), 3.78 (s, 3 6 H), 3.90 (s, 3 H), 3.99-4.09 (m, 1 H), 4.68 (br. s., 1 H), 4.86-4.97 (m, 2 H), 5.59 (s, 2 H), 6.38 (d, J = 8.8 Hz, 1 H), 7.14 (d, J = 5.5 Hz, 1 H), 7.49 (s, 1 H), 8.23 (d, J = 5.5 Hz, 1 H) |
| 215 | 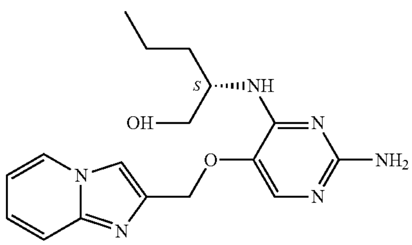 | 342.18 | 343 | 0.6, D | ¹H NMR (400 MHz, DMSO-d₆) δ ppm 0.85 (t, J = 7.3 Hz, 3 H), 1.14-1.33 (m, 2 H), 1.49-1.72 (m, 2 H), 3.47-3.61 (m, 2 H), 4.21-4.33 (m, 1 H), 5.41 (s, 2 6 H), 7.50 (td, J = 6.5, 1.5 Hz, 1 H), 7.61 (br. s., 2 H), 7.78 (s, 1 H), 7.91-8.03 (m, 2 H), 8.22 (d, J = 9.0 Hz, 1 H), 8.48 (s, 1 H), 8.97 (d, J = 6.8 Hz, 1 H), 12.42 (br. s., 1 H) |
| 216 | 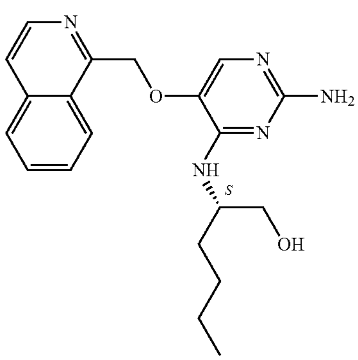 | 367.20 | 368 | 0.82, D | ¹H NMR (400 MHz, DMSO-d₆) δ ppm 0.80 (t, J = 7.2 Hz, 3 H), 1.08-1.18 (m, 2 H), 1.18-1.27 (m, 2 H), 1.27-1.37 (m, 1 H), 1.49-1.61 (m, 1 H), 3.27-6 3.33 (m, 2 H), 3.92-4.04 (m, 1 H), 4.65 (br. s., 1 H), 5.47-5.63 (m, 4 H), 6.08 (d, J = 9.0 Hz, 1 H), 7.51 (s, 1 H), 7.66-7.74 (m, 1 H), 7.78-7.83 (m, 1 H), 7.85 (d, J = 5.5 Hz, 1 H), 8.02 (d, J = 8.0 Hz, 1 H), 8.40 (d, J = 8.5 Hz, 1 H), 8.48 (d, J = 5.8 Hz, 1 H) |
| 217 | 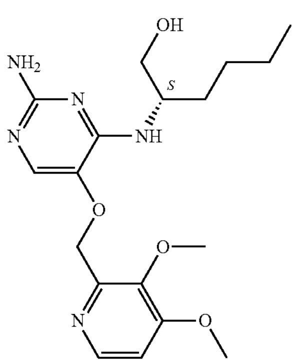 | 377.21 | 378 | 0.73, D | ¹H NMR (400 MHz, DMSO-d₆) δ ppm 0.84 (t, J = 6.9 Hz, 3 H), 1.15-1.37 (m, 4 H), 1.58-1.79 (m, 2 H), 3.50-3.64 (m, 2 H), 3.93 (s, 3 H), 4.16 (s, 3 H), 6 4.25-4.37 (m, 1 H), 5.37-5.47 (m, 2 H), 7.58 (br. s., 2 H), 7.71 (d, J = 6.8 Hz, 1 H), 7.81 (d, J = 4.3 Hz, 1 H), 8.62 (d, J = 6.8 Hz, 1 H), 8.89 (d, J = 8.8 Hz, 1 H), 12.30-12.47 (m, 1 H) |

TABLE I-continued

| | STRUCTURE | Exact Mass | Mass Found [M + H] | LCMS Ret Time, Method | 1H NMR |
|---|---|---|---|---|---|
| 218 | 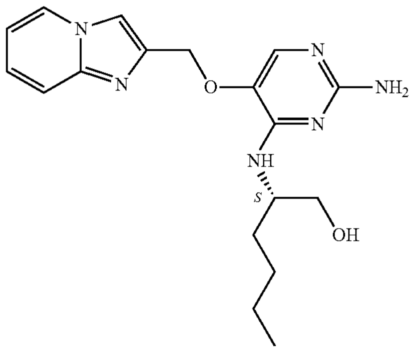 | 356.20 | 357 | 0.68, D | ¹H NMR (400 MHz, DMSO-d₆) δ ppm 0.82 (t, J = 7.0 Hz, 3 H), 1.09-1.36 (m, 4 H), 1.61 (q, J = 7.2 Hz, 2 H), 3.45-3.59 (m, 2 H), 4.18-4.31 (m, 1 H), 5.33-6 5.45 (m, 2 H), 7.47 (t, J = 6.7 Hz, 1 H), 7.59 (br. s., 2 H), 7.76 (s, 1 H), 7.86-8.02 (m, 2 H), 8.20 (d, J = 9.0 Hz, 1 H), 8.45 (s, 1 H), 8.94 (d, J = 6.8 Hz, 1 H), 12.33 (br. s., 1 H) |
| 219 | 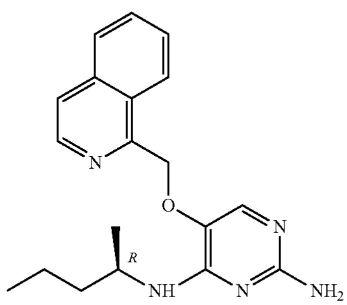 | 337.19 | 338 | 0.94, D | ¹H NMR (400 MHz, DMSO-d₆) δ ppm 0.85 (t, J = 7.3 Hz, 3 H), 1.18 (d, J = 6.5 Hz, 3 H), 1.20-1.29 (m, 2 H), 1.41-1.56 (m, 1 H), 1.67 (dd, J = 13.4, 6.7 Hz, 1H), 4.24-4.36 (m, 1 H), 5.84 (br. s., 2 H), 7.47 (br. s., 2 H), 7.70 (br. s., 1 H), 7.80-7.89 (m, 1 H), 7.98 (t, J = 7.2 Hz, 1 H), 8.11 (br. s., 1 H), 8.17 (d, J = 8.3 Hz, 1 H), 8.50 (d, J = 8.3 Hz, 1 H), 8.57 (d, J = 6.0 Hz, 1 H), 8.71 (br. s., 1 H), 11.79 (br. s., 1 H) |
| 220 | 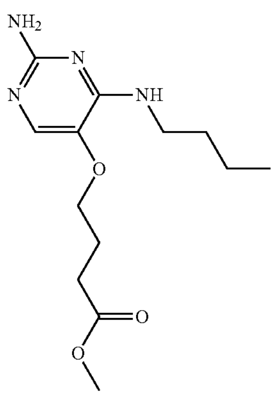 [SMILES: CCCCNc1nc(N)ncc1OCCCC(=O)OC] | 282.17 | 283 | 0.76, D | ¹H NMR (400 MHz, DMSO-d₆) δ ppm 0.90 (t, J = 7.4 Hz, 3 H), 1.30 (dq, J = 14.9, 7.3 Hz, 2 H), 1.54 (dt, J = 14.5, 7.4 Hz, 2 H), 1.97 (quin, J = 6.7 Hz, 2 H), 2.55 6 (t, J = 7.4 Hz, 2 H), 3.37-3.45 (m, 2 H), 3.61 (s, 3 H), 3.93 (t, J = 6.1 Hz, 2 H), 7.39 (s, 1 H), 7.47 (br. s., 2 H), 8.34 (t, J = 5.8 Hz, 1 H), 11.96 (br. s., 1 H) |
| 221 | 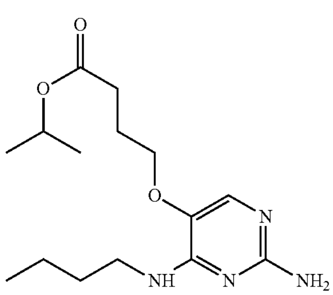 [SMILES: CCCCNc1nc(N)ncc1OCCCC(=O)OC(C)C] | 310.20 | 311 | 0.91, D | ¹H NMR (400 MHz, DMSO-d₆) δ ppm 0.90 (t, J = 7.3 Hz, 3 H), 1.19 (d, J = 6.3 Hz, 6 H), 1.30 (dq, J = 14.9, 7.4 Hz, 2 H), 1.54 (dt, J = 14.5, 7.4 Hz, 2 H), 1.89-6 2.02 (m, 2 H), 3.36-3.44 (m, 2 H), 3.92 (t, J = 6.1 Hz, 2 H), 4.90 (quin, J = 6.3 Hz, 1 H), 7.36 (s, 1 H), 7.41 (br. s., 2 H), 8.35 (t, J = 6.0 Hz, 1 H), 11.73 (br. s., 1 H) |

TABLE I-continued

| | STRUCTURE | Exact Mass | Mass Found [M + H] | LCMS Ret Time, Method | 1H NMR |
|---|---|---|---|---|---|
| 222 | 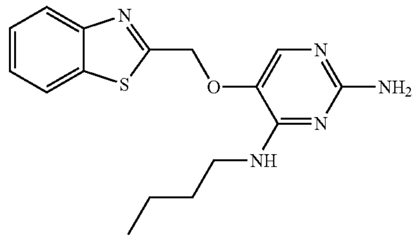 [SMILES: CCCCNc1nc(N)ncc1OCc1nc2ccccc2s1] | 329.13 | 330 | 0.27, D | ¹H NMR (400 MHz, DMSO-d₆) δ ppm 0.89 (t, J = 7.28 Hz, 2 H) 1.22-1.40 (m, 2 H) 1.42-1.58 (m, 2 H) 3.25-3.38 (m, 2 H) 5.39 (s, 2 H) 5.63 (s, 1 H) 6.56 (t, J = 5.77 Hz, 1 H) 7.43-7.61 (m, 2 H) 8.01 (d, J = 7.53 Hz, 1 H) 8.13 (dd, J = 7.91, 0.63 Hz, 1 H) |
| 223 | 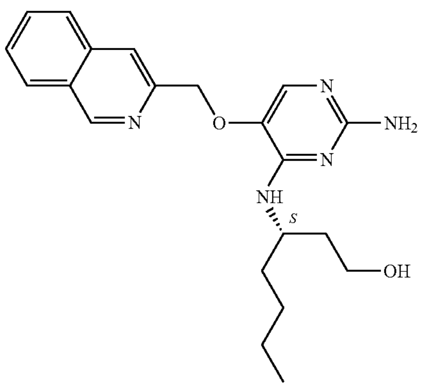 | 381.22 | 382 | 0.86, D | ¹H NMR (400 MHz, DMSO-d₆) δ ppm 0.83 (t, J = 7.00 Hz, 3 H) 1.17-1.34 (m, 4 H) 1.53-1.67 (m, 2 H) 1.71-1.83 (m, 2 H) 3.46 (t, J = 6.30 Hz, 2 H) 4.34 (m, J = 7.80 Hz, 1 H) 5.33 (s, 2 H) 7.49 (br. s., 2 H) 7.64 (d, J = 5.52 Hz, 1 H) 7.79 (t, J = 7.50 Hz, 1 H) 7.91 (t, J = 7.53 Hz, 1 H) 8.10 (s, 1 H) 8.06 (d, J = 8.30 Hz, 1 H) 8.26 (d, J = 8.28 Hz, 1 H) 8.46 (d, J = 8.78 Hz, 1 H) 9.48 (s, 1 H) |
| 224 | 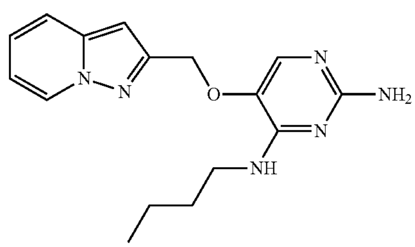 [SMILES: CCCCNc1nc(N)ncc1OCc1cc2ccccn2n1] | 312.17 | 313 | 0.26, D | ¹H NMR (400 MHz, DMSO-d₆) δ ppm 0.88 (t, J = 7.40 Hz, 3 H) 1.19-1.31 (m, 2 H) 1.51 (quin, J = 7.28 Hz, 2 H) 3.39 (m, J = 6.80, 6.80, 6.80 Hz, 2 H) 5.24 (s, 2 H) 6.78 (s, 1 H) 6.92 (t, J = 6.90 Hz, 1 H) 7.25 (dd, J = 8.28, 7.28 Hz, 1 H) 7.47 (br. s., 2 H) 7.55 (d, J = 5.77 Hz, 1 H) 7.70 (d, J = 9.03 Hz, 1 H) 8.42 (t, J = 5.77 Hz, 1 H) 8.65 (d, J = 7.03 Hz, 1 H) 11.74 (d, J = 5.77 Hz, 1 H) |
| 225 | 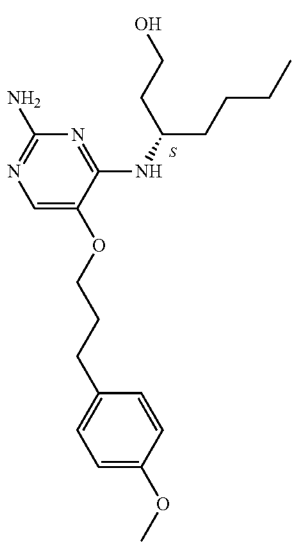 | 388.25 | 389 | 2.51, F | ¹H NMR (300 MHz, CHLOROFORM-d) δ ppm 0.74-0.88 (m, 3 H), 1.14-1.36 (m, 4 H), 1.40-1.65 (m, 2 H), 1.77-1.93 (m, 2 H), 2.00 (quin, J = 6.9 Hz, 2 H), 2.64 (td, J = 7.4, 2.4 Hz, 2 H), 3.38-3.42 (m, 1 H), 3.46 (dd, J = 11.4, 2.6 Hz, 1 H), 3.52 (dd, J = 5.1, 2.2 Hz, 1 H), 3.72 (s, 3 H), 3.84 (td, J = 6.3, 1.8 Hz, 2 H), 4.06 (d, J = 2.7 Hz, 1 H), 4.48 (br. s., 2 H), 4.89 (d, J = 8.7 Hz, 1 H), 6.72-6.80 (m, 2 H), 7.02 (d, J = 8.7 Hz, 2 H), 7.25 (s, 1 H) |

TABLE I-continued

| | STRUCTURE | Exact Mass | Mass Found [M + H] | LCMS Ret Time, Method | 1H NMR |
|---|---|---|---|---|---|
| 226 | 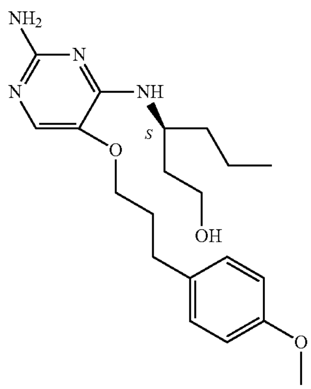 | 374.23 | 375 | 2.36, F | ¹H NMR (300 MHz, CHLOROFORM-d) δ ppm 0.85 (t, J = 7.2 Hz, 3 H), 1.24-1.39 (m, 3 H), 1.41-1.54 (m, 2 H), 1.85 (d, J = 5.4 Hz, 1 H), 2.00 (t, J = 6.9 Hz, 2 H), 2.64 (td, J = 7.4, 2.1 Hz, 2 H), 3.42 (s, 1 H), 3.46 (dd, J = 11.4, 2.6 Hz, 1 H), 3.52 (d, J = 2.6 Hz, 1 H), 3.72 (s, 3 H), 3.84 (td, J = 6.4, 1.4 Hz, 2 H), 4.01-4.17 (m, 1 H), 4.46 (br. s., 2 H), 4.85 (br. s., 1 H), 6.71-6.82 (m, 2 H), 6.97-7.08 (m, 2 H), 7.26 (s, 1 H) |
| 227 | 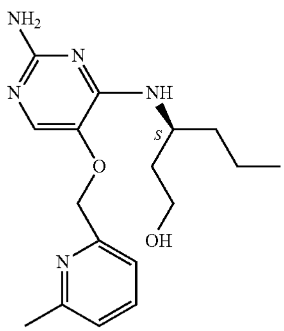 | 331.20 | 332 | 1.5, F | ¹H NMR (300 MHz, CHLOROFORM-d) δ ppm 0.90 (t, J = 7.3 Hz, 3 H), 1.22-1.50 (m, 4 H), 1.52-1.67 (m, 2 H), 1.83-2.05 (m, 1 H), 2.58 (s, 3 H), 3.43-3.55 (m, 1 H), 3.56-3.65 (m, 1 H), 4.20 (br. s., 1 H), 4.60-4.76 (m, 2 H), 4.99 (s, 2 H), 5.82 (d, J = 8.7 Hz, 1 H), 7.14 (t, J = 6.8 Hz, 2 H), 7.50 (s, 1 H), 7.61 (t, J = 7.7 Hz, 1 H) |
| 228 | 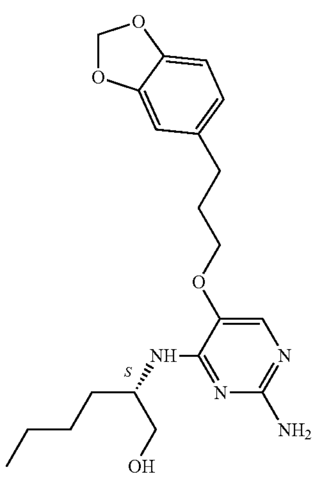 | 388.21 | 389 | 2.4, F | ¹H NMR (300 MHz, CHLOROFORM-d) δ ppm 0.92 (t, J = 1.0 Hz, 3 H), 1.22-1.43 (m, 5 H), 1.47-1.71 (m, 2 H), 1.97-2.12 (m, 2 H), 2.64-2.75 (m, 2 H), 3.63 (dd, J = 10.9, 6.8 Hz, 1 H), 3.74-3.83 (m, 1 H), 3.91 (t, J = 6.3 Hz, 2 H), 3.97-4.10 (m, 1 H), 4.57 (br. s., 2 H), 5.26 (d, J = 6.7 Hz, 1 H), 5.94 (s, 2 H), 6.59-6.66 (m, 1 H), 6.69 (d, J = 1.5 Hz, 1 H), 6.72-6.78 (m, 1 H), 7.35 (s, 1 H) |
| 229 | 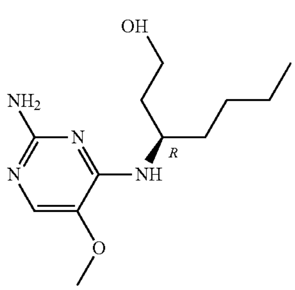 | 254.17 | 255 | 1.59, F | ¹H NMR (300 MHz, CHLOROFORM-d) δ ppm 0.90 (t, J = 1.0 Hz, 3 H), 1.30-1.46 (m, 5 H), 1.48-1.73 (m, 3 H), 1.95 (tdd, J = 11.2, 11.2, 5.5, 2.7 Hz, 1 H), 3.54 (dd, J = 11.3, 2.7 Hz, 1 H), 3.58-3.67 (m, 1 H), 3.79 (s, 3 H), 4.16 (dd, J = 5.7, 3.0 Hz, 1 H), 4.99 (br. s., 2 H), 5.10 (d, J = 8.5 Hz, 1 H), 7.32 (s, 1 H) |

TABLE I-continued

| | STRUCTURE | Exact Mass | Mass Found [M + H] | LCMS Ret Time, Method | 1H NMR |
|---|---|---|---|---|---|
| 230 | 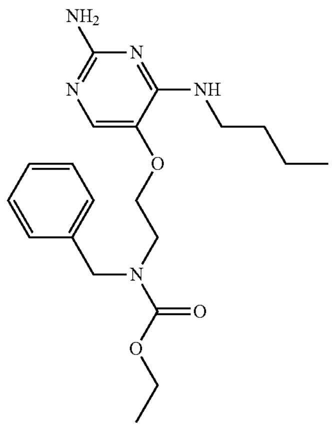 [SMILES: CCCCNc1nc(N)ncc1OCCN(Cc1ccccc1)C(=O)OCC] | 387.23 | 388 | 5.75, G | nl ¹H NMR (360 MHz, DMSO-d₆) δ ppm 0.89 (t, J = 7.32 Hz, 3 H) 1.03-1.20 (m, 3 H) 1.29 (m, J = 7.70 Hz, 2 H) 1.52 (d, J = 6.95 Hz, 2 H) 3.38 (m, J = 7.00 Hz, 2 H) 3.48-3.63 (m, 2 H) 4.07 (q, J = 7.20 Hz, 4 H), 4.53 (s, 2 H) 7.19-7.29 (m, 3 H) 7.30-7.38 (m, 2 H) 7.42 (s, 1 H) 7.45-7.56 (m, 2 H) 8.09-8.32 (m, 1 H) 11.84-12.01 (m, 1 H) |
| 231 | 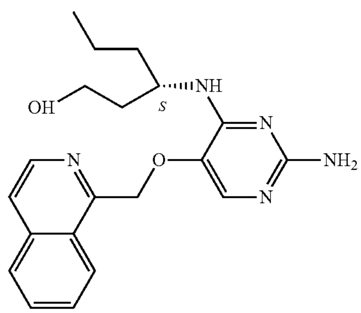 | 367.20 | 368 | 0.8, D | ¹H NMR (400 MHz, DMSO-d₆) δ ppm 0.86 (t, J = 7.40 Hz, 3 H) 1.19-1.30 (m, 2 H) 1.48-1.58 (m, 1 H) 1.65-1.78 (m, 2 H) 1.82-1.92 (m, 1 H) 3.35-3.45 (m, 2 H) 4.37-4.45 (m, 1 H) 5.93 (s, 2 H) 7.49 (br. s., 2 H) 7.80 (br. s., 1 H) 7.90 (t, J = 7.40 Hz, 1 H) 8.04 (t, J = 6.90 Hz, 1 H), 8.22 (d, J = 8.03 Hz, 2 H) 8.54-8.63 (m, 2 H) 8.88 (br. s., 1 H) 12.04 (br. s., 1 H) |
| 232 | 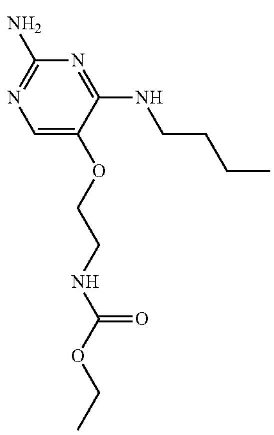 [SMILES: CCCCNc1nc(N)ncc1OCCNC(=O)OCC] | 297.18 | 298 | 4.18, G | ¹H NMR (360 MHz, DMSO-d₆) δ ppm 0.91 (t, J = 7.32 Hz, 3 H) 1.17 (t, J = 7.14 Hz, 3 H) 1.32 (m, J = 7.40, 7.40, 7.40, 7.40, 7.40 Hz, 2 H) 1.56 (m, J = 7.30, 7.30, 7.30, 7.30 Hz, 2 H) 3.38-3.48 (m, 2 H) 3.88 (t, J = 5.12 Hz, 2 H) 4.01 (q, J = 7.20 Hz, 2 H) 7.32-7.40 (m, 2 H) 7.44 (br. s., 2 H) 8.32 (t, J = 5.67 Hz, 1 H) 11.71 (br. s., 1 H) |
| 233 | 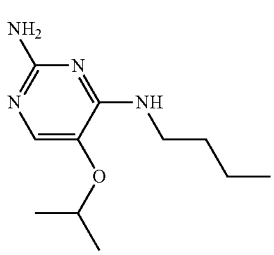 [SMILES: CCCCNc1nc(N)ncc1OC(C)C] | 224.16 | 225 | 4.53, G | ¹H NMR (360 MHz, DMSO-d₆) δ ppm 0.90 (t, J = 7.32 Hz, 3 H) 1.19-1.34 (m, 8 H) 1.45-1.58 (m, 2 H) 3.35-3.43 (m, 2 H) 4.41 (m, J = 6.00, 6.00, 6.00, 6.00 Hz, 1 H) 7.35-7.54 (m, 3 H) 8.26 (t, J = 6.04 Hz, 1 H) 11.89 (br. s., 1 H) |

TABLE I-continued

| | STRUCTURE | Exact Mass | Mass Found [M + H] | LCMS Ret Time, Method | 1H NMR |
|---|---|---|---|---|---|
| 234 | 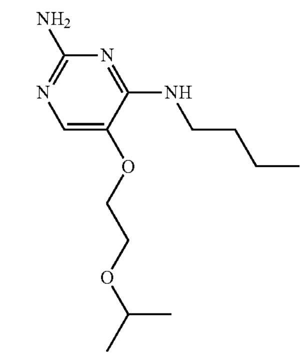 [SMILES: CCCCNc1nc(N)ncc1OCCOC(C)C] | 268.19 | 269 | 0.84, D | ¹H NMR (400 MHz, DMSO-d₆) δ ppm 0.90 (t, J = 7.4 Hz, 3 H), 1.10 (d, J = 6.0 Hz, 6 H), 1.24-1.35 (m, 2 H), 1.54 (quin, J = 7.3 Hz, 2 H), 3.40 (q, J = 6.9 Hz, 2 6 H), 3.62 (dt, J = 12.2, 6.1 Hz, 1 H), 3.68 (dd, J = 5.3, 4.0 Hz, 2 H), 4.01-4.07 (m, 2 H), 7.36-7.52 (m, 3 H), 8.27 (t, J = 5.9 Hz, 1 H), 11.77 (br. s., 1 H) |
| 235 | 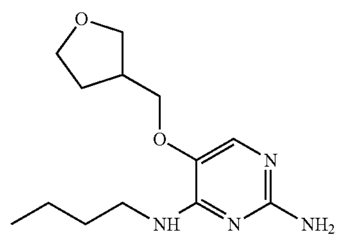 [SMILES: CCCCNc1nc(N)ncc1OCC1CCOC1] | 266.17 | 267 | 0.71, D | ¹H NMR (400 MHz, DMSO-d₆) δ ppm 0.90 (t, J = 7.3 Hz, 3 H), 1.30 (dq, J = 14.9, 7.3 Hz, 2 H), 1.49-1.57 (m, 2 H), 1.57-1.67 (m, 1 H), 1.97-2.09 (m, 1 H), 6 2.59-2.71 (m, 1 H), 3.40 (q, J = 6.8 Hz, 2 H), 3.52 (dd, J = 8.7, 5.4 Hz, 1 H), 3.65 (q, J = 7.7 Hz, 1 H), 3.72-3.85 (m, 3 H), 3.86-3.93 (m, 1 H), 7.32-7.48 (m, 3 H), 8.30 (t, J = 5.9 Hz, 1 H), 11.88 (br. s., 1 H) |
| 236 | 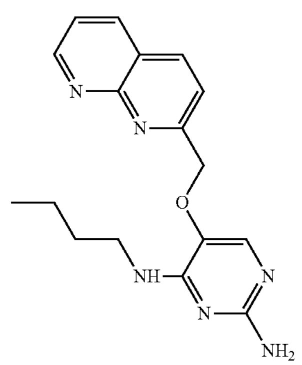 [SMILES: CCCCNc1nc(N)ncc1OCc1ccc2cccnc2n1] | 324.17 | 325 | 0.71, D | ¹H NMR (400 MHz, DMSO-d₆) δ ppm 0.91 (t, J = 7.4 Hz, 3 H), 1.32 (sxt, J = 7.4 Hz, 2 H), 1.52-1.65 (m, 2 H), 3.46 (q, J = 6.8 Hz, 2 H), 5.43 (s, 2 H), 7.59 (br. 6 s., 2 H), 7.65 (d, J = 4.5 Hz, 1 H), 7.81 (dd, J = 8.2, 4.4 Hz, 1 H), 8.05 (d, J = 8.5 Hz, 1 H), 8.64-8.77 (m, 3 H), 9.20 (dd, J = 4.4, 1.9 Hz, 1 H), 12.13 (br. s., 1 H) |
| 237 | 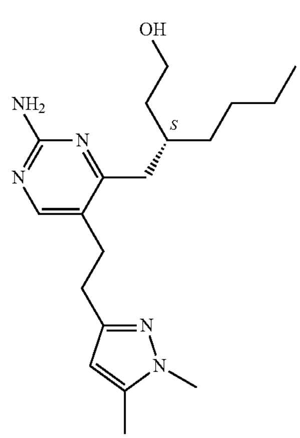 | 348.23 | 349 | 0.73, D | ¹H NMR (400 MHz, DMSO-d₆) δ ppm 0.84 (m, J = 7.20, 7.20 Hz, 3 H) 1.14-1.34 (m, 4 H) 1.55 (m, J = 16.10, 8.00, 8.00 Hz, 2 H) 1.62-1.78 (m, 2 H) 2.23 (s, 2 H) 3.39 (m, J = 6.40, 6.40 Hz, 2 H) 3.69 (s, 3 H) 4.23-4.33 (m, 1 H) 4.93 (s, 2 H) 6.15 (s, 1 H) 7.46 (br. s., 1 H) 7.52 (s, 1 H) 8.04 (d, J = 9.03 Hz, 1 H) 11.92 (d, J = 5.27 Hz, 1 H) |

TABLE I-continued

| | STRUCTURE | Exact Mass | Mass Found [M + H] | LCMS Ret Time, Method | 1H NMR |
|---|---|---|---|---|---|
| 238 | 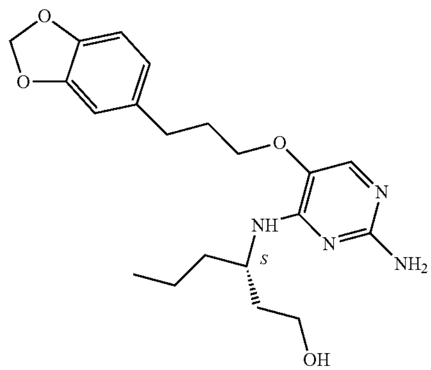 | 388.21 | 389 | 2.34, F | ¹H NMR (300 MHz, CHLOROFORM-d) δ ppm 0.93 (t, J = 7.2 Hz, 3 H), 1.29-1.47 (m, 3H), 1.49-1.64 (m, 3 H), 1.87-2.00 (m, 1 H), 2.07 (quin, J = 6.9 Hz, 2 H), 2.66-2.73 (m, 2 H), 3.46-3.57 (m, 1 H), 3.58-3.68 (m, 1 H), 3.91 (td, J = 6.4, 1.4 Hz, 2 H), 4.16 (ddd, J = 11.2, 5.4, 3.0 Hz, 1 H), 4.52 (s, 2 H), 4.93 (d, J = 8.7 Hz, 1 H), 5.94 (s, 2 H), 6.60-6.65 (m, 1 H), 6.69 (d, J = 1.5 Hz, 1 H), 6.72-6.77 (m, 1 H), 7.34 (s, 1 H) |
| 239 | 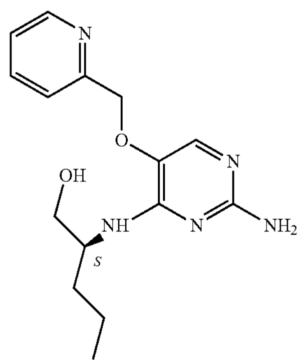 | 303.17 | 304 | 1.42, F | ¹H NMR (300 MHz, CHLOROFORM-d) δ ppm 0.88-1.01 (m, 3 H), 1.22-1.51 (m, 3 H), 1.54-1.71 (m, 2 H), 3.62 (dd, J = 11.0, 6.7 Hz, 1 H), 3.78 (dd, J = 11.0, 3.2 Hz, 1 H), 4.11 (td, J = 6.8, 3.0 Hz, 1 H), 4.56 (br. s., 2 H), 4.92-5.13 (m, 2 H), 6.21 (d, J = 7.0 Hz, 1 H), 7.30 (m, J = 5.4 Hz, 1 H), 7.36 (d, J = 7.7 Hz, 1 H), 7.52 (s, 1 H), 7.74 (td, J = 7.7, 1.6 Hz, 1 H), 8.61 (d, J = 4.7 Hz, 1 H) |
| 240 | 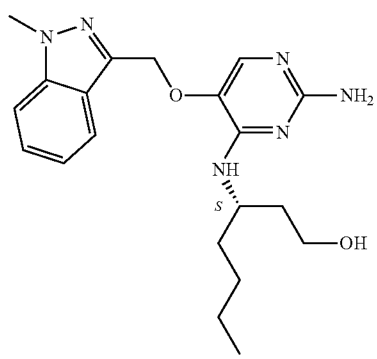 | 384.23 | 385 | 0.88, D | ¹H NMR (400 MHz, DMSO-d₆) δ ppm 0.73-0.87 (m, 3 H) 1.08-1.19 (m, 2 H) 1.19-1.31 (m, 2 H) 1.43-1.59 (m, 2 H) 1.59-1.75 (m, 2 H) 3.35-3.42 (m, 2 H) 4.03 (s, 3 H) 4.20-4.33 (m, 1 H) 5.44 (s, 2 H) 7.16 (t, J = 7.40 Hz, 1 H) 7.43 (br. s., 1 H) 7.43 (t, J = 7.70 Hz, 1 H) 7.51 (s, 1 H) 7.65 (d, J = 8.53 Hz, 1 H) 7.88 (d, J = 8.03 Hz, 1 H) 8.08 (d, J = 8.78 Hz, 1 H) 11.70 (s, 1 H) |
| 241 | 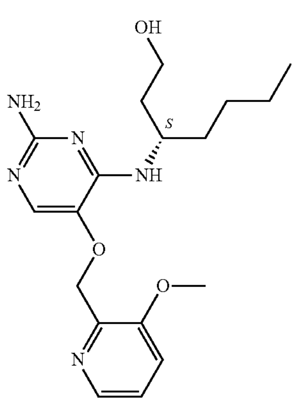 | 361.21 | 362 | 0.88, D | ¹H NMR (400 MHz, DMSO-d₆) δ ppm 0.84 (m , J = 7.00, 7.00 Hz, 3 H) 1.14-1.35 (m, 4 H) 1.53-1.66 (m, 2 H) 1.68-1.83 (m, 2 H) 3.40 (m, J = 6.70, 6.70 Hz, 2 H) 3.91 (s, 3 H) 4.28-4.41 (m, 1 H) 5.22 (s, 2 H) 7.49 (br. s., 2 H) 7.61 (d, J = 1.00 Hz, 1 H) 7.61 (s, 1 H) 7.77 (d, J = 7.78 Hz, 1 H) 8.26 (d, J = 4.52 Hz, 1 H) 8.53 (d, J = 8.03 Hz, 1 H) 11.84 (d, J = 5.50 Hz, 1 H) |

TABLE I-continued

| | STRUCTURE | Exact Mass | Mass Found [M + H] | LCMS Ret Time, Method | 1H NMR |
|---|---|---|---|---|---|
| 242 | 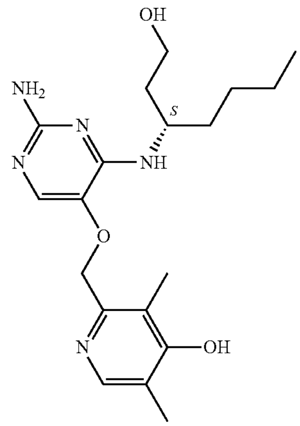 | 375.23 | 376 | , D | ¹H NMR (400 MHz, DMSO-d₆) δ ppm 0.79-0.87 (m, 3 H) 1.16-1.34 (m, 4 H) 1.54-1.63 (m, 1 H) 1.68-1.79 (m, 2 H) 1.85-1.95 (m, 1 H) 2.17 (s, 3 H) 2.24 (s, 3 H) 3.38-3.46 (m, 2 H) 4.33-4.43 (m, 1 H) 5.30 (s, 2 H) 7.48 (br. s., 2 H) 7.74 (d, J = 4.77 Hz, 1 H) 8.29 (s, 1 H) 8.87 (d, J = 8.53 Hz, 1 H) 11.99 (br. s., 1 H)" |
| 243 | 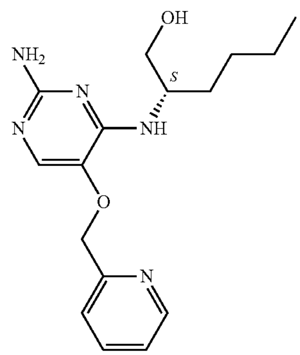 | 317.19 | 318 | 1.66, F | ¹H NMR (300 MHz, CHLOROFORM-d) δ ppm 0.90 (t, J = 1.0 Hz, 3 H), 1.30-1.46 (m, 5 H), 1.51-1.75 (m, 2 H), 3.57-3.68 (m, 1 H), 3.75-3.84 (m, 1 H), 4.09 (td, J = 6.9, 2.9 Hz, 1 H), 4.63 (br. s., 2 H), 4.94-5.12 (m, 2 H), 6.25 (d, J = 7.0 Hz, 1 H), 7.28-7.32 (m, 1 H), 7.37 (d, J = 7.7 Hz, 1 H), 7.52 (s, 1 H), 7.74 (td, J = 7.7, 1.8 Hz, 1 H), 8.62 (d, J = 4.1 Hz, 1 H) |
| 244 | 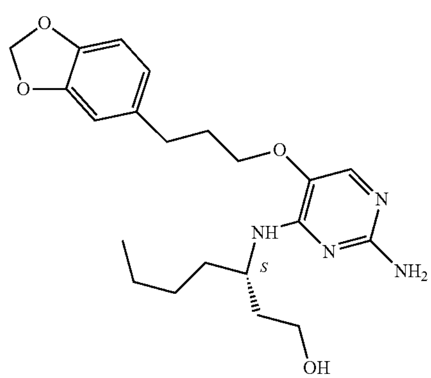 | 402.23 | 403 | 2.46, F | ¹H NMR (300 MHz, CHLOROFORM-d) δ 0.85-0.94 (m, 3 H), 1.23-1.44 (m, 5 H), 1.46-1.71 (m, 2 H), 1.94 (m, J = 14.0, 11.3, 5.3, 3.0 Hz, 2 H), 2.06 (quin, J = 6.9 Hz, 2 H), 2.70 (td, J = 7.4, 1.6 Hz, 2 H), 3.45-3.57 (m, 1 H), 3.58-3.68 (m, 1 H), 3.85-3.98 (m, 2 H), 4.13 (ddd, J = 11.2, 5.4, 3.0 Hz, 1 H), 4.53 (s, 2 H), 4.94 (d, J = 8.7 Hz, 1 H), 5.93 (s, 2 H), 6.60-6.65 (m, 1 H), 6.68 (d, J = 1.5 Hz, 1 H), 6.71-6.77 (m, 1 H), 7.35 (s, 1 H) |
| 245 | 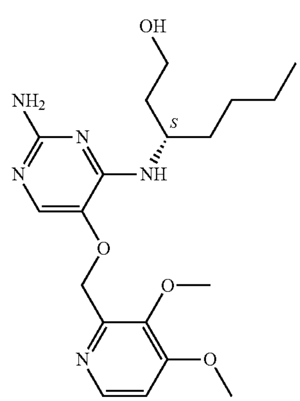 | 391.22 | 392 | 0.77, D | ¹H NMR (400 MHz, DMSO-d₆) δ ppm 0.78-0.87 (m, 3 H) 1.16-1.33 (m, 4 H) 1.52-1.62 (m, 1 H) 1.63-1.78 (m, 2 H) 1.81-1.91 (m, 1 H) 3.35-3.42 (m, 2 H) 3.89 (s, 3 H) 4.08 (s, 3 H) 4.32-4.41 (m, 1 H) 5.29 (s, 2 H) 7.52 (s, 1 H) 7.51 (s, 2 H) 7.68 (d, J = 5.52 Hz, 1 H) 8.51 (d, J = 6.02 Hz, 1 H) 8.74 (br. s., 1 H) 11.90 (s, 1 H)" |

TABLE I-continued

| | STRUCTURE | Exact Mass | Mass Found [M + H] | LCMS Ret Time, Method | 1H NMR |
|---|---|---|---|---|---|
| 246 | 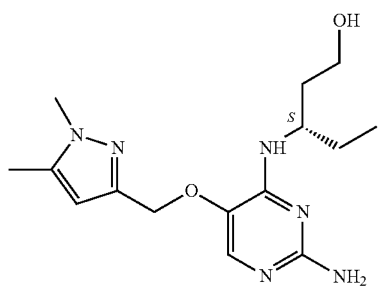 | 334.21 | 335 | 0.66, D | ¹H NMR (400 MHz, DMSO-d₆) δ ppm 0.78-0.90 (m, 3 H) 1.15-1.29 (m, 2 H) 1.40-1.62 (m, 2 H) 1.63-1.78 (m, 2 H) 2.23 (s, 3 H) 3.32-3.43 (m, 2 H) 3.70 (s, 3 H) 4.25-4.33 (m, 2 H) 4.93 (s, 2 H) 6.15 (s, 1 H) 7.47 (br. s., 2 H) 7.52 (s, 1 H) 8.04 (d, J = 8.78 Hz, 1 H) 11.93 (s, 1 H) |
| 247 | 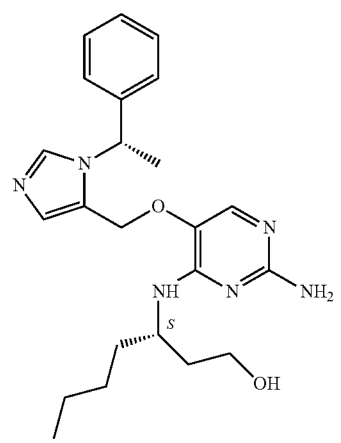 | 424.26 | 425 | 0.27, D | ¹H NMR (400 MHz, DMSO-d₆) δ ppm −0.05-0.01 (m, 2 H) 0.77-0.87 (m, 3 H) 1.12-1.35 (m, 4 H) 1.48-1.59 (m, 2 H) 1.66-1.79 (m, 2 H) 1.90 (d, J = 7.03 Hz, 3 H) 3.41-3.47 (m, 2 H) 4.25-4.36 (m, 1 H) 4.85 (d, J = 13.30 Hz, 1 H) 5.12 (d, J = 13.05 Hz, 1 H) 5.81 (d, J = 7.03 Hz, 1 H) 7.27-7.43 (m, 5 H) 7.45-7.61 (m, 2 H) 7.54 (br. s, 1 H) 7.95-8.05 (m, 1 H) 9.47 (s, 1 H) 12.16 (br. s., 1 H) |
| 248 | 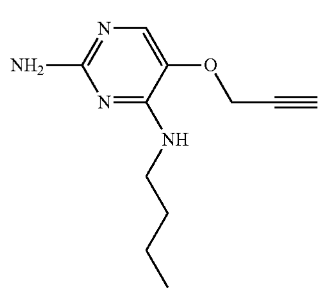 [SMILES: C#CCOc1cnc(N)nc1NCCCC] | 220.13 | 221 | 0.75, D | ¹H NMR (400 MHz, DMSO-d₆) δ ppm 0.87-0.93 (m, 3 H) 1.22-1.35 (m, 2 H) 1.54 (m, J = 1.00, 1.00, 1.00 Hz, 2 H) 3.33-3.43 (m, 2 H) 4.79 (d, J = 2.51 Hz, 2 H) 7.50 (d, J = 4.02 Hz, 1 H) 7.56 (br. s., 2 H) 8.51 (t, J = 5.77 Hz, 1 H) 12.02 (br. s., 1 H) |
| 249 | 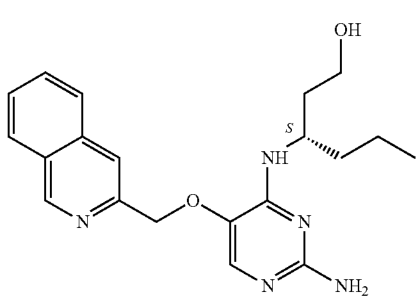 | 367.20 | 368 | 0.84, D | ¹H NMR (400 MHz, DMSO-d₆) δ ppm 0.87 (t, J = 7.40 Hz, 3 H) 1.21-1.31 (m, 2 H) 1.49-1.58 (m, 1 H) 1.58-1.69 (m, 1 H) 1.70-1.85 (m, 2 H) 3.38-3.50 (m, 2 H) 4.30-4.42 (m, 1 H) 5.35 (s, 2 H) 7.51 (br. s., 2 H) 7.65 (d, J = 5.52 Hz, 1 H) 7.81 (t, J = 7.53 Hz, 1 H) 7.93 (t, J = 7.40 Hz, 1 H) 8.08 (d, J = 8.03 Hz, 1 H) 8.13 (s, 1 H) 8.29 (d, J = 8.28 Hz, 1 H) 8.46 (d, J = 8.78 Hz, 1 H) 9.52 (s, 1 H) 11.84 (d, J = 5.27 Hz, 1 H) |

TABLE I-continued

| | STRUCTURE | Exact Mass | Mass Found [M + H] | LCMS Ret Time, Method | 1H NMR |
|---|---|---|---|---|---|
| 250 | 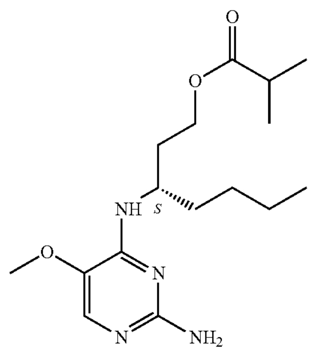 | 324.22 | 325 | 1.02, D | ¹H NMR (600 MHz, DMSO-d₆) δ ppm 0.84 (t, J = 7.0 Hz, 3 H), 1.05 (d, J = 7.0 Hz, 3 H), 1.06 (d, J = 7.0 Hz, 3 H), 1.16-1.32 (m, 4 H), 1.45-1.55 (m, 2 H), 6 1.80 (q, J = 6.9 Hz, 2 H), 2.48 (spt, J = 6.9 Hz, 1 H), 3.67 (s, 3 H), 3.95-4.03 (m, 2 H), 4.13-4.21 (m, 1 H), 5.37 (s, 2 H), 6.20 (d, J = 9.1 Hz, 1 H), 7.35 (s, 1 H) |
| 251 | 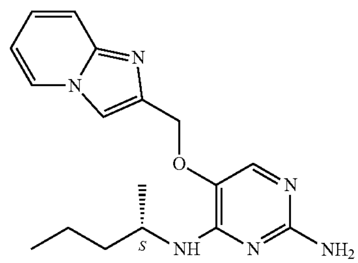 | 326.19 | 327 | 0.79, D | ¹H NMR (400 MHz, DMSO-d₆) δ ppm 0.85 (t, J = 7.4 Hz, 3 H), 1.20 (d, J = 6.8 Hz, 3 H), 1.21-1.28 (m, 2 H), 1.44-1.56 (m, 1 H), 1.71 (dd, J = 13.4, 7.4 Hz, 1H), 4.21-4.36 (m, 1 H), 5.37 (d, J = 1.8 Hz, 2 H), 7.47 (t, J = 6.7 Hz, 1 H), 7.59 (br. s., 2 H), 7.73 (s, 1 H), 7.86-8.00 (m, 2 H), 8.36-8.46 (m, 2 H), 8.93 (d, J = 6.5 Hz, 1 H), 12.24 (br. s., 1 H) |
| 252 | 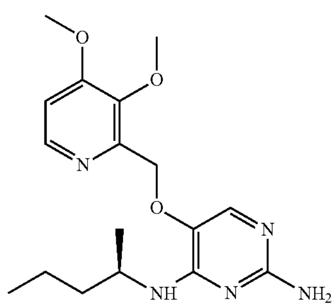 [SMILES: CCC[C@@H](C)Nc1nc(N)ncc1OCc1nccc(OC)c1OC] | 347.20 | 348 | 0.86, D | ¹H NMR (400 MHz, DMSO-d₆) δ ppm 0.87 (t, J = 7.4 Hz, 3 H), 1.24 (d, J = 6.4 Hz, 3 H), 1.25-1.33 (m, 2 H), 1.47-1.60 (m, 1 H), 1.71-1.86 (m, 1 H), 3.91 6 (s, 3 H), 4.12 (s, 3 H), 4.28-4.42 (m, 1 H), 5.36 (s, 2 H), 7.57 (br. s, 2 H), 7.63 (d, J = 6.5 Hz, 1 H), 7.72-7.80 (m, 1 H), 8.56 (d, J = 6.5 Hz, 1 H), 8.99-9.10 (m, 1 H), 12.27 (br. s., 1 H) |
| 253 | 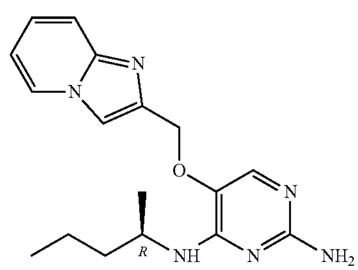 | 326.19 | 327 | 0.79, D | ¹H NMR (400 MHz, DMSO-d₆) δ ppm 0.85 (t, J = 7.4 Hz, 3 H), 1.21 (d, J = 6.5 Hz, 3 H), 1.23-1.29 (m, 2 H), 1.45-1.58 (m, 1 H), 1.66-1.80 (m, 1 H), 4.21-6 4.38 (m, 1 H), 5.33-5.45 (m, 2 H), 7.44-7.55 (m, 1 H), 7.62 (br. s., 2 H), 7.76 (s, 1 H), 7.89-8.02 (m, 2 H), 8.40-8.52 (m, 2 H), 8.96 (d, J = 6.8 Hz, 1 H), 12.39 (br. s., 1 H) |
| 254 | 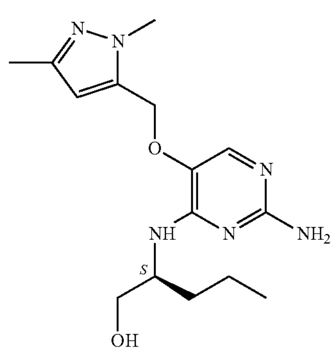 | 320.20 | 321 | 0.62, D | ¹H NMR (400 MHz, DMSO-d₆) δ ppm 0.86 (t, J = 7.3 Hz, 3 H), 1.17-1.35 (m, 2 H), 1.36-1.47 (m, 1 H), 1.47-1.60 (m, 1 H), 2.11 (s, 3 H), 3.36-3.47 (m, 2 6 H), 3.73 (s, 3 H), 4.05 (td, J = 8.8, 4.9 Hz, 1 H), 4.66 (br. s., 1 H), 4.94 (s, 2 H), 5.58 (s, 2 H), 5.86 (d, J = 9.0 Hz, 1 H), 6.10 (s, 1 H), 7.43 (s, 1 H) |

TABLE I-continued

| | STRUCTURE | Exact Mass | Mass Found [M + H] | LCMS Ret Time, Method | 1H NMR |
|---|---|---|---|---|---|
| 255 | 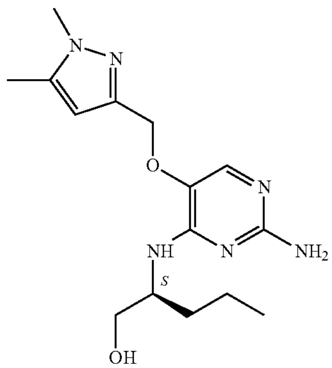 | 334.21 | 335 | 0.72, D | $^1$H NMR (400 MHz, DMSO-d$_6$) δ ppm 0.84 (t, J = 7.0 Hz, 3 H), 1.11-1.38 (m, 4 H), 1.39-1.67 (m, 2 H), 2.23 (s, 3 H), 3.38-3.52 (m, 2 H), 3.70 (s, 3 H), 6 4.13-4.24 (m, 1 H), 4.93 (s, 2 H), 6.16 (s, 1 H), 7.47 (br. s., 2 H), 7.53 (d, J = 5.3 Hz, 1 H), 7.79 (d, J = 9.0 Hz, 1 H), 11.96 (d, J = 5.3 Hz, 1 H) |
| 256 | 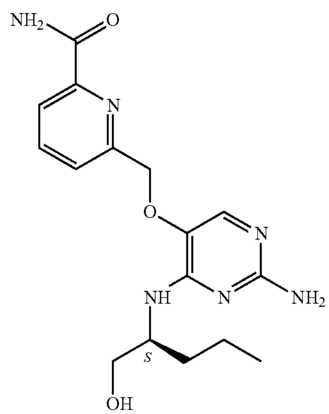 | 346.18 | 347 | 0.55, D | $^1$H NMR (400 MHz, DMSO-d$_6$) δ ppm 0.86 (t, J = 7.3 Hz, 3 H), 1.17-1.33 (m, 2 H), 1.39-1.50 (m, 1 H), 1.50-1.62 (m, 1 H), 3.37-3.48 (m, 2 H), 4.01-6 4.14 (m, 1 H), 4.69 (br. s., 1 H), 5.10 (s, 2 H), 5.54 (s, 2 H), 6.00 (d, J = 9.0 Hz, 1 H), 7.46 (s, 1 H), 7.68 (br. s., 1 H), 7.72 (dd, J = 7.5, 1.3 Hz, 1 H), 7.94-8.03 (m, 2 H), 8.03 (s, 1 H) |
| 257 | 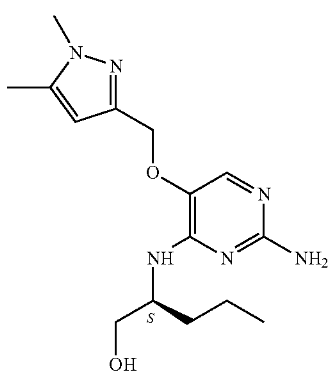 | 320.20 | 321 | 0.63, D | $^1$H NMR (400 MHz, DMSO-d$_6$) δ ppm 0.86 (t, J = 7.3 Hz, 3 H), 1.13-1.34 (m, 2 H), 1.46-1.60 (m, 2 H), 2.24 (s, 3 H), 3.38-3.53 (m, 2 H), 3.70 (s, 3 H), 4.18-4.28 (m, 1 H), 4.93 (s, 2 H), 6.16 (s, 1 H), 7.48 (br. s., 2 H), 7.54 (d, J = 5.5 Hz, 1 H), 7.78 (d, J = 8.8 Hz, 1 H), 11.97 (d, J = 5.5 Hz, 1 H) |
| 258 | 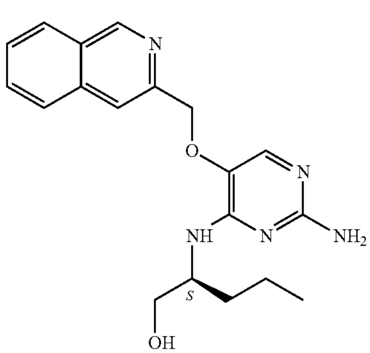 | 353.19 | 354 | 0.79, D | $^1$H NMR (400 MHz, DMSO-d$_6$) δ ppm 0.87 (t, J = 7.4 Hz, 3 H), 1.18-1.37 (m, 2 H), 1.58 (q, J = 7.7 Hz, 2 H), 3.45-3.58 (m, 2 H), 4.21-4.32 (m, 1 H), 5.37 6 (s, 2 H), 7.54 (br. s., 2 H), 7.69 (d, J = 5.0 Hz, 1 H), 7.84 (t, J = 7.5 Hz, 1 H), 7.97 (t, J = 7.5 Hz, 1 H), 8.11 (d, J = 8.3 Hz, 1 H), 8.21 (s, 1 H), 8.32 (t, J = 8.5 Hz, 2 H), 9.58 (s, 1 H), 11.98 (d, J = 5.0 Hz, 1 H) |

TABLE I-continued

| | STRUCTURE | Exact Mass | Mass Found [M + H] | LCMS Ret Time, Method | 1H NMR |
|---|---|---|---|---|---|
| 259 | 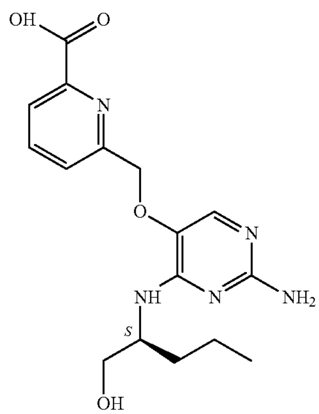 | 361.18 | 362 | 0.5, D | ¹H NMR (400 MHz, DMSO-d₆) δ ppm 0.84 (t, J = 6.8 Hz, 3 H), 1.15-1.35 (m, 4 H), 1.38-1.57 (m, 1 H), 1.57-1.68 (m, 1 H), 3.38-3.50 (m, 2 H), 4.04-6 4.17 (m, 1 H), 5.12 (s, 2 H), 6.51 (br. s., 2 H), 6.71 (d, J = 7.8 Hz, 1 H), 7.62-7.74 (m, 2 H), 7.90-7.98 (m, 2 H) |
| 260 | 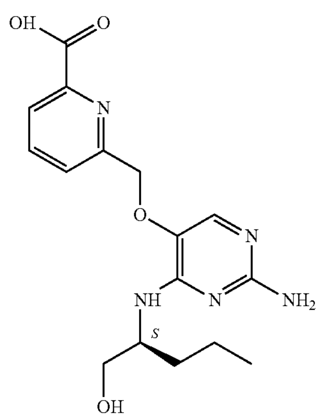 | 347.16 | 348 | 0.44, D | ¹H NMR (400 MHz, DMSO-d₆) δ ppm 0.86 (t, J = 7.3 Hz, 3 H), 1.26 (dq, J = 14.9, 7.3 Hz, 2 H), 1.43-1.63 (m, 2 H), 3.38-3.50 (m, 2 H), 4.13 (td, J = 8.7, 5.1 Hz, 1 H), 5.12 (s, 2 H), 6.50 (br. s., 2 H), 6.69 (d, J = 8.5 Hz, 1 H), 7.63-7.70 (m, 2 H), 7.93-7.97 (m, 2 H) |
| 261 | 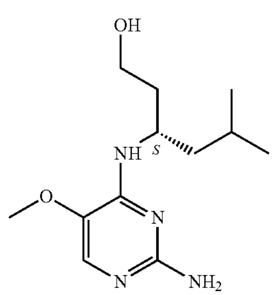 | 254.17 | 255 | 3.71, G | ¹H NMR (400 MHz, DMSO-d₆) δ ppm 0.86 (dd, J = 6.02, 4.52 Hz, 67 H) 1.14-1.29 (m, 1 H) 1.46-1.67 (m, 4 H) 3.34-3.43 (m, 2 H) 3.66 (s, 3 H) 4.22 (m, J = 8.70, 8.70, 4.40 Hz, 1 H) 4.37 (t, J = 5.40 Hz, 1 H) 5.43 (s, 2 H) 6.12 (d, J = 9.03 Hz, 1 H) 7.34 (s, 1 H) |
| 262 | 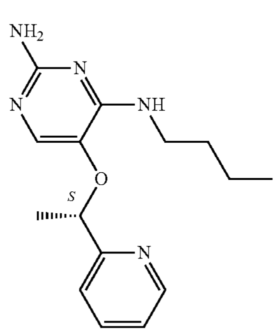 | 287.17 | 288 | 4.59, G | ¹H NMR (360 MHz, DMSO-d₆) δ ppm 0.91 (t, J = 7.50 Hz, 3 H) 1.31 (dq, J = 14.96, 7.46 Hz, 2 H) 1.58 (quin, J = 7.41 Hz, 2 H) 1.66 (d, J = 6.22 Hz, 3 H) 3.43 (q, J = 6.59 Hz, 2 H) 5.66 (q, J = 6.10 Hz, 1 H) 7.57 (m, J = 4.80 Hz, 3 H) 7.71 (t, J = 5.90 Hz, 1 H) 7.87 (d, J = 8.05 Hz, 1 H) 8.25 (t, J = 7.50 Hz, 1 H) 8.75 (d, J = 4.76 Hz, 1 H) 8.84 (t, J = 5.85 Hz, 1 H) 12.10 (d, J = 4.39 Hz, 1 H) |

TABLE I-continued

| | STRUCTURE | Exact Mass | Mass Found [M + H] | LCMS Ret Time, Method | 1H NMR |
|---|---|---|---|---|---|
| 263 | 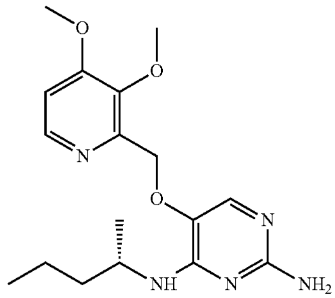 [SMILES: CCC[C@H](C)Nc1nc(N)ncc1OCc1nccc(OC)c1OC] | 347.20 | 348 | 0.86, D | $^1$H NMR (400 MHz, CHLOROFORM-d) δ ppm 0.90 (t, J = 7.2 Hz, 3 H), 1.17 (d, J = 6.5 Hz, 3 H), 1.29-1.40 (m, 2 H), 1.40-1.59 (m, 2 H), 3.86 (s, 3 H), 3.93 (s, 3 H), 4.07-4.20 (m, 1 H), 4.71 (br. s., 2 H), 5.02 (s, 2 H), 6.28 (d, J = 8.3 Hz, 1 H), 6.85 (d, J = 5.5 Hz, 1 H), 7.59 (s, 1 H), 8.26 (d, J = 5.5 Hz, 1 H) |
| 264 | 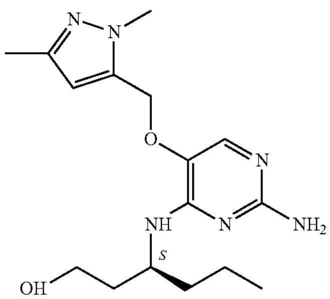 | 334.21 | 335 | 0.65, D | $^1$H NMR (400 MHz, DMSO-d$_6$) δ ppm 0.86 (t, J = 7.3 Hz, 3 H), 1.16-1.30 (m, 2 H), 1.43-1.63 (m, 2 H), 1.63-1.80 (m, 2 H), 2.14 (s, 3 H), 3.40 (t, J = 6.4 Hz, 6 2 H) 3.75 (s, 3 H), 4.26-4.39 (m, 1 H), 5.08 (s, 2 H), 6.23 (s, 1 H), 7.53 (br. s., 2 H), 7.59 (d, J = 4.8 Hz, 1 H), 8.10 (d, J = 8.8 Hz, 1 H), 12.22 (d, J = 5.0 Hz, 1 H) |
| 265 | 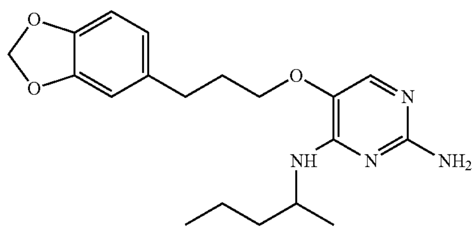 [SMILES: CCCC(C)Nc1nc(N)ncc1OCCCc1ccc2c(c1)OCO2] | 358.20 | 359 | 2.62, F | $^1$H NMR (300 MHz, CHLOROFORM-d) δ ppm 0.94 (t, J = 1.0 Hz, 3 H), 1.19 (d, J = 6.5 Hz, 3 H), 1.31-1.44 (m, 2 H), 1.45-1.58 (m, 2 H), 1.98-2.11 (m, 2 H), 2.70 (t, J = 7.5 Hz, 2 H), 3.89 (t, J = 6.3 Hz, 2 H), 4.15 (m, J = 8.4, 6.6, 6.6, 6.6 Hz, 1 H), 4.44 (s, 2 H), 4.90 (d, J = 8.4 Hz, 1 H), 5.94 (s, 2 H), 6.60-6.66 (m, 1 H), 6.69 (d, J = 1.5 Hz, 1 H), 6.72-6.77 (m, 1 H), 7.32 (s, 1 H) |
| 266 | 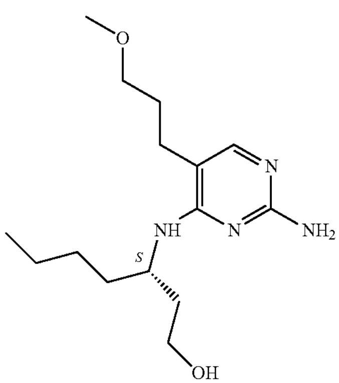 | 298.20 | 299 | 1.7, F | $^1$H NMR (300 MHz, CHLOROFORM-d) δ ppm 0.86-0.94 (m, 3 H), 1.25-1.45 (m, 5 H), 1.46-1.69 (m, 2 H), 1.86-2.00 (m, 1 H), 2.05 (s, 1 H), 3.43 (s, 3 H), 3.46-3.56 (m, 1 H), 3.57-3.63 (m, 1 H), 3.64-3.69 (m, 2 H), 3.96-4.04 (m, 2 H), 4.06-4.24 (m, 1 H), 5.18 (br. s., 2 H), 5.72 (d, J = 8.8 Hz, 1 H), 7.45 (s, 1 H) |
| 267 | 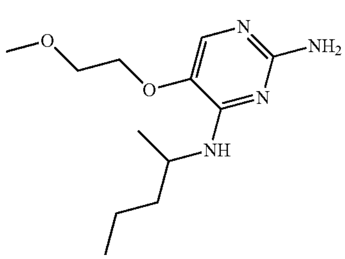 [SMILES: CCCC(C)Nc1nc(N)ncc1OCCOC] | 254.17 | 255 | 1.75, F | $^1$H NMR (300 MHz, CHLOROFORM-d) δ ppm 0.93 (t, J = 1.0 Hz, 3 H), 1.18 (d, J = 6.5 Hz, 3 H), 1.29-1.60 (m, 4 H), 3.44 (s, 3 H), 3.60-3.70 (m, 2 H), 3.95-4.02 (m, 2 H), 4.05-4.21 (m, 1 H), 4.53 (br. s., 2 H), 5.51 (d, J = 7.8 Hz, 1 H), 7.46 (s, 1 H) |

TABLE I-continued

| | STRUCTURE | Exact Mass | Mass Found [M + H] | LCMS Ret Time, Method | 1H NMR |
|---|---|---|---|---|---|
| 268 | 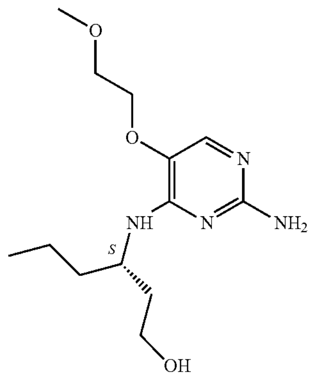 | 284.18 | 285 | 1.46, F | ¹H NMR (300 MHz, CHLOROFORM-d) δ ppm 0.92 (t, J = 7.2 Hz, 3 H), 1.30-1.49 (m, 4 H), 1.51-1.65 (m, 2 H), 1.85-1.98 (m, 1 H), 3.43 (s, 3 H), 3.52 (dd, J = 11.4, 2.6 Hz, 1 H), 3.60 (td, J = 5.9, 2.5 Hz, 1 H), 3.63-3.69 (m, 2 H), 3.95-4.03 (m, 2 H), 4.14 (ddd, J = 8.3, 5.5, 2.7 Hz, 1 H), 4.85 (br. s., 2 H), 5.65 (d, J = 8.7 Hz, 1 H), 7.48 (s, 1 H) |
| 269 | 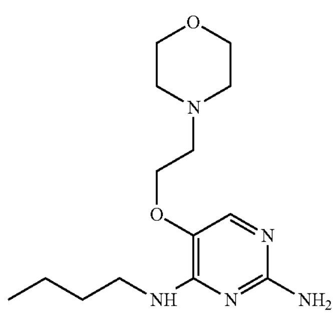 [SMILES: CCCCNc1nc(N)ncc1OCCN1CCOCC1] | 295.20 | 296 | 0.63, D | ¹H NMR (400 MHz, DMSO-d₆) δ ppm 0.74-0.93 (m, 3 H) 1.30 (m, J = 1.00, 1.00, 1.00 Hz, 2 H) 1.43-1.65 (m, 2 H) 3.09-3.18 (m, 2 H) 3.40-3.45 (m, 2 H) 3.49-3.60 (m, 2 H) 3.72-3.88 (m, 1 H) 3.88-4.13 (m, 5 H) 4.25 (t, J = 4.77 Hz, 2 H) 7.45 (s, 1 H) 7.51 (br. s., 2 H) 9.31 (t, J = 5.77 Hz, 1 H) 11.69 (br. s., 1 H) 12.01 (br. s., 1 H) |
| 270 | 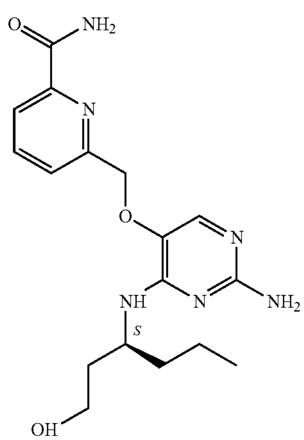 | 360.19 | 361 | 0.61, D | ¹H NMR (400 MHz, DMSO-d₆) δ ppm 0.85 (t, J = 7.4 Hz, 3 H), 1.24 (dq, J = 14.7, 7.4 Hz, 2 H), 1.39-1.56 (m, 2 H), 1.56-1.73 (m, 2 H), 3.41 (br. s., 2 H), 6 4.09-4.22 (m, 1 H), 4.44 (br. s., 1 H), 5.10 (s, 2 H), 5.54 (s, 2 H), 6.26 (d, J = 9.0 Hz, 1 H), 7.45 (s, 1 H) 7.68 (br. s., 1 H), 7.74 (d, J = 7.5 Hz, 1 H), 7.93-8.03 (m, 2 H), 8.06 (br. s., 1 H) |
| 271 | 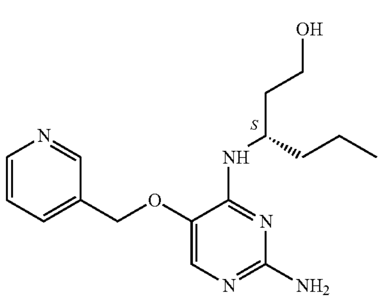 | 317.19 | 318 | 0.64, D | ¹H NMR (400 MHz, DMSO-d₆) δ ppm 0.80-0.92 (m, 3 H) 1.17-1.36 (m, 4 H) 1.47-1.65 (m, 2 H) 1.67-1.81 (m, 2 H) 4.29-4.37 (m, 1 H) 5.26 (s, 2 H) 7.52 (br. s., 2 H) 7.62 (d, J = 5.02 Hz, 1 H) 7.99 (dd, J = 8.03, 5.52 Hz, 1 H) 8.19 (d, J = 8.78 Hz, 1 H) 8.51 (d, J = 8.03 Hz, 1 H) 8.87 (d, J = 5.02 Hz, 1 H) 9.02 (s, 1 H) 11.98 (s, 1 H) |

TABLE I-continued

| | STRUCTURE | Exact Mass | Mass Found [M + H] | LCMS Ret Time, Method | 1H NMR |
|---|---|---|---|---|---|
| 272 | 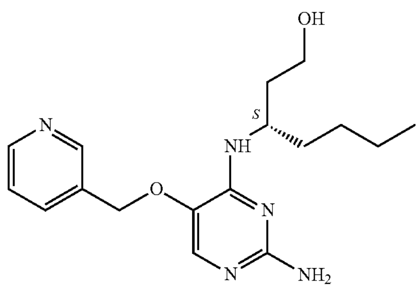 | 331.20 | 332 | 0.72, D | ¹H NMR (400 MHz, DMSO-d₆) δ ppm 0.85 (t, J = 7.15 Hz, 3 H) 1.10-1.38 (m, 4 H) 1.56 (dd, J = 14.56-7.53 Hz, 2 H) 1.74 (dd, J = 13.68, 5.90 Hz, 2 H) 4.25-4.39 (m, 2 H) 4.25-4.39 (m, 1 H) 5.19 (s, 2 H) 7.52 (br. s., 2 H) 7.61 (s, 1 H) 7.66 (dd, J = 7.78, 5.02 Hz, 1 H) 8.16 (t, J = 8.41 Hz, 2 H), 8.69 (d, J = 4.27 Hz, 1 H) 8.83 (s, 1 H) 12.08 (br. s., 1 H) |
| 273 | 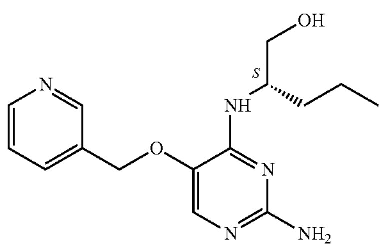 | 303.17 | 304 | 0.59, D | ¹H NMR (400 MHz, DMSO-d₆) δ ppm 0.81-0.91 (m, 3 H) 1.17-1.32 (m, 2 H) 1.47-1.60 (m, 2 H) 3.41-3.54 (m, 2 H) 4.20-4.34 (m, 1 H) 5.21 (s, 2 H) 7.50 (br. s., 2 H) 7.59 (d, J = 4.77 Hz, 1 H) 7.78 (dd, J = 7.65, 5.40 Hz, 1 H) 8.00 (d, J = 9.03 Hz, 1 H) 8.29 (d, J = 7.53 Hz, 1 H) 8.75 (d, J = 4.27 Hz, 1 H) 8.92 (s, 1 H) 11.95 (br. s., 1 H) |
| 274 | 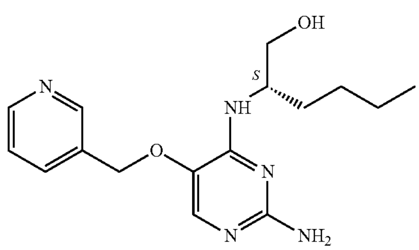 | 317.19 | 318 | 0.57, D | ¹H NMR (400 MHz, DMSO-d₆) δ ppm 0.85 (t, J = 7.03 Hz, 3 H) 1.13-1.36 (m, 4 H) 1.47-1.66 (m, 2 H) 3.40-3.52 (m, 2 H) 4.16-4.30 (m, 1 H) 5.24 (s, 2 H) 7.53 (br. s., 2 H) 7.62 (d, J = 4.02 Hz, 1 H) 7.86 (dd, J = 7.91, 5.40 Hz, 1 H) 8.02 (d, J = 8.78 Hz, 1 H) 8.39 (d, J = 8.03 Hz, 1 H) 8.80 (d, J = 4.27 Hz, 1 H) 8.98 (s, 1 H) 12.08 (br. s., 1 H) |
| 275 | 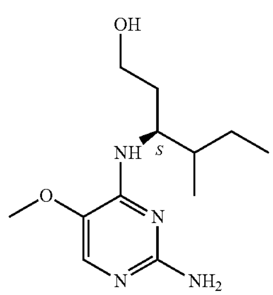 | 254.17 | 255 | 0.67, D | ¹H NMR (400 MHz, DMSO-d₆) δ ppm 0.73-0.91 (m, 6 H) 0.94-1.16 (m, 1 H) 1.33-1.47 (m, 1 H) 1.49-1.75 (m, 3 H) 3.38 (m, J = 9.00 Hz, 2 H) 3.67 (s, 3 H) 3.93-4.18 (m, 1 H) 4.34 (t, J = 1.00 Hz, 1 H) 5.44 (br. s., 2 H) 5.94 (d, J = 1.00 Hz, 1 H) 7.35 (s, 1 H) |
| 276 | 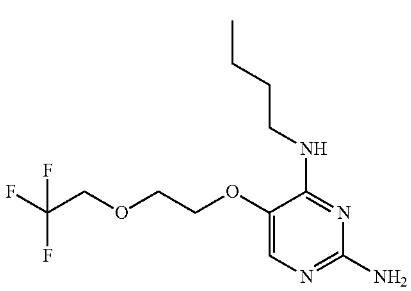 [SMILES: CCCCNc1nc(N)ncc1OCCOCC(F)(F)F] | 308.15 | 309 | 4.89, G | ¹H NMR (400 MHz, DMSO-d₆) δ ppm 0.90 (t, J = 7.28 Hz, 3 H) 1.30 (sxt, J = 7.43 Hz, 2 H) 1.47-1.60 (m, 2 H) 3.41 (q, J = 6.78 Hz, 2 H) 3.90-3.97 (m, 2 H) 4.09-4.13 (m, 2 H) 4.18 (q, J = 1.00 Hz, 2 H) 7.46 (s, 1 H) 7.49 (br. s., 1 H) 8.32 (t, J = 5.90 Hz, 1 H) |

TABLE I-continued

| | STRUCTURE | Exact Mass | Mass Found [M + H] | LCMS Ret Time, Method | 1H NMR |
|---|---|---|---|---|---|
| 277 | 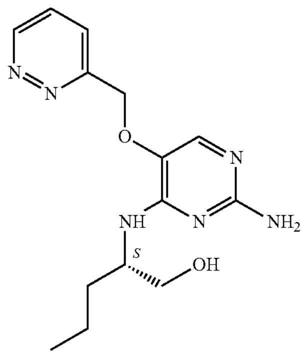 | 304.16 | 305 | 0.5, D | ¹H NMR (400 MHz, DMSO-d₆) δ ppm 0.87 (t, J = 7.4 Hz, 3 H), 1.17-1.35 (m, 2 H), 1.47-1.62 (m, 2 H), 3.43-3.54 (m, 2 H), 4.19-4.31 (m, 1 H), 5.39 (s, 2 6 H), 7.55 (br. s., 2 H), 7.65 (d, J = 4.0 Hz, 1 H), 7.85 (dd, J = 8.5, 5.0 Hz, 1 H), 8.00 (dd, J = 8.4, 1.6 Hz, 1 H), 8.07 (d, J = 8.8 Hz, 1 H), 9.27 (dd, J = 4.9, 1.6 Hz, 1 H), 12.03-12.17 (m, 1 H) |
| 278 | 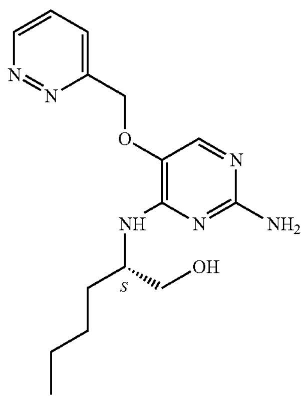 | 318.18 | 319 | 0.58, D | ¹H NMR (400 MHz, DMSO-d₆) δ ppm 0.85 (t, J = 7.0 Hz, 3 H), 1.14-1.38 (m, 4 H), 1.45-1.71 (m, 2 H), 3.42-3.53 (m, 2 H), 4.23 (td, J = 9.0, 5.4 Hz, 1 H), 6 5.39 (s, 2 H), 7.55 (br. s., 2 H), 7.65 (d, J = 3.3 Hz, 1 H), 7.84 (dd, J = 8.4, 4.9 Hz, 1 H), 8.00 (dd, J = 8.5, 1.5 Hz, 1 H), 8.07 (d, J = 8.8 Hz, 1 H), 9.27 (dd, J = 5.0, 1.8 Hz, 1 H), 12.10 (br. s., 1 H) |
| 279 | 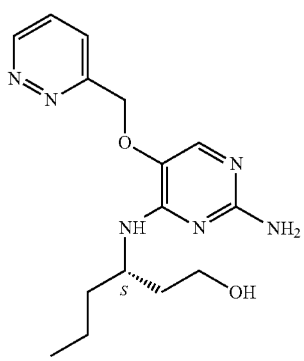 | 318.18 | 319 | 0.54, D | ¹H NMR (400 MHz, DMSO-d₆) δ ppm 0.87 (t, J = 7.3 Hz, 3 H), 1.25 (dq, J = 14.9, 7.4 Hz, 2 H), 1.45-1.66 (m, 2 H), 1.66-1.83 (m, 2 H), 3.43 (t, J = 6.4 Hz, 2 H), 4.28-4.40 (m, 1 H), 5.39 (s, 2 H), 7.56 (br. s., 2 H), 7.66 (d, J = 4.0 Hz, 1 H), 7.85 (dd, J = 8.5, 5.0 Hz, 1 H), 7.98 (dd, J = 8.5, 1.5 Hz, 1 H), 8.26 (d, J = 9.0 Hz, 1 H), 9.27 (dd, J = 4.9, 1.6 Hz, 1 H), 12.13 (br. s., 1 H) |
| 280 | 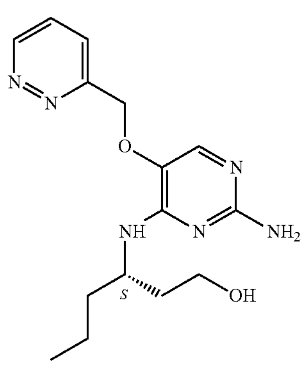 | 332.20 | 333 | 0.62, D | ¹H NMR (400 MHz, DMSO-d₆) δ ppm 0.85 (t, J = 7.0 Hz, 3 H), 1.15-1.35 (m, 4 H), 1.49-1.66 (m, 2 H), 1.68-1.80 (m, 2 H), 3.43 (t, J = 6.4 Hz, 2 H), 4.26-6 4.39 (m, 1 H), 5.39 (s, 2 H), 7.55 (br. s., 2 H), 7.66 (d, J = 4.3 Hz, 1 H), 7.85 (dd, J = 8.5, 5.0 Hz, 1 H), 7.97 (dd, J = 8.5, 1.5 Hz, 1 H), 8.26 (d, J = 8.8 Hz, 1 H), 9.27 (dd, J = 5.0, 1.5 Hz, 1 H), 12.05-12.16 (m, 1 H) |

TABLE I-continued

| | STRUCTURE | Exact Mass | Mass Found [M + H] | LCMS Ret Time, Method | 1H NMR |
|---|---|---|---|---|---|
| 281 | 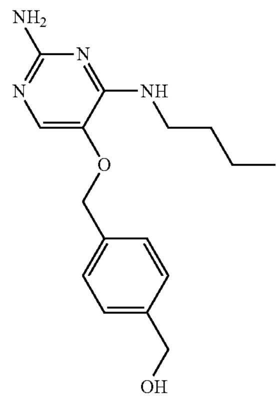 [SMILES: CCCCNc1nc(N)ncc1OCc1ccc(CO)cc1] | 302.17 | 303 | 0.71, D | ¹H NMR (400 MHz, DMSO-d₆) δ ppm 0.89 (t, J = 7.3 Hz, 3 H), 1.28 (dq, J = 14.9, 7.3 Hz, 2 H), 1.49 (quin, J = 7.3 Hz, 2 H), 3.23-3.31 (m, 2 H), 4.49 (br. s., 2 6 H), 4.93 (s, 2 H), 5.17 (br. s., 1 H), 5.47 (s, 2 H), 6.37 (t, J = 5.8 Hz, 1 H), 7.26-7.33 (m, 2 H), 7.33-7.42 (m, 3 H) |
| 282 | 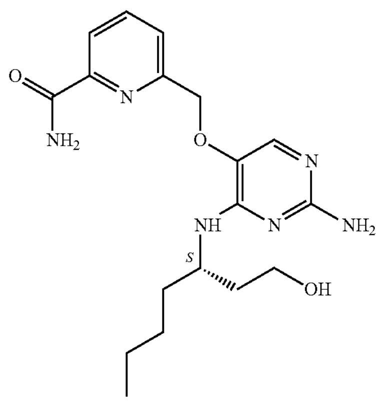 | 374.21 | 375 | 0.66, D | ¹H NMR (400 MHz, DMSO-d₆) δ ppm 0.84 (t, J = 7.0 Hz, 3 H), 1.13-1.33 (m, 4 H), 1.42-1.56 (m, 2 H), 1.56-1.73 (m, 2 H), 3.40 (br. s., 2 H), 4.06-4.20 6 (m, 1 H), 4.44 (br. s., 1 H), 5.10 (s, 2 H), 5.55 (s, 2 H), 6.28 (d, J = 8.8 Hz, 1 H), 7.45 (s, 1 H), 7.67 (br. s., 1 H), 7.71-7.76 (m, 1 H), 7.93-8.03 (m, 2 H), 8.06 (br. s., 1 H) |
| 283 | 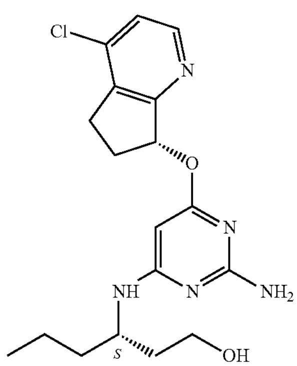 | 377.16 | 378 | 0.91, D | ¹H NMR (400 MHz, DMSO-d₆) δ ppm 0.82 (t, J = 7.40 Hz, 3 H) 1.11-1.22 (m, 2 H) 1.43-1.55 (m, 2 H) 1.66-1.76 (m, 2 H) 2.25-2.34 (m, 1 H) 2.52-2.65 (m, 1 H) 2.88-2.97 (m, 1 H) 3.10-3.22 (m, 1 H) 3.43 (t, J = 6.40 Hz, 2 H) 4.24-4.34 (m, 1 H) 5.61 (dd, J = 7.40, 4.14 Hz, 1 H) 7.51 (d, J = 7.60 Hz, 1 H) 7.53 (br. s, 2 H) 7.84 (s, 1 H) 8.17 (d, J = 8.78 Hz, 1 H) 8.44 (d, J = 5.52 Hz, 1 H) 11.77 (br. s., 1 H) |
| 284 | 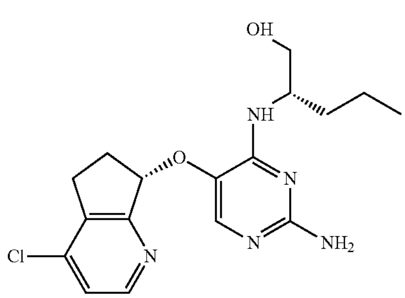 [SMILES: CCC[C@@H](CO)Nc1nc(N)ncc1O[C@H]1CCc2c(Cl)ccnc21] | 377.16 | 378 | 0.92, D | ¹H NMR (400 MHz, DMSO-d₆) δ ppm 0.82 (t, J = 7.40 Hz, 3 H) 1.11-1.22 (m, 2 H) 1.43-1.55 (m, 2 H) 1.66-1.76 (m, 2 H) 2.25-2.34 (m, 1 H) 2.52-2.65 (m, 1 H) 2.88-2.97 (m, 1 H) 3.10-3.22 (m, 1 H) 3.43 (t, J = 6.40 Hz, 2 H) 4.24-4.34 (m, 1 H) 5.61 (dd, J = 7.40, 4.14 Hz, 1 H) 7.51 (d, J = 7.60 Hz, 1 H) 7.53 (br. s, 2 H) 7.84 (s, 1 H) 8.17 (d, J = 8.78 Hz, 1 H) 8.44 (d, J = 5.52 Hz, 1 H) 11.77 (br. s., 1 H) |

TABLE I-continued

| | STRUCTURE | Exact Mass | Mass Found [M + H] | LCMS Ret Time, Method | 1H NMR |
|---|---|---|---|---|---|
| 285 | 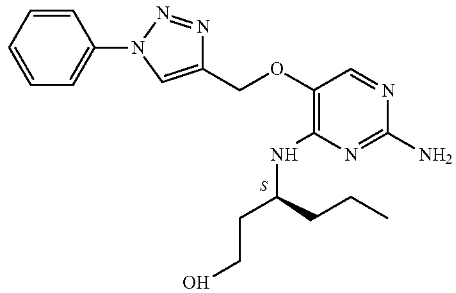 | 383.21 | 384 | 0.8, D | $^1$H NMR (400 MHz, DMSO-d$_6$) δ ppm 0.62-0.92 (m, 3 H) 1.14-1.31 (m, 2 H) 1.42-1.63 (m, 2 H) 1.63-1.82 (m, 2 H) 3.40 (t, J = 6.40 Hz, 2 H) 4.25-4.36 (m, 1 H) 5.22 (s, 2 H) 7.47-7.59 (m, 1 H) 7.47-7.59 (m, 2 H) 7.59-7.67 (m, 2 H) 7.72 (br. s., 1 H) 7.85-7.98 (m, 2 H) 8.08 (d, J = 8.78 Hz, 1 H) 9.07 (s, 1 H) 12.16 (br. s., 1 H) |
| 286 | 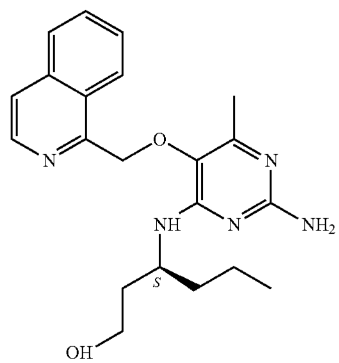 | 381.22 | 382 | 0.89, D | $^1$H NMR (400 MHz, DMSO-d$_6$) δ ppm 0.84 (t, J = 7.28 Hz, 3 H) 1.18-1.30 (m, 2 H) 1.50-1.64 (m, 2 H) 1.75 (dt, J = 12.80, 6.40 Hz, 2 H) 2.14 (s, 3 H) 3.40-3.44 (m, 2 H) 4.31 (m, J = 7.50 Hz, 1 H) 5.64 (s, 2 H) 7.46 (br. s., 2 H) 7.78-7.85 (m, 1 H) 7.91 (t, J = 7.65 Hz, 1 H) 8.00 (d, J = 6.02 Hz, 1 H) 8.11 (d, J = 8.28 Hz, 1 H) 8.37 (d, J = 8.28 Hz, 1 H) 8.56 (d, J = 5.77 Hz, 1 H) 9.30 (br. s., 1 H) 12.20 (s, 1 H) |
| 287 | 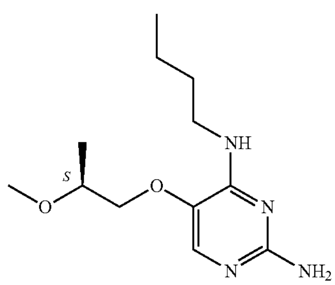 | 254.17 | 255 | 4.21, G | $^1$H NMR (400 MHz, DMSO-d$_6$) δ ppm 0.90 (t, J = 7.40 Hz, 3 H) 1.17 (d, J = 6.52 Hz, 3 H) 1.23-1.38 (m, 2 H) 1.54 (quin, J = 7.34 Hz, 2 H) 3.30 (s, 3 H) 3.41 (q, J = 6.69 Hz, 2 H) 3.60-3.75 (m, 1 H) 3.78-3.98 (m, 2 H) 7.32-7.58 (m, 3 H) 8.24 (t, J = 5.77 Hz, 1 H) |
| 288 | 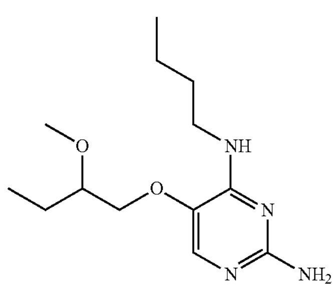 [SMILES: CCCCNc1nc(N)ncc1OCC(CC)OC] | 268.19 | 269 | 0.86, D | $^1$H NMR (400 MHz, DMSO-d$_6$) δ ppm 0.90 (tt, J = 7.40, 3.50 Hz, 6 H) 1.23-1.36 (m, 2 H) 1.47-1.69 (m, 4 H) 3.33 (s, 3 H) 3.36-3.52 (m, 3 H) 3.92 (d, J = 4.77 Hz, 2 H) 7.19-7.68 (m, 3 H) 8.21 (t, J = 6.02 Hz, 1 H) |
| 289 | 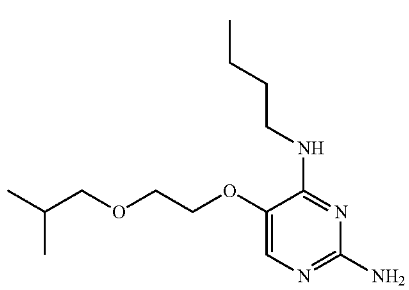 [SMILES: CCCCNc1nc(N)ncc1OCCOCC(C)C] | 282.21 | 283 | 5.45, G | $^1$H NMR (400 MHz, DMSO-d$_6$) δ ppm 0.85 (d, J = 6.78 Hz, 6 H) 0.90 (t, J = 7.40 Hz, 3 H) 1.22-1.37 (m, 2 H) 1.54 (quin, J = 7.28 Hz, 2 H) 1.78 (m, J = 13.40, 6.70, 6.70 Hz, 1 H) 3.21 (d, J = 6.52 Hz, 2 H) 3.40 (q, J = 6.69 Hz, 2 H) 3.56-3.75 (m, 2 H) 3.99-4.14 (m, 2 H) 7.32-7.60 (m, 3 H) 8.29 (t, J = 5.65 Hz, 1 H) |

TABLE I-continued

| | STRUCTURE | Exact Mass | Mass Found [M + H] | LCMS Ret Time, Method | 1H NMR |
|---|---|---|---|---|---|
| 290 | (structure) | 240.16 | 241 | 3.38, G | ¹H NMR (400 MHz, DMSO-d₆) δ ppm 0.91 (t, J = 7.28 Hz, 3 H) 1.12 (d, J = 6.52 Hz, 3 H) 1.31 (sxt, J = 7.43 Hz, 2 H) 1.56 (quin, J = 7.34 Hz, 2 H) 3.34-3.48 (m, 2 H) 3.61 (dd, J = 9.41, 7.40 Hz, 1 H) 3.83 (dd, J = 9.54, 3.51 Hz, 1 H) 3.90-4.02 (m, 1 H) 6.10 (br. s., 1 H) 7.40 (d, J = 5.27 Hz, 1 H) 7.48 (br. s., 2 H) 8.54 (t, J = 5.65 Hz, 1 H) 12.02 (br. s., 1 H) |
| 291 | (structure) | 331.20 | 332 | 0.7, D | ¹H NMR (400 MHz, CHLOROFORM-d) δ ppm 0.90 (t, J = 6.9 Hz, 3 H), 1.27-1.45 (m, 5 H), 1.47-1.69 (m, 2 H) 1.87-1.99 (m, 1 H), 3.49-3.58 (m, 1 H), 3.60-3.66 (m, 1 H), 4.17 (ddd, J = 10.8, 5.5, 3.0 Hz, 1 H), 5.00 (s, 2 H), 5.15 (d, J = 8.5 Hz, 1 H), 7.25-7.32 (m, 2 H), 7.39 (s, 1 H), 8.57-8.67 (m, 2 H) supports structure but don't see exchangables. |
| 292 | (structure) | 250.18 | 251 | 4.51, B | ¹H NMR (400 MHz, CHLOROFORM-d) δ ppm 0.82-0.93 (m, 3 H), 1.22-1.37 (m, 4 H), 1.40-1.51 (m, 1 H), 1.52-1.63 (m, 1 H), 2.20-2.39 (m, 2 H), 3.75 (s, 3 H), 4.09-4.23 (m, 1 H), 4.72 (br. s., 2 H), 5.04 (s, 1 H), 5.08 (d, J = 4.8 Hz, 2 H), 5.70-5.87 (m, 1 H), 7.30 (s, 1 H) |
| 293 | (structure) | 317.19 | 318 | 1.55, F | ¹H NMR (300 MHz, CHLOROFORM-d) δ ppm 0.92 (t, J = 7.3 Hz, 3 H), 1.31-1.50 (m, 3 H), 1.55-1.67 (m, 2 H), 1.94 (m, J = 11.2, 11.2, 5.5, 2.6 Hz, 2 H), 3.42-3.54 (m, 1 H), 3.56-3.69 (m, 1 H), 4.17 (d, J = 7.3 Hz, 1 H), 4.53 (br. s., 2 H), 5.04 (s, 2 H), 6.05 (d, J = 8.5 Hz, 1 H), 7.29-7.38 (m, 2 H), 7.54 (s, 1 H), 7.74 (td, J = 7.7, 1.6 Hz, 1 H), 8.63 (d, J = 4.7 Hz, 1 H) |
| 294 | (structure) | 331.20 | 332 | 1.76, F | ¹H NMR (300 MHz, CHLOROFORM-d) δ ppm 0.80 (t, J = 6.9 Hz, 3 H), 1.13-1.39 (m, 5 H), 1.44-1.60 (m, 3 H), 1.80-1.95 (m, 1 H), 3.35-3.47 (m, 1 H), 3.48-3.59 (m, 1 H), 4.08 (ddd, J = 11.0, 5.5, 2.7 Hz, 1 H), 4.49 (s, 2 H), 4.97 (s, 2 H), 6.04 (d, J = 8.2 Hz, 1 H), 7.20-7.24 (m, 1 H), 7.27 (d, J = 7.7 Hz, 1 H), 7.45 (s, 1 H), 7.66 (td, J = 7.7, 2.2 Hz, 1 H), 8.51-8.60 (m, 1 H) |

| | STRUCTURE | Exact Mass | Mass Found [M + H] | LCMS Ret Time, Method | 1H NMR |
|---|---|---|---|---|---|
| 295 | 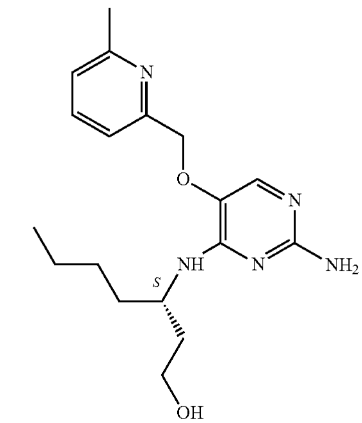 | 345.22 | 346 | 1.7, F | ¹H NMR (300 MHz, CHLOROFORM-d) δ ppm 0.88 (t, J = 7.0 Hz, 3 H), 1.17-1.45 (m, 4 H), 1.50-1.81 (m, 4 H), 1.95 (tdd, J = 11.2, 11.2, 5.5, 2.6 Hz, 1 H), 2.59 (s, 3 H), 3.42-3.54 (m, 1 H), 3.56-3.66 (m, 1 H), 4.17 (m, J = 11.1, 5.6, 2.8 Hz, 1 H), 4.51 (br. s., 2 H), 5.00 (s, 2 H), 5.77 (d, J = 8.7 Hz, 1 H), 7.14 (t, J = 6.7 Hz, 2 H), 7.53 (s, 1 H), 7.62 (t, J = 7.6 Hz, 1 H) |
| 296 | 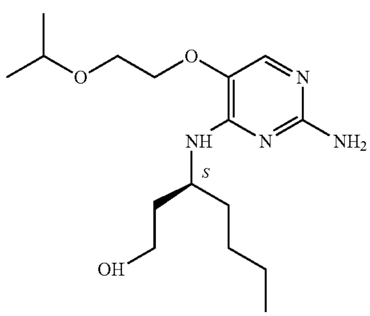 | 326.23 | 327 | 0.84, D | ¹H NMR (400 MHz, DMSO-d₆) δ ppm 0.85 (t, J = 6.8 Hz, 3 H), 1.12 (d, J = 6.3 Hz, 6 H), 1.18-1.36 (m, 4 H), 1.41-1.73 (m, 4 H), 3.41 (t, J = 6.4 Hz, 2 H), 3.55-3.67 (m, 3 H), 3.82-3.90 (m, 2 H), 4.04-4.18 (m, 1 H), 4.40 (br. s., 1 H), 5.58 (s, 2 H), 5.86 (d, J = 9.0 Hz, 1 H), 7.43 (s, 1 H) |
| 297 | 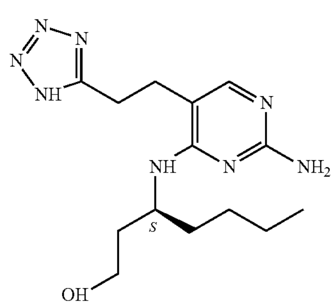 | 322.19 | 323 | 0.48, D | ¹H NMR (400 MHz, DMSO-d₆) δ ppm 0.85 (t, J = 7.00 Hz, 3 H) 1.13-1.39 (m 4 H) 1.51-1.65 (m, 2 H) 1.66-1.81 (m, 2 H) 3.36-3.45 (m, 2 H) 4.28-4.39 (m, 1 H) 5.46 (s, 2 H) 7.51 (br. s., 2 H) 7.62 (s, 1 H) 8.23 (d, J = 9.03 Hz, 1 H) 11.85 (br. s., 1 H) |
| 298 | 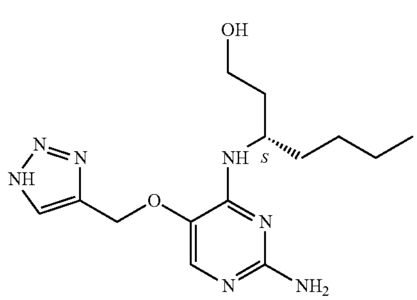 | 321.19 | 322 | 0.58, D | ¹H NMR (400 MHz, DMSO-d₆) δ ppm 0.84 (t, J = 7.15 Hz, 3 H) 1.09-1.34 (m, 4 H) 1.46-1.61 (m, 2 H) 1.61-1.77 (m, 2 H) 4.24-4.34 (m, 1 H) 5.17 (s, 2 H) 7.47 (br. s., 2 H) 7.59 (d, J = 5.52 Hz, 1 H) 8.05 (s, 1 H) 7.99-8.11 (m, 1 H) 11.89 (d, J = 5.52 Hz, 1 H) |

TABLE I-continued

| | STRUCTURE | Exact Mass | Mass Found [M + H] | LCMS Ret Time, Method | 1H NMR |
|---|---|---|---|---|---|
| 299 | 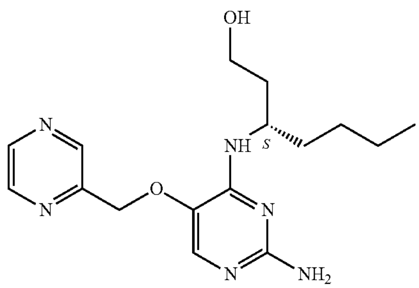 | 318.18 | 319 | 0.58, D | ¹H NMR (400 MHz, DMSO-d₆) δ ppm 0.87 (t, J = 7.40 Hz, 3 H) 1.16-1.32 (m, 2 H) 1.47-1.65 (m, 2 H) 1.67-1.80 (m, 2 H) 4.29-4.40 (m, 1 H) 5.03-5.20 (m, 2 H) 5.23 (s, 2 H) 7.53 (br. s., 2 H) 7.63 (d, J = 5.27 Hz, 1 H) 8.18 (d, J = 8.78 Hz, 1 H) 8.61-8.71 (m, 2 H) 8.94 (s, 1 H) 12.05 (d, J = 5.02 Hz, 1 H) |
| 300 | 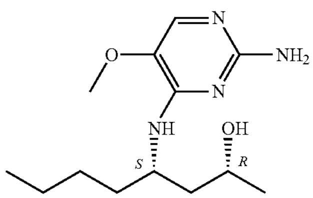 | 268.19 | 269 | 4.13, B | ¹H NMR (400 MHz, CHLOROFORM-d) δ ppm 0.89 (t, J = 7.0 Hz, 3 H), 1.16 (d, J = 6.3 Hz, 3 H), 1.26-1.44 (m, 6 H), 1.51 (dd, J = 8.7, 4.6 Hz, 1 H), 1.57-1.67 (m, 2 H), 3.63-3.75 (m, 1 H), 3.78 (s, 3 H), 4.07-4.24 (m, 1 H), 4.62 (br. s., 2 H), 5.07 (d, J = 8.5 Hz, 1 H), 7.34 (s, 1 H) |
| 301 | 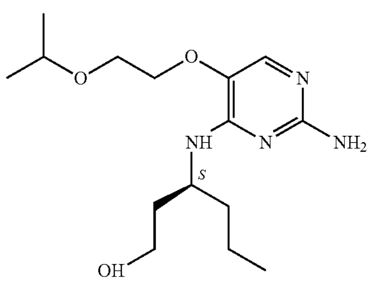 | 312.22 | 313 | 0.75, D | ¹H NMR (400 MHz, DMSO-d₆) δ ppm 0.86 (t, J = 7.3 Hz, 3 H), 1.12 (d, J = 6.0 Hz, 6 H), 1.28 (dt, J = 14.7, 7.5 Hz, 2 H), 1.48 (q, J = 7.4 Hz, 2 H), 1.54-1.62 (m, 1 H), 1.63-1.74 (m, 1 H), 3.38-3.46 (m, 2 H), 3.54-3.68 (m, 3 H), 3.86 (dd, J = 5.5, 4.0 Hz, 2 H), 4.14 (d, J = 4.8 Hz, 1 H), 4.34-4.48 (m, 1 H), 5.58 (s, 2 H), 5.86 (d, J = 9.0 Hz, 1 H), 7.43 (s, 1 H) |
| 302 | 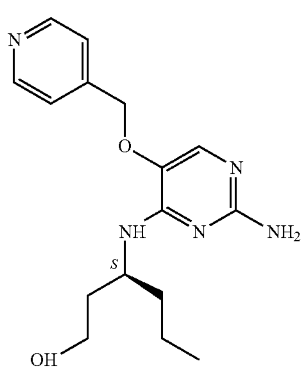 | 317.19 | 318 | 0.61, D | ¹H NMR (400 MHz, DMSO-d₆) δ ppm 0.87 (t, J = 7.4 Hz, 3 H), 1.19-1.34 (m, 2 H), 1.41-1.60 (m, 2 H), 1.66 (s, 2 H), 3.44 (d, J = 6.5 Hz, 2 H), 4.09-4.26 (m, 1 H), 4.41-4.50 (m, 1 H), 5.04 (s, 2 H), 5.61 (br. s., 2 H), 6.36 (d, J = 8.5 Hz, 1 H), 7.39 (s, 1 H), 7.42-7.46 (m, 2 H), 8.52-8.61 (m, 2 H) |

Analytical Methods.

All compounds were characterized by LC-MS. The following LC-MS methods were used:

Method A. Waters Aquity UPLC equipped with a PDA detector (210-400 nm) and a Waters SQD with a dual mode ion source ES+/−. The column used was a Halo C18, 2.7 μm, 2.1×50 mm, heated to 50° C. A gradient of 95% aqueous formic acid (0.1%)/5% acetonitrile to 100% acetonitrile was ramped over 1.5 minutes, held for 0.6 minutes, then returns to 100% aqueous formic acid (0.1%) for 0.5 minutes. The flow rate was 0.6 mL/min.

Method B.

| Column | YMC-PACK ODS-AQ, 50 × 2.0 mm 5 μm |
| --- | --- |
| Mobile Phase | A: H₂O (0.1% TFA) |
| | B: acetonitrile (0.05% TFA) |
| Gradient | StopTime: 10 min |
| | PostTime: OFF |

| TIME(min) | A % | B % |
| --- | --- | --- |
| 0 | 100 | 0 |
| 1 | 100 | 0 |
| 5 | 40 | 60 |
| 7.5 | 40 | 60 |
| 8 | 100 | 0 |

| Flow Rate | 0.8 ml/min |
| --- | --- |
| Wavelength | UV 220 nm |
| Column Temperture | 50° C. |
| MS polarity | positive |
| LCMS | Agilent 1100 |

Method C.

| Column | YMC-PACK ODS-AQ, 50 × 2.0 mm 5 μm |
| --- | --- |
| Mobile Phase | A: H₂O (0.1% TFA) |
| | B: acetonitrile (0.05% TFA) |
| Gradient | StopTime: 10 min |
| | Post Time: OFF |

| TIME(min) | A % | B % |
| --- | --- | --- |
| 0 | 90 | 10 |
| 0.8 | 90 | 10 |
| 4.5 | 20 | 80 |
| 7.5 | 20 | 80 |
| 8 | 90 | 10 |

| Flow Rate | 0.8 ml/min |
| --- | --- |
| Wavelength | UV 220 nm |
| Oven Tem. | 50° C. |
| MS polarity | positive |
| LCMS | Agilent 1100 |

Method D. Reversed phase UPLC (Ultra Performance Liquid Chromatography) was carried out on a bridged ethylsiloxane/silica hybrid (BEH) C18 column (1.7 μm, 2.1×50 mm; Waters Acquity) with a flow rate of 0.8 ml/min. Two mobile phases (10 mM ammonium acetate in H₂O/acetonitrile 95/5; mobile phase B: acetonitrile) were used to run a gradient condition from 95% A and 5% B to 5% A and 95% B in 1.3 minutes and hold for 0.7 minutes. An injection volume of 0.75 μl was used. Cone voltage was 30 V for positive ionization mode and 30 V for negative ionization mode.

Method E. Using a Phenomenex Kinetex column(XB-C18 50×4.6 mm I.D. 2.6 u) held at 35° C. MS detection: API-ES Positive ionization mode, Mass range 100-1200. PDA detection (λ=190-400 nm). The following gradient was used with a 2 μL injection:

| Solvent A | H₂O + 0.1% Formic Acid |
| --- | --- |
| Solvent B | Acetonitrile |

| Time (min) | % A | % B | Flow (ml/min) |
| --- | --- | --- | --- |
| 0.0 | 95 | 5 | 3.0 |
| 4.2 | 5 | 95 | 3.0 |
| 4.9 | 5 | 95 | 3.0 |
| 5.0 | 95 | 5 | 3.0 |

Method F. Using a YMC ODS-AQ C-18; 50×4.6 mm, ID=3 μm held at 35° C. MS detection: API-ES Positive ionization mode, Mass range 100-1400. PDA detection (λ=190-400 nm). The following gradient was used with a 2 μL injection:

| Solvent A | H₂O + 0.1% Formic Acid |
| --- | --- |
| Solvent B | Acetonitrile |

| Time (min) | % A | % B | Flow (ml/min) |
| --- | --- | --- | --- |
| 0.0 | 95 | 5 | 2.6 |
| 4.8 | 5 | 95 | 2.6 |
| 5.8 | 5 | 95 | 2.6 |
| 6.0 | 95 | 5 | 2.6 |

Method G. Alliance HT 2790 (Waters) system comprising a quaternary pump with degasser, an autosampler, a column oven (set at 40° C.). Flow from the column was split to a MS spectrometer. The MS detector was configured with an electrospray ionization source. The capillary needle voltage was 3 kV and the source temperature was maintained at 140° C. Nitrogen was used as the nebulizer gas. Xterra MS C18 column (3.5 μm, 4.6×100 mm) with a flow rate of 1.6 mL/min. Three mobile phases (mobile phase A: 95% 25 mM ammoniumacetate+5% acetonitrile; mobile phase B: acetonitrile; mobile phase C: methanol) were employed to run a gradient condition from 100% A to 50% B and 50% C in 6.5 minutes, to 100% B in 0.5 minute, 100% B for 1 minute and re-equilibrate with 100% A for 1.5 minutes. An injection volume of 10 μl was used.

Method H. Reversed phase UPLC (Ultra Performance Liquid Chromato-graphy) was carried out on a bridged ethylsiloxane/silica hybrid (BEH) C18 column (1.7 μm, 2.1×50 mm; Waters Acquity) with a flow rate of 0.8 mL/min. Two mobile phases (mobile phase A: 10 mM ammonium acetate in H₂O/acetonitrile 95/5; mobile phase B: acetonitrile) were used to run a gradient condition from 95% A and 5% B to 5% A and 95% B in 1.3 minutes and hold for 0.2 minutes. An injection volume of 0.5 μl was used. Cone voltage was 10 V for positive ionization mode and 20 V for negative ionization mode.

Biological Activity of Compounds of Formula (I)

Description of Biological Assays

Assessment of TLR7 and TLR8 Activity

The ability of compounds to activate human TLR7 and/or TLR8 was assessed in a cellular reporter assay using HEK293 cells transiently transfected with a TLR7 or TLR8 expression vector and NFκB-luc reporter construct. In one instance the TLR expression construct expresses the respective wild type sequence or a mutant sequence comprising a deletion in the second leucine-rich repeat of the TLR. Such mutant TLR proteins have previously been shown to be more susceptible to agonist activation (U.S. Pat. No. 7,498,409).

Briefly, HEK293 cells were grown in culture medium (DMEM supplemented with 10% FCS and 2 mM Glutamine). For transfection of cells in 10 cm dishes, cells were detached with Trypsin-EDTA, transfected with a mix of CMV-TLR7 or TLR8 plasmid (750 ng), NFκB-luc plasmid (375 ng) and a transfection reagent and incubated for 48 hours at 37° C. in a humidified 5% $CO_2$ atmosphere. Transfected cells were then detached with Trypsin-EDTA, washed in PBS and resuspended in medium to a density of $1.67 \times 10^5$ cells/mL. Thirty microliters of cells were then dispensed into each well in 384-well plates, where 10 μL of compound in 4% DMSO was already present. Following 6 hours incubation at 37° C., 5% $CO_2$, the luciferase activity was determined by adding 15 μl of Steady Lite Plus substrate (Perkin Elmer) to each well and readout performed on a ViewLux ultraHTS microplate imager (Perkin Elmer). Dose response curves were generated from measurements performed in quadruplicates. Lowest effective concentrations (LEC) values, defined as the concentration that induces an effect which is at least two fold above the standard deviation of the assay, were determined for each compound.

Compound toxicity was determined in parallel using a similar dilution series of compound with 30 μL per well of cells transfected with the CMV-TLR7 construct alone ($1.67 \times 10^5$ cells/mL), in 384-well plates. Cell viability was measured after 6 hours incubation at 37° C., 5% $CO_2$ by adding 15 μL of ATP lite (Perkin Elmer) per well and reading on a ViewLux ultraHTS microplate imager (Perkin Elmer). Data was reported as $CC_{50}$.

Suppression of HCV Replicon Replication

Activation of human TLR7 results in robust production of interferon by plasmacytoid dendritic cells present in human blood. The potential of compounds to induce interferon was evaluated by looking at the antiviral activity in the HCV replicon system upon incubation with conditioned media from peripheral blood mononuclear cells (PBMC). The HCV replicon assay is based on a bicistronic expression construct, as described by Lohmann et al. (Science (1999) 285: 110-113; Journal of Virology (2003) 77: 3007-15 3019) with modifications described by Krieger et al. (Journal of Virology (2001) 75: 4614-4624). The assay utilized the stably transfected cell line Huh-7 luc/neo harboring an RNA encoding a bicistronic expression construct comprising the wild type NS3-NS5B regions of HCV type 1 b translated from an Internal Ribosome Entry Site (IRES) from encephalomyocarditis virus (EMCV), preceded by a reporter gene (Firefly-luciferase) and a selectable marker gene (neoR, neomycine phosphotransferase). The construct is flanked by 5' and 3' NTRs (non-translated regions) from HCV type 1 b. Continued culture of the replicon cells in the presence of G418 (neoR) is dependent on the replication of the HCV RNA. The stably transfected replicon cells that replicate HCV RNA autonomously and to high levels, encoding inter alia luciferase, were used for profiling of the conditioned cell culture media.

Briefly, PBMCs were prepared from buffy coats of at least two donors using a standard Ficoll centrifugation protocol. Isolated PBMCs were resuspended in RPMI medium supplemented with 10% human AB serum and $2 \times 10^5$ cells/well were dispensed into 384-well plates containing compounds (70 μL total volume). After overnight incubation, 10 μL of supernatant was transferred to 384-well plates containing $2.2 \times 10^3$ replicon cells/well in 30 μL (plated the day before). Following 24 hours of incubation, replication was measured by assaying luciferase activity using 40 μL/well Steady Lite Plus substrate (Perkin Elmer) and measured with ViewLux ultraHTS microplate imager (Perkin Elmer). The inhibitory activity of each compound on the Huh7-luc/neo cells were reported as $EC_{50}$ values, defined as the compound concentration applied to the PBMCs resulting in a 50% reduction of luciferase activity which in turn indicates the degree of replication of the replicon RNA on transfer of a defined amount of PBMC culture medium. Recombinant interferon α-2a (Roferon-A) was used as a standard control compound.

Biological activity of compounds of formula (I). All compounds showed CC50 of >22 uM in the HEK 293 TOX assay described above.

Activation of ISRE Promoter Elements

The potential of compounds to induce IFN-I was also evaluated by measuring the activation of interferon-stimulated responsive elements (ISRE) by conditioned media from PBMC. The ISRE element of sequence GAAACT-GAAACT (SEQ ID NO: 1) is highly responsive to the STAT1-STAT2-IRF9 transcription factor, activated upon binding of IFN-I to their receptor IFNAR (Clontech, PT3372-5W). The plasmid pISRE-Luc from Clontech (ref. 631913) contains 5 copies of this ISRE element, followed by the firefly luciferase ORF. A HEK293 cell line stably transfected with pISRE-Luc (HEK-ISREluc) was established to profile of the conditioned PBMC cell culture media.

Briefly, PBMCs were prepared from buffy coats of at least two donors using a standard Ficoll centrifugation protocol. Isolated PBMCs were resuspended in RPMI medium supplemented with 10% human AB serum and $2 \times 10^5$ cells/well were dispensed into 384-well plates containing compounds (70 μL total volume). After overnight incubation, 10 μL of supernatant was transferred to 384-well plates containing $5 \times 10^3$ HEK-ISREluc cells/well in 30 μL (plated the day before). Following 24 hours of incubation, activation of the ISRE elements was measured by assaying luciferase activity using 40 μL/well Steady Lite Plus substrate (Perkin Elmer) and measured with ViewLux ultraHTS microplate imager (Perkin Elmer). The stimulating activity of each compound on the HEK-ISREluc cells was reported as LEC value, defined as the compound concentration applied to the PBMCs resulting in a luciferase activity at least two fold above the standard deviation of the assay. The LEC in turn indicates the degree of ISRE activation on transfer of a defined amount of PBMC culture medium. Recombinant interferon α-2a (Roferon-A) was used as a standard control compound.

For a given compound, the LEC value obtained from this assay were in the same range as the $EC_{50}$ values obtained from the "suppression of HCV replication assay." Thus, it is possible to compare the potential of compounds to induce IFN-I by PBMC, measured by either of the 2 assays.

TABLE II
| | BIOLOGICAL ACTIVITY OF THE COMPOUNDS. | | | | | |
|---|---|---|---|---|---|---|
| | STRUCTURE | TLR7-wt_LEC | TLR7-dIRR2_LEC | TLR8-wt_LEC | TLR8-dIRR2_LEC | PBMC-HUH7_EC$_5$ |
| 1 | 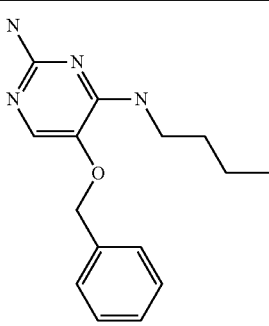 | 0.90 | 0.55 | 2.42 | 1.30 | 0.70 |
| 2 | 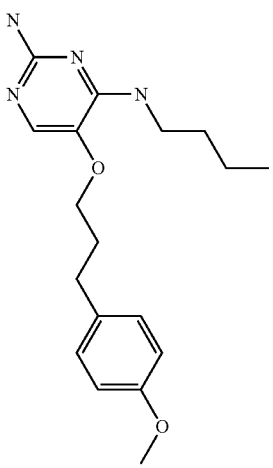 [SMILES: CCCCNc1nc(N)ncc1OCCCc1ccc(OC)cc1] | | 0.02 | 1.34 | 0.31 | 0.04 |
| 3 | 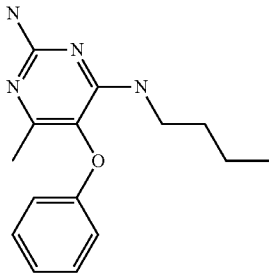 [SMILES: CCCCNc1nc(N)nc(C)c1Oc1ccccc1] | | 21.69 | 4.91 | 1.66 | 10.80 |
| 4 | 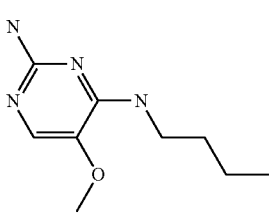 | 6.71 | 1.17 | 2.56 | 1.10 | 1.14 |

TABLE II-continued

| | | | | | | |
|---|---|---|---|---|---|---|
| 5 | *(pyrimidine structure with N-butyl amine and O-propyl ether)* | 6.18 | 1.69 | 4.53 | 2.30 | 2.65 |
| 6 | *(pyrimidine structure with N-butyl amine and O-CH2-(3,5-dimethyl-4-methoxypyridyl))* | 0.01 | 0.16 | 0.10 | 0.02 | |
| 7 | *(6-methylpyrimidine with N-butyl amine and O-(2-methoxyphenyl))* | 1.11 | 5.84 | 3.03 | 3.11 | |
| 8 | *(pyrimidine with N-butyl amine and O-CH2-(2-fluorophenyl))* | 0.38 | 1.88 | 0.81 | 0.37 | |
| 9 | *(pyrimidine with N-butyl amine and O-isopentyl)* | 1.55 | 19.00 | 9.70 | 9.72 | |

TABLE II-continued

| | | | | | |
|---|---|---|---|---|---|
| 10 | *(pyrimidine structure with N-butyl and O-butyl substituents)* | 1.28 | 8.14 | 2.82 | 1.58 |
| 11 | *(pyrimidine structure with N-butyl and O-CH2-(3,4-dichlorophenyl) substituents)* | 0.60 | 4.52 | 3.50 | 0.78 |
| 12 | *(pyrimidine structure with N-butyl and O-CH2-(4-methoxycarbonylphenyl) substituents)* | 0.26 | 1.49 | 1.12 | 2.76 |
| 13 | *(pyrimidine structure with N-butyl and O-CH2CH2-phenyl substituents)* | 2.26 | 13.18 | 5.23 | 2.53 |

TABLE II-continued
| | | | | | | |
|---|---|---|---|---|---|---|
| 14 | 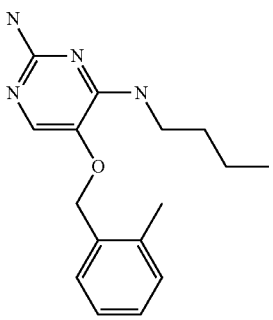 | | 0.91 | 4.92 | 0.91 | 1.81 |
| 15 | 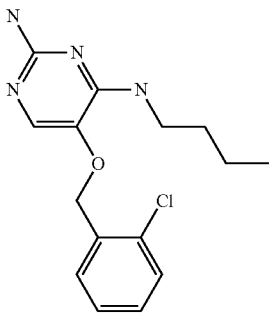 [SMILES: CCCCNc1nc(N)ncc1OCc1ccccc1Cl] | | 0.17 | 2.31 | 1.06 | 0.17 |
| 16 | 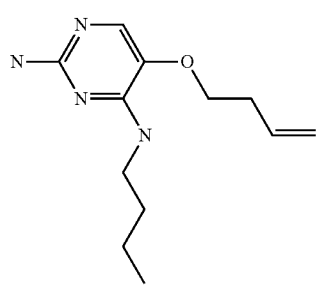 [SMILES: C=CCCOc1cnc(N)nc1NCCCC] | | 0.49 | 2.68 | 0.59 | 0.79 |
| 17 | 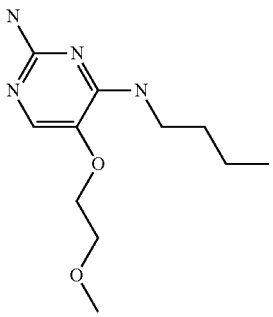 [SMILES: CCCCNc1nc(N)ncc1OCCOC] | | 0.34 | 2.03 | 0.67 | 0.71 |
| 18 | 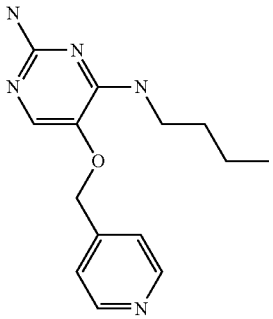 [SMILES: CCCCNc1nc(N)ncc1OCc1ccncc1] | | 0.83 | 1.87 | 0.85 | 0.63 |

TABLE II-continued
| | | | | | | |
|---|---|---|---|---|---|---|
| 19 | 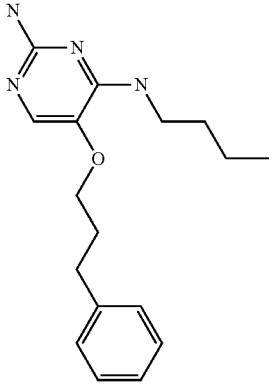 [SMILES: CCCCNc1nc(N)ncc1OCCCc1ccccc1] | 1.53 | 0.16 | 7.94 | 2.36 | 0.43 |
| 20 | 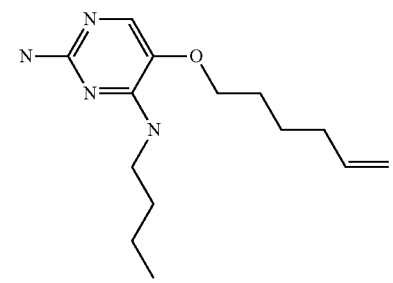 [SMILES: C=CCCCCOc1cnc(N)nc1NCCCC] | | 0.79 | 10.21 | 2.87 | 1.33 |
| 21 | 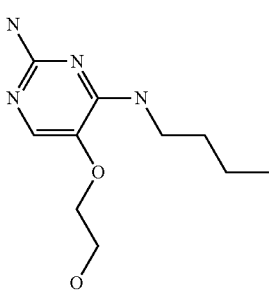 [SMILES: CCCCNc1nc(N)ncc1OCCO] | | 1.61 | 2.69 | 0.64 | 3.08 |
| 22 | 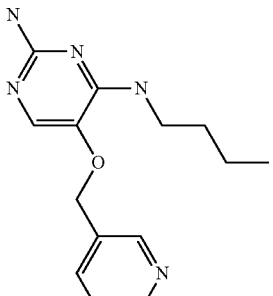 | | 0.31 | 2.35 | 0.94 | 0.25 |
| 23 | 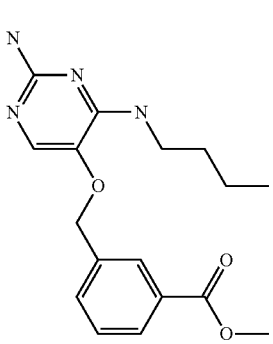 [SMILES: CCCCNc1nc(N)ncc1OCc1cccc(C(=O)OC)c1] | | 0.26 | 2.55 | 1.45 | 10.84 |

TABLE II-continued

| | | | | | |
|---|---|---|---|---|---|
| 24 | | 1.99 | 2.42 | 1.50 | 2.75 |
| 25 | | 0.64 | >25 | >25 | 1.55 |
| 26 | | 0.49 | 3.90 | 1.52 | 0.58 |
| 27 | | 0.78 | 5.36 | 0.64 | 1.03 |

TABLE II-continued

| # | Structure | | | | |
|---|---|---|---|---|---|
| 28 | (pyrimidine with NH-butyl, O-(CH2)3-C(=O)-NH2) | 2.47 | 9.18 | 6.99 | 1.75 |
| 29 | (pyrimidine with NH-butyl, O-(CH2)3-CN) | | 1.32 | 2.86 | 1.19 | 2.97 |
| 30 | (pyrimidine with NH-butyl, O-CH2CH2-NH2) | >25 | 6.44 | 1.16 | 9.07 |
| 31 | (pyrimidine with NH-butyl, O-isobutyl) | >24.59 | 5.27 | 17.53 | 6.46 | 10.36 |
| 32 | (pyrimidine with NH-butyl, O-pentyl) | 10.60 | 1.35 | 9.97 | 4.43 | 1.06 |

TABLE II-continued

| 33 | [structure] | 0.36 | 1.78 | 1.17 | 1.48 |
| --- | --- | --- | --- | --- | --- |
| 34 | [structure] | 0.06 | 0.83 | 0.61 | 0.05 |
| 35 | [structure] | 0.39 | 1.67 | 1.66 | 1.50 |
| 36 | [structure] | 0.58 | 1.68 | 0.82 | 0.70 |

TABLE II-continued
| | | | | | | |
|---|---|---|---|---|---|---|
| 37 | 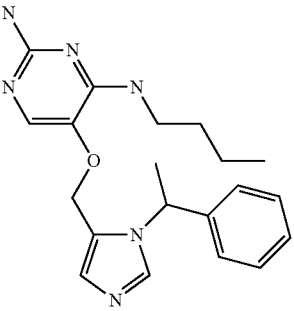 | | 0.04 | 9.22 | 5.69 | 0.12 |
| 38 | 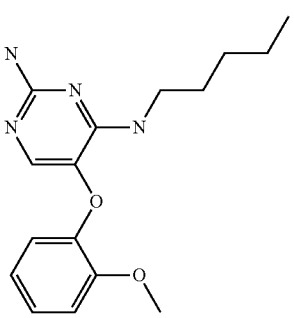 [SMILES: CCCCCNc1nc(N)ncc1Oc1ccccc1OC] | 21.97 | 2.46 | >50 | 22.88 | 11.28 |
| 39 | 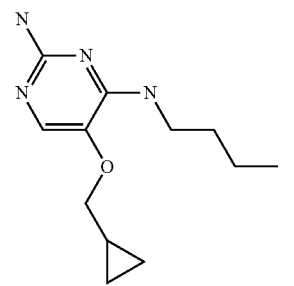 [SMILES: CCCCNc1nc(N)ncc1OCC1CC1] | | 3.01 | 14.41 | 7.10 | |
| 40 | 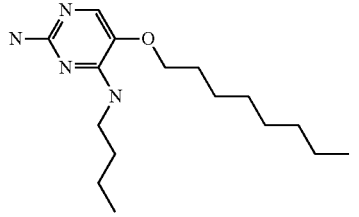 [SMILES: CCCCCCCCOc1cnc(N)nc1NCCCC] | | 2.69 | >25 | >25 | |
| 41 | 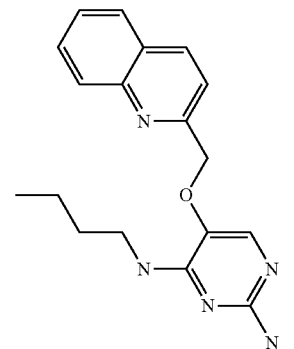 [SMILES: CCCCNc1nc(N)ncc1OCc1ccc2ccccc2n1] | | 0.03 | 0.83 | 0.51 | 0.10 |

TABLE II-continued
| | | | | | |
|---|---|---|---|---|---|
| 42 | 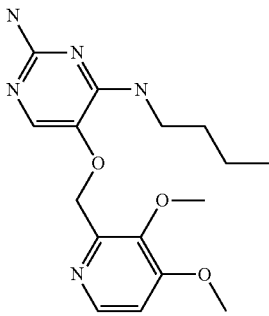 [SMILES: CCCCNc1nc(N)ncc1OCc1nccc(OC)c1OC] | 0.04 | 1.15 | 0.41 | 0.04 |
| 43 | 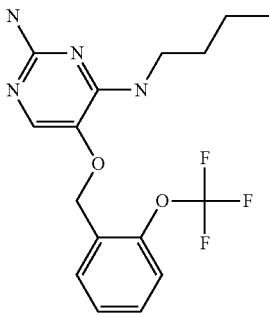 [SMILES: CCCCNc1nc(N)ncc1OCc1ccccc1OC(F)(F)F] | 0.08 | 8.22 | 1.66 | 0.79 |
| 44 | 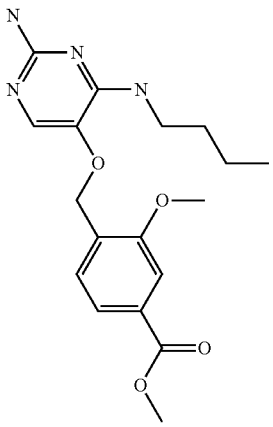 [SMILES: CCCCNc1nc(N)ncc1OCc1ccc(C(=O)OC)cc1OC] | 0.16 | 3.11 | 1.96 | 0.59 |
| 45 | 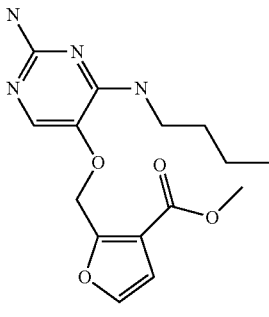 [SMILES: CCCCNc1nc(N)ncc1OCc1occc1C(=O)OC] | 0.17 | 0.58 | 0.40 | 0.17 |

TABLE II-continued
| | | | | | |
|---|---|---|---|---|---|
| 46 | 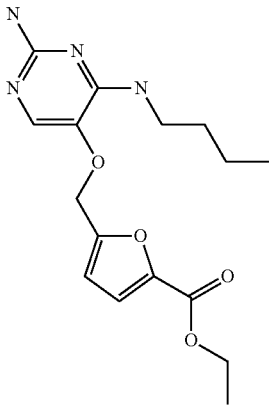 [SMILES: CCCCNc1nc(N)ncc1OCc1ccc(C(=O)OCC)o1] | 0.19 | 3.85 | 1.96 | 2.51 |
| 47 | 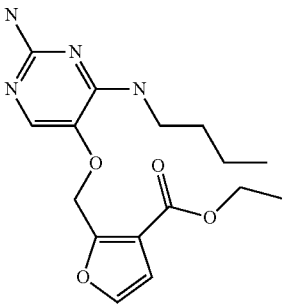 [SMILES: CCCCNc1nc(N)ncc1OCc1occc1C(=O)OCC] | 0.20 | 1.87 | 0.66 | 0.33 |
| 48 | 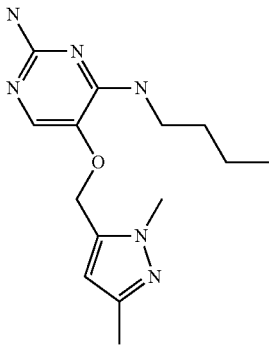 [SMILES: CCCCNc1nc(N)ncc1OCc1cc(C)nn1C] | 0.28 | 1.75 | 0.60 | 0.64 |
| 49 | 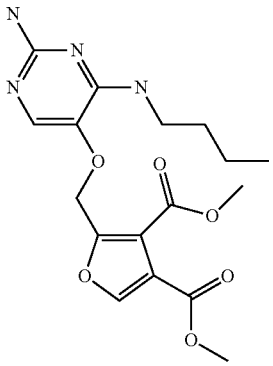 [SMILES: CCCCNc1nc(N)ncc1OCc1occ(C(=O)OC)c1C(=O)OC] | 0.31 | 3.72 | 2.07 | 0.55 |

TABLE II-continued

| | | | | | |
|---|---|---|---|---|---|
| 50 | (structure) | 0.51 | >25 | >25 | 0.78 |
| 51 | (structure) | 0.58 | 3.92 | 2.09 | 0.50 |
| 52 | (structure) | 0.63 | 3.61 | 1.65 | 0.26 |
| 53 | (structure) | 0.64 | 3.06 | 2.15 | 0.60 |
| 54 | (structure) | 0.68 | 1.40 | 0.69 | 0.75 |

TABLE II-continued
| | | | | | | |
|---|---|---|---|---|---|---|
| 55 | 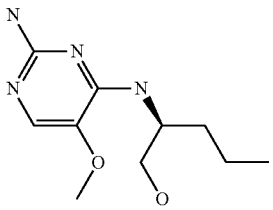 [SMILES: CCC[C@@H](CO)Nc1nc(N)ncc1OC] | | 0.72 | 0.16 | 0.12 | 0.41 |
| 56 | 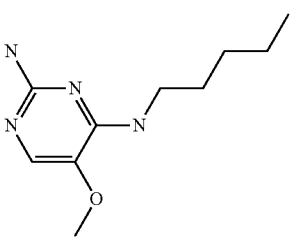 | 12.02 | 0.84 | 5.55 | 1.47 | 0.80 |
| 57 | 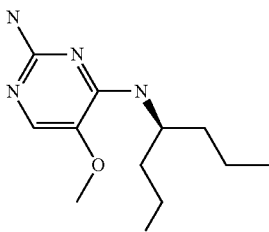 | | 0.88 | 1.80 | 0.74 | 0.80 |
| 58 | 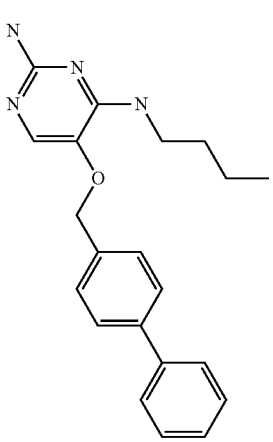 [SMILES: CCCCNc1nc(N)ncc1OCc1ccc(-c2ccccc2)cc1] | 6.48 | 0.99 | 3.84 | 2.17 | 2.99 |
| 59 | 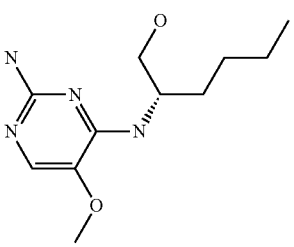 [SMILES: CCCC[C@@H](CO)Nc1nc(N)ncc1OC] | | 1.20 | 0.36 | 0.13 | 0.40 |
| 60 | 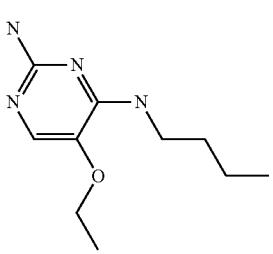 | 5.58 | 1.38 | 2.08 | 0.65 | 1.91 |

TABLE II-continued
| | | | | | | |
|---|---|---|---|---|---|---|
| 61 | 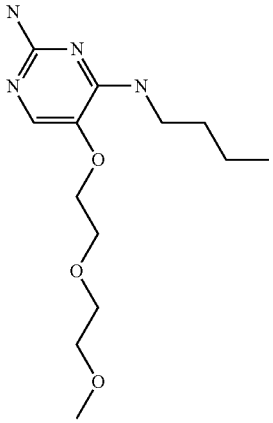 [SMILES: CCCCNc1nc(N)ncc1OCCOCCOC] | | 1.38 | 3.59 | 1.56 | 1.91 |
| 62 | 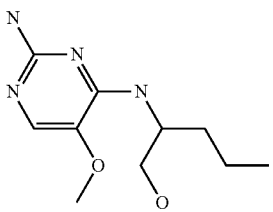 [SMILES: CCCC(CO)Nc1nc(N)ncc1OC] | 21.26 | 1.76 | 0.55 | 0.15 | 0.74 |
| 63 | 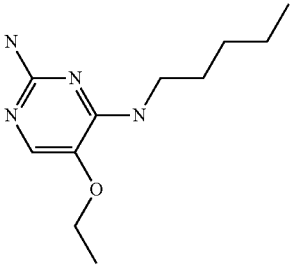 [SMILES: CCCCCNc1nc(N)ncc1OCC] | 2.78 | 1.79 | 6.35 | 1.94 | 2.69 |
| 64 | 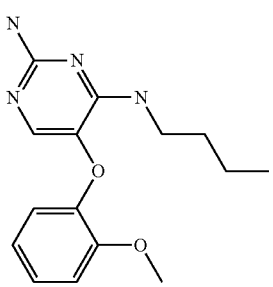 [SMILES: CCCCNc1nc(N)ncc1Oc1ccccc1OC] | 8.47 | 2.03 | 18.43 | 7.65 | 4.29 |
| 65 | 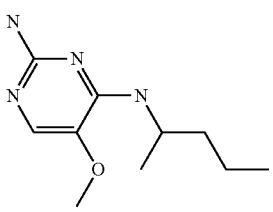 | 21.59 | 2.04 | 3.68 | 1.13 | 2.30 |

TABLE II-continued
| | | | | | | |
|---|---|---|---|---|---|---|
| 66 | 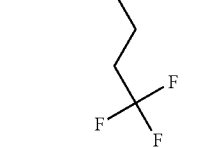 | 2.29 | 9.03 | 1.89 | 2.27 | |
| 67 | 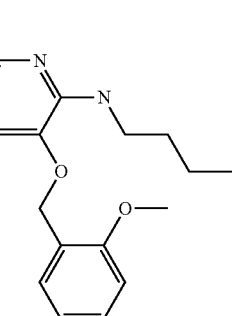 | 2.31 | >24.59 | >24.59 | 2.43 | |
| 68 | 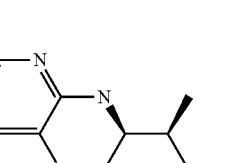 | 2.54 | 0.56 | 0.43 | 1.17 | |
| 69 | 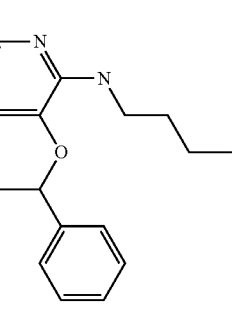 | 3.75 | 6.43 | 2.22 | 6.16 | |
| 70 | 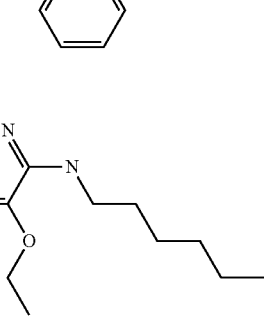 | 15.84 | 4.96 | >24.59 | >24.59 | >23.81 |

TABLE II-continued
| | Structure | | | | |
|---|---|---|---|---|---|
| 71 | 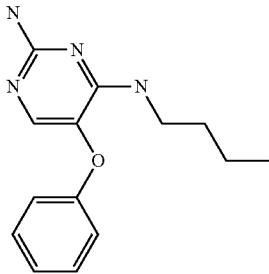 [SMILES: CCCCNc1nc(N)ncc1Oc1ccccc1] | >24.59 | >24.59 | >24.59 | 4.96 |
| 72 | 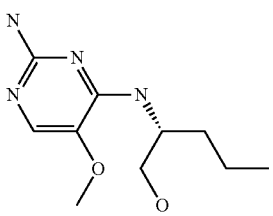 | >25 | 6.57 | 6.24 | 17.50 |
| 73 | 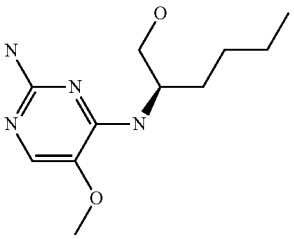 [SMILES: CCCC[C@H](CO)Nc1nc(N)ncc1OC] | >25 | 0.80 | 0.47 | 1.39 |
| | Structure | TLR 7 wt LEC | TLR 8 wt LEC | PBMC HUH-7 EC$_{50}$ | HEK-ISREluc LEC |
|---|---|---|---|---|---|
| 74 | 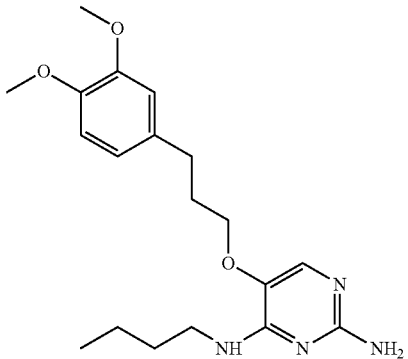 [SMILES: CCCCNc1nc(N)ncc1OCCCc1ccc(OC)c(OC)c1] | 0.713 | 1.720 | 0.157 | ND |
| 75 | 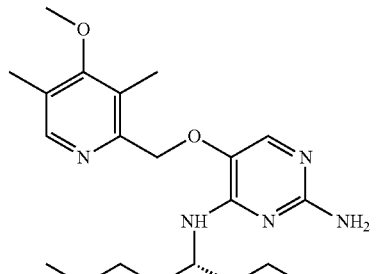 | 0.023 | 0.218 | 0.007 | ND |

TABLE II-continued

| | | | | | |
|---|---|---|---|---|---|
| 76 | [structure] | 0.021 | 0.055 | ND | 0.008 |
| 77 | [structure] | 0.449 | 0.623 | ND | 0.137 |
| 78 | [structure] | 0.519 | 0.827 | ND | 0.123 |
| 79 | [structure] | 1.620 | 0.329 | ND | 0.235 |
| 80 | [structure] | 0.560 | 0.041 | ND | 0.027 |

TABLE II-continued

| | | | | | |
|---|---|---|---|---|---|
| 81 | (structure) | 0.101 | 0.429 | ND | 0.086 |
| 82 | (structure) | 4.420 | 13.590 | 14.020 | ND |
| 83 | (structure) | 0.997 | 1.610 | 0.204 | ND |
| 84 | (structure) | 0.860 | 0.250 | 0.076 | ND |
| 85 | (structure) | 0.509 | 2.960 | 0.209 | ND |

TABLE II-continued

| | | | | | |
|---|---|---|---|---|---|
| 86 | [structure: 2-amino-4-(butylamino)-5-((1H-1,2,3-triazol-4-yl)methoxy)pyrimidine] | 0.646 | 3.750 | ND | 0.131 |
| 87 | [structure: 2-amino-4-[(S)-pentan-3-ylamino with hydroxyethyl]-5-((3,4-dimethoxypyridin-2-yl)methoxy)pyrimidine] | 0.013 | 0.567 | 0.012 | ND |
| 88 | [structure: 2-amino-4-[(S)-pentan-3-ylamino with hydroxyethyl]-5-((3-methoxy-4-oxo-1,4-dihydropyridin-2-yl)methoxy)pyrimidine] | 3.090 | 6.960 | ND | 0.050 |
| 89 | [structure: ethylcarbamate of 2-amino-4-[(S)-heptan-3-ylamino]-5-methoxypyrimidine derivative] | 1.670 | 6.670 | ND | 0.526 |
| 90 | [structure: 2-amino-4-(allylamino)-5-methoxypyrimidine] | >25 | 8.460 | 6.950 | ND |

TABLE II-continued

| # | Structure | | | | |
|---|---|---|---|---|---|
| 91 | (structure) | >25 | 20.850 | 7.650 | ND |
| 92 | (structure) | >25 | 14.570 | 20.160 | ND |
| 93 | (structure) | >25 | 15.880 | 9.050 | ND |
| 94 | (structure) | 1.590 | 3.170 | 0.696 | ND |
| 95 | (structure) | 2.730 | 2.010 | 0.726 | ND |
| 96 | (structure) | >25 | 6.340 | 4.310 | ND |

| | | | | | |
|---|---|---|---|---|---|
| 97 | 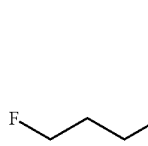 | 21.810 | 5.070 | 2.640 | ND |
| 98 |  | >25 | 10.100 | 21.960 | ND |
| 99 |  | 8.980 | 1.820 | 1.280 | ND |
| 100 | 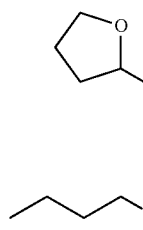 | 18.950 | 6.160 | 5.120 | ND |
| 101 | 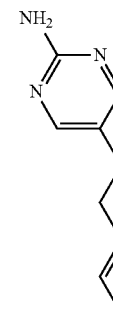 | 0.277 | 0.597 | 0.055 | ND |

TABLE II-continued
| | | | | | |
|---|---|---|---|---|---|
| 102 | 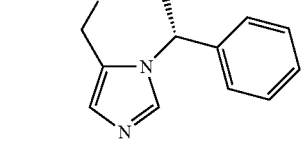 | 0.141 | 5.690 | 0.012 | ND |
| 103 | 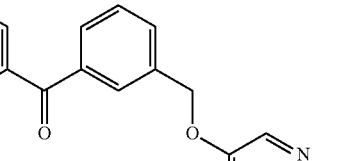 | 1.190 | 1.270 | 0.725 | ND |
| 104 | 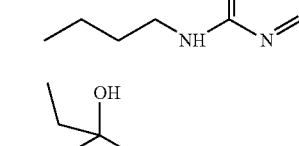 | >25 | 12.390 | >23.81 | ND |
| 105 | 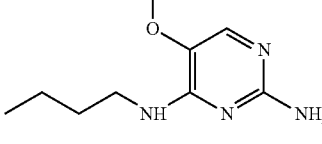 | >25 | 22.020 | 19.050 | ND |
| 106 | 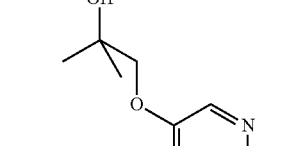 | 16.100 | 5.940 | 3.150 | ND |
| 107 | 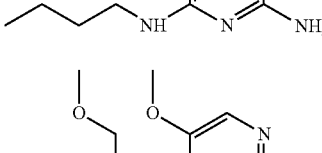 | 2.460 | 3.940 | 1.590 | ND |

TABLE II-continued

| | | | | | |
|---|---|---|---|---|---|
| 108 | (structure) | 6.580 | >25 | 6.770 | ND |
| 109 | (structure) | 0.790 | 2.230 | 0.393 | ND |
| 110 | (structure) | 2.380 | 3.780 | 0.740 | ND |
| 111 | (structure) | 0.257 | ND | 0.096 | ND |

TABLE II-continued
| | | | | | |
|---|---|---|---|---|---|
| 112 | 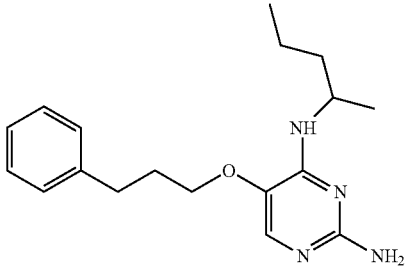 [SMILES: CCCC(C)Nc1nc(N)ncc1OCCCc1ccccc1] | 3.960 | 5.560 | 3.350 | ND |
| 113 | 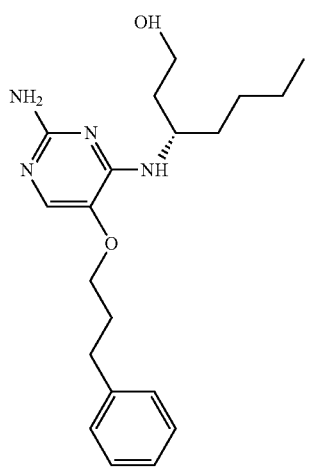 [SMILES: CCCC[C@@H](CCO)Nc1nc(N)ncc1OCCCc1ccccc1] | 0.433 | 2.240 | 0.251 | ND |
| 114 | 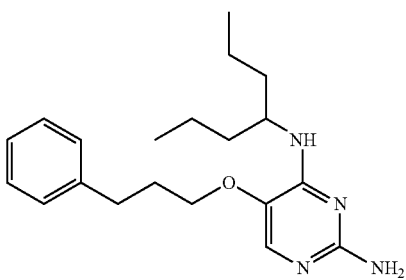 [SMILES: CCCC(CCC)Nc1nc(N)ncc1OCCCc1ccccc1] | 2.020 | >25 | 2.000 | ND |
| 115 | 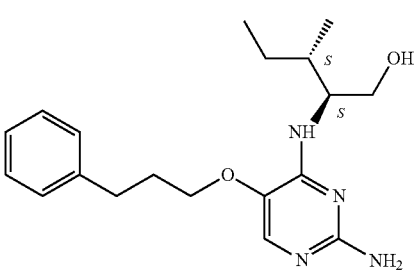 | 6.180 | 6.510 | 3.730 | ND |

TABLE II-continued

| 116 | [structure: 2-amino-4-(butylamino)pyrimidine with 5-O-CH2-isoxazole-furan] | 0.652 | 1.610 | 0.066 | ND |
| 117 | [structure: 2-amino-4-(butylamino)pyrimidine with 5-O-CH2-(1,5-dimethylpyrazole)] | 0.335 | 1.120 | 0.088 | ND |
| 118 | [structure: 2-amino-4-(butylamino)pyrimidine with 5-O-CH2-(3-methyl-5-phenylisoxazole)] | 1.670 | 3.710 | 0.976 | ND |
| 119 | [structure: 2-amino-4-(butylamino)pyrimidine with 5-O-CH2-(5-trifluoromethylfuran)] | 1.720 | 6.120 | 0.193 | ND |

TABLE II-continued
| 120 | 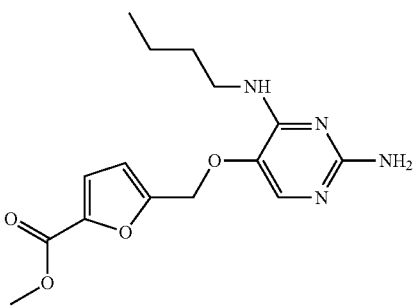 [SMILES: CCCCNc1nc(N)ncc1OCc1ccc(C(=O)OC)o1] | 0.649 | 3.910 | 0.273 | ND |
| 121 | 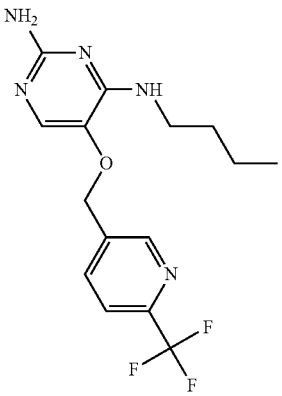 [SMILES: CCCCNc1nc(N)ncc1OCc1ccc(C(F)(F)F)nc1] | 0.797 | 3.020 | 0.272 | ND |
| 122 | 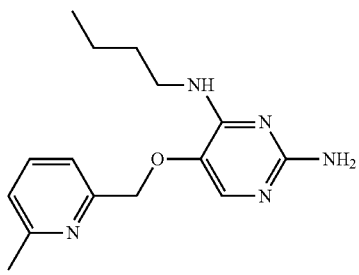 [SMILES: CCCCNc1nc(N)ncc1OCc1cccc(C)n1] | 0.118 | 0.628 | 0.025 | ND |
| 123 | 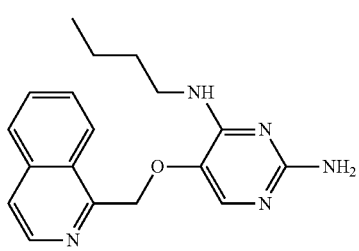 [SMILES: CCCCNc1nc(N)ncc1OCc1nccc2ccccc12] | 0.008 | 0.143 | 0.002 | ND |
| 124 | 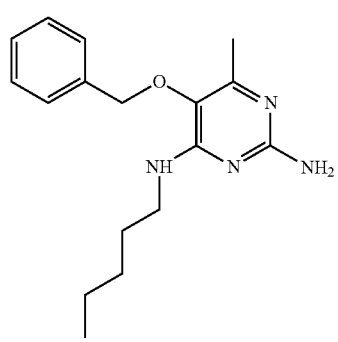 [SMILES: CCCCCNc1nc(N)nc(C)c1OCc1ccccc1] | 15.610 | 13.650 | >23.81 | ND |

TABLE II-continued

| # | Structure | | | | |
|---|---|---|---|---|---|
| 125 | (structure) | 1.630 | 0.598 | 0.336 | ND |
| 126 | (structure) | 1.000 | 1.020 | 0.264 | ND |
| 127 | (structure) | 1.0303 | 2.050 | 0.256 | ND |
| 128 | (structure) | 2.430 | 3.740 | 0.284 | ND |
| 129 | (structure) | 2.090 | 3.250 | 0.432 | ND |

TABLE II-continued

| | | | | | |
|---|---|---|---|---|---|
| 130 | [structure] | 0.676 | 6.560 | 0.103 | ND |
| 131 | [structure] | 1.700 | >25 | 0.806 | ND |
| 132 | [structure] | 1.470 | >25 | 0.634 | ND |
| 133 | [structure] | 1.500 | 3.090 | 0.585 | ND |
| 134 | [structure] | 2.010 | 2.110 | 0.935 | ND |

TABLE II-continued
| 135 | 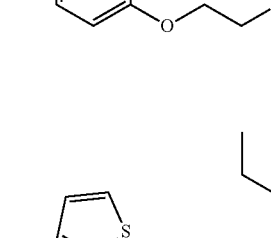 | 3.230 | 1.970 | 3.190 | ND |
| --- | --- | --- | --- | --- | --- |
| 136 | 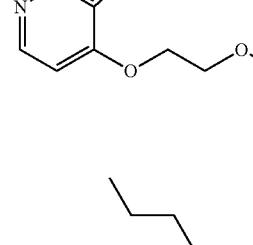 | 2.000 | 2.030 | 0.275 | ND |
| 137 | 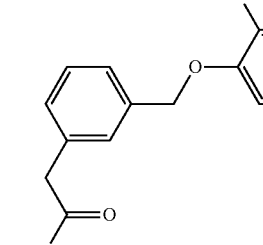 | 0.757 | 1.760 | 22.760 | ND |
| 138 | 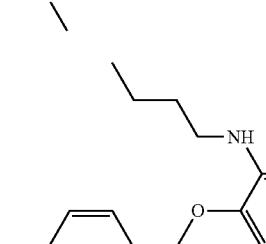 | 1.040 | 1.050 | 0.570 | ND |
| 139 | 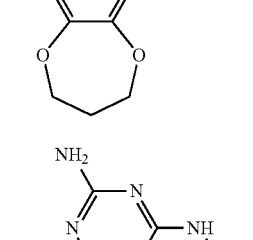 | 0.025 | 0.286 | 0.009 | ND |

TABLE II-continued

| # | Structure | | | | |
|---|---|---|---|---|---|
| 140 | (structure) | 0.617 | 2.250 | 0.175 | ND |
| 141 | (structure) | 4.360 | 0.704 | 0.733 | ND |
| 142 | (structure) | >25 | 2.370 | 19.680 | ND |
| 143 | (structure) | 1.810 | 0.880 | 0.443 | ND |
| 144 | (structure) | 13.010 | 20.790 | 1.320 | ND |

TABLE II-continued
| | | | | | |
|---|---|---|---|---|---|
| 145 | 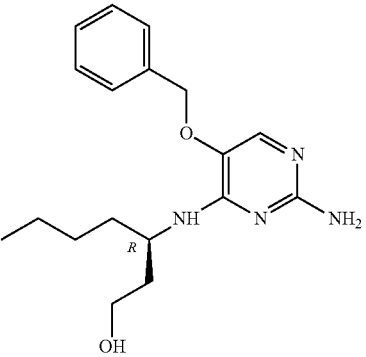 | 2.140 | 1.920 | 0.632 | ND |
| 146 | 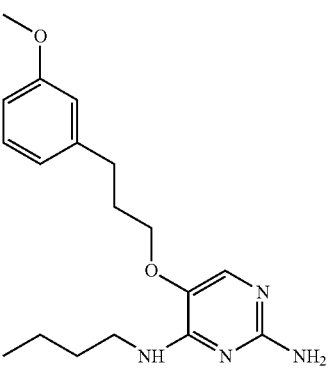 [SMILES: CCCCNc1nc(N)ncc1OCCCc1cccc(OC)c1] | 1.230 | 2.300 | 0.707 | ND |
| 147 | 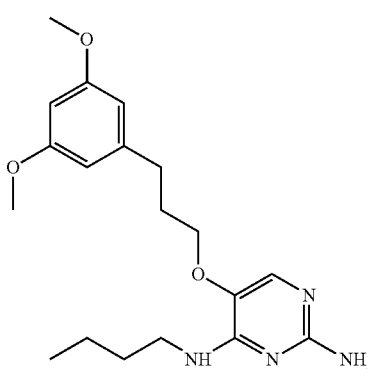 | 2.520 | 4.340 | 0.746 | ND |
| 148 | 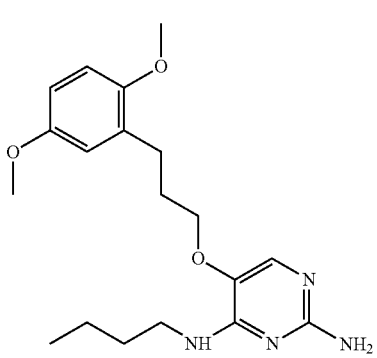 [SMILES: CCCCNc1nc(N)ncc1OCCCc1cc(OC)ccc1OC] | 0.691 | 4.850 | 0.634 | ND |

TABLE II-continued
| 149 | 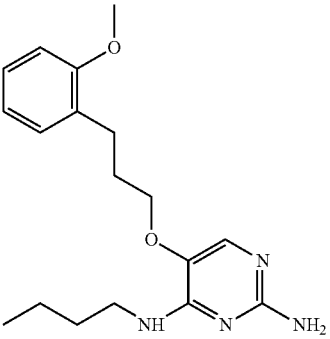 [SMILES: CCCCNc1nc(N)ncc1OCCCc1ccccc1OC] | 2.080 | 5.850 | 0.703 | ND |
| 150 | 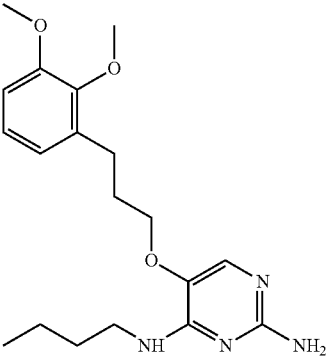 [SMILES: CCCCNc1nc(N)ncc1OCCCc1cccc(OC)c1OC] | 1.180 | 4.310 | 0.689 | ND |
| 151 | 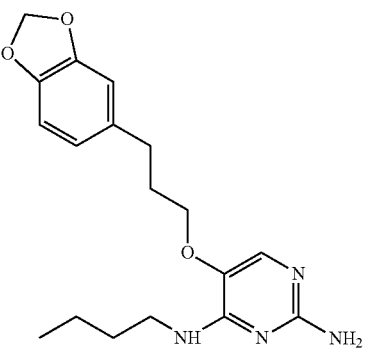 [SMILES: CCCCNc1nc(N)ncc1OCCCc1ccc2c(c1)OCO2] | 0.4331 | 1.860 | 0.188 | ND |
| 152 | 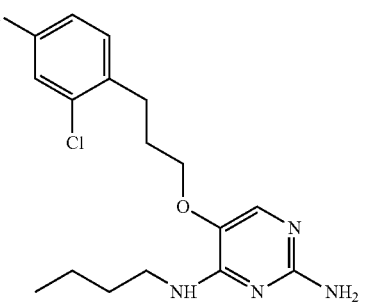 | 5.410 | >25 | 3.350 | ND |

TABLE II-continued
| 153 | 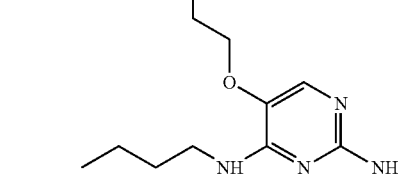 | 10.640 | ND | 3.430 | ND |
| 154 | 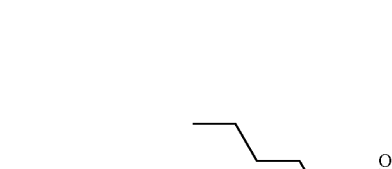 | 3.710 | 2.960 | 3.020 | ND |
| 155 | 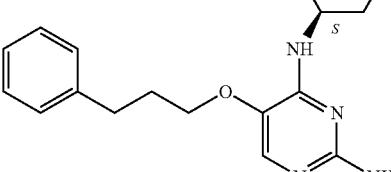 | 2.660 | 4.560 | 3.440 | ND |
| 156 |  | 0.828 | 2.060 | 0.697 | ND |

TABLE II-continued
| | | | | | |
|---|---|---|---|---|---|
| 157 | 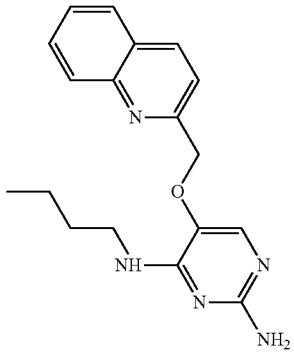 [SMILES: CCCCNc1nc(N)ncc1OCc1ccc2ccccc2n1] | 0.333 | 1.110 | 0.162 | ND |
| 158 | 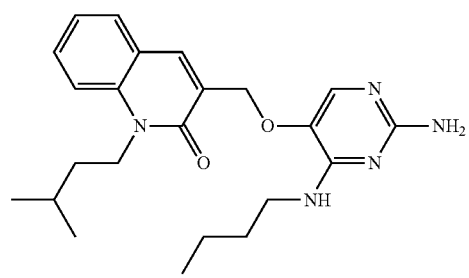 [SMILES: CCCCNc1nc(N)ncc1OCc1cc2ccccc2n(CCC(C)C)c1=O] | 3.080 | >25 | 3.310 | ND |
| 159 | 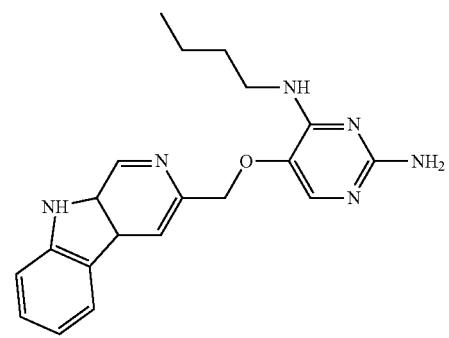 [SMILES: CCCCNc1nc(N)ncc1OCC1=CC2c3ccccc3NC2C=N1] | 0.159 | 1.080 | 0.018 | ND |
| 160 | 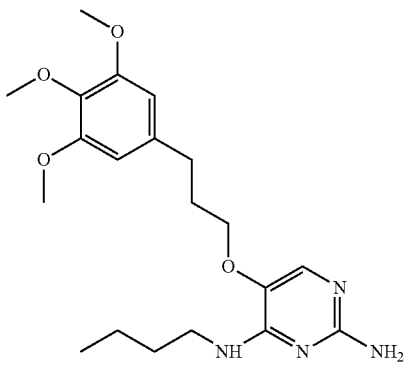 [SMILES: CCCCNc1nc(N)ncc1OCCCc1cc(OC)c(OC)c(OC)c1] | 0.756 | 2.710 | 0.634 | ND |

TABLE II-continued

| # | Structure | | | | |
|---|---|---|---|---|---|
| 161 | (2,4,5-trimethoxyphenyl-propoxy pyrimidine structure) | 0.672 | 3.480 | 0.629 | ND |
| 162 | (2-trifluoromethylphenyl-propoxy pyrimidine structure) | 11.850 | >25 | ND | ND |
| 163 | (2,4-dimethoxyphenyl-propoxy pyrimidine structure) | 0.573 | 2.500 | 0.728 | ND |
| 164 | (2,3,4-trimethoxyphenyl-propoxy pyrimidine structure) | 0.606 | 23.030 | 0.769 | ND |

TABLE II-continued
| | | | | | |
|---|---|---|---|---|---|
| 165 | 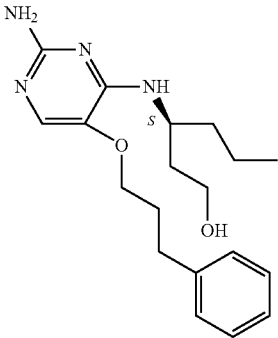 | 0.683 | 1.800 | 0.187 | ND |
| 166 | 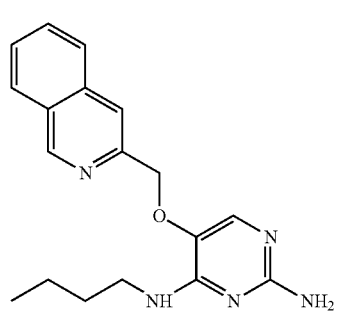 [SMILES: CCCCNc1nc(N)ncc1OCc1cc2ccccc2cn1] | 0.128 | 0.980 | 0.046 | ND |
| 167 | 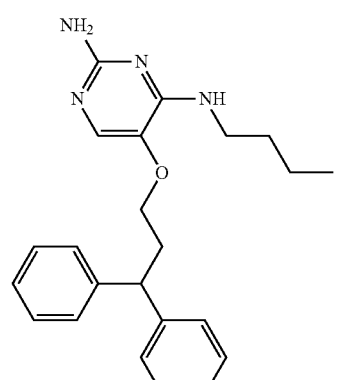 | 1.200 | >25 | 0.764 | ND |
| 168 | 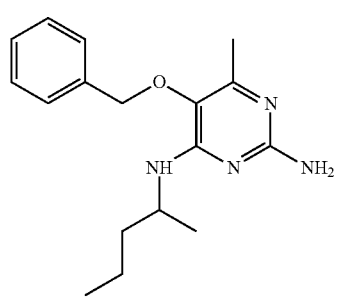 [SMILES: CCCC(C)Nc1nc(N)nc(C)c1OCc1ccccc1] | >25 | 14.900 | 11.740 | ND |

TABLE II-continued
| 169 | 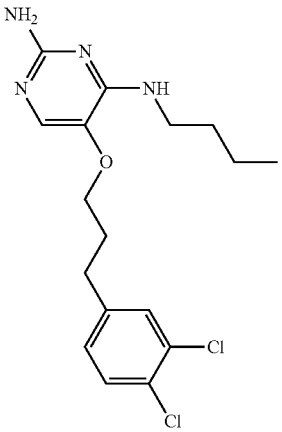 [SMILES: CCCCNc1nc(N)ncc1OCCCc1ccc(Cl)c(Cl)c1] | 5.110 | >25 | 3.130 | ND |
| --- | --- | --- | --- | --- | --- |
| 170 | 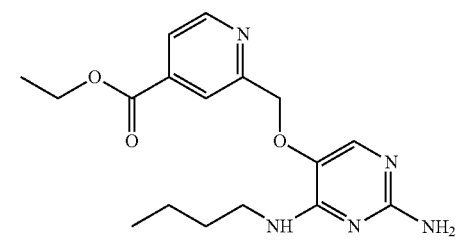 [SMILES: CCCCNc1nc(N)ncc1OCc1cc(C(=O)OCC)ccn1] | 0.319 | 1.750 | 2.630 | ND |
| 171 | 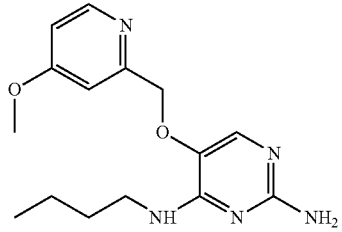 [SMILES: CCCCNc1nc(N)ncc1OCc1cc(OC)ccn1] | 0.396 | 1.060 | 0.158 | ND |
| 172 | 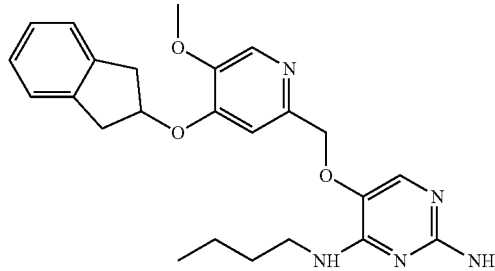 | 0.187 | 2.000 | 0.045 | ND |
| 173 | 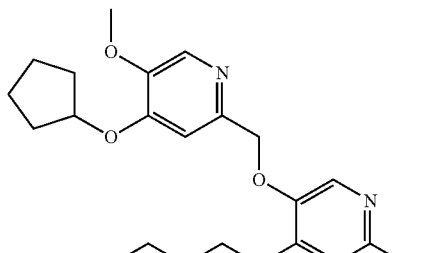 | 0.222 | 2.550 | 0.086 | ND |

TABLE II-continued

| # | Structure | | | | |
|---|---|---|---|---|---|
| 174 | (structure) | 0.447 | 2.610 | 0.052 | ND |
| 175 | (structure) | 0.367 | 2.480 | 0.167 | ND |
| 176 | (structure) | 0.868 | 0.463 | 0.173 | ND |
| 177 | (structure) | 0.795 | 0.819 | 0.197 | ND |
| 178 | (structure) | 0.810 | 0.410 | 0.302 | ND |

TABLE II-continued
| | | | | | |
|---|---|---|---|---|---|
| 179 | 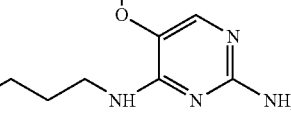 | 0.078 | 0.142 | 0.021 | ND |
| 180 | 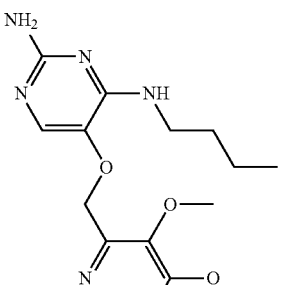 | 0.135 | 0.524 | 0.047 | ND |
| 181 | 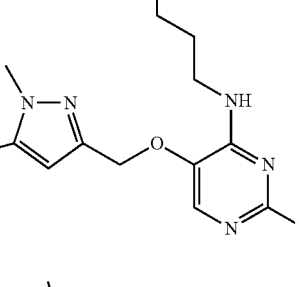 | 0.146 | 1.210 | 0.096 | ND |
| 182 | 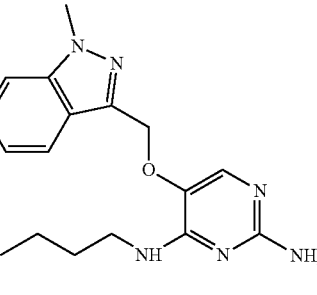 | 0.014 | 0.178 | 0.007 | ND |
| 183 | 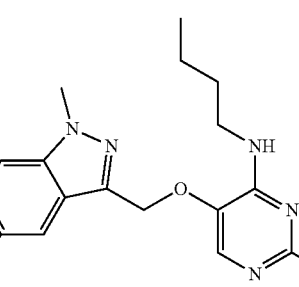 | 0.056 | 1.580 | 0.023 | ND |

TABLE II-continued

| # | Structure | | | | |
|---|---|---|---|---|---|
| 184 | (quinoline-8-CH2-O-pyrimidine with NH-butyl and NH2) | 0.157 | 1.650 | 0.053 | ND |
| 185 | (quinoline-2-CH2-O-pyrimidine with NH-sec-pentyl and NH2) | 0.743 | 2.340 | 0.488 | ND |
| 186 | (quinoline-2-CH2-O-pyrimidine with NH-(S)-CH(butyl)CH2CH2OH and NH2) | 0.122 | 0.680 | 0.065 | ND |
| 187 | (4-methoxy-3,5-dimethylpyridin-2-CH2-O-pyrimidine with NH-(S)-CH(propyl)CH2CH2OH and NH2) | 0.074 | 0.178 | 0.022 | ND |
| 188 | (quinoline-2-CH2-O-pyrimidine with NH-(S)-CH(propyl)CH2CH2OH and NH2) | 0.237 | 0.530 | 0.086 | ND |
| 189 | (quinoline-2-CH2-O-pyrimidine with NH-CH(CH3)-hexyl and NH2) | 11.990 | >25 | 17.570 | ND |

TABLE II-continued
| | | | | | |
|---|---|---|---|---|---|
| 190 | 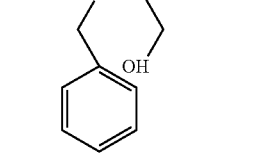 | 8.620 | 4.330 | 3.230 | ND |
| 191 | 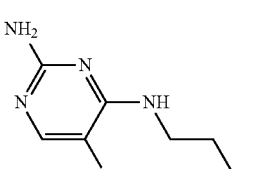 | 0.286 | 0.743 | 0.066 | ND |
| 192 | 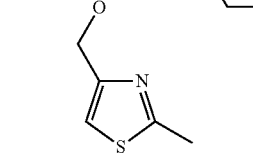 | 0.080 | 0.220 | 0.044 | ND |
| 193 | 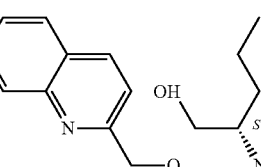 | 0.032 | 0.654 | 0.017 | ND |
| 194 | 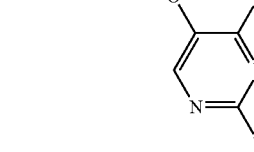 | 0.031 | 0.164 | 0.019 | ND |

TABLE II-continued

| # | Structure | | | | |
|---|---|---|---|---|---|
| 195 | (structure) | 0.003 | 0.056 | 0.003 | ND |
| 196 | (structure) | 1.900 | 0.469 | 0.687 | ND |
| 197 | (structure) | 2.650 | 0.624 | 0.767 | ND |
| 198 | (structure) | 0.076 | 0.511 | 0.089 | ND |

TABLE II-continued

| | | | | | |
|---|---|---|---|---|---|
| 199 | [structure] | 0.512 | 2.280 | 0.218 | ND |
| 200 | [structure] | 0.253 | 0.181 | 0.200 | ND |
| 201 | [structure] | 0.566 | 0.647 | 0.758 | ND |
| 202 | [structure] | 0.164 | 0.089 | 0.049 | ND |

TABLE II-continued
| | | | | | |
|---|---|---|---|---|---|
| 203 | 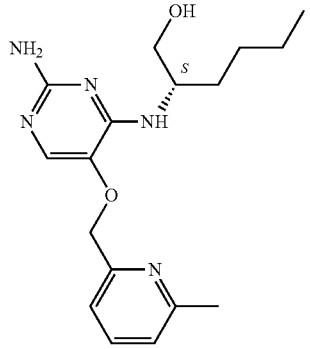 | 0.124 | 0.160 | 0.054 | ND |
| 204 | 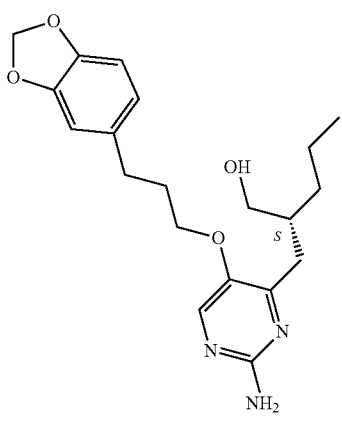 | 0.791 | 0.791 | 0.493 | ND |
| 205 | 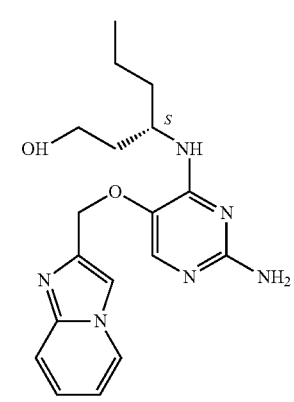 | 0.369 | 1.110 | 0.047 | ND |
| 206 | 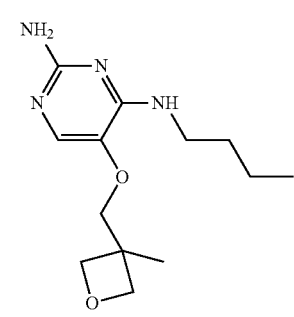 [SMILES: CCCCNc1nc(N)ncc1OCC1(C)COC1] | >25 | 9.450 | >23.81 | ND |

TABLE II-continued

| | | | | | |
|---|---|---|---|---|---|
| 207 | (structure) | 0.177 | 1.450 | 0.063 | ND |
| 208 | (structure) | 0.001 | 0.093 | 0.000 | ND |
| 209 | (structure) | 0.074 | 0.667 | 0.076 | ND |
| 210 | (structure) | 0.686 | 0.896 | 0.237 | ND |
| 211 | (structure) | 0.208 | 1.040 | 0.097 | ND |

TABLE II-continued

| # | Structure | | | | |
|---|---|---|---|---|---|
| 212 | (structure) | 0.007 | 0.148 | 0.005 | ND |
| 213 | (structure) | 0.225 | 0.207 | ND | 0.032 |
| 214 | (structure) | 0.134 | 0.593 | ND | 0.027 |
| 215 | (structure) | 0.171 | 0.300 | ND | 0.029 |
| 216 | (structure) | 0.008 | 0.111 | ND | 0.002 |

TABLE II-continued
| 217 | 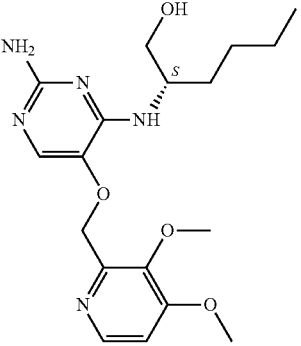 | 0.106 | 0.433 | ND | 0.007 |
| 218 | 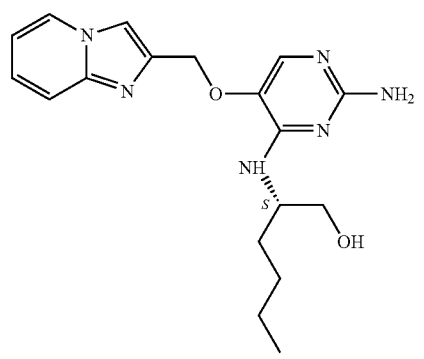 | 0.154 | 0.352 | ND | 0.032 |
| 219 | 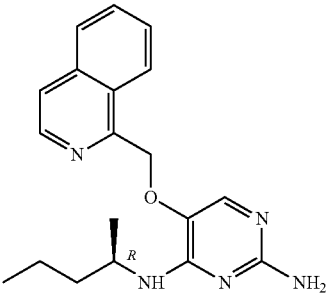 | 0.125 | 1.640 | ND | 0.029 |
| 220 | 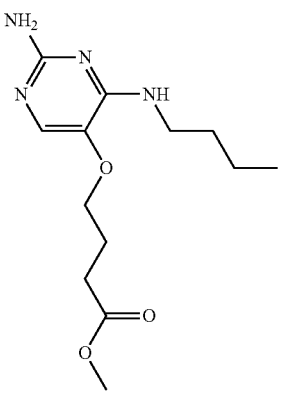 [SMILES: CCCCNc1nc(N)ncc1OCCCC(=O)OC] | 1.940 | 1.450 | ND | 1.720 |

TABLE II-continued
| 221 | 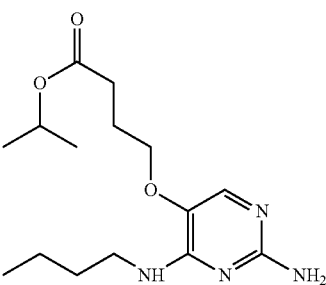 [SMILES: CCCCNc1nc(N)ncc1OCCCC(=O)OC(C)C] | 0.654 | 0.859 | ND | 0.496 |
| --- | --- | --- | --- | --- | --- |
| 222 | 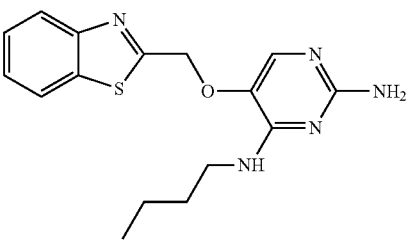 | 0.277 | 2.600 | ND | 0.106 |
| 223 | 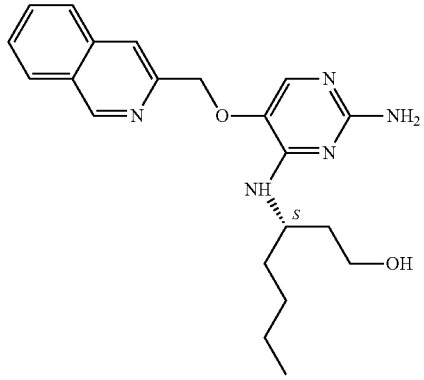 | 0.100 | 1.400 | ND | 0.033 |
| 224 | 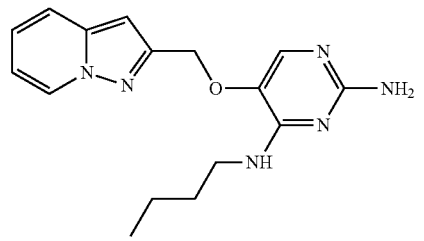 [SMILES: CCCCNc1nc(N)ncc1OCc1cc2ccccn2n1] | 0.206 | 1.270 | ND | 0.037 |

TABLE II-continued

| | | | | | |
|---|---|---|---|---|---|
| 225 | (structure) | 0.385 | 2.180 | ND | 0.129 |
| 226 | (structure) | 0.274 | 1.050 | ND | 0.036 |
| 227 | (structure) | 0.170 | 0.717 | ND | 0.030 |

TABLE II-continued

| # | Structure | | | | |
|---|---|---|---|---|---|
| 228 | (structure) | 1.410 | 1.510 | ND | 0.112 |
| 229 | (structure) | >25 | 8.850 | ND | 7.790 |
| 230 | (structure) | 0.593 | 3.470 | ND | 0.138 |
| 231 | (structure) | 0.001 | 0.052 | ND | <0.001 |

TABLE II-continued

| # | Structure | | | | |
|---|---|---|---|---|---|
| 232 | (2-amino-pyrimidin-4-yl)-butylamine with 5-O-CH2CH2-NH-C(=O)-O-ethyl | 0.967 | 1.680 | ND | 0.110 |
| 233 | (2-amino-pyrimidin-4-yl)-butylamine with 5-O-isopropyl | 10.070 | 0.662 | ND | 0.503 |
| 234 | (2-amino-pyrimidin-4-yl)-butylamine with 5-O-CH2CH2-O-isopropyl | 1.850 | 1.170 | ND | 0.464 |
| 235 | (tetrahydrofuran-3-yl)methoxy-pyrimidine with butylamine and NH2 | >25 | 10.410 | ND | 1.890 |
| 236 | 1,8-naphthyridin-2-yl-methoxy-pyrimidine with butylamine and NH2 | 0.241 | 0.333 | ND | 0.031 |

TABLE II-continued
| | | | | | |
|---|---|---|---|---|---|
| 237 | 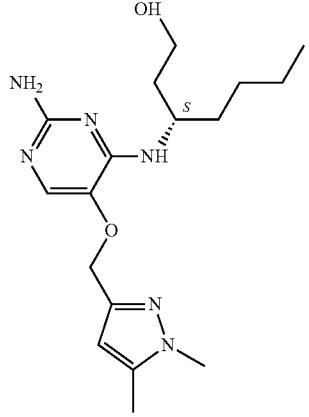 | 0.156 | 1.830 | ND | 0.051 |
| 238 | 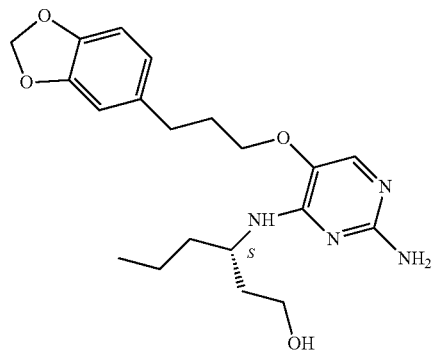 | 0.234 | 1.920 | ND | 0.091 |
| 239 | 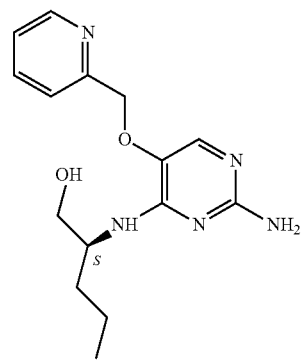 | 0.464 | 0.247 | ND | 0.145 |
| 240 | 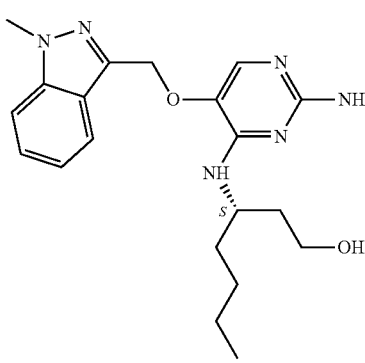 | 0.008 | 0.442 | ND | 0.005 |

TABLE II-continued
| | | | | | | |
|---|---|---|---|---|---|---|
| 241 | 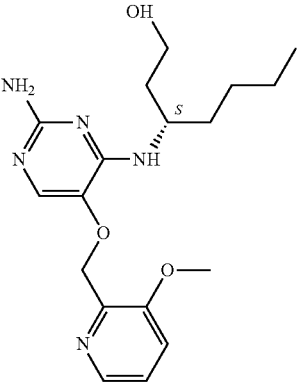 | 0.008 | 0.304 | ND | 0.004 |
| 242 | 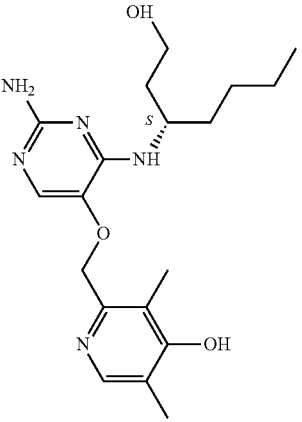 | 5.400 | 3.010 | ND | 0.006 |
| 243 | 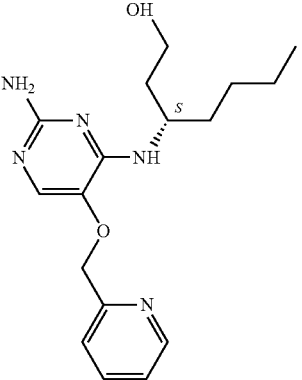 | 0.343 | 0.103 | ND | 0.190 |
| 244 | 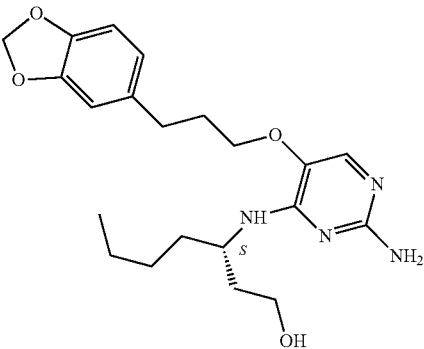 | 0.202 | 1.400 | ND | 0.104 |

TABLE II-continued
| | | | | | |
|---|---|---|---|---|---|
| 245 | 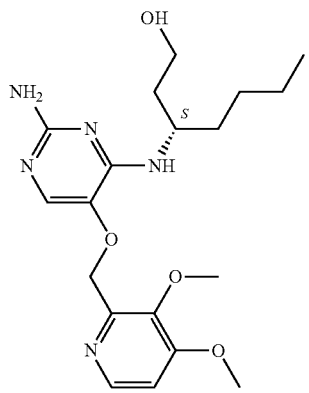 | 0.040 | 0.507 | ND | 0.011 |
| 246 | 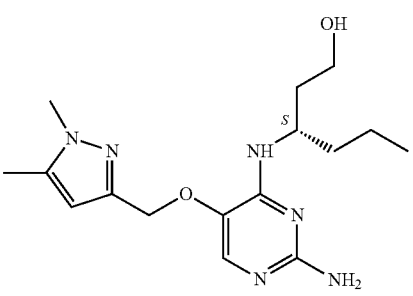 | 0.157 | 1.150 | ND | 0.048 |
| 247 | 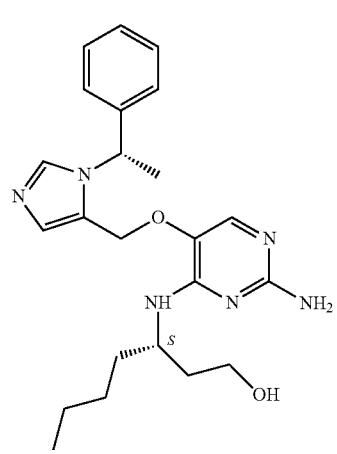 | 12.390 | 8.240 | ND | 3.200 |
| 248 | 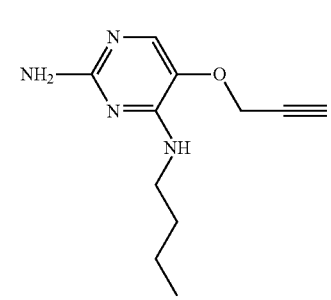 | 2.120 | 0.654 | ND | 0.529 |

TABLE II-continued

| | | | | | |
|---|---|---|---|---|---|
| 249 | (structure) | 0.039 | 0.172 | ND | 0.036 |
| 250 | (structure) | 0.724 | 3.250 | ND | 0.580 |
| 251 | (structure) | 0.164 | 0.556 | ND | 0.087 |
| 252 | (structure) | 4.020 | >25 | ND | 1.310 |
| 253 | (structure) | 12.760 | >25 | ND | 6.230 |

TABLE II-continued
| 254 | 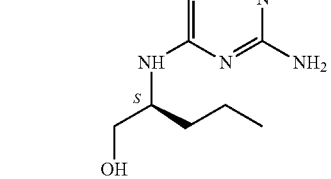 | 1.770 | 0.467 | ND | 0.364 |
| 255 | 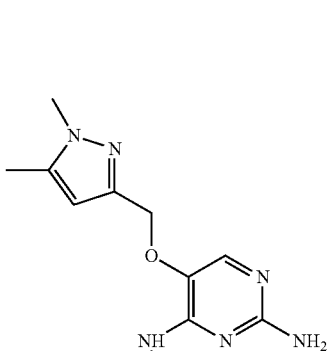 | 0.552 | 0.515 | ND | 0.315 |
| 256 | 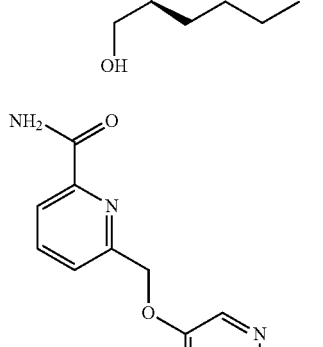 | 1.630 | 0.100 | ND | 0.039 |
| 257 | 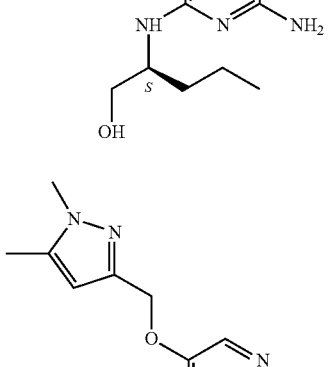 | 0.697 | 0.444 | ND | 0.304 |

TABLE II-continued
| | | | | | |
|---|---|---|---|---|---|
| 258 | 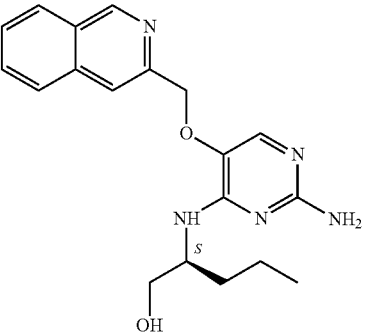 | 0.074 | 0.153 | ND | 0.060 |
| 259 | 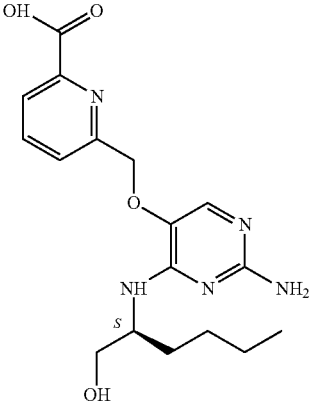 | 6.980 | 3.150 | ND | 1.250 |
| 260 | 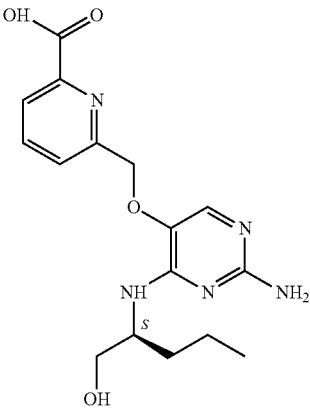 | 4.850 | 2.830 | ND | >8.14 |
| 261 | 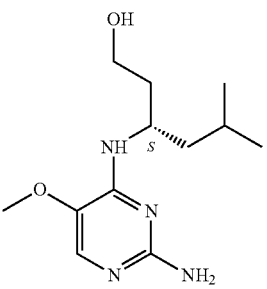 | 10.790 | 2.300 | ND | 7.460 |

TABLE II-continued

| | | | | | |
|---|---|---|---|---|---|
| 262 | (structure) | 0.658 | 0.168 | ND | 0.363 |
| 263 | (structure) | 0.049 | 0.159 | ND | 0.056 |
| 264 | (structure) | 0.215 | 0.489 | ND | 0.087 |
| 265 | (structure) | 0.752 | 3.700 | ND | 0.591 |
| 266 | (structure) | 1.070 | 1.890 | ND | 0.557 |

TABLE II-continued

| | | | | | |
|---|---|---|---|---|---|
| 267 | [structure] | 4.880 | 0.719 | ND | 1.710 |
| 268 | [structure] | 2.100 | 1.800 | ND | 1.170 |
| 269 | [structure] | 24.550 | 8.280 | ND | 9.750 |
| 270 | [structure] | 0.109 | 0.131 | ND | 0.006 |
| 271 | [structure] | 0.261 | 0.511 | ND | 0.088 |

TABLE II-continued

| | | | | | |
|---|---|---|---|---|---|
| 272 | (structure) | 0.207 | 1.110 | ND | 0.084 |
| 273 | (structure) | 1.100 | 0.516 | ND | 0.552 |
| 274 | (structure) | 1.140 | 0.303 | ND | 0.357 |
| 275 | (structure) | 10.380 | 2.600 | ND | 2.230 |
| 276 | (structure) | 3.260 | 0.707 | ND | 0.652 |

TABLE II-continued

| # | Structure | | | | |
|---|---|---|---|---|---|
| 277 | (pyridazin-3-ylmethoxy pyrimidine with 2-amino, NH-(S)-pentan-1-ol) | 1.180 | 0.438 | ND | 0.135 |
| 278 | (pyridazin-3-ylmethoxy pyrimidine with 2-amino, NH-(S)-hexan-1-ol) | 0.880 | 0.270 | ND | 0.136 |
| 279 | (pyridazin-3-ylmethoxy pyrimidine with 2-amino, NH-(S)-pentan-3-yl ethanol) | 0.724 | 1.100 | ND | 0.034 |
| 280 | (pyridazin-3-ylmethoxy pyrimidine with 2-amino, NH-(S)-hexan-3-yl ethanol) | 0.392 | 1.450 | ND | 0.038 |

TABLE II-continued
| | | | | | |
|---|---|---|---|---|---|
| 281 | 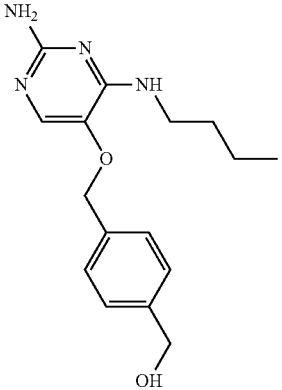 [SMILES: CCCCNc1nc(N)ncc1OCc1ccc(CO)cc1] | 0.472 | 1.630 | ND | 0.191 |
| 282 | 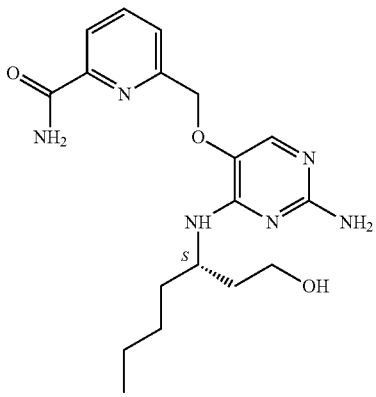 | 0.133 | 0.502 | ND | 0.005 |
| 283 | 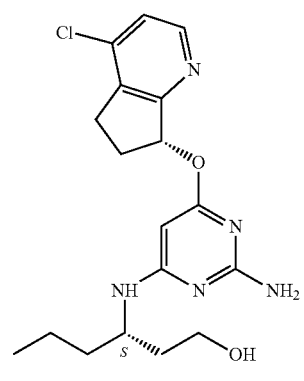 | 17.180 | 8.320 | ND | 4.350 |
| 284 | 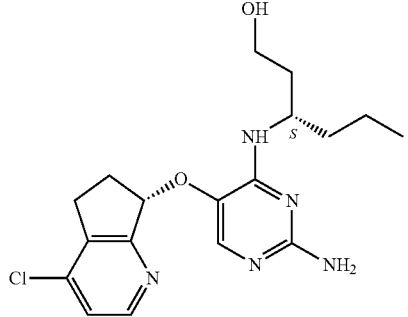 | 9.910 | 10.300 | ND | 2.150 |

TABLE II-continued

| | | | | | |
|---|---|---|---|---|---|
| 285 | [structure] | 0.266 | 0.530 | ND | 0.036 |
| 286 | [structure] | 0.620 | 7.660 | ND | 0.128 |
| 287 | [structure] | 15.530 | 5.380 | ND | 3.560 |
| 288 | [structure] | >25 | 10.200 | ND | 1.4890 |
| 289 | [structure] | 0.875 | 0.930 | ND | 0.647 |

TABLE II-continued

| | | | | | |
|---|---|---|---|---|---|
| 290 | (structure) | >25 | 9.110 | ND | 12.460 |
| 291 | (structure) | 0.120 | 0.407 | ND | 0.106 |
| 292 | (structure) | 0.913 | 3.082 | ND | ND |
| 293 | (structure) | 0.197 | 0.530 | ND | 0.088 |
| 294 | (structure) | 0.133 | 0.521 | ND | 0.042 |

TABLE II-continued

| # | Structure | | | | |
|---|---|---|---|---|---|
| 295 | 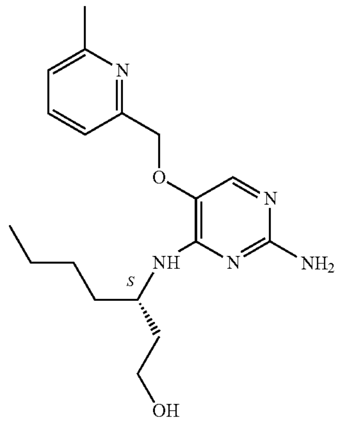 | 0.047 | 0.430 | ND | 0.034 |
| 296 | 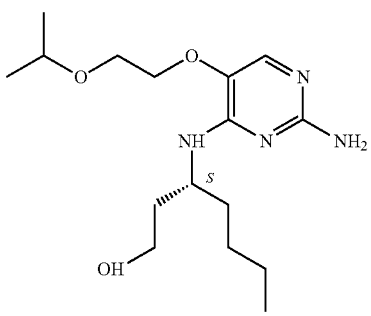 | 0.664 | 2.540 | ND | 0.310 |
| 297 | 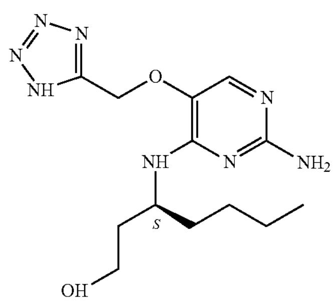 | 2.810 | >25 | ND | 2.540 |
| 298 | 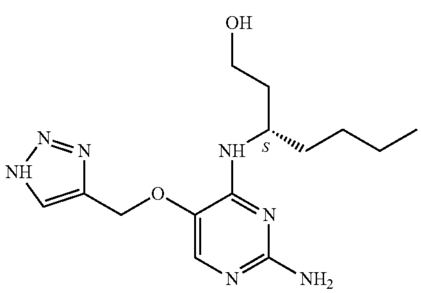 | 0.394 | 2.840 | ND | 0.058 |
| 299 | 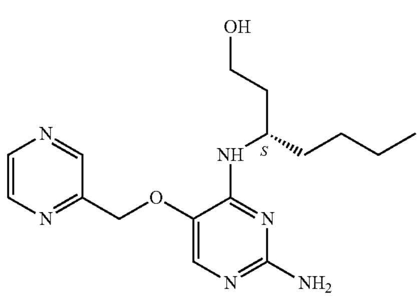 | 0.211 | 0.433 | ND | 0.159 |

TABLE II-continued

| | | | | | |
|---|---|---|---|---|---|
| 300 | [structure: 5-methoxy-pyrimidine-2-amine with NH-CH(butyl)-CH(OH)-CH3, S,R] | 1.740 | 0.720 | ND | 0.475 |
| 301 | [structure: 5-(2-isopropoxyethoxy)pyrimidine-2-amine with NH-CH(S)(CH2CH2OH)(butyl)] | 1.170 | 2.640 | ND | 0.534 |
| 302 | [structure: 5-(pyridin-4-ylmethoxy)pyrimidine-2-amine with NH-CH(S)(CH2CH2OH)(propyl)] | 0.385 | 0.487 | ND | 0.070 |

ND = Not done.

---

The invention claimed is:

1. A method for the treatment of a disorder or disease in a subject in which the modulation of TLR7 and/or TLR8 is involved, said method comprising administering to the subject an effective amount of a compound of formula (I)

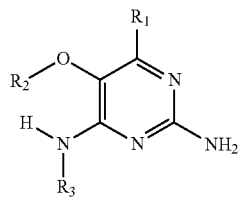

or a pharmaceutically acceptable salt, tautomer(s), solvate or polymorph thereof, wherein $R_1$ is hydrogen, $C_{1-4}$alkyl, cyclopropyl, $C_{1-6}$alkoxy, halogen, hydroxyl, or trifluoromethyl;

$R_2$ is $C_{1-8}$alkyl optionally substituted by one or more substituents independently selected from the group consisting of halogen, hydroxyl, amino, $C_{1-6}$alkyl, di-($C_{1-6}$)alkylamino, $C_{1-6}$alkylamino, $C_{1-6}$alkoxy, $C_{3-6}$cycloalkyl, carboxylic acid, carboxylic ester, carboxylic amide, heterocycle, aryl, alkenyl, alkynyl, arylalkyl, heteroaryl, heteroarylalkyl, and nitrile, wherein said aryl, heterocycle, or heteroaryl is further optionally substituted by $C_{1-3}$alkyl, alkoxy, carboxylic ester or carboxylic amide;

and $R_3$ is $C_{4-8}$alkyl, $C_{4-8}$alkoxy, $C_{2-6}$alkenyl or $C_{2-6}$ alkynyl, each of which is optionally substituted by one or more substituents independently selected from the group consisting of halogen, hydroxyl, amino, $C_{1-3}$alkyl, $C_{1-3}$alkoxy or $C_{3-6}$ cycloalkyl, and nitrile.

2. A method for the treatment of viral infections in a subject comprising administering to the subject an effective amount of a compound of formula (I)

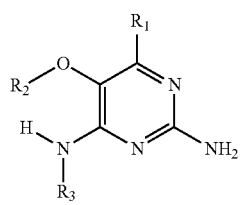

or a pharmaceutically acceptable salt, tautomer, solvate or polymorph thereof, wherein $R_1$ is hydrogen, $C_{1-4}$alkyl, cyclopropyl, $C_{1-6}$alkoxy, halogen, hydroxyl, or trifluoromethyl;

$R_2$ is $C_{1-8}$alkyl optionally substituted by one or more substituents independently selected from the group consisting of halogen, hydroxyl, amino, $C_{1-6}$alkyl, di-($C_{1-6}$)alkylamino, $C_{1-6}$alkylamino, $C_{1-6}$alkoxy, $C_{3-6}$cycloalkyl, carboxylic acid, carboxylic ester, carboxylic amide, heterocycle, aryl, alkenyl, alkynyl, arylalkyl, heteroaryl, heteroarylalkyl, and nitrile, wherein said aryl, heterocycle, or heteroaryl is further optionally substituted by $C_{1-3}$alkyl, alkoxy, carboxylic ester or carboxylic amide;

and $R_3$ is $C_{4-8}$alkyl, $C_{4-8}$alkoxy, $C_{2-6}$alkenyl or $C_{2-6}$alkynyl, each of which is optionally substituted by one or more substituents independently selected from the group consisting of halogen, hydroxyl, amino, $C_{1-3}$alkyl, $C_{1-3}$alkoxy or $C_{3-6}$cycloalkyl, and nitrile.

3. A method for treating viral infection in a subject through modulation of TLR7 and/or TLR8, said method comprising administering to the subject an effective amount of a compound of formula (I)

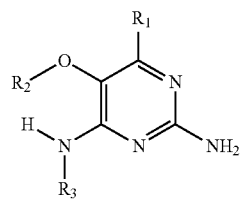

or a pharmaceutically acceptable salt, tautomer(s), solvate or polymorph thereof, wherein $R_1$ is hydrogen, $C_{1-4}$alkyl, cyclopropyl, $C_{1-6}$alkoxy, halogen, hydroxyl, or trifluoromethyl;

$R_2$ is $C_{1-8}$alkyl optionally substituted by one or more substituents independently selected from the group consisting of halogen, hydroxyl, amino, $C_{1-6}$alkyl, di-($C_{1-6}$)alkylamino, $C_{1-6}$alkylamino, $C_{1-6}$alkoxy, $C_{3-6}$cycloalkyl, carboxylic acid, carboxylic ester, carboxylic amide, heterocycle, aryl, alkenyl, alkynyl, arylalkyl, heteroaryl, heteroarylalkyl, and nitrile, wherein said aryl, heterocycle, or heteroaryl is further optionally substituted by $C_{1-3}$alkyl, alkoxy, carboxylic ester or carboxylic amide;

and $R_3$ is $C_{4-8}$alkyl, $C_{4-8}$alkoxy, $C_{2-6}$alkenyl or $C_{2-6}$ alkynyl, each of which is optionally substituted by one or more substituents independently selected from the group consisting of halogen, hydroxyl, amino, $C_{1-3}$alkyl, $C_{1-3}$alkoxy or $C_{3-6}$ cycloalkyl, and nitrile.

4. The method of claim 3 wherein the compound of formula (I) is selected from the group consisting of:

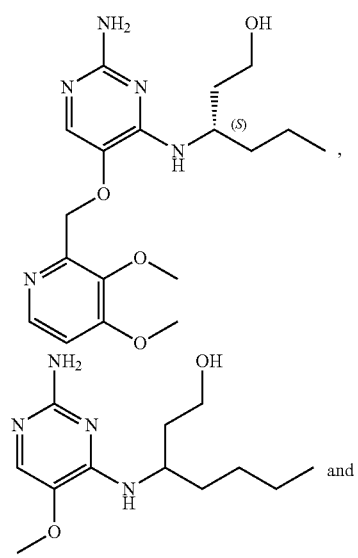

-continued

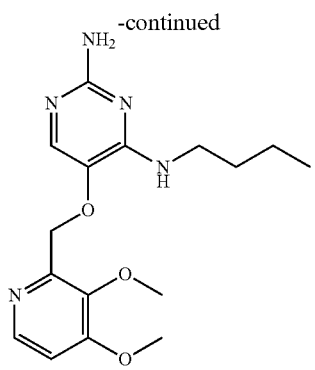

or a pharmaceutically acceptable salt, tautomer, solvate or polymorph thereof.

5. A method for modulating TLR7 and/or TLR8, said method comprising contacting said TLR7 and/or TLR8 with a compound of formula (I)

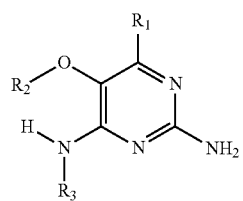

or a pharmaceutically acceptable salt, tautomer(s), solvate or polymorph thereof, wherein $R_1$ is hydrogen, $C_{1-4}$alkyl, cyclopropyl, $C_{1-6}$alkoxy, halogen, hydroxyl, or trifluoromethyl;

$R_2$ is $C_{1-8}$alkyl optionally substituted by one or more substituents independently selected from the group consisting of halogen, hydroxyl, amino, $C_{1-6}$alkyl, di-($C_{1-6}$)alkylamino, $C_{1-6}$alkylamino, $C_{1-6}$alkoxy, $C_{3-6}$cycloalkyl, carboxylic acid, carboxylic ester, carboxylic amide, heterocycle, aryl, alkenyl, alkynyl, arylalkyl, heteroaryl, heteroarylalkyl, and nitrile, wherein said aryl, heterocycle, or heteroaryl is further optionally substituted by $C_{1-3}$alkyl, alkoxy, carboxylic ester or carboxylic amide;

and $R_3$ is $C_{4-8}$alkyl, $C_{4-8}$alkoxy, $C_{2-6}$alkenyl or $C_{2-6}$alkynyl, each of which is optionally substituted by one or more substituents independently selected from the group consisting of halogen, hydroxyl, amino, $C_{1-3}$alkyl, $C_{1-3}$alkoxy or $C_{3-6}$cycloalkyl, and nitrile.

6. The method of claim 5, wherein the compound of formula (I) is selected from the group consisting of:

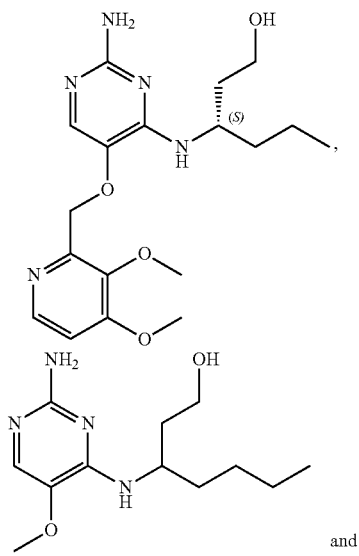

or a pharmaceutically acceptable salt, tautomer, solvate or polymorph thereof.

7. The method of claim 1 wherein the compound of formula (I) is selected from the group consisting of:

-continued

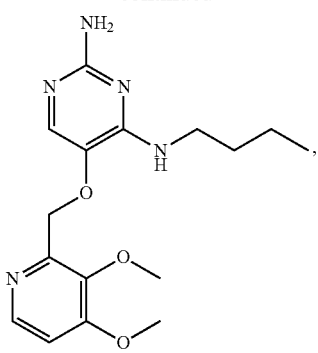

or a pharmaceutically acceptable salt, tautomer, solvate or polymorph thereof.

8. The method of claim 1 wherein in the compound of formula (I), $R_3$ is selected from the group consisting of:

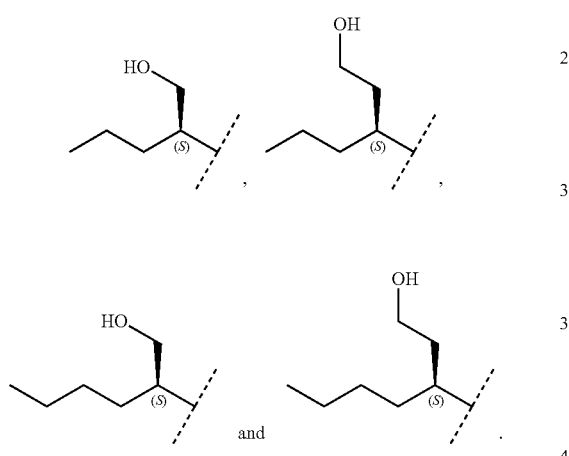

9. The method of claim 1 wherein in the compound of formula (I), $R_2$ is selected from the group consisting of:

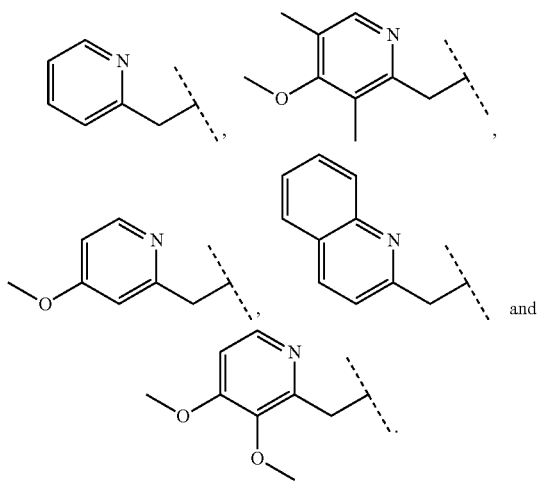

10. The method of claim 1 wherein in the compound of formula (I) is

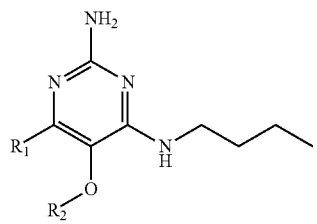

wherein
$R_1$ is selected from the group consisting of $C_{1-4}$alkyl, cyclopropyl, $C_{1-6}$alkoxy and trifluoromethyl; and
$R_2$ is $C_{1-8}$alkyl optionally substituted by one or more substituents independently selected from the group consisting of halogen, hydroxyl, amino, $C_{1-6}$alkyl, di-($C_{1-6}$)alkylamino, $C_{1-6}$alkylamino, $C_{1-6}$alkoxy, $C_{3-6}$cycloalkyl, carboxylic acid, carboxylic ester, carboxylic amide, heterocycle, aryl, alkenyl, alkynyl, arylalkyl, heteroaryl, heteroarylalkyl, and nitrile, wherein said aryl, heterocycle, or heteroaryl is further optionally substituted by $C_{1-3}$alkyl, alkoxy, carboxylic ester or carboxylic amide.

11. The method of claim 2 wherein the compound of formula (I) is selected from the group consisting of:

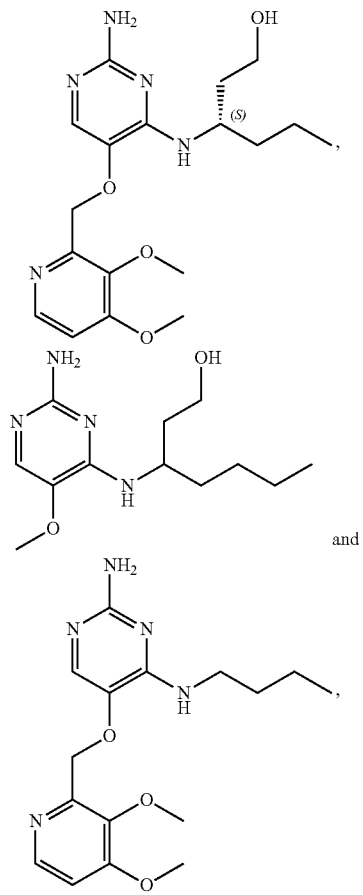

or a pharmaceutically acceptable salt, tautomer, solvate or polymorph thereof.

12. The method of claim 2 wherein in the compound of formula (I), $R_3$ is selected from the group consisting of:

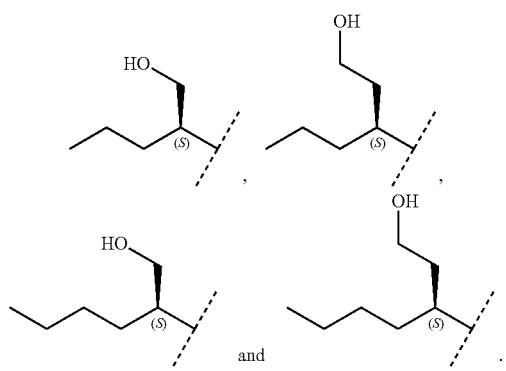

13. The method of claim 2 wherein in the compound of formula (I), $R_2$ is selected from the group consisting of:

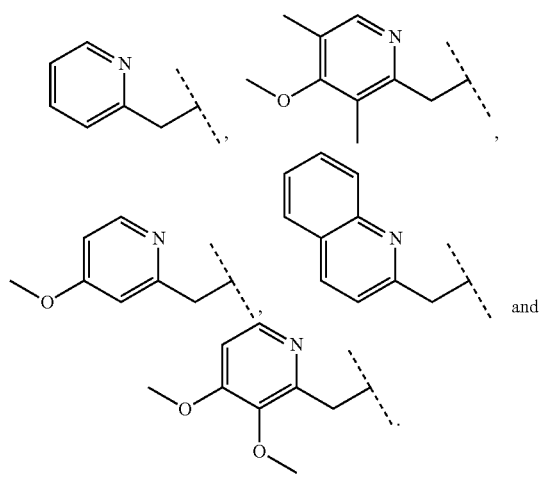

14. The method of claim 2 wherein in the compound of formula (I) is

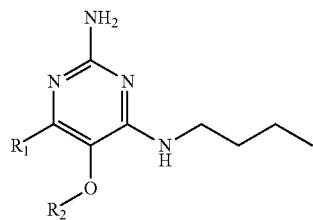

wherein
$R_1$ is selected from the group consisting of $C_{1-4}$alkyl, cyclopropyl, $C_{1-6}$alkoxy and trifluoromethyl; and
$R_2$ is $C_{1-8}$alkyl optionally substituted by one or more substituents independently selected from the group consisting of halogen, hydroxyl, amino, $C_{1-6}$alkyl, di-$(C_{1-6})$alkylamino, $C_{1-6}$alkylamino, $C_{1-6}$alkoxy, $C_{3-6}$cycloalkyl, carboxylic acid, carboxylic ester, carboxylic amide, heterocycle, aryl, alkenyl, alkynyl, arylalkyl, heteroaryl, heteroarylalkyl, and nitrile, wherein said aryl, heterocycle, or heteroaryl is further optionally substituted by $C_{1-3}$alkyl, alkoxy, carboxylic ester or carboxylic amide.

15. The method of claim 3 wherein in the compound of formula (I), $R_3$ is selected from the group consisting of:

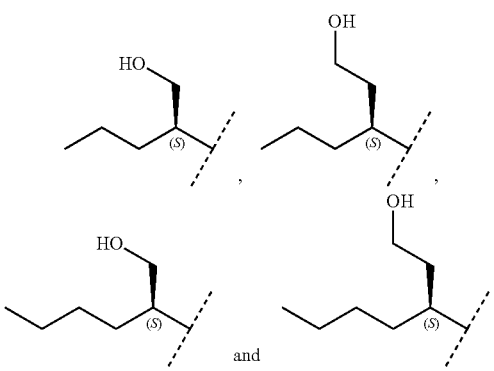

16. The method of claim 3 wherein in the compound of formula (I), $R_2$ is selected from the group consisting of:

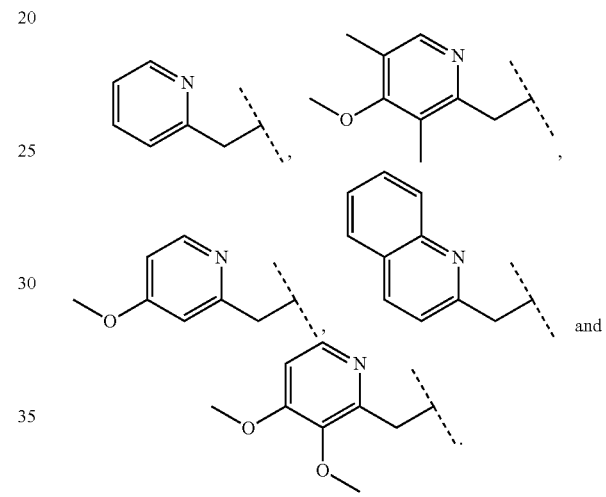

17. The method of claim 3 wherein in the compound of formula (I) is

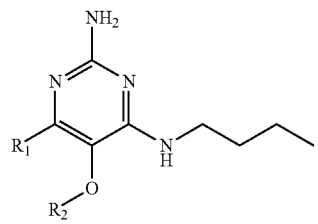

wherein
$R_1$ is selected from the group consisting of $C_{1-4}$alkyl, cyclopropyl, $C_{1-6}$alkoxy and trifluoromethyl; and
$R_2$ is $C_{1-8}$alkyl optionally substituted by one or more substituents independently selected from the group consisting of halogen, hydroxyl, amino, $C_{1-6}$alkyl, di-$(C_{1-6})$alkylamino, $C_{1-6}$alkylamino, $C_{1-6}$alkoxy, $C_{3-6}$cycloalkyl, carboxylic acid, carboxylic ester, carboxylic amide, heterocycle, aryl, alkenyl, alkynyl, arylalkyl, heteroaryl, heteroarylalkyl, and nitrile, wherein said aryl, heterocycle, or heteroaryl is further optionally substituted by $C_{1-3}$alkyl, alkoxy, carboxylic ester or carboxylic amide.

18. The method of claim 5 wherein in the compound of formula (I), $R_3$ is selected from the group consisting of:

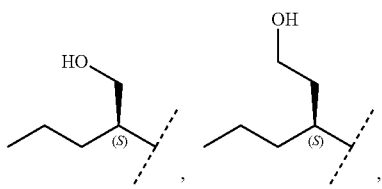

,

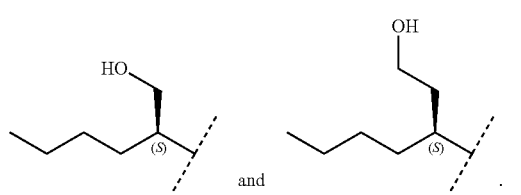

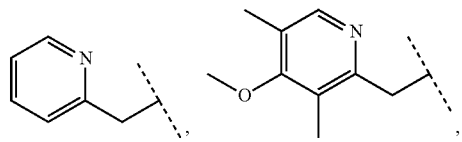

and 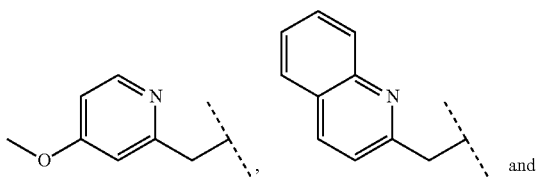.

19. The method of claim 5 wherein in the compound of formula (I), R$_2$ is selected from the group consisting of:

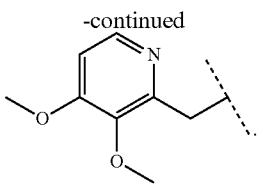

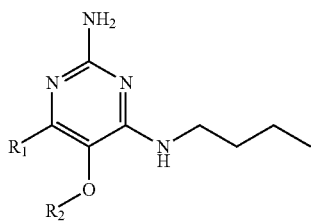

and

20. The method of claim 5 wherein in the compound of formula (I) is wherein
R$_1$ is selected from the group consisting of C$_{1-4}$alkyl, cyclopropyl, C$_{1-6}$alkoxy and trifluoromethyl; and R$_2$ is C$_{1-8}$alkyl optionally substituted by one or more substituents independently selected from the group consisting of halogen, hydroxyl, amino, C$_{1-6}$alkyl, di-(C$_{1-6}$)alkylamino, C$_{1-6}$alkylamino, C$_{1-6}$alkoxy, C$_{3-6}$cycloalkyl, carboxylic acid, carboxylic ester, carboxylic amide, heterocycle, aryl, alkenyl, alkynyl, arylalkyl, heteroaryl, heteroarylalkyl, and nitrile, wherein said aryl, heterocycle, or heteroaryl is further optionally substituted by C$_{1-3}$alkyl, alkoxy, carboxylic ester or carboxylic amide.

* * * * *